US012529701B2

(12) United States Patent
Ogasawara et al.

(10) Patent No.: US 12,529,701 B2
(45) Date of Patent: Jan. 20, 2026

(54) METHOD FOR PREDICTING SENSITIVITY OF CANCER CELL TO GPX4 INHIBITOR

(71) Applicant: Chugai Seiyaku Kabushiki Kaisha, Tokyo (JP)

(72) Inventors: Kiyomoto Ogasawara, Kanagawa (JP); Keisuke Hashimoto, Kanagawa (JP); Kenji Kashima, Kanagawa (JP); Hiroshi Sakamoto, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 860 days.

(21) Appl. No.: 17/785,484

(22) PCT Filed: Dec. 25, 2020

(86) PCT No.: PCT/JP2020/048811
§ 371 (c)(1),
(2) Date: Jun. 15, 2022

(87) PCT Pub. No.: WO2021/132592
PCT Pub. Date: Jul. 1, 2021

(65) Prior Publication Data

US 2023/0204589 A1 Jun. 29, 2023

(30) Foreign Application Priority Data

Dec. 26, 2019 (JP) ................................ 2019-236516

(51) Int. Cl.
*G01N 33/574* (2006.01)
*C12Q 1/6886* (2018.01)
*G01N 33/50* (2006.01)

(52) U.S. Cl.
CPC ..... *G01N 33/57488* (2013.01); *C12Q 1/6886* (2013.01); *G01N 33/5011* (2013.01); *G01N 33/5023* (2013.01); *C12Q 2600/106* (2013.01); *C12Q 2600/158* (2013.01)

(58) Field of Classification Search
CPC ................................................ G01N 33/57488
USPC ........................................................ 435/7.23
See application file for complete search history.

(56) References Cited

FOREIGN PATENT DOCUMENTS

WO WO 2018/218087 A1 * 11/2018
WO WO 2019/006005 A2 * 1/2019

OTHER PUBLICATIONS

Carcamo et al (Cell Reports, 2022, 39, 110637: 1-15 and e1-e9).*
English translation of International Preliminary Report on Patentability for App. Ser. No. PCT/JP2020/048811, dated Jun. 28, 2022, 5 pages.
Eaton et al., "Targeting a Therapy-Resistant Cancer Cell State Using Masked Electrophiles as GPX4 Inhibitors," bioRxiv, Sep. 5, 2018, pp. 1-38.
Eaton et al., "Diacylfuroxans are Masked Nitrile Oxides that Inhibit GPX4 Covalently," J Am Chem Soc, Dec. 26, 2019, 141(51):20407-20415.
Shi et al., "Ferroptosis in Carcinoma: Regulatory Mechanisms and New Method for Cancer Therapy," Onco Targets and Therapy, Dec. 1, 2019, 12:11291-11304.
Viswanathan et al., "Dependency of a therapy-resistant state of cancer cells on a lipid peroxidase pathway," Nature, Jul. 27, 2017, 547(7664):453-457.
Wilson et al., "ARID1A and PI3-kinase pathway mutations in the endometrium drive epithelial transdifferentiation and collective invasion," Nature Communications, Aug. 7, 2019, 10(1):3554, 18 pages.
Camidge et al., "Updated Efficacy and Safety Data and Impact of the EML4-ALK Fusion Variant on the Efficacy of Alectinib in Untreated ALK-Positive Advanced Non-Small Cell Lung Cancer in the Global Phase III ALEX Study," J Thorac Oncol, Jul. 2019, 14(7):1233-1243.
Chapman et al., "Improved Survival with Vemurafenib in Melanoma with BRAF V600E Mutation," NEJM, Jun. 30, 2011, 364(26):2507-2516.
Deribe et al., "Mutations in the SWI/SNF complex induce a targetable dependence on oxidative phosphorylation in lung cancer," Nat Med, Jul. 2018, 24:1047-1057.
Maemondo et al., "Gefitinib or Chemotherapy for Non-Small-Cell Lung Cancer with Mutated EGFR," NEJM, Jun. 24, 2010, 362(25):2380-2388.
Ogiwara et al., "Targeting the Vulnerability of Glutathione Metabolism in ARIDIA-Deficient Cancers," Cancer Cell, 2019, 35:177-190.
Tagal et al., "SMARCA4-inactivating mutations increase sensitivity to Aurora kinase A inhibitor VX-680 in non-small cell lung cancers," Nat Commun, 2017, 8:14098, 13 pages.
Xue et al., "SMARCA4 loss is synthetic lethal with CDK4/6 inhibition in non-small cell lung cancer," Nat Commun, 2019, 10:557, 13 pages.
Zou et al., "A GPX4-dependent cancer cell state underlies the clear-cell morphology and confers sensitivity to ferroptosis," Nat Commun, Apr. 8, 2019, 10(1617):1-13.
International Search Report for PCT/JP2020/048811, mailed Mar. 2, 2021, 1 page.

* cited by examiner

*Primary Examiner* — Sean E Aeder
(74) *Attorney, Agent, or Firm* — Fish & Richardson P.C.

(57) ABSTRACT

Provided are a cancer therapeutic drug comprising a compound which inhibits GPX4 as an active ingredient, the cancer therapeutic drug treating cancer containing a cancer cell having a suppressed function of a SWI/SNF complex factor detected; and a method for predicting sensitivity of a cancer cell to a GPX4 inhibitor, the method comprising the step of predicting a cancer cell having a suppressed function of a SWI/SNF complex factor detected in the cancer cell, as having sensitivity to the GPX4 inhibitor.

20 Claims, 9 Drawing Sheets

Specification includes a Sequence Listing.

SEQUENCE LISTING

<160> NUMBER OF SEQ ID NOS: 91

<210> SEQ ID NO 1
<211> LENGTH: 851
<212> TYPE: DNA
<213> ORGANISM: Homo sapiens

<400> SEQUENCE: 1

```
attggtcggc tggacgaggg gaggagccgc tggctcccag ccccgccgcg atgagcctcg     60

gccgcctttg ccgcctactg aagccggcgc tgctctgtgg ggctctggcc gcgcctggcc    120

tggccgggac catgtgcgcg tcccgggacg actggcgctg tgcgcgctcc atgcacgagt    180

tttccgccaa ggacatcgac gggcacatgg ttaacctgga caagtaccgg ggcttcgtgt    240

gcatcgtcac caacgtggcc tcccagtgag gcaagaccga agtaaactac actcagctcg    300

tcgacctgca cgcccgatac gctgagtgtg gtttgcggat cctggccttc ccgtgtaacc    360

agttcgggaa gcaggagcca gggagtaacg aagagatcaa agagttcgcc gcgggctaca    420

acgtcaaatt cgatatgttc agcaagatct gcgtgaacgg ggacgacgcc cacccgctgt    480

ggaagtggat gaagatccaa cccaagggca agggcatcct gggaaatgcc atcaagtgga    540

acttcaccaa gttcctcatc gacaagaacg gctgcgtggt gaagcgctac ggacccatgg    600

aggagcccct ggtgatagag aaggacctgc cccactattt ctagctccac aagtgtgtgg    660

ccccgcccga gcccctgccc acgcccttgg agccttccac cggcactcat gacggcctgc    720

ctgcaaacct gctggtgggg cagacccgaa aatccagcgt gcaccccgcc ggaggaaggt    780

cccatggcct gctgggcttg gctcggcgcc cccacccctg gctaccttgt gggaataaac    840

agacaaatta g                                                         851
```

<210> SEQ ID NO 2
<211> LENGTH: 197
<212> TYPE: PRT
<213> ORGANISM: Homo sapiens
<220> FEATURE:
<221> NAME/KEY: MISC_FEATURE
<222> LOCATION: (73)..(73)
<223> OTHER INFORMATION: Xaa represents seleonocysteine

<400> SEQUENCE: 2

```
Met Ser Leu Gly Arg Leu Cys Arg Leu Leu Lys Pro Ala Leu Leu Cys
1               5                   10                  15

Gly Ala Leu Ala Ala Pro Gly Leu Ala Gly Thr Met Cys Ala Ser Arg
            20                  25                  30

Asp Asp Trp Arg Cys Ala Arg Ser Met His Glu Phe Ser Ala Lys Asp
        35                  40                  45

Ile Asp Gly His Met Val Asn Leu Asp Lys Tyr Arg Gly Phe Val Cys
    50                  55                  60

Ile Val Thr Asn Val Ala Ser Gln Xaa Gly Lys Thr Glu Val Asn Tyr
65                  70                  75                  80

Thr Gln Leu Val Asp Leu His Ala Arg Tyr Ala Glu Cys Gly Leu Arg
                85                  90                  95

Ile Leu Ala Phe Pro Cys Asn Gln Phe Gly Lys Gln Glu Pro Gly Ser
            100                 105                 110

Asn Glu Glu Ile Lys Glu Phe Ala Ala Gly Tyr Asn Val Lys Phe Asp
        115                 120                 125

Met Phe Ser Lys Ile Cys Val Asn Gly Asp Asp Ala His Pro Leu Trp
    130                 135                 140
```

-continued

```
Lys Trp Met Lys Ile Gln Pro Lys Gly Lys Gly Ile Leu Gly Asn Ala
145                 150                 155                 160

Ile Lys Trp Asn Phe Thr Lys Phe Leu Ile Asp Lys Asn Gly Cys Val
                165                 170                 175

Val Lys Arg Tyr Gly Pro Met Glu Glu Pro Leu Val Ile Glu Lys Asp
            180                 185                 190

Leu Pro His Tyr Phe
        195


<210> SEQ ID NO 3
<211> LENGTH: 5879
<212> TYPE: DNA
<213> ORGANISM: Homo sapiens

<400> SEQUENCE: 3

tcagaagaaa gccccgagat cacagagacc cggcgagatc acagagaccc ggcctgaagg     60

aacgtggaaa gaccaatgta cctgttttga ccggttgcct ggagcaagaa gttccagttg    120

gggagaattt tcagaagata aagtcggaga ttgtggaaag acttgacttg cagcattact    180

ctactgactg gcagagacag gagaggtaga tgtccacgcc cacagaccct ggtgcgatgc    240

cccacccagg gccttcgccg gggcctgggc cttcccctgg gccaattctt gggcctagtc    300

caggaccagg accatcccca ggttccgtcc acagcatgat ggggccaagt cctggacctc    360

caagtgtctc ccatcctatg ccgacgatgg ggtccacaga cttcccacag gaaggcatgc    420

atcaaatgca taagcccatc gatggtatac atgacaaggg gattgtagaa gacatccatt    480

gtggatccat gaagggcact ggtatgcgac cacctcaccc aggcatgggc cctccccaga    540

gtccaatgga tcaacacagc caaggttata tgtcaccaca cccatctcca ttaggagccc    600

cagagcacgt ctccagccct atgtctggag gaggcccaac tccacctcag atgccaccaa    660

gccagccggg ggccctcatc ccaggtgatc cgcaggccat gagccagccc aacagaggtc    720

cctcaccttt cagtcctgtc cagctgcatc agcttcgagc tcagatttta gcttataaaa    780

tgctggcccg aggccagccc ctccccgaaa cgctgcagct tgcagtccag gggaaaagga    840

cgttgcctgg cttgcagcaa caacagcagc agcaacagca gcagcagcag cagcagcagc    900

agcagcagca gcagcaacag cagccgcagc agcagccgcc gcaaccacag acgcagcaac    960

aacagcagcc ggcccttgtt aactacaaca gaccatctgg cccggggccg gagctgagcg   1020

gcccgagcac cccgcagaag ctgccggtgc ccgcgcccgg cggccggccc tcgcccgcgc   1080

cccccgcagc cgcgcagccg cccgcggccg cagtgcccgg gccctcagtg ccgcagccgg   1140

ccccggggca gccctcgccc gtcctccagc tgcagcagaa gcagagccgc atcagcccca   1200

tccagaaacc gcaaggcctg gaccccgtgg aaattctgca agagcgggaa tacagacttc   1260

aggcccgcat agctcatagg atacaagaac tggaaaatct gcctggctct ttgccaccag   1320

atttaagaac caaagcaacc gtggaactaa aagcacttcg gttactcaat ttccagcgtc   1380

agctgagaca ggaggtggtg gcctgcatgc gcagggacac gaccctggag acggctctca   1440

actccaaagc atacaaacgg agcaagcgcc agactctgag agaagctcgc atgaccgaga   1500

agctggagaa gcagcagaag attgagcagg agaggaaacg ccgtcagaaa caccaggaat   1560

acctgaacag tattttgcaa catgcaaaag attttaagga atatcatcgg tctgtggccg   1620

gaaagatcca gaagctctcc aaagcagtgg caacttggca tgccaacact gaaagagagc   1680

agaagaagga gacagagcgg attgaaaagg agagaatgcg gcgactgatg gctgaagatg   1740

aggagggtta tagaaaactg attgatcaaa agaaagacag gcgtttagct tacctttttgc  1800
```

-continued

```
agcagaccga tgagtatgta gccaatctga ccaatctggt ttgggagcac aagcaagccc   1860
aggcagccaa agagaagaag aagaggagga ggaggaagaa gaaggctgag gagaatgcag   1920
agggtgggga gtctgccctg ggaccggatg gagagcccat agatgagagc agccagatga   1980
gtgacctccc tgtcaaagtg actcacacag aaaccggcaa ggttctgttc ggaccagaag   2040
cacccaaagc aagtcagctg gacgcctggc tggaaatgaa tcctggttat gaagttgccc   2100
ctagatctga cagtgaagag agtgattctg attatgagga agaggatgag gaagaagagt   2160
ccagtaggca ggaaaccgaa gagaaaatac tcctggatcc aaatagcgaa gaagtttctg   2220
agaaggatgc taagcagatc attgagacag ctaagcaaga cgtggatgat gaatacagca   2280
tgcagtacag tgccaggggc tcccagtcct actacaccgt ggctcatgcc atctcggaga   2340
gggtggagaa acagtctgcc ctcctaatta atgggaccct aaagcattac cagctccagg   2400
gcctggaatg gatggtttcc ctgtataata acaacttgaa cggaatctta gccgatgaaa   2460
tggggcttgg aaagaccata cagaccattg cactcatcac ttatctgatg gagcacaaaa   2520
gactcaatgg cccctatctc atcattgttc ccctttcgac tctatctaac tggacatatg   2580
aatttgacaa atgggctcct tctgtggtga agatttctta caagggtact cctgccatgc   2640
gtcgctccct tgtcccccag ctacggagtg gcaaattcaa tgtcctcttg actacttatg   2700
agtatattat aaaagacaag cacattcttg caaagattcg gtggaaatac atgatagtgg   2760
acgaaggcca ccgaatgaag aatcaccact gcaagctgac tcaggtcttg aacactcact   2820
atgtggcccc cagaaggatc ctcttgactg ggaccccgct gcagaataag ctccctgaac   2880
tctgggccct cctcaacttc ctcctcccaa caatttttaa gagctgcagc acatttgaac   2940
aatggttcaa tgctccattt gccatgactg gtgaaagggt ggacttaaat gaagaagaaa   3000
ctatattgat catcaggcgt ctacataagg tgttaagacc atttttacta aggagactga   3060
agaaagaagt tgaatcccag cttcccgaaa aagtggaata tgtgatcaag tgtgacatgt   3120
cagctctgca gaagattctg tatcgccata tgcaagccaa ggggatcctt ctcacagatg   3180
gttctgagaa agataagaag gggaaaggag gtgctaagac acttatgaac actattatgc   3240
agttgagaaa aatctgcaac cacccatata tgtttcagca cattgaggaa tcctttgctg   3300
aacacctagg ctattcaaat ggggtcatca atggggctga actgtatcgg gcctcaggga   3360
agtttgagct gcttgatcgt attctgccaa aattgagagc gactaatcac cgagtgctgc   3420
ttttctgcca gatgacatct ctcatgacca tcatggagga ttattttgct tttcggaact   3480
tcctttacct acgccttgat ggcaccacca agtctgaaga tcgtgctgct ttgctgaaga   3540
aattcaatga acctggatcc cagtatttca ttttcttgct gagcacaaga gctggtggcc   3600
tgggcttaaa tcttcaggca gctgatacag tggtcatctt tgacagcgac tggaatcctc   3660
atcaggatct gcaggcccaa gaccgagctc accgcatcgg gcagcagaac gaggtccggg   3720
tactgaggct ctgtaccgtg aacagcgtgg aggaaaagat cctcgcggcc gcaaaataca   3780
agctgaacgt ggatcagaaa gtgatccagg cgggcatgtt tgaccaaaag tcttcaagcc   3840
acgagcggag ggcattcctg caggccatct tggagcatga ggaggaaaat gaggaagaag   3900
atgaagtacc ggacgatgag actctgaacc aaatgattgc tcgacgagaa gaagaatttg   3960
acctttttat gcggatggac atggaccggc ggagggaaga tgcccggaac ccgaaacgga   4020
agccccgttt aatggaggag gatgagctgc cctcctggat cattaaggat gacgctgaag   4080
tagaaaggct cacctgtgaa gaagaggagg agaaaatatt tgggaggggg tcccgccagc   4140
```

```
gccgtgacgt ggactacagt gacgccctca cggagaagca gtggctaagg gccatcgaag   4200

acggcaattt ggaggaaatg gaagaggaag tacggcttaa gaagcgaaaa agacgaagaa   4260

atgtggataa agatcctgca aaagaagatg tggaaaaagc taagaagaga agaggccgcc   4320

ctcccgctga gaaactgtca ccaaatcccc ccaaactgac aaagcagatg aacgctatca   4380

tcgatactgt gataaactac aaagataggt gtaacgtgga gaaggtgccc agtaattctc   4440

agttggaaat agaaggaaac agttcagggc gacagctcag tgaagtcttc attcagttac   4500

cttcaaggaa agaattacca gaatactatg aattaattag gaagccagtg gatttcaaaa   4560

aaataaagga aaggattcgt aatcataagt accggagcct aggcgacctg gagaaggatg   4620

tcatgcttct ctgtcacaac gctcagacgt tcaacctgga gggatcccag atctatgaag   4680

actccatcgt cttacagtca gtgtttaaga gtgcccggca gaaaattgcc aaagaggaag   4740

agagtgagga tgaaagcaat gaagaggagg aagaggaaga tgaagaagag tcagagtccg   4800

aggcaaaatc agtcaaggtg aaaattaagc tcaataaaaa agatgacaaa ggccgggaca   4860

aagggaaagg caagaaaagg ccaaatcgag gaaaagccaa acctgtagtg agcgattttg   4920

acagcgatga ggagcaggat gaacgtgaac agtcagaagg aagtgggacg gatgatgagt   4980

gatcagtatg gaccttttc cttggtagaa ctgaattcct tcctcccctg tctcatttct    5040

acccagtgag ttcatttgtc atataggcac tgggttgttt ctatatcatc atcgtctata   5100

aactagcttt aggatagtgc cagacaaaca tatgatatca tggtgtaaaa aacacacaca   5160

tacacaaata tttgtaacat attgtgacca aatgggcctc aaagattcag attgaaacaa   5220

acaaaaagct tttgatggaa aatatgtggg tggatagtat atttctatgg gtgggtctaa   5280

tttggtaacg gtttgattgt gcctggtttt atcacctgtt cagatgagaa gatttttgtc   5340

ttttgtagca ctgataacca ggagaagcca ttaaaagcca ctggttattt tatttttcat   5400

caggcaattt tcgaggtttt tatttgttcg gtattgtttt tttacactgt ggtacatata   5460

agcaacttta ataggtgata aatgtacagt agttagattt cacctgcata tacatttttc   5520

cattttatgc tctatgatct gaacaaaagc tttttgaatt gtataagatt tatgtctact   5580

gtaaacattg cttaattttt ttgctcttga tttaaaaaaa agttttgttg aaagcgctat   5640

tgaatattgc aatctatata gtgtattgga tggcttcttt tgtcaccctg atctcctatg   5700

ttaccaatgt gtatcgtctc cttctcccta aagtgtactt aatctttgct ttctttgcac   5760

aatgtctttg gttgcaagtc ataagcctga ggcaaataaa attccagtaa tttcgaagaa   5820

tgtggtgttg gtgctttcct aataaagaaa taatttagct tgacaaaaaa aaaaaaaaa    5879
```

<210> SEQ ID NO 4
<211> LENGTH: 1590
<212> TYPE: PRT
<213> ORGANISM: Homo sapiens

<400> SEQUENCE: 4

```
Met Ser Thr Pro Thr Asp Pro Gly Ala Met Pro His Pro Gly Pro Ser
1               5                   10                  15

Pro Gly Pro Gly Pro Ser Pro Gly Pro Ile Leu Gly Pro Ser Pro Gly
            20                  25                  30

Pro Gly Pro Ser Pro Gly Ser Val His Ser Met Met Gly Pro Ser Pro
        35                  40                  45

Gly Pro Pro Ser Val Ser His Pro Met Pro Thr Met Gly Ser Thr Asp
    50                  55                  60
```

-continued

```
Phe Pro Gln Glu Gly Met His Gln Met His Lys Pro Ile Asp Gly Ile
65                  70                  75                  80

His Asp Lys Gly Ile Val Glu Asp Ile His Cys Gly Ser Met Lys Gly
                85                  90                  95

Thr Gly Met Arg Pro Pro His Pro Gly Met Gly Pro Pro Gln Ser Pro
            100                 105                 110

Met Asp Gln His Ser Gln Gly Tyr Met Ser Pro His Pro Ser Pro Leu
        115                 120                 125

Gly Ala Pro Glu His Val Ser Ser Pro Met Ser Gly Gly Gly Pro Thr
    130                 135                 140

Pro Pro Gln Met Pro Pro Ser Gln Pro Gly Ala Leu Ile Pro Gly Asp
145                 150                 155                 160

Pro Gln Ala Met Ser Gln Pro Asn Arg Gly Pro Ser Pro Phe Ser Pro
                165                 170                 175

Val Gln Leu His Gln Leu Arg Ala Gln Ile Leu Ala Tyr Lys Met Leu
            180                 185                 190

Ala Arg Gly Gln Pro Leu Pro Glu Thr Leu Gln Leu Ala Val Gln Gly
        195                 200                 205

Lys Arg Thr Leu Pro Gly Leu Gln Gln Gln Gln Gln Gln Gln Gln Gln
    210                 215                 220

Gln Gln Gln Gln Gln Gln Gln Gln Gln Gln Gln Gln Gln Gln Pro Gln
225                 230                 235                 240

Gln Gln Pro Pro Gln Pro Gln Thr Gln Gln Gln Gln Gln Pro Ala Leu
                245                 250                 255

Val Asn Tyr Asn Arg Pro Ser Gly Pro Gly Pro Glu Leu Ser Gly Pro
            260                 265                 270

Ser Thr Pro Gln Lys Leu Pro Val Pro Ala Pro Gly Gly Arg Pro Ser
        275                 280                 285

Pro Ala Pro Pro Ala Ala Ala Gln Pro Pro Ala Ala Ala Val Pro Gly
    290                 295                 300

Pro Ser Val Pro Gln Pro Ala Pro Gly Gln Pro Ser Pro Val Leu Gln
305                 310                 315                 320

Leu Gln Gln Lys Gln Ser Arg Ile Ser Pro Ile Gln Lys Pro Gln Gly
                325                 330                 335

Leu Asp Pro Val Glu Ile Leu Gln Glu Arg Glu Tyr Arg Leu Gln Ala
            340                 345                 350

Arg Ile Ala His Arg Ile Gln Glu Leu Glu Asn Leu Pro Gly Ser Leu
        355                 360                 365

Pro Pro Asp Leu Arg Thr Lys Ala Thr Val Glu Leu Lys Ala Leu Arg
    370                 375                 380

Leu Leu Asn Phe Gln Arg Gln Leu Arg Gln Glu Val Val Ala Cys Met
385                 390                 395                 400

Arg Arg Asp Thr Thr Leu Glu Thr Ala Leu Asn Ser Lys Ala Tyr Lys
                405                 410                 415

Arg Ser Lys Arg Gln Thr Leu Arg Glu Ala Arg Met Thr Glu Lys Leu
            420                 425                 430

Glu Lys Gln Gln Lys Ile Glu Gln Glu Arg Lys Arg Arg Gln Lys His
        435                 440                 445

Gln Glu Tyr Leu Asn Ser Ile Leu Gln His Ala Lys Asp Phe Lys Glu
    450                 455                 460

Tyr His Arg Ser Val Ala Gly Lys Ile Gln Lys Leu Ser Lys Ala Val
465                 470                 475                 480
```

-continued

```
Ala Thr Trp His Ala Asn Thr Glu Arg Glu Gln Lys Lys Glu Thr Glu
                485                 490                 495

Arg Ile Glu Lys Glu Arg Met Arg Arg Leu Met Ala Glu Asp Glu Glu
            500                 505                 510

Gly Tyr Arg Lys Leu Ile Asp Gln Lys Lys Asp Arg Arg Leu Ala Tyr
        515                 520                 525

Leu Leu Gln Gln Thr Asp Glu Tyr Val Ala Asn Leu Thr Asn Leu Val
    530                 535                 540

Trp Glu His Lys Gln Ala Gln Ala Ala Lys Glu Lys Lys Lys Arg Arg
545                 550                 555                 560

Arg Arg Lys Lys Lys Ala Glu Glu Asn Ala Glu Gly Gly Glu Ser Ala
                565                 570                 575

Leu Gly Pro Asp Gly Glu Pro Ile Asp Glu Ser Ser Gln Met Ser Asp
            580                 585                 590

Leu Pro Val Lys Val Thr His Thr Glu Thr Gly Lys Val Leu Phe Gly
        595                 600                 605

Pro Glu Ala Pro Lys Ala Ser Gln Leu Asp Ala Trp Leu Glu Met Asn
    610                 615                 620

Pro Gly Tyr Glu Val Ala Pro Arg Ser Asp Ser Glu Glu Ser Asp Ser
625                 630                 635                 640

Asp Tyr Glu Glu Glu Asp Glu Glu Glu Glu Ser Ser Arg Gln Glu Thr
                645                 650                 655

Glu Glu Lys Ile Leu Leu Asp Pro Asn Ser Glu Glu Val Ser Glu Lys
            660                 665                 670

Asp Ala Lys Gln Ile Ile Glu Thr Ala Lys Gln Asp Val Asp Asp Glu
        675                 680                 685

Tyr Ser Met Gln Tyr Ser Ala Arg Gly Ser Gln Ser Tyr Tyr Thr Val
    690                 695                 700

Ala His Ala Ile Ser Glu Arg Val Glu Lys Gln Ser Ala Leu Leu Ile
705                 710                 715                 720

Asn Gly Thr Leu Lys His Tyr Gln Leu Gln Gly Leu Glu Trp Met Val
                725                 730                 735

Ser Leu Tyr Asn Asn Asn Leu Asn Gly Ile Leu Ala Asp Glu Met Gly
            740                 745                 750

Leu Gly Lys Thr Ile Gln Thr Ile Ala Leu Ile Thr Tyr Leu Met Glu
        755                 760                 765

His Lys Arg Leu Asn Gly Pro Tyr Leu Ile Ile Val Pro Leu Ser Thr
    770                 775                 780

Leu Ser Asn Trp Thr Tyr Glu Phe Asp Lys Trp Ala Pro Ser Val Val
785                 790                 795                 800

Lys Ile Ser Tyr Lys Gly Thr Pro Ala Met Arg Arg Ser Leu Val Pro
                805                 810                 815

Gln Leu Arg Ser Gly Lys Phe Asn Val Leu Leu Thr Thr Tyr Glu Tyr
            820                 825                 830

Ile Ile Lys Asp Lys His Ile Leu Ala Lys Ile Arg Trp Lys Tyr Met
        835                 840                 845

Ile Val Asp Glu Gly His Arg Met Lys Asn His His Cys Lys Leu Thr
    850                 855                 860

Gln Val Leu Asn Thr His Tyr Val Ala Pro Arg Arg Ile Leu Leu Thr
865                 870                 875                 880

Gly Thr Pro Leu Gln Asn Lys Leu Pro Glu Leu Trp Ala Leu Leu Asn
                885                 890                 895
```

-continued

```
Phe Leu Leu Pro Thr Ile Phe Lys Ser Cys Ser Thr Phe Glu Gln Trp
            900                 905                 910

Phe Asn Ala Pro Phe Ala Met Thr Gly Glu Arg Val Asp Leu Asn Glu
        915                 920                 925

Glu Glu Thr Ile Leu Ile Ile Arg Arg Leu His Lys Val Leu Arg Pro
    930                 935                 940

Phe Leu Leu Arg Arg Leu Lys Lys Glu Val Glu Ser Gln Leu Pro Glu
945                 950                 955                 960

Lys Val Glu Tyr Val Ile Lys Cys Asp Met Ser Ala Leu Gln Lys Ile
                965                 970                 975

Leu Tyr Arg His Met Gln Ala Lys Gly Ile Leu Leu Thr Asp Gly Ser
            980                 985                 990

Glu Lys Asp Lys Lys Gly Lys Gly  Gly Ala Lys Thr Leu  Met Asn Thr
        995                 1000                 1005

Ile Met  Gln Leu Arg Lys Ile  Cys Asn His Pro Tyr  Met Phe Gln
    1010                 1015                 1020

His Ile  Glu Glu Ser Phe Ala  Glu His Leu Gly Tyr  Ser Asn Gly
    1025                 1030                 1035

Val Ile  Asn Gly Ala Glu Leu  Tyr Arg Ala Ser Gly  Lys Phe Glu
    1040                 1045                 1050

Leu Leu  Asp Arg Ile Leu Pro  Lys Leu Arg Ala Thr  Asn His Arg
    1055                 1060                 1065

Val Leu  Leu Phe Cys Gln Met  Thr Ser Leu Met Thr  Ile Met Glu
    1070                 1075                 1080

Asp Tyr  Phe Ala Phe Arg Asn  Phe Leu Tyr Leu Arg  Leu Asp Gly
    1085                 1090                 1095

Thr Thr  Lys Ser Glu Asp Arg  Ala Ala Leu Leu Lys  Lys Phe Asn
    1100                 1105                 1110

Glu Pro  Gly Ser Gln Tyr Phe  Ile Phe Leu Leu Ser  Thr Arg Ala
    1115                 1120                 1125

Gly Gly  Leu Gly Leu Asn Leu  Gln Ala Ala Asp Thr  Val Val Ile
    1130                 1135                 1140

Phe Asp  Ser Asp Trp Asn Pro  His Gln Asp Leu Gln  Ala Gln Asp
    1145                 1150                 1155

Arg Ala  His Arg Ile Gly Gln  Gln Asn Glu Val Arg  Val Leu Arg
    1160                 1165                 1170

Leu Cys  Thr Val Asn Ser Val  Glu Glu Lys Ile Leu  Ala Ala Ala
    1175                 1180                 1185

Lys Tyr  Lys Leu Asn Val Asp  Gln Lys Val Ile Gln  Ala Gly Met
    1190                 1195                 1200

Phe Asp  Gln Lys Ser Ser Ser  His Glu Arg Arg Ala  Phe Leu Gln
    1205                 1210                 1215

Ala Ile  Leu Glu His Glu Glu  Glu Asn Glu Glu Glu  Asp Glu Val
    1220                 1225                 1230

Pro Asp  Asp Glu Thr Leu Asn  Gln Met Ile Ala Arg  Arg Glu Glu
    1235                 1240                 1245

Glu Phe  Asp Leu Phe Met Arg  Met Asp Met Asp Arg  Arg Arg Glu
    1250                 1255                 1260

Asp Ala  Arg Asn Pro Lys Arg  Lys Pro Arg Leu Met  Glu Glu Asp
    1265                 1270                 1275

Glu Leu  Pro Ser Trp Ile Ile  Lys Asp Asp Ala Glu  Val Glu Arg
    1280                 1285                 1290
```

-continued

```
Leu Thr  Cys Glu Glu Glu Glu  Glu Lys Ile Phe Gly  Arg Gly Ser
    1295                 1300                 1305

Arg Gln  Arg Arg Asp Val Asp  Tyr Ser Asp Ala Leu  Thr Glu Lys
    1310                 1315                 1320

Gln Trp  Leu Arg Ala Ile Glu  Asp Gly Asn Leu Glu  Glu Met Glu
    1325                 1330                 1335

Glu Glu  Val Arg Leu Lys Lys  Arg Lys Arg Arg Arg  Asn Val Asp
    1340                 1345                 1350

Lys Asp  Pro Ala Lys Glu Asp  Val Glu Lys Ala Lys  Lys Arg Arg
    1355                 1360                 1365

Gly Arg  Pro Pro Ala Glu Lys  Leu Ser Pro Asn Pro  Pro Lys Leu
    1370                 1375                 1380

Thr Lys  Gln Met Asn Ala Ile  Ile Asp Thr Val Ile  Asn Tyr Lys
    1385                 1390                 1395

Asp Arg  Cys Asn Val Glu Lys  Val Pro Ser Asn Ser  Gln Leu Glu
    1400                 1405                 1410

Ile Glu  Gly Asn Ser Ser Gly  Arg Gln Leu Ser Glu  Val Phe Ile
    1415                 1420                 1425

Gln Leu  Pro Ser Arg Lys Glu  Leu Pro Glu Tyr Tyr  Glu Leu Ile
    1430                 1435                 1440

Arg Lys  Pro Val Asp Phe Lys  Lys Ile Lys Glu Arg  Ile Arg Asn
    1445                 1450                 1455

His Lys  Tyr Arg Ser Leu Gly  Asp Leu Glu Lys Asp  Val Met Leu
    1460                 1465                 1470

Leu Cys  His Asn Ala Gln Thr  Phe Asn Leu Glu Gly  Ser Gln Ile
    1475                 1480                 1485

Tyr Glu  Asp Ser Ile Val Leu  Gln Ser Val Phe Lys  Ser Ala Arg
    1490                 1495                 1500

Gln Lys  Ile Ala Lys Glu Glu  Glu Ser Glu Asp Glu  Ser Asn Glu
    1505                 1510                 1515

Glu Glu  Glu Glu Glu Asp Glu  Glu Glu Ser Glu Ser  Glu Ala Lys
    1520                 1525                 1530

Ser Val  Lys Val Lys Ile Lys  Leu Asn Lys Lys Asp  Asp Lys Gly
    1535                 1540                 1545

Arg Asp  Lys Gly Lys Gly Lys  Lys Arg Pro Asn Arg  Gly Lys Ala
    1550                 1555                 1560

Lys Pro  Val Val Ser Asp Phe  Asp Ser Asp Glu Glu  Gln Asp Glu
    1565                 1570                 1575

Arg Glu  Gln Ser Glu Gly Ser  Gly Thr Asp Asp Glu
    1580                 1585                 1590
```

<210> SEQ ID NO 5
<211> LENGTH: 2464
<212> TYPE: DNA
<213> ORGANISM: Homo sapiens

<400> SEQUENCE: 5

```
gggacggagc gatgtcgggc cgaggcgcgg gcgggttccc gctgccccccg ctaagccctg     60

gcggcggcgc cgtggctgcg gccctgggag cgccgcctcc ccccgcggga cccggcatgc    120

tgcccggacc ggcgctccgg ggaccgggtc cggcaggagg cgtggggggc cccggggccg    180

ccgccttccg ccccatgggc cccgcgggcc ccgcggcgca gtaccagcga cctggcatgt    240

caccagggaa ccggatgccc atggctggct tgcaggtggg acccccctgct ggctccccat    300

ttggtgcagc agctccgctt cgacctggca tgccacccac catgatggat ccattccgaa    360
```

-continued

```
aacgcctgct tgtgccccag gcgcagcctc ccatgcctgc ccagcgccgg gggttaaaga    420
ggaggaagat ggcagataag gttctacctc agcgaatccg ggagcttgtt ccagagtctc    480
aggcgtacat ggatctcttg gcttttgagc ggaagctgga ccagaccatt gctcgcaagc    540
ggatggagat ccaggaggcc atcaaaaagc ctctgacaca aaagcgaaag cttcggatct    600
acatttccaa tacgttcagt cccagcaagg cggaaggcga tagtgcagga actgcaggga    660
cccctggggg aaccccagca ggggacaagg tggcttcctg ggaactccga gtggaaggaa    720
aactgctgga tgatcctagc aaacagaaga ggaagttttc ttcattcttt aagagcctcg    780
tcattgagct ggacaaggag ctgtacgggc ctgacaatca cctggtggag tggcaccgga    840
tgcccaccac ccaggagaca gatggcttcc aagtaaaacg gcctggagac ctcaacgtca    900
agtgcaccct cctgctcatg ctggatcatc agcctcccca gtacaaattg gacccccgat    960
tggcaaggct gctgggagtg cacacgcaga cgagggccgc catcatgcag gccctgtggc   1020
tttacatcaa gcacaaccag ctgcaggatg ggcacgagcg ggagtacatc aactgcaacc   1080
gttacttccg ccagatcttc agttgtggcc gactccgttt ctccgagatt cccatgaagc   1140
tggcagggtt gctgcagcat ccagacccca ttgtcatcaa ccatgtcatt agtgtcgacc   1200
ctaacgacca gaagaagaca gcctgttacg acatcgatgt ggaggtggac gacccactga   1260
aggcccaaat gagcaatttt ctggcctcta ccaccaatca gcaggagatc gcctcccttg   1320
atgtcaagat ccatgagacc attgagtcca tcaaccagct gaagacccag agagatttca   1380
tgctcagttt tagcaccgac ccccaggact tcatccagga atggctccgt tcccagcgcc   1440
gagacctcaa gatcatcact gatgtgattg gaaatcctga ggaggagaga cgagctgctt   1500
tctaccacca gccctgggcc caggaagcag taggcaggca catctttgcc aaggtgcagc   1560
agcgaaggca ggaactggaa caggtgctgg gaattcgcct gacctaactg ctcagggatc   1620
tttcttccca gccctggagc ctggagggag accaccctct gggtccttgc tggggccgca   1680
gacacgtagg ctggggtgag gagtgtctgc tgtcaccctc tactctccag ctttagtctt   1740
ataaatgtag tgataggatt ccttgttgct tggtccccaa agccttatac tttttgcatt   1800
ggctttaatt gggttcagca gatgcctcct ctgcccccct gcaggcaggc ccaagtagga   1860
ctgctggagg ctgtgctttg acattgtaag acatttccga accaaaggct gctgggtttg   1920
catgtttaca gactccccct ggggcgaggg tcagagctgg ctctggggag ctgggctagg   1980
aagaggaggt gcagcccaga ctcttcctag cctttctaaa ccaaagttct ttgccattcc   2040
tacaagccca gccttgctgc tggtttttc ctttcctttg ggtatttgca ctattttggg   2100
agcaagtttt ctatgtggga gccacttttt ttgtacaggg gtaagttggg ggttttcagg   2160
gagcctgtta ggtgcctcct tcttttcttt cctcaatcta tgcaagcggc tctggccgcc   2220
atcatctcct gggatgccag agggctgcct ctccagcggc ttgggccggg gaggggacac   2280
tccagttctc tagcatggcc tgaggtatgg ggtatgtgca tgtggaggcc agggtaaggt   2340
gaatggggag gctgggagga ctggtgttgc cctttggagc ttggtgagga gggtgggcct   2400
agggcttggc gagtgccaca tctggcaggt ttggaaattt ccaaataaat ccttttgtct   2460
attg                                                                2464
```

<210> SEQ ID NO 6
<211> LENGTH: 531
<212> TYPE: PRT
<213> ORGANISM: Homo sapiens

<400> SEQUENCE: 6

```
Met Ser Gly Arg Gly Ala Gly Gly Phe Pro Leu Pro Pro Leu Ser Pro
1               5                   10                  15

Gly Gly Gly Ala Val Ala Ala Ala Leu Gly Ala Pro Pro Pro Pro Ala
            20                  25                  30

Gly Pro Gly Met Leu Pro Gly Pro Ala Leu Arg Gly Pro Gly Pro Ala
        35                  40                  45

Gly Gly Val Gly Gly Pro Gly Ala Ala Ala Phe Arg Pro Met Gly Pro
    50                  55                  60

Ala Gly Pro Ala Ala Gln Tyr Gln Arg Pro Gly Met Ser Pro Gly Asn
65                  70                  75                  80

Arg Met Pro Met Ala Gly Leu Gln Val Gly Pro Pro Ala Gly Ser Pro
                85                  90                  95

Phe Gly Ala Ala Ala Pro Leu Arg Pro Gly Met Pro Pro Thr Met Met
            100                 105                 110

Asp Pro Phe Arg Lys Arg Leu Leu Val Pro Gln Ala Gln Pro Pro Met
        115                 120                 125

Pro Ala Gln Arg Arg Gly Leu Lys Arg Arg Lys Met Ala Asp Lys Val
    130                 135                 140

Leu Pro Gln Arg Ile Arg Glu Leu Val Pro Glu Ser Gln Ala Tyr Met
145                 150                 155                 160

Asp Leu Leu Ala Phe Glu Arg Lys Leu Asp Gln Thr Ile Ala Arg Lys
                165                 170                 175

Arg Met Glu Ile Gln Glu Ala Ile Lys Lys Pro Leu Thr Gln Lys Arg
            180                 185                 190

Lys Leu Arg Ile Tyr Ile Ser Asn Thr Phe Ser Pro Ser Lys Ala Glu
        195                 200                 205

Gly Asp Ser Ala Gly Thr Ala Gly Thr Pro Gly Gly Thr Pro Ala Gly
    210                 215                 220

Asp Lys Val Ala Ser Trp Glu Leu Arg Val Glu Gly Lys Leu Leu Asp
225                 230                 235                 240

Asp Pro Ser Lys Gln Lys Arg Lys Phe Ser Ser Phe Phe Lys Ser Leu
                245                 250                 255

Val Ile Glu Leu Asp Lys Glu Leu Tyr Gly Pro Asp Asn His Leu Val
            260                 265                 270

Glu Trp His Arg Met Pro Thr Thr Gln Glu Thr Asp Gly Phe Gln Val
        275                 280                 285

Lys Arg Pro Gly Asp Leu Asn Val Lys Cys Thr Leu Leu Leu Met Leu
    290                 295                 300

Asp His Gln Pro Pro Gln Tyr Lys Leu Asp Pro Arg Leu Ala Arg Leu
305                 310                 315                 320

Leu Gly Val His Thr Gln Thr Arg Ala Ala Ile Met Gln Ala Leu Trp
                325                 330                 335

Leu Tyr Ile Lys His Asn Gln Leu Gln Asp Gly His Glu Arg Glu Tyr
            340                 345                 350

Ile Asn Cys Asn Arg Tyr Phe Arg Gln Ile Phe Ser Cys Gly Arg Leu
        355                 360                 365

Arg Phe Ser Glu Ile Pro Met Lys Leu Ala Gly Leu Leu Gln His Pro
    370                 375                 380

Asp Pro Ile Val Ile Asn His Val Ile Ser Val Asp Pro Asn Asp Gln
385                 390                 395                 400

Lys Lys Thr Ala Cys Tyr Asp Ile Asp Val Glu Val Asp Asp Pro Leu
                405                 410                 415
```

-continued

```
Lys Ala Gln Met Ser Asn Phe Leu Ala Ser Thr Thr Asn Gln Gln Glu
            420                 425                 430

Ile Ala Ser Leu Asp Val Lys Ile His Glu Thr Ile Glu Ser Ile Asn
        435                 440                 445

Gln Leu Lys Thr Gln Arg Asp Phe Met Leu Ser Phe Ser Thr Asp Pro
    450                 455                 460

Gln Asp Phe Ile Gln Glu Trp Leu Arg Ser Gln Arg Arg Asp Leu Lys
465                 470                 475                 480

Ile Ile Thr Asp Val Ile Gly Asn Pro Glu Glu Glu Arg Arg Ala Ala
                485                 490                 495

Phe Tyr His Gln Pro Trp Ala Gln Glu Ala Val Gly Arg His Ile Phe
            500                 505                 510

Ala Lys Val Gln Gln Arg Arg Gln Glu Leu Glu Gln Val Leu Gly Ile
        515                 520                 525

Arg Leu Thr
    530
```

<210> SEQ ID NO 7
<211> LENGTH: 5673
<212> TYPE: DNA
<213> ORGANISM: Homo sapiens

<400> SEQUENCE: 7

```
gggcgcgcgc gcgaggcttc ccctcgtttg gcggcggcgg cggcttcttt gtttcgtgaa     60

gagaagcgag acgcccattc tgcccccggc cccgcgcgga ggggcggggg aggcgccggg    120

aagtcgacgg cgccggcggc tcctgcagga ggccactgtc tgcagctccc gtgaagatgt    180

ccactccaga cccacccctg ggcggaactc ctcggccagg tccttccccg ggccctggcc    240

cttcccctgg agccatgctg ggccctagcc cgggtccctc gccgggctcc gcccacagca    300

tgatggggcc cagcccaggg ccgccctcag caggacaccc catccccacc caggggcctg    360

gagggtaccc tcaggacaac atgcaccaga tgcacaagcc catggagtcc atgcatgaga    420

agggcatgtc ggacgacccg cgctacaacc agatgaaagg aatggggatg cggtcagggg    480

gccatgctgg gatggggccc ccgcccagcc ccatggacca gcactcccaa ggttacccct    540

cgcccctggg tggctctgag catgcctcta gtccagttcc agccagtggc ccgtcttcgg    600

ggccccagat gtcttccggg ccaggaggtg ccccgctgga tggtgctgac ccccaggcct    660

tggggcagca gaaccggggc ccaaccccat ttaaccagaa ccagctgcac cagctcagag    720

ctcagatcat ggcctacaag atgctggcca gggggcagcc cctccccgac cacctgcaga    780

tggcggtgca gggcaagcgg ccgatgcccg ggatgcagca gcagatgcca acgctacctc    840

caccctcggt gtccgcaaca ggacccggcc ctggccctgg ccctggcccc ggcccgggtc    900

ccggcccggc acctccaaat tacagcaggc ctcatggtat gggagggccc aacatgcctc    960

ccccaggacc ctcgggcgtg ccccccggga tgccaggcca gcctcctgga gggcctccca   1020

agccctggcc tgaaggaccc atggcgaatg ctgctgcccc cacgagcacc cctcagaagc   1080

tgattccccc gcagccaacg ggccgccctt cccccgcgcc ccctgccgtc ccacccgccg   1140

cctcgcccgt gatgccaccg cagacccagt cccccgggca gccggcccag cccgcgccca   1200

tggtgccact gcaccagaag cagagccgca tcacccccat ccagaagccg cggggcctcg   1260

accctgtgga gatcctgcag gagcgcgagt acaggctgca ggctcgcatc gcacaccgaa   1320

ttcaggaact tgaaaacctt cccgggtccc tggccgggga tttgcgaacc aaagcgacca   1380
```

ttgagctcaa ggccctcagg ctgctgaact tccagaggca gctgcgccag gaggtggtgg 1440
tgtgcatgcg gagggacaca gcgctggaga cagccctcaa tgctaaggcc tacaagcgca 1500
gcaagcgcca gtccctgcgc gaggcccgca tcactgagaa gctggagaag cagcagaaga 1560
tcgagcagga gcgcaagcgc cggcagaagc accaggaata cctcaatagc attctccagc 1620
atgccaagga tttcaaggaa tatcacagat ccgtcacagg caaaatccag aagctgacca 1680
aggcagtggc cacgtaccat gccaacacgg agcgggagca gaagaaagag aacgagcgga 1740
tcgagaagga gcgcatgcgg aggctcatgg ctgaagatga ggaggggtac cgcaagctca 1800
tcgaccagaa gaaggacaag cgcctggcct acctcttgca gcagacagac gagtacgtgg 1860
ctaacctcac ggagctggtg cggcagcaca aggctgccca ggtcgccaag gagaaaaaga 1920
agaaaaagaa aaagaagaag gcagaaaatg cagaaggaca gacgcctgcc attgggccgg 1980
atggcgagcc tctggacgag accagccaga tgagcgacct cccggtgaag gtgatccacg 2040
tggagagtgg gaagatcctc acaggcacag atgcccccaa agccgggcag ctggaggcct 2100
ggctcgagat gaacccgggg tatgaagtag ctccgaggtc tgatagtgaa gaaagtggct 2160
cagaagaaga ggaagaggag gaggaggaag agcagccgca ggcagcacag cctcccaccc 2220
tgcccgtgga ggagaagaag aagattccag atccagacag cgatgacgtc tctgaggtgg 2280
acgcgcggca catcattgag aatgccaagc aagatgtcga tgatgaatat ggcgtgtccc 2340
aggcccttgc acgtggcctg cagtcctact atgccgtggc ccatgctgtc actgagagag 2400
tggacaagca gtcagcgctt atggtcaatg gtgtcctcaa acagtaccag atcaaaggtt 2460
tggagtggct ggtgtccctg tacaacaaca acctgaacgg catcctggcc gacgagatgg 2520
gcctggggaa gaccatccag accatcgcgc tcatcacgta cctcatggag cacaaacgca 2580
tcaatgggcc cttcctcatc atcgtgcctc tctcaacgct gtccaactgg gcgtacgagt 2640
ttgacaagtg ggcccccctcc gtggtgaagg tgtcttacaa gggatcccca gcagcaagac 2700
gggcctttgt cccccagctc cggagtggga agttcaacgt cttgctgacg acgtacgagt 2760
acatcatcaa agacaagcac atcctcgcca agatccgttg gaagtacatg attgtggacg 2820
aaggtcaccg catgaagaac caccactgca agctgacgca ggtgctcaac acgcactatg 2880
tggcaccccg ccgcctgctg ctgacgggca caccgctgca gaacaagctt cccgagctct 2940
gggcgctgct caacttcctg ctgcccacca tcttcaagag ctgcagcacc ttcgagcagt 3000
ggtttaacgc accctttgcc atgaccgggg aaaaggtgga cctgaatgag gaggaaacca 3060
ttctcatcat ccggcgtctc cacaaagtgc tgcggccctt cttgctccga cgactcaaga 3120
aggaagtcga ggcccagttg cccgaaaagg tggagtacgt catcaagtgc gacatgtctg 3180
cgctgcagcg agtgctctac cgccacatgc aggccaaggg cgtgctgctg actgatggct 3240
ccgagaagga caagaagggc aaaggcggca ccaagaccct gatgaacacc atcatgcagc 3300
tgcggaagat ctgcaaccac ccctacatgt tccagcacat cgaggagtcc ttttccgagc 3360
acttggggtt cactggcggc attgtccaag ggctggacct gtaccgagcc tcgggtaaat 3420
ttgagcttct tgatagaatt cttcccaaac tccgagcaac caaccacaaa gtgctgctgt 3480
tctgccaaat gacctccctc atgaccatca tggaagatta ctttgcgtat cgcggcttta 3540
aatacctcag gcttgatgga accacgaagg cggaggaccg gggcatgctg ctgaaaacct 3600
tcaacgagcc cggctctgag tacttcatct tcctgctcag cacccgggct ggggggctcg 3660
gcctgaacct ccagtcggca gacactgtga tcatttttga cagcgactgg aatcctcacc 3720
aggacctgca agcgcaggac cgagcccacc gcatcgggca gcagaacgag gtgcgtgtgc 3780
tccgcctctg caccgtcaac agcgtggagg agaagatcct agctgcagcc aagtacaagc 3840
tcaacgtgga ccagaaggtg atccaggccg gcatgttcga ccagaagtcc tccagccatg 3900
agcggcgcgc cttcctgcag gccatcctgg agcacgagga gcaggatgag agcagacact 3960
gcagcacggg cagcggcagt gccagcttcg cccacactgc ccctccgcca gcgggcgtca 4020
accccgactt ggaggagcca cctctaaagg aggaagacga ggtgcccgac gacgagaccg 4080
tcaaccagat gatcgcccgg cacgaggagg agtttgatct gttcatgcgc atggacctgg 4140
accgcaggcg cgaggaggcc cgcaacccca agcggaagcc gcgcctcatg gaggaggacg 4200
agctcccctc gtggatcatc aaggacgacg cggaggtgga gcggctgacc tgtgaggagg 4260
aggaggagaa gatgttcggc cgtggctccc gccaccgcaa ggaggtggac tacagcgact 4320
cactgacgga gaagcagtgg ctcaagaaaa ttacaggaaa agatatccat gacacagcca 4380
gcagtgtggc acgtgggcta caattccagc gtggccttca gttctgcaca cgtgcgtcaa 4440
aggccatcga ggagggcacg ctggaggaga tcgaagagga ggtccggcag aagaaatcat 4500
cacggaagcg caagcgagac agcgacgccg gctcctccac cccgaccacc agcacccgca 4560
gccgcgacaa ggacgacgag agcaagaagc agaagaagcg cgggcggccg cctgccgaga 4620
aactctcccc taacccaccc aacctcacca agaagatgaa gaagattgtg gatgccgtga 4680
tcaagtacaa ggacagcagc agtggacgtc agctcagcga ggtcttcatc cagctgccct 4740
cgcgaaagga gctgcccgag tactacgagc tcatccgcaa gcccgtggac ttcaagaaga 4800
taaaggagcg cattcgcaac cacaagtacc gcagcctcaa cgacctagag aaggacgtca 4860
tgctcctgtg ccagaacgca cagaccttca acctggaggg ctccctgatc tatgaagact 4920
ccatcgtctt gcagtcggtc ttcaccagcg tgcggcagaa aatcgagaag gaggatgaca 4980
gtgaaggcga ggagagtgag gaggaggaag agggcgagga ggaaggctcc gaatccgaat 5040
ctcggtccgt caaagtgaag atcaagcttg gccggaagga gaaggcacag gaccggctga 5100
agggcggccg gcggcggccg agccgagggt cccgagccaa gccggtcgtg agtgacgatg 5160
acagtgagga ggaacaagag gaggaccgct caggaagtgg cagcgaagaa gactgagccc 5220
cgacattcca gtctcgaccc cgagcccctc gttccagagc tgagatggca taggccttag 5280
cagtaacggg tagcagcaga tgtagtttca gacttggagt aaaactgtat aaacaaaaga 5340
atcttccata tttatacagc agagaagctg taggactgtt tgtgactggc cctgtcctgg 5400
catcagtagc atctgtaaca gcattaactg tcttaaagag agagagagag aattccgaat 5460
tggggaacac acgatacctg tttttctttt ccgttgctgg cagtactgtt gcgccgcagt 5520
ttggagtcac tgtagttaag tgtggatgca tgtgcgtcac cgtccactcc tcctactgta 5580
ttttattgga caggtcagac tcgccggggg cccggcgagg gtatgtcagt gtcactggat 5640
gtcaaacagt aataaattaa accaacaaca aaa 5673

<210> SEQ ID NO 8
<211> LENGTH: 1679
<212> TYPE: PRT
<213> ORGANISM: Homo sapiens

<400> SEQUENCE: 8

Met Ser Thr Pro Asp Pro Pro Leu Gly Gly Thr Pro Arg Pro Gly Pro
1 5 10 15

Ser Pro Gly Pro Gly Pro Ser Pro Gly Ala Met Leu Gly Pro Ser Pro
20 25 30

-continued

```
Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
    290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Val Cys Met Arg Arg Asp Thr Ala Leu Glu Thr
            420                 425                 430

Ala Leu Asn Ala Lys Ala Tyr Lys Arg Ser Lys Arg Gln Ser Leu Arg
        435                 440                 445
```

-continued

```
Glu Ala Arg Ile Thr Glu Lys Leu Glu Lys Gln Gln Lys Ile Glu Gln
    450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
                485                 490                 495

Ile Gln Lys Leu Thr Lys Ala Val Ala Thr Tyr His Ala Asn Thr Glu
            500                 505                 510

Arg Glu Gln Lys Lys Glu Asn Glu Arg Ile Glu Lys Glu Arg Met Arg
        515                 520                 525

Arg Leu Met Ala Glu Asp Glu Glu Gly Tyr Arg Lys Leu Ile Asp Gln
    530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
                565                 570                 575

Ala Lys Glu Lys Lys Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
        595                 600                 605

Thr Ser Gln Met Ser Asp Leu Pro Val Lys Val Ile His Val Glu Ser
    610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
            660                 665                 670

Gln Pro Gln Ala Ala Gln Pro Pro Thr Leu Pro Val Glu Glu Lys Lys
        675                 680                 685

Lys Ile Pro Asp Pro Asp Ser Asp Asp Val Ser Glu Val Asp Ala Arg
    690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
            740                 745                 750

Val Leu Lys Gln Tyr Gln Ile Lys Gly Leu Glu Trp Leu Val Ser Leu
        755                 760                 765

Tyr Asn Asn Asn Leu Asn Gly Ile Leu Ala Asp Glu Met Gly Leu Gly
    770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
        835                 840                 845

Arg Ser Gly Lys Phe Asn Val Leu Leu Thr Thr Tyr Glu Tyr Ile Ile
    850                 855                 860
```

-continued

```
Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
            900                 905                 910

Pro Leu Gln Asn Lys Leu Pro Glu Leu Trp Ala Leu Leu Asn Phe Leu
        915                 920                 925

Leu Pro Thr Ile Phe Lys Ser Cys Ser Thr Phe Glu Gln Trp Phe Asn
    930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met  Ser Ala Leu Gln Arg  Val Leu Tyr
        995                 1000                1005

Arg His  Met Gln Ala Lys Gly  Val Leu Leu Thr Asp  Gly Ser Glu
    1010                1015                1020

Lys Asp  Lys Lys Gly Lys Gly  Gly Thr Lys Thr Leu  Met Asn Thr
    1025                1030                1035

Ile Met  Gln Leu Arg Lys Ile  Cys Asn His Pro Tyr  Met Phe Gln
    1040                1045                1050

His Ile  Glu Glu Ser Phe Ser  Glu His Leu Gly Phe  Thr Gly Gly
    1055                1060                1065

Ile Val  Gln Gly Leu Asp Leu  Tyr Arg Ala Ser Gly  Lys Phe Glu
    1070                1075                1080

Leu Leu  Asp Arg Ile Leu Pro  Lys Leu Arg Ala Thr  Asn His Lys
    1085                1090                1095

Val Leu  Leu Phe Cys Gln Met  Thr Ser Leu Met Thr  Ile Met Glu
    1100                1105                1110

Asp Tyr  Phe Ala Tyr Arg Gly  Phe Lys Tyr Leu Arg  Leu Asp Gly
    1115                1120                1125

Thr Thr  Lys Ala Glu Asp Arg  Gly Met Leu Leu Lys  Thr Phe Asn
    1130                1135                1140

Glu Pro  Gly Ser Glu Tyr Phe  Ile Phe Leu Leu Ser  Thr Arg Ala
    1145                1150                1155

Gly Gly  Leu Gly Leu Asn Leu  Gln Ser Ala Asp Thr  Val Ile Ile
    1160                1165                1170

Phe Asp  Ser Asp Trp Asn Pro  His Gln Asp Leu Gln  Ala Gln Asp
    1175                1180                1185

Arg Ala  His Arg Ile Gly Gln  Gln Asn Glu Val Arg  Val Leu Arg
    1190                1195                1200

Leu Cys  Thr Val Asn Ser Val  Glu Glu Lys Ile Leu  Ala Ala Ala
    1205                1210                1215

Lys Tyr  Lys Leu Asn Val Asp  Gln Lys Val Ile Gln  Ala Gly Met
    1220                1225                1230

Phe Asp  Gln Lys Ser Ser Ser  His Glu Arg Arg Ala  Phe Leu Gln
    1235                1240                1245

Ala Ile  Leu Glu His Glu Glu  Gln Asp Glu Ser Arg  His Cys Ser
    1250                1255                1260
```

-continued

```
Thr Gly  Ser Gly Ser Ala Ser  Phe Ala His Thr Ala  Pro Pro Pro
    1265                 1270                 1275

Ala Gly  Val Asn Pro Asp Leu  Glu Glu Pro Pro Leu  Lys Glu Glu
    1280                 1285                 1290

Asp Glu  Val Pro Asp Asp Glu  Thr Val Asn Gln Met  Ile Ala Arg
    1295                 1300                 1305

His Glu  Glu Glu Phe Asp Leu  Phe Met Arg Met Asp  Leu Asp Arg
    1310                 1315                 1320

Arg Arg  Glu Glu Ala Arg Asn  Pro Lys Arg Lys Pro  Arg Leu Met
    1325                 1330                 1335

Glu Glu  Asp Glu Leu Pro Ser  Trp Ile Ile Lys Asp  Asp Ala Glu
    1340                 1345                 1350

Val Glu  Arg Leu Thr Cys Glu  Glu Glu Glu Glu Lys  Met Phe Gly
    1355                 1360                 1365

Arg Gly  Ser Arg His Arg Lys  Glu Val Asp Tyr Ser  Asp Ser Leu
    1370                 1375                 1380

Thr Glu  Lys Gln Trp Leu Lys  Lys Ile Thr Gly Lys  Asp Ile His
    1385                 1390                 1395

Asp Thr  Ala Ser Ser Val Ala  Arg Gly Leu Gln Phe  Gln Arg Gly
    1400                 1405                 1410

Leu Gln  Phe Cys Thr Arg Ala  Ser Lys Ala Ile Glu  Glu Gly Thr
    1415                 1420                 1425

Leu Glu  Glu Ile Glu Glu Glu  Val Arg Gln Lys Lys  Ser Ser Arg
    1430                 1435                 1440

Lys Arg  Lys Arg Asp Ser Asp  Ala Gly Ser Ser Thr  Pro Thr Thr
    1445                 1450                 1455

Ser Thr  Arg Ser Arg Asp Lys  Asp Asp Glu Ser Lys  Lys Gln Lys
    1460                 1465                 1470

Lys Arg  Gly Arg Pro Pro Ala  Glu Lys Leu Ser Pro  Asn Pro Pro
    1475                 1480                 1485

Asn Leu  Thr Lys Lys Met Lys  Lys Ile Val Asp Ala  Val Ile Lys
    1490                 1495                 1500

Tyr Lys  Asp Ser Ser Ser Gly  Arg Gln Leu Ser Glu  Val Phe Ile
    1505                 1510                 1515

Gln Leu  Pro Ser Arg Lys Glu  Leu Pro Glu Tyr Tyr  Glu Leu Ile
    1520                 1525                 1530

Arg Lys  Pro Val Asp Phe Lys  Lys Ile Lys Glu Arg  Ile Arg Asn
    1535                 1540                 1545

His Lys  Tyr Arg Ser Leu Asn  Asp Leu Glu Lys Asp  Val Met Leu
    1550                 1555                 1560

Leu Cys  Gln Asn Ala Gln Thr  Phe Asn Leu Glu Gly  Ser Leu Ile
    1565                 1570                 1575

Tyr Glu  Asp Ser Ile Val Leu  Gln Ser Val Phe Thr  Ser Val Arg
    1580                 1585                 1590

Gln Lys  Ile Glu Lys Glu Asp  Asp Ser Glu Gly Glu  Glu Ser Glu
    1595                 1600                 1605

Glu Glu  Glu Glu Gly Glu Glu  Glu Gly Ser Glu Ser  Glu Ser Arg
    1610                 1615                 1620

Ser Val  Lys Val Lys Ile Lys  Leu Gly Arg Lys Glu  Lys Ala Gln
    1625                 1630                 1635

Asp Arg  Leu Lys Gly Gly Arg  Arg Arg Pro Ser Arg  Gly Ser Arg
    1640                 1645                 1650
```

-continued

```
Ala Lys Pro Val Val Ser Asp Asp Asp Ser Glu Glu Glu Gln Glu
    1655                1660                1665

Glu Asp Arg Ser Gly Ser Gly Ser Glu Glu Asp
    1670                1675


<210> SEQ ID NO 9
<211> LENGTH: 1907
<212> TYPE: DNA
<213> ORGANISM: Homo sapiens

<400> SEQUENCE: 9

actccgctcg agtagaagtg tgagagagcc cagcaggact cagaggggag agttggagga     60

aaaaaaaagg cagaaaaggg aaagaaagag gaagagagag agagagtgag aggagccgct    120

gagcccaccc cgatggccgc ggacgaagtt gccggagggg cgcgcaaagc cacgaaaagc    180

aaactttttg agtttctggt ccatggggtg cgcccccgga tgccgtctgg agcccggatg    240

ccccaccagg gggcgcccat gggccccccg ggctccccgt acatgggcag ccccgccgtg    300

cgacccggcc tggcccccgc gggcatggag cccgcccgca agcgagcagc gcccccgccc    360

gggcagagcc aggcacagag ccagggccag ccggtgccca ccgcccccgc gcggagccgc    420

agtgccaaga ggaggaagat ggctgacaaa atcctccctc aaaggattcg ggagctggtc    480

cccgagtccc aggcttacat ggacctcttg gcatttgaga ggaaactgga tcaaaccatc    540

atgcggaagc gggtggacat ccaggaggct ctgaagaggc ccatgaagca aaagcggaag    600

ctgcgactct atatctccaa cacttttaac cctgcgaagc ctgatgctga ggattccgac    660

ggcagcattg cctcctggga gctacgggtg gaggggaagc tcctggatga tcccagcaaa    720

cagaagcgga agttctcttc tttcttcaag agtttggtca tcgagctgga caaagatctt    780

tatggccctg acaaccacct cgttgagtgg catcggacac ccacgaccca ggagacggac    840

ggcttccagg tgaaacggcc tggggacctg agtgtgcgct gcacgctgct cctcatgctg    900

gactaccagc ctccccagtt caaactggat ccccgcctag cccggctgct ggggctgcac    960

acacagagcc gctcagccat tgtccaggcc ctgtggcagt atgtgaagac caacaggctg   1020

caggactccc atgacaagga atacatcaat ggggacaagt atttccagca gatttttgat   1080

tgtccccggc tgaagttttc tgagattccc cagcgcctca cagccctgct attgccccct   1140

gacccaattg tcatcaacca tgtcatcagc gtggaccctt cagaccagaa gaagacggcg   1200

tgctatgaca ttgacgtgga ggtggaggag ccattaaagg ggcagatgag cagcttcctc   1260

ctatccacgg ccaaccagca ggagatcagt gctctggaca gtaagatcca tgagacgatt   1320

gagtccataa accagctcaa gatccagagg gacttcatgc taagcttctc cagagacccc   1380

aaaggctatg tccaagacct gctccgctcc cagagccggg acctcaaggt gatgacagat   1440

gtagccggca accctgaaga ggagcgccgg gctgagttct accaccagcc ctggtcccag   1500

gaggccgtca gtcgctactt ctactgcaag atccagcagc gcaggcagga gctggagcag   1560

tcgctggttg tgcgcaacac ctaggagccc aaaaataagc agcacgacgg aactttcagc   1620

cgtgtcccgg gccccagcat tttgccccgg gctccagcat cactcctctg ccaccttggg   1680

gtgtggggct ggattaaaag tcattcatct gacagcagcc gtgtggtcat tggaaactgg   1740

ggaggggagg gggagagaag gggaagggaa gaaggtgggg aggcagtggg tccctcggga   1800

cgactcccca ttcccttccc ttggattctt ctccttactc aattttccct agacctaaaa   1860

acagtttggc agaagacatg tttaataaca ttttcatatt taaaaaa                 1907
```

<210> SEQ ID NO 10
<211> LENGTH: 483
<212> TYPE: PRT
<213> ORGANISM: Homo sapiens

<400> SEQUENCE: 10

```
Met Ala Ala Asp Glu Val Ala Gly Gly Ala Arg Lys Ala Thr Lys Ser
1               5                   10                  15

Lys Leu Phe Glu Phe Leu Val His Gly Val Arg Pro Gly Met Pro Ser
            20                  25                  30

Gly Ala Arg Met Pro His Gln Gly Ala Pro Met Gly Pro Pro Gly Ser
        35                  40                  45

Pro Tyr Met Gly Ser Pro Ala Val Arg Pro Gly Leu Ala Pro Ala Gly
    50                  55                  60

Met Glu Pro Ala Arg Lys Arg Ala Ala Pro Pro Pro Gly Gln Ser Gln
65                  70                  75                  80

Ala Gln Ser Gln Gly Gln Pro Val Pro Thr Ala Pro Ala Arg Ser Arg
                85                  90                  95

Ser Ala Lys Arg Arg Lys Met Ala Asp Lys Ile Leu Pro Gln Arg Ile
            100                 105                 110

Arg Glu Leu Val Pro Glu Ser Gln Ala Tyr Met Asp Leu Leu Ala Phe
        115                 120                 125

Glu Arg Lys Leu Asp Gln Thr Ile Met Arg Lys Arg Val Asp Ile Gln
    130                 135                 140

Glu Ala Leu Lys Arg Pro Met Lys Gln Lys Arg Lys Leu Arg Leu Tyr
145                 150                 155                 160

Ile Ser Asn Thr Phe Asn Pro Ala Lys Pro Asp Ala Glu Asp Ser Asp
                165                 170                 175

Gly Ser Ile Ala Ser Trp Glu Leu Arg Val Glu Gly Lys Leu Leu Asp
            180                 185                 190

Asp Pro Ser Lys Gln Lys Arg Lys Phe Ser Ser Phe Phe Lys Ser Leu
        195                 200                 205

Val Ile Glu Leu Asp Lys Asp Leu Tyr Gly Pro Asp Asn His Leu Val
    210                 215                 220

Glu Trp His Arg Thr Pro Thr Thr Gln Glu Thr Asp Gly Phe Gln Val
225                 230                 235                 240

Lys Arg Pro Gly Asp Leu Ser Val Arg Cys Thr Leu Leu Leu Met Leu
                245                 250                 255

Asp Tyr Gln Pro Pro Gln Phe Lys Leu Asp Pro Arg Leu Ala Arg Leu
            260                 265                 270

Leu Gly Leu His Thr Gln Ser Arg Ser Ala Ile Val Gln Ala Leu Trp
        275                 280                 285

Gln Tyr Val Lys Thr Asn Arg Leu Gln Asp Ser His Asp Lys Glu Tyr
    290                 295                 300

Ile Asn Gly Asp Lys Tyr Phe Gln Gln Ile Phe Asp Cys Pro Arg Leu
305                 310                 315                 320

Lys Phe Ser Glu Ile Pro Gln Arg Leu Thr Ala Leu Leu Leu Pro Pro
                325                 330                 335

Asp Pro Ile Val Ile Asn His Val Ile Ser Val Asp Pro Ser Asp Gln
            340                 345                 350

Lys Lys Thr Ala Cys Tyr Asp Ile Asp Val Glu Val Glu Glu Pro Leu
        355                 360                 365

Lys Gly Gln Met Ser Ser Phe Leu Leu Ser Thr Ala Asn Gln Gln Glu
    370                 375                 380
```

-continued

```
Ile Ser Ala Leu Asp Ser Lys Ile His Glu Thr Ile Glu Ser Ile Asn
385                 390                 395                 400

Gln Leu Lys Ile Gln Arg Asp Phe Met Leu Ser Phe Ser Arg Asp Pro
                405                 410                 415

Lys Gly Tyr Val Gln Asp Leu Leu Arg Ser Gln Ser Arg Asp Leu Lys
            420                 425                 430

Val Met Thr Asp Val Ala Gly Asn Pro Glu Glu Glu Arg Arg Ala Glu
        435                 440                 445

Phe Tyr His Gln Pro Trp Ser Gln Glu Ala Val Ser Arg Tyr Phe Tyr
    450                 455                 460

Cys Lys Ile Gln Gln Arg Arg Gln Glu Leu Glu Gln Ser Leu Val Val
465                 470                 475                 480

Arg Asn Thr
```

<210> SEQ ID NO 11
<211> LENGTH: 8595
<212> TYPE: DNA
<213> ORGANISM: Homo sapiens

<400> SEQUENCE: 11

```
ctcctttctc cggcagcaga aagcggagag tcacagcggg gccaggccct ggggagcgga      60

gcctccaccg cccccctcat tcccaggcaa gggcttgggg ggaatgagcc gggagagccg     120

ggtcccgagc ctacagagcc gggagcagct gagccgccgg cgcctcggcc gccgccgccg     180

cctcctcctc ctccgccgcc gccagcccgg agcctgagcc ggcggggcgg gggggagagg     240

agcgagcgca gcgcagcagc ggagccccgc gaggcccgcc cgggcgggtg gggagggcag     300

cccgggggac tgggccccgg ggcggggtgg gagggggggga gaagacgaag acagggccgg     360

gtctctccgc ggacgagaca gcggggatca tggccgcgca ggtcgccccc gccgccgcca     420

gcagcctggg caacccgccg ccgccgccgc cctcggagct gaagaaagcc gagcagcagc     480

agcgggagga ggcgggggggc gaggcggcgg cggcggcagc ggccgagcgc ggggaaatga     540

aggcagccgc cgggcaggaa agcgagggcc ccgccgtggg gccgccgcag ccgctgggaa     600

aggagctgca ggacggggcc gagagcaatg gggggtggcgg cggcggcgga gccggcagcg     660

gcggcgggcc cggcgcggag ccggacctga agaactcgaa cgggaacgcg ggccctaggc     720

ccgccctgaa caataacctc acggagccgc ccggcggcgg cggtggcggc agcagcgatg     780

gggtgggggc gcctcctcac tcagccgcgg ccgccttgcc gcccccagcc tacggcttcg     840

ggcaacccta cggccggagc ccgtctgccg tcgccgccgc cgcggccgcc gtcttccacc     900

aacaacatgg cggacaacaa agccctggcc tggcagcgct gcagagcggc ggcggcgggg     960

gcctggagcc ctacgcgggg ccccagcaga actctcacga ccacggcttc cccaaccacc    1020

agtacaactc ctactacccc aaccgcagcg cctacccccc gcccgccccg gcctacgcgc    1080

tgagctcccc gagaggtggc actccgggct ccggcgcggc ggcggctgcc ggctccaagc    1140

cgcctccctc ctccagcgcc tccgcctcct cgtcgtcttc gtccttcgct cagcagcgct    1200

tcggggccat ggggggaggc ggcccctccg cggccggcgg gggaactccc cagcccaccg    1260

ccacccccac cctcaaccaa ctgctcacgt cgcccagctc ggcccggggc taccagggct    1320

accccggggg cgactacagt ggcgggcccc aggacggggg cgccggcaag ggcccggcgg    1380

acatggcctc gcagtgttgg ggggctgcgg cggcggcagc tgcggcggcg gccgcctcgg    1440

gaggggccca acaaaggagc caccacgcgc ccatgagccc cgggagcagc ggcggcgggg    1500

ggcagccgct cgcccggacc cctcagccat ccagtccaat ggatcagatg ggcaagatga    1560
```

```
gacctcagcc atatggcggg actaacccat actcgcagca acagggacct ccgtcaggac   1620
cgcagcaagg acatgggtac ccagggcagc catacgggtc ccagaccccg cagcggtacc   1680
cgatgaccat gcagggccgg gcgcagagtg ccatgggcgg cctctcttat acacagcaga   1740
ttcctcctta tggacaacaa ggccccagcg ggtatggtca acagggccag actccatatt   1800
acaaccagca aagtcctcac cctcagcagc agcagccacc ctactcccag caaccaccgt   1860
cccagacccc tcatgcccaa ccttcgtatc agcagcagcc acagtctcaa ccaccacagc   1920
tccagtcctc tcagcctcca tactcccagc agccatccca gcctccacat cagcagtccc   1980
cggctccata cccctcccag cagtcgacga cacagcagca cccccagagc cagcccccct   2040
actcacagcc acaggctcag tctccttacc agcagcagca acctcagcag ccagcacccct  2100
cgacgctctc ccagcaggct gcgtatcctc agccccagtc tcagcagtcc cagcaaactg   2160
cctattccca gcagcgcttc cctccaccgc aggagctatc tcaagattca tttgggtctc   2220
aggcatcctc agcccccctca atgacctcca gtaagggagg gcaagaagat atgaacctga  2280
gccttcagtc aagaccctcc agcttgcctg atctatctgg ttcaatagat gacctcccca   2340
tggggacaga aggagctctg agtcctggag tgagcacatc agggatttcc agcagccaag   2400
gagagcagag taatccagct cagtctcctt tctctcctca tacctcccct cacctgcctg   2460
gcatccgagg ccccttccccg tcccctgttg gctctcccgc cagtgttgct cagtctcgct  2520
caggaccact ctcgcctgct gcagtgccag gcaaccagat gccacctcgg ccacccagtg   2580
gccagtcgga cagcatcatg catccttcca tgaaccaatc aagcattgcc caagatcgag   2640
gttatatgca gaggaacccc cagatgcccc agtacagttc cccccagccc ggctcagcct   2700
tatctccgcg tcagccttcc ggaggacaga tacacacagg catgggctcc taccagcaga   2760
actccatggg gagctatggt ccccaggggg gtcagtatgg cccacaaggt ggctacccca   2820
ggcagccaaa ctataatgcc ttgcccaatg ccaactaccc cagtgcaggc atggctggag   2880
gcataaaccc catgggtgcc ggaggtcaaa tgcatggaca gcctggcatc ccaccttatg   2940
gcacactccc tccagggagg atgagtcacg cctccatggg caaccggcct tatggcccta   3000
acatggccaa tatgccacct caggttgggt cagggatgtg tcccccacca gggggcatga   3060
accggaaaac ccaagaaact gctgtcgcca tgcatgttgc tgccaactct atccaaaaca   3120
ggccgccagg ctaccccaat atgaatcaag gggggcatgat gggaactgga cctccttatg  3180
gacaagggat taatagtatg gctggcatga tcaaccctca gggaccccca tattccatgg   3240
gtggaaccat ggccaacaat tctgcaggga tggcagccag cccagagatg atgggccttg   3300
gggatgtaaa gttaactcca gccaccaaaa tgaacaacaa ggcagatggg acacccaaga   3360
cagaatccaa atccaagaaa tccagttctt ctactacaac caatgagaag atcaccaagt   3420
tgtatgagct gggtggtgag cctgagagga agatgtgggt ggaccgttat ctggccttca   3480
ctgaggagaa ggccatgggc atgacaaatc tgcctgctgt gggtaggaaa cctctggacc   3540
tctatcgcct ctatgtgtct gtgaaggaga ttggtggatt gactcaggtc aacaagaaca   3600
aaaaatggcg ggaacttgca accaacctca atgtgggcac atcaagcagt gctgccagct   3660
ccttgaaaaa gcagtatatc cagtgtctct atgcctttga atgcaagatt gaacggggag   3720
aagaccctcc cccagacatc tttgcagctg ctgattccaa gaagtcccag cccaagatcc   3780
agcctccctc tcctgcggga tcaggatcta tgcagggggcc ccagactccc cagtcaacca  3840
gcagttccat ggcagaagga ggagacttaa agccaccaac tccagcatcc acaccacaca   3900
```

-continued

```
gtcagatccc cccattgcca ggcatgagca ggagcaattc agttgggatc caggatgcct   3960
ttaatgatgg aagtgactcc acattccaga agcggaattc catgactcca aaccctgggt   4020
atcagcccag tatgaatacc tctgacatga tggggcgcat gtcctatgag ccaaataagg   4080
atccttatgg cagcatgagg aaagctccag ggagtgatcc cttcatgtcc tcagggcagg   4140
gccccaacgg cgggatgggt gacccctaca gtcgtgctgc cggccctggg ctaggaaatg   4200
tggcgatggg accacgacag cactatccct atggaggtcc ttatgacaga gtgaggacgg   4260
agcctggaat agggcctgag ggaaacatga gcactggggc cccacagccg aatctcatgc   4320
cttccaaccc agactcgggg atgtattctc ctagccgcta ccccccgcag cagcagcagc   4380
agcagcagca acgacatgat tcctatggca atcagttctc cacccaaggc accccttctg   4440
gcagcccctt ccccagccag cagactacaa tgtatcaaca gcaacagcag aattacaagc   4500
ggccaatgga tggcacatat ggccctcctg ccaagcggca cgaaggggag atgtacagcg   4560
tgccatacag cactgggcag gggcagcctc agcagcagca gttgccccca gcccagcccc   4620
agcctgccag ccagcaacaa gctgcccagc cttcccctca gcaagatgta tacaaccagt   4680
atggcaatgc ctatcctgcc actgccacag ctgctactga gcgccgacca gcaggcggcc   4740
cccagaacca atttccattc cagtttggcc gagaccgtgt ctctgcaccc cctggcacca   4800
atgcccagca aaacatgcca ccacaaatga tgggcggccc catacaggca tcagctgagg   4860
ttgctcagca aggcaccatg tggcaggggc gtaatgacat gacctataat tatgccaaca   4920
ggcagagcac gggctctgcc ccccagggcc ccgcctatca tggcgtgaac cgaacagatg   4980
aaatgctgca cacagatcag agggccaacc acgaaggctc gtggccttcc catggcacac   5040
gccagccccc atatggtccc tctgccccctg tgccccccat gacaaggccc cctccatcta   5100
actaccagcc cccaccaagc atgcagaatc acattcctca ggtatccagc cctgctcccc   5160
tgccccggcc aatggagaac cgcacctctc ctagcaagtc tccattcctg cactctggga   5220
tgaaaatgca gaaggcaggt cccccagtac ctgcctcgca catagcacct gcccctgtgc   5280
agcccccat gattcggcgg gatatcacct tcccacctgg ctctgttgaa gccacacagc   5340
ctgtgttgaa gcagaggagg cggctcacaa tgaaagacat tggaaccccg gaggcatggc   5400
gggtaatgat gtccctcaag tctggtctcc tggcagagag cacatgggca ttagatacca   5460
tcaacatcct gctgtatgat gacaacagca tcatgacctt caacctcagt cagctcccag   5520
ggttgctaga gctccttgta gaatatttcc gacgatgcct gattgagatc tttggcattt   5580
taaaggagta tgaggtgggt gacccaggac agagaacgct actggatcct gggaggttca   5640
gcaaggtgtc tagtccagct cccatggagg gtggggaaga agaagaagaa cttctaggtc   5700
ctaaactaga agaggaagaa gaagaggaag tagttgaaaa tgatgaggag atagcctttt   5760
caggcaagga caagccagct tcagagaata gtgaggagaa gctgatcagt aagtttgaca   5820
agcttccagt aaagatcgta cagaagaatg atccatttgt ggtggactgc tcagataagc   5880
ttgggcgtgt gcaggagttt gacagtggcc tgctgcactg gcggattggt ggggggggaca   5940
ccactgagca tatccagacc cacttcgaga gcaagacaga gctgctgcct tcccggcctc   6000
acgcaccctg cccaccagcc cctcggaagc atgtgacaac agcagagggt acaccaggga   6060
caacagacca ggaggggccc ccacctgatg gacctccaga aaaacggatc acagccacta   6120
tggatgacat gttgtctact cggtctagca ccttgaccga ggatggagct aagagttcag   6180
aggccatcaa ggagagcagc aagtttccat ttggcattag cccagcacag agccaccgga   6240
acatcaagat cctagaggac gaaccccaca gtaaggatga gaccccactg tgtacccttc   6300
```

-continued

```
tggactggca ggattctctt gccaagcgct gcgtctgtgt gtccaatacc attcgaagcc   6360
tgtcatttgt gccaggcaat gactttgaga tgtccaaaca cccagggctg ctgctcatcc   6420
tgggcaagct gatcctgctg caccacaagc acccagaacg gaagcaggca ccactaactt   6480
atgaaaagga ggaggaacag gaccaagggg tgagctgcaa caaagtggag tggtggtggg   6540
actgcttgga gatgctccgg gaaaacacct tggttacact cgccaacatc tcggggcagt   6600
tggacctatc tccatacccc gagagcattt gcctgcctgt cctggacgga ctcctacact   6660
gggcagtttg cccttcagct gaagcccagg accccttttc caccctgggc cccaatgccg   6720
tcctttcccc gcagagactg gtcttggaaa ccctcagcaa actcagcatc caggacaaca   6780
atgtggacct gattctggcc acaccccccct tcagccgcct ggagaagttg tatagcacta   6840
tggtgcgctt cctcagtgac cgaaagaacc cggtgtgccg ggagatggct gtggtactgc   6900
tggccaacct ggctcagggg gacagcctgg cagctcgtgc cattgcagtg cagaagggca   6960
gtatcggcaa cctcctgggc ttcctagagg acagccttgc cgccacacag ttccagcaga   7020
gccaggccag cctcctccac atgcagaacc caccctttga gccaactagt gtggacatga   7080
tgcggcgggc tgcccgcgcg ctgcttgcct tggccaaggt ggacgagaac cactcagagt   7140
ttactctgta cgaatcacgg ctgttggaca tctcggtatc accgttgatg aactcattgg   7200
tttcacaagt catttgtgat gtactgtttt tgattggcca gtcatgacag ccgtgggaca   7260
cctccccccc ccgtgtgtgt gtgcgtgtgt ggagaactta gaaactgact gttgcccttt   7320
atttatgcaa aaccacctca gaatccagtt taccctgtgc tgtccagctt ctcccttggg   7380
aaaaagtctc tcctgtttct ctctcctcct tccacctccc ctccctccat cacctcacgc   7440
ctttctgttc cttgtcctca ccttactccc ctcaggaccc taccccaccc tctttgaaaa   7500
gacaaagctc tgcctacata gaagactttt tttattttaa ccaaagttac tgttgtttac   7560
agtgagtttg gggaaaaaaa ataaaataaa aatggctttc ccagtccttg catcaacggg   7620
atgccacatt tcataactgt ttttaatggt aaaaaaaaaa aaaaaaaata caaaaaaaaa   7680
ttctgaagga caaaaaaggt gactgctgaa ctgtgtgtgg tttattgttg tacattcaca   7740
atcttgcagg agccaagaag ttcgcagttg tgaacagacc ctgttcactg gagaggcctg   7800
tgcagtagag tgtagaccct ttcatgtact gtactgtaca cctgatactg taaacatact   7860
gtaataataa tgtctcacat ggaaacagaa aacgctgggt cagcagcaag ctgtagtttt   7920
taaaaatgtt tttagttaaa cgttgaggag aaaaaaaaaa aaggcttttc ccccaaagta   7980
tcatgtgtga acctacaaca ccctgacctc tttctctcct ccttgattgt atgaataacc   8040
ctgagatcac ctcttagaac tggttttaac ctttagctgc agcggctacg ctgccacgtg   8100
tgtatatata tgacgttgta cattgcacat acccttggat ccccacagtt tggtcctcct   8160
cccagctacc cctttatagt atgacgagtt aacaagttgg tgacctgcac aaagcgagac   8220
acagctattt aatctcttgc cagatatcgc ccctcttggt gcgatgctgt acaggtctct   8280
gtaaaaagtc cttgctgtct cagcagccaa tcaacttata gtttattttt ttctgggttt   8340
ttgttttgtt ttgttttctt tctaatcgag gtgtgaaaaa gttctaggtt cagttgaagt   8400
tctgatgaag aaacacaatt gagatttttt cagtgataaa atctgcatat ttgtatttca   8460
acaatgtagc taaaacttga tgtaaattcc tcctttttttt cctttttttgg cttaatgaat   8520
atcatttatt cagtatgaaa tctttatact atatgttcca cgtgttaaga ataaatgtac   8580
attaaatctt ggtaa                                                   8595
```

<210> SEQ ID NO 12
<211> LENGTH: 2285
<212> TYPE: PRT
<213> ORGANISM: Homo sapiens

<400> SEQUENCE: 12

Met Ala Ala Gln Val Ala Pro Ala Ala Ala Ser Ser Leu Gly Asn Pro
1 5 10 15

Pro Pro Pro Pro Pro Ser Glu Leu Lys Lys Ala Glu Gln Gln Gln Arg
20 25 30

Glu Glu Ala Gly Gly Glu Ala Ala Ala Ala Ala Ala Ala Glu Arg Gly
35 40 45

Glu Met Lys Ala Ala Ala Gly Gln Glu Ser Glu Gly Pro Ala Val Gly
50 55 60

Pro Pro Gln Pro Leu Gly Lys Glu Leu Gln Asp Gly Ala Glu Ser Asn
65 70 75 80

Gly Gly Gly Gly Gly Gly Gly Ala Gly Ser Gly Gly Gly Pro Gly Ala
85 90 95

Glu Pro Asp Leu Lys Asn Ser Asn Gly Asn Ala Gly Pro Arg Pro Ala
100 105 110

Leu Asn Asn Asn Leu Thr Glu Pro Pro Gly Gly Gly Gly Gly Gly Ser
115 120 125

Ser Asp Gly Val Gly Ala Pro Pro His Ser Ala Ala Ala Ala Leu Pro
130 135 140

Pro Pro Ala Tyr Gly Phe Gly Gln Pro Tyr Gly Arg Ser Pro Ser Ala
145 150 155 160

Val Ala Ala Ala Ala Ala Ala Val Phe His Gln Gln His Gly Gly Gln
165 170 175

Gln Ser Pro Gly Leu Ala Ala Leu Gln Ser Gly Gly Gly Gly Gly Leu
180 185 190

Glu Pro Tyr Ala Gly Pro Gln Gln Asn Ser His Asp His Gly Phe Pro
195 200 205

Asn His Gln Tyr Asn Ser Tyr Tyr Pro Asn Arg Ser Ala Tyr Pro Pro
210 215 220

Pro Ala Pro Ala Tyr Ala Leu Ser Ser Pro Arg Gly Gly Thr Pro Gly
225 230 235 240

Ser Gly Ala Ala Ala Ala Ala Gly Ser Lys Pro Pro Pro Ser Ser Ser
245 250 255

Ala Ser Ala Ser Ser Ser Ser Ser Ser Phe Ala Gln Gln Arg Phe Gly
260 265 270

Ala Met Gly Gly Gly Gly Pro Ser Ala Ala Gly Gly Gly Thr Pro Gln
275 280 285

Pro Thr Ala Thr Pro Thr Leu Asn Gln Leu Leu Thr Ser Pro Ser Ser
290 295 300

Ala Arg Gly Tyr Gln Gly Tyr Pro Gly Gly Asp Tyr Ser Gly Gly Pro
305 310 315 320

Gln Asp Gly Gly Ala Gly Lys Gly Pro Ala Asp Met Ala Ser Gln Cys
325 330 335

Trp Gly Ala Ala Ala Ala Ala Ala Ala Ala Ala Ala Ala Ser Gly Gly
340 345 350

Ala Gln Gln Arg Ser His His Ala Pro Met Ser Pro Gly Ser Ser Gly
355 360 365

Gly Gly Gly Gln Pro Leu Ala Arg Thr Pro Gln Pro Ser Ser Pro Met
370 375 380

```
Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415

Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
        435                 440                 445

Gln Gln Ile Pro Pro Tyr Gly Gln Gln Gly Pro Ser Gly Tyr Gly Gln
    450                 455                 460

Gln Gly Gln Thr Pro Tyr Tyr Asn Gln Gln Ser Pro His Pro Gln Gln
465                 470                 475                 480

Gln Gln Pro Pro Tyr Ser Gln Gln Pro Pro Ser Gln Thr Pro His Ala
                485                 490                 495

Gln Pro Ser Tyr Gln Gln Gln Pro Gln Ser Gln Pro Pro Gln Leu Gln
            500                 505                 510

Ser Ser Gln Pro Pro Tyr Ser Gln Gln Pro Ser Gln Pro Pro His Gln
        515                 520                 525

Gln Ser Pro Ala Pro Tyr Pro Ser Gln Gln Ser Thr Thr Gln Gln His
    530                 535                 540

Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Gln Thr Ala Tyr
            580                 585                 590

Ser Gln Gln Arg Phe Pro Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
    690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gly Gln Ile His Thr Gly
    770                 775                 780

Met Gly Ser Tyr Gln Gln Asn Ser Met Gly Ser Tyr Gly Pro Gln Gly
785                 790                 795                 800
```

-continued

```
Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
    930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
            980                 985                 990

Ser Lys Ser Lys Lys Ser Ser Ser  Ser Thr Thr Thr Asn  Glu Lys Ile
        995                 1000                1005

Thr Lys  Leu Tyr Glu Leu Gly  Gly Glu Pro Glu Arg  Lys Met Trp
    1010                1015                1020

Val Asp  Arg Tyr Leu Ala Phe  Thr Glu Glu Lys Ala  Met Gly Met
    1025                1030                1035

Thr Asn  Leu Pro Ala Val Gly  Arg Lys Pro Leu Asp  Leu Tyr Arg
    1040                1045                1050

Leu Tyr  Val Ser Val Lys Glu  Ile Gly Gly Leu Thr  Gln Val Asn
    1055                1060                1065

Lys Asn  Lys Lys Trp Arg Glu  Leu Ala Thr Asn Leu  Asn Val Gly
    1070                1075                1080

Thr Ser  Ser Ser Ala Ala Ser  Ser Leu Lys Lys Gln  Tyr Ile Gln
    1085                1090                1095

Cys Leu  Tyr Ala Phe Glu Cys  Lys Ile Glu Arg Gly  Glu Asp Pro
    1100                1105                1110

Pro Pro  Asp Ile Phe Ala Ala  Ala Asp Ser Lys Lys  Ser Gln Pro
    1115                1120                1125

Lys Ile  Gln Pro Pro Ser Pro  Ala Gly Ser Gly Ser  Met Gln Gly
    1130                1135                1140

Pro Gln  Thr Pro Gln Ser Thr  Ser Ser Ser Met Ala  Glu Gly Gly
    1145                1150                1155

Asp Leu  Lys Pro Pro Thr Pro  Ala Ser Thr Pro His  Ser Gln Ile
    1160                1165                1170

Pro Pro  Leu Pro Gly Met Ser  Arg Ser Asn Ser Val  Gly Ile Gln
    1175                1180                1185

Asp Ala  Phe Asn Asp Gly Ser  Asp Ser Thr Phe Gln  Lys Arg Asn
    1190                1195                1200
```

```
Ser Met  Thr Pro Asn Pro Gly  Tyr Gln Pro Ser Met  Asn Thr Ser
    1205                 1210                 1215

Asp Met  Met Gly Arg Met Ser  Tyr Glu Pro Asn Lys  Asp Pro Tyr
    1220                 1225                 1230

Gly Ser  Met Arg Lys Ala Pro  Gly Ser Asp Pro Phe  Met Ser Ser
    1235                 1240                 1245

Gly Gln  Gly Pro Asn Gly Gly  Met Gly Asp Pro Tyr  Ser Arg Ala
    1250                 1255                 1260

Ala Gly  Pro Gly Leu Gly Asn  Val Ala Met Gly Pro  Arg Gln His
    1265                 1270                 1275

Tyr Pro  Tyr Gly Gly Pro Tyr  Asp Arg Val Arg Thr  Glu Pro Gly
    1280                 1285                 1290

Ile Gly  Pro Glu Gly Asn Met  Ser Thr Gly Ala Pro  Gln Pro Asn
    1295                 1300                 1305

Leu Met  Pro Ser Asn Pro Asp  Ser Gly Met Tyr Ser  Pro Ser Arg
    1310                 1315                 1320

Tyr Pro  Pro Gln Gln Gln Gln  Gln Gln Gln Gln Arg  His Asp Ser
    1325                 1330                 1335

Tyr Gly  Asn Gln Phe Ser Thr  Gln Gly Thr Pro Ser  Gly Ser Pro
    1340                 1345                 1350

Phe Pro  Ser Gln Gln Thr Thr  Met Tyr Gln Gln Gln  Gln Gln Asn
    1355                 1360                 1365

Tyr Lys  Arg Pro Met Asp Gly  Thr Tyr Gly Pro Pro  Ala Lys Arg
    1370                 1375                 1380

His Glu  Gly Glu Met Tyr Ser  Val Pro Tyr Ser Thr  Gly Gln Gly
    1385                 1390                 1395

Gln Pro  Gln Gln Gln Gln Leu  Pro Pro Ala Gln Pro  Gln Pro Ala
    1400                 1405                 1410

Ser Gln  Gln Gln Ala Ala Gln  Pro Ser Pro Gln Gln  Asp Val Tyr
    1415                 1420                 1425

Asn Gln  Tyr Gly Asn Ala Tyr  Pro Ala Thr Ala Thr  Ala Ala Thr
    1430                 1435                 1440

Glu Arg  Arg Pro Ala Gly Gly  Pro Gln Asn Gln Phe  Pro Phe Gln
    1445                 1450                 1455

Phe Gly  Arg Asp Arg Val Ser  Ala Pro Pro Gly Thr  Asn Ala Gln
    1460                 1465                 1470

Gln Asn  Met Pro Pro Gln Met  Met Gly Gly Pro Ile  Gln Ala Ser
    1475                 1480                 1485

Ala Glu  Val Ala Gln Gln Gly  Thr Met Trp Gln Gly  Arg Asn Asp
    1490                 1495                 1500

Met Thr  Tyr Asn Tyr Ala Asn  Arg Gln Ser Thr Gly  Ser Ala Pro
    1505                 1510                 1515

Gln Gly  Pro Ala Tyr His Gly  Val Asn Arg Thr Asp  Glu Met Leu
    1520                 1525                 1530

His Thr  Asp Gln Arg Ala Asn  His Glu Gly Ser Trp  Pro Ser His
    1535                 1540                 1545

Gly Thr  Arg Gln Pro Pro Tyr  Gly Pro Ser Ala Pro  Val Pro Pro
    1550                 1555                 1560

Met Thr  Arg Pro Pro Pro Ser  Asn Tyr Gln Pro Pro  Pro Ser Met
    1565                 1570                 1575

Gln Asn  His Ile Pro Gln Val  Ser Ser Pro Ala Pro  Leu Pro Arg
    1580                 1585                 1590
```

-continued

```
Pro Met  Glu Asn Arg Thr Ser  Pro Ser Lys Ser Pro  Phe Leu His
    1595                 1600                 1605

Ser Gly  Met Lys Met Gln Lys  Ala Gly Pro Pro Val  Pro Ala Ser
    1610                 1615                 1620

His Ile  Ala Pro Ala Pro Val  Gln Pro Pro Met Ile  Arg Arg Asp
    1625                 1630                 1635

Ile Thr  Phe Pro Pro Gly Ser  Val Glu Ala Thr Gln  Pro Val Leu
    1640                 1645                 1650

Lys Gln  Arg Arg Arg Leu Thr  Met Lys Asp Ile Gly  Thr Pro Glu
    1655                 1660                 1665

Ala Trp  Arg Val Met Met Ser  Leu Lys Ser Gly Leu  Leu Ala Glu
    1670                 1675                 1680

Ser Thr  Trp Ala Leu Asp Thr  Ile Asn Ile Leu Leu  Tyr Asp Asp
    1685                 1690                 1695

Asn Ser  Ile Met Thr Phe Asn  Leu Ser Gln Leu Pro  Gly Leu Leu
    1700                 1705                 1710

Glu Leu  Leu Val Glu Tyr Phe  Arg Arg Cys Leu Ile  Glu Ile Phe
    1715                 1720                 1725

Gly Ile  Leu Lys Glu Tyr Glu  Val Gly Asp Pro Gly  Gln Arg Thr
    1730                 1735                 1740

Leu Leu  Asp Pro Gly Arg Phe  Ser Lys Val Ser Ser  Pro Ala Pro
    1745                 1750                 1755

Met Glu  Gly Gly Glu Glu Glu  Glu Glu Leu Leu Gly  Pro Lys Leu
    1760                 1765                 1770

Glu Glu  Glu Glu Glu Glu Glu  Val Val Glu Asn Asp  Glu Glu Ile
    1775                 1780                 1785

Ala Phe  Ser Gly Lys Asp Lys  Pro Ala Ser Glu Asn  Ser Glu Glu
    1790                 1795                 1800

Lys Leu  Ile Ser Lys Phe Asp  Lys Leu Pro Val Lys  Ile Val Gln
    1805                 1810                 1815

Lys Asn  Asp Pro Phe Val Val  Asp Cys Ser Asp Lys  Leu Gly Arg
    1820                 1825                 1830

Val Gln  Glu Phe Asp Ser Gly  Leu Leu His Trp Arg  Ile Gly Gly
    1835                 1840                 1845

Gly Asp  Thr Thr Glu His Ile  Gln Thr His Phe Glu  Ser Lys Thr
    1850                 1855                 1860

Glu Leu  Leu Pro Ser Arg Pro  His Ala Pro Cys Pro  Pro Ala Pro
    1865                 1870                 1875

Arg Lys  His Val Thr Thr Ala  Glu Gly Thr Pro Gly  Thr Thr Asp
    1880                 1885                 1890

Gln Glu  Gly Pro Pro Pro Asp  Gly Pro Pro Glu Lys  Arg Ile Thr
    1895                 1900                 1905

Ala Thr  Met Asp Asp Met Leu  Ser Thr Arg Ser Ser  Thr Leu Thr
    1910                 1915                 1920

Glu Asp  Gly Ala Lys Ser Ser  Glu Ala Ile Lys Glu  Ser Ser Lys
    1925                 1930                 1935

Phe Pro  Phe Gly Ile Ser Pro  Ala Gln Ser His Arg  Asn Ile Lys
    1940                 1945                 1950

Ile Leu  Glu Asp Glu Pro His  Ser Lys Asp Glu Thr  Pro Leu Cys
    1955                 1960                 1965

Thr Leu  Leu Asp Trp Gln Asp  Ser Leu Ala Lys Arg  Cys Val Cys
    1970                 1975                 1980
```

-continued

Val Ser Asn Thr Ile Arg Ser Leu Ser Phe Val Pro Gly Asn Asp
1985 1990 1995

Phe Glu Met Ser Lys His Pro Gly Leu Leu Leu Ile Leu Gly Lys
2000 2005 2010

Leu Ile Leu Leu His His Lys His Pro Glu Arg Lys Gln Ala Pro
2015 2020 2025

Leu Thr Tyr Glu Lys Glu Glu Glu Gln Asp Gln Gly Val Ser Cys
2030 2035 2040

Asn Lys Val Glu Trp Trp Trp Asp Cys Leu Glu Met Leu Arg Glu
2045 2050 2055

Asn Thr Leu Val Thr Leu Ala Asn Ile Ser Gly Gln Leu Asp Leu
2060 2065 2070

Ser Pro Tyr Pro Glu Ser Ile Cys Leu Pro Val Leu Asp Gly Leu
2075 2080 2085

Leu His Trp Ala Val Cys Pro Ser Ala Glu Ala Gln Asp Pro Phe
2090 2095 2100

Ser Thr Leu Gly Pro Asn Ala Val Leu Ser Pro Gln Arg Leu Val
2105 2110 2115

Leu Glu Thr Leu Ser Lys Leu Ser Ile Gln Asp Asn Asn Val Asp
2120 2125 2130

Leu Ile Leu Ala Thr Pro Pro Phe Ser Arg Leu Glu Lys Leu Tyr
2135 2140 2145

Ser Thr Met Val Arg Phe Leu Ser Asp Arg Lys Asn Pro Val Cys
2150 2155 2160

Arg Glu Met Ala Val Val Leu Leu Ala Asn Leu Ala Gln Gly Asp
2165 2170 2175

Ser Leu Ala Ala Arg Ala Ile Ala Val Gln Lys Gly Ser Ile Gly
2180 2185 2190

Asn Leu Leu Gly Phe Leu Glu Asp Ser Leu Ala Ala Thr Gln Phe
2195 2200 2205

Gln Gln Ser Gln Ala Ser Leu Leu His Met Gln Asn Pro Pro Phe
2210 2215 2220

Glu Pro Thr Ser Val Asp Met Met Arg Arg Ala Ala Arg Ala Leu
2225 2230 2235

Leu Ala Leu Ala Lys Val Asp Glu Asn His Ser Glu Phe Thr Leu
2240 2245 2250

Tyr Glu Ser Arg Leu Leu Asp Ile Ser Val Ser Pro Leu Met Asn
2255 2260 2265

Ser Leu Val Ser Gln Val Ile Cys Asp Val Leu Phe Leu Ile Gly
2270 2275 2280

Gln Ser
2285

<210> SEQ ID NO 13
<211> LENGTH: 5150
<212> TYPE: DNA
<213> ORGANISM: Homo sapiens

<400> SEQUENCE: 13
caaagggaag cgaagccgga gctgcgggcg ctttttctgc ccgcggtgtc tcagattcat 60
tcttaaggaa ctgagaactt aatcttccaa aatgtcaaaa agaccatctt atgccccacc 120 tcccaccccca gctcctgcaa cacaaatgcc cagcacacca gggtttgtgg gatacaatcc 180
atacagtcat ctcgcctaca acaactacag gctgggaggg aacccgggca ccaacagccg 240

-continued

```
ggtcacggca tcctctggta tcacgattcc aaaaccccca aagccaccag ataagccgct    300
gatgccctac atgaggtaca gcagaaaggt ctgggaccaa gtaaaggctt ccaaccctga    360
cctaaagttg tgggagattg gcaagattat tggtggcatg tggcgagatc tcactgatga    420
agaaaaacaa gaatatttaa acgaatacga agcagaaaag atagagtaca atgaatctat    480
gaaggcctat cataattccc ccgcgtacct tgcttacata aatgcaaaaa gtcgtgcaga    540
agctgcttta gaggaagaaa gtcgacagag acaatctcgc atggagaaag gagaaccgta    600
catgagcatt cagcctgctg aagatccaga tgattatgat gatggctttt caatgaagca    660
tacagccacc gcccgtttcc agagaaacca ccgcctcatc agtgaaattc ttagtgagag    720
tgtggtgcca gacgttcggt cagttgtcac aacagctaga atgcaggtcc tcaaacggca    780
ggtccagtcc ttaatggttc atcagcgaaa actagaagct gaacttcttc aaatagagga    840
acgacaccag gagaagaaga ggaaattcct ggaaagcaca gattcattta acaatgaact    900
taaaaggttg tgcggtctga aagtagaagt ggatatggag aaaattgcag ctgagattgc    960
acaggcagag gaacaggccc gcaaaaggca ggaggaaagg gagaaggagg ccgcagagca   1020
agctgagcgc agtcagagca gcatcgttcc tgaggaagaa caagcagcta acaaaggcga   1080
ggagaagaaa gacgacgaga acattccgat ggagacagag gagacacacc ttgaagaaac   1140
aacagagagc caacagaatg gtgaagaagg cacgtctact cctgaggaca aggagagtgg   1200
gcaggagggg gtcgacagta tggcagagga aggaaccagt gatagtaaca ctggctcgga   1260
gagcaacagt gcaacagtgg aggagccacc aacagatccc ataccagaag atgagaaaaa   1320
agaataagtg ttgccttgtt ttgtgtgttc taaatacttt ttttaatgaa aaaatgtttt   1380
ttggttttaa tggtgttacg tggtttgtgt attaattttt tttcttgtcc atatcacacc   1440
accaaaggct tttggaccat ttagcatcat gagcctaatg gctcagtcag tcacctttct   1500
taagtgttgt gaagatggct cttttctttg gatcttgttt ctagccctca actgctgaaa   1560
gcctcagaat ttagattaat tgagaaaaca cccacctctt ttagagaatt atcctttgat   1620
gctgcagaat ctactcttac aatgccttcc tacagctcac tggggtgctt accaaagcca   1680
tagctttaaa ccttcccagt ccccatcagt agcttcctga aagtctcctc tcttgtttac   1740
ttctgcaaag ggtagcttct taaaaacgtg atcatgtatg agtatgtatt tgttcactta   1800
cccttttta cttttaatca atgtcagata ccaagagttg tgttaagctg agtgtagtgt   1860
gtaactaact acacttggat cttactgatc cagaaatagt ccccatagtt agagtagtta   1920
cttatgaagt ggttattaaa gtgaacacag cacatataca ttatctatac tgctttttgt   1980
tatgattaat actgggtatg ttctggtaaa tccatcctta ttgtatagaa aaaaaattac   2040
tttttacca ggttttccaa agacagaata gatcacaaag ctcaaggaat ttaatattct   2100
tgtaatggac tagataattc aaactgatta gcccattcca gaagaaaaac agctgggaat   2160
taagttaatc cacttgaaat tgttttacaa taatcagaac atccaaacct caaggctcag   2220
gatcccatag accagagccc accttttga taaacttagt aaagtcttgg agactagaag   2280
caagatagtt tgtgacacat aagcttccca aaaactagaa tagattttta ctgaatagtg   2340
gtatatctga tggtatatgt ttcttaaagg tccaaatgta ataaaaaaaa aaatgaaaaa   2400
aaggtctcag tgtttttaat gcactacata tttgtatgca agacaagcat ccagtttttt   2460
tctgtaatgc agtgacagtg tggaatgacc actcagccat tataaatttg tgtactcagg   2520
gcccttgtct cacccaacta tctctataaa ctgctgcagt agcttatttg tacaagacac   2580
```

-continued

```
ttgtgaaaat cagttttctt acattatagt cattgtcaca tatggaagtt ggtctttgat   2640
tccaaaagta aagggaatat gtttctacat taacaggaat atggagaaat ctgtaacgtt   2700
tgaattatct ttgaaagaat ggctaaatga taaatgttaa gtcctgtgcc tatatggaga   2760
ggactctgta ccagcatgag ttaatttaag tggattcact gctattcagt tcatagcaca   2820
ttagtgacta ggaatgtgtg ttcagcctcc tgagagagga ggggaggaag cttgatactg   2880
ggtggaaaca actcttgaca tctgtttcct tgtgtgtcaa agaacgaatt tgtatcaaat   2940
agatctgttt tgagctttgg ccattatttg gctaagaact tcagccatct catctcagac   3000
aaattggaca gcctctttga tacattttct agtagtcaaa atggggcaga tgtagtttaa   3060
tatgggtgga aaactgcccc agcaagatac caggttattt actgtggtat cgaaagctct   3120
aagagaatgg aagtggttct tttgcccggc tggaaatagc agtgggaaga caagtctatc   3180
cagaccaagc ctgtccatac aacactggca atcagttgat gagggaatta agtcagatgg   3240
gagacgtctc aatctgtcgc ccaggttgga gtgcagtggt ggcgatctca gctcactgca   3300
acctccacct cccaggttca agcaattctc tctgcctcag cctctagagc agctgggatt   3360
acaggctctc gccaccatgc ccggttaatt tttgtatttt ttagtagaga tggggtttca   3420
ccatgttagc caggctgatc ttgaactcgt gacctcaggt gatccgcctg cctcagtctc   3480
ccaaagtgct gggattacag gcgtgagcca ctgtgcccgg cctcagttgg gatttgacag   3540
ctctgaacct cagcagggga agattgatgt aaaaatccac ttggtcagag tgatatatgt   3600
agacttgatg tttgagatgg ttctcagttt agagaatgtg ggatatggta gaggtctttg   3660
tttttttccc atgtcccaaa aggtgctggg caagtagctt gaactcgagc ctgttttaat   3720
tataaaatag atcaaactgc tctttcttgg tgcccttact gctccttgat ttttagtgca   3780
tttattttga gtatgaatgc ataaagtctg agggcctaaa ttttgttaat ttttttttaac   3840
aaatgggaga ggggaatcct cgatagtcac ccaattttcc ttttttttttg agacagtctg   3900
actgttgccc aggctggagt gtaatggcgc catctcggct cactgcaaca tccagctcct   3960
gggtttcagc aattctcctg cctcagcctc ctgagtagct gggattacag gcgcccgcca   4020
ccacgcccgg ctaatttttg tatttttagt agagacagga ttttgccatg tttgccagcc   4080
tggtctcgaa ctcttgacct cctgatccac cctcctctgc ctcccaaagt gctgggatta   4140
caggcgtgag ccaccgcgcc cagccccata gtccccccaat tttctaacag ttttaaattc   4200
tgtaacttct cctgtctgta aacaaggctg tcttttcaaa tggctctcct acaggatgtg   4260
ataattatct attctataaa gccgaggttt ggagaggtaa atagctattt cacattaaca   4320
caataatgtc aatgccctat ggaaaagata aaatacttgg actatatttt aaaggggaat   4380
ctggggtcat gcatattgaa gtttaactag atccctccag atttttggtt ttgatcctac   4440
acatttagat actagttttg gattttagac agttggtgct gacagtgtga aactcctatt   4500
gcctgcagtt aaattgaagc tttggtttct cgtgaacagg cagtgaagct ggtattatac   4560
tttaagtcct catttcagaa atagtttccc tccaccccca agcactacca cacatggtct   4620
ccccacctgg tttcagctag tgcattagtt ttatcttgtt ttttaccgct gggcaaacct   4680
tgctggaaca acaactgact tcatgatttg cacatttgga gggcttaacg tctttgcaaa   4740
tgaaaaatcc actgtacaat aacaagctca aaggaactcg gagccttttt agaagaaatc   4800
gtgctgaatt ataatgtggc ttactgcaat aatgtttctt tgatcaggat ggaaaggaaa   4860
atactgagtt tagcagaaaa cgatgtctaa atgtatttgt aatgatacaa ttgtttataa   4920
atgttttact attaggttga accataagaa attgccagtg tacaatttca tctacaaaat   4980
```

```
gactggctta acctaaattc tgcattttat actccaagaa taagctcttc gtggcagctt   5040

tctaagtgtg aaatgatgga actttctatt tgccagaatg acctacactt ctctaatagt   5100

ttatctcata ttgttagcca aacgctgatt aaaatgcaaa tttcaaacta              5150


<210> SEQ ID NO 14
<211> LENGTH: 411
<212> TYPE: PRT
<213> ORGANISM: Homo sapiens

<400> SEQUENCE: 14

Met Ser Lys Arg Pro Ser Tyr Ala Pro Pro Pro Thr Pro Ala Pro Ala
1               5                   10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Pro Lys
    50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
            100                 105                 110

Gln Glu Tyr Leu Asn Glu Tyr Glu Ala Glu Lys Ile Glu Tyr Asn Glu
        115                 120                 125

Ser Met Lys Ala Tyr His Asn Ser Pro Ala Tyr Leu Ala Tyr Ile Asn
    130                 135                 140

Ala Lys Ser Arg Ala Glu Ala Ala Leu Glu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
            180                 185                 190

Thr Ala Arg Phe Gln Arg Asn His Arg Leu Ile Ser Glu Ile Leu Ser
        195                 200                 205

Glu Ser Val Val Pro Asp Val Arg Ser Val Val Thr Thr Ala Arg Met
    210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285

Ile Ala Gln Ala Glu Glu Gln Ala Arg Lys Arg Gln Glu Glu Arg Glu
    290                 295                 300

Lys Glu Ala Ala Glu Gln Ala Glu Arg Ser Gln Ser Ser Ile Val Pro
305                 310                 315                 320

Glu Glu Glu Gln Ala Ala Asn Lys Gly Glu Glu Lys Lys Asp Asp Glu
                325                 330                 335
```

```
Asn Ile Pro Met Glu Thr Glu Glu Thr His Leu Glu Glu Thr Thr Glu
            340                 345                 350

Ser Gln Gln Asn Gly Glu Glu Gly Thr Ser Thr Pro Glu Asp Lys Glu
        355                 360                 365

Ser Gly Gln Glu Gly Val Asp Ser Met Ala Glu Glu Gly Thr Ser Asp
    370                 375                 380

Ser Asn Thr Gly Ser Glu Ser Asn Ser Ala Thr Val Glu Glu Pro Pro
385                 390                 395                 400

Thr Asp Pro Ile Pro Glu Asp Glu Lys Lys Glu
                405                 410


<210> SEQ ID NO 15
<211> LENGTH: 10190
<212> TYPE: DNA
<213> ORGANISM: Homo sapiens

<400> SEQUENCE: 15

aagccatgct gggcccgata ggctcagcta gtcgtgtatt tacccatatc cgggctagag     60

aggaaaagag aaaagtttca tttaaacctg aactaaaaac tttcaccatg aaagcacaca    120

gcaggagcag gcccagagcg taaggcgtgc ccggcccggc gctccggcgg ggcctgcgga    180

gggggagggg gtcgcggctt cccggcgggc cgcgtggatg cgcacaggag gggccgcggc    240

ctgaaaagtg ggggttattg tctccccccg ccccccgccc ggcctcgcca cgccgcggcg    300

atcatggccg cgcgggcagc agcggcggcg gcggcggcgg cggcgcgggc gcgggcgcgg    360

gcaggcagcg gcgaacggcg ggcgcccccc gggccgcggc cggcgcccgg agcccgggac    420

ctggaggcgg gggcgcgcgg cgcggcggcg gcggcggcgg caccgggacc catgctgggg    480

ggcggcggcg acggcggcgg cggcctgaac agtgtgcacc accacccccct gctcccccgt    540

cacgaactca acatggccca taacgcgggc gccgcggccg ccgccggcac ccacagcgcc    600

aagagcggcg gctccgaggc ggctctcaag gagggtggaa gcgccgccgc gctgtcctcc    660

tcctcctcct cctccgcggc ggcagcggcg gcatcctctt cctcctcgtc gggcccgggc    720

tcggccatgg agacggggct gctccccaac cacaaactga aaaccgttgg cgaagccccc    780

gccgcgccgc cccaccagca gcaccaccac caccaccatg cccaccacca ccaccaccat    840

gcccaccacc tccaccacca ccacgcacta cagcagcagc taaaccagtt ccagcagcag    900

cagcagcagc agcaacagca gcagcagcag cagcagcaac agcaacatcc catttccaac    960

aacaacagct tgggcggcgc gggcggcggc gcgcctcagc ccggccccga catggagcag   1020

ccgcaacatg gaggcgccaa ggacagtgct gcgggcggcc aggccgaccc cccgggcccg   1080

ccgctgctga gcaagccggg cgacgaggac gacgcgccgc ccaagatggg ggagccggcg   1140

ggcggccgct acgagcaccc gggcttgggc gccctgggca cgcagcagcc gccggtcgcc   1200

gtgcccgggg gcggcggcgg cccggcggcc gtcccggagt ttaataatta ctatggcagc   1260

gctgcccctg cgagcggcgg ccccggcggc cgcgctgggc cttgctttga tcaacatggc   1320

ggacaacaaa gccccgggat ggggatgatg cactccgcct ccgccgccgc cgccggggcc   1380

cccggcagca tggacccccct gcagaactcc cacgaagggt accccaacag ccagtgcaac   1440

cattatccgg gctacagccg gcccggcgcg ggcggcggcg gcggcggcgg cggcggagga   1500

ggaggaggca gcggaggagg aggaggagga ggaggagcag gagcaggagg agcaggagcg   1560

ggagctgtgg cggcggcggc cgcggcggcg gcggcagcag caggaggcgg cggcggcggc   1620

ggctatgggg gctcgtccgc ggggtacggg gtgctgagct ccccccggca gcagggcggc   1680
```

-continued

```
ggcatgatga tgggccccgg gggcggcggg gccgcgagcc tcagcaaggc ggccgccggc   1740
tcggcggcgg ggggcttcca gcgcttcgcc ggccagaacc agcacccgtc gggggccacc   1800
ccgaccctca atcagctgct cacctcgccc agccccatga tgcggagcta cggcggcagc   1860
taccccgagt acagcagccc cagcgcgccg ccgccgccgc cgtcgcagcc ccagtcccag   1920
gcggcggcgg cgggggcggc ggcgggcggc cagcaggcgg ccgcgggcat gggcttgggc   1980
aaggacatgg gcgcccagta cgccgctgcc agcccggcct gggcggccgc gcaacaaagg   2040
agtcacccgg cgatgagccc cggcaccccc ggaccgacca tgggcagatc ccagggcagc   2100
ccaatggatc caatggtgat gaagagacct cagttgtatg gcatgggcag taaccctcat   2160
tctcagcctc agcagagcag tccgtaccca ggaggttcct atggccctcc aggcccacag   2220
cggtatccaa ttggcatcca gggtcggact cccggggcca tggccggaat gcagtaccct   2280
cagcagcagg actctggaga tgccacatgg aaagaaacat tctggttgat gccacctcag   2340
tatggacagc aaggtgtgag tggttactgc cagcagggcc aacagccata ttacagccag   2400
cagccgcagc cccgcacct cccaccccag gcgcagtatc tgccgtccca gtcccagcag   2460
aggtaccagc cgcagcagga catgtctcag gaaggctatg gaactagatc tcaacctcct   2520
ctggcccccg gaaaacctaa ccatgaagac ttgaacttaa tacagcaaga aagaccatca   2580
agtttaccag atctgtctgg ctccattgat gacctcccca cgggaacgga agcaactttg   2640
agctcagcag tcagtgcatc cgggtccacg agcagccaag gggatcagag caacccggcg   2700
cagtcgcctt tctccccaca tgcgtcccct catctctcca gcatcccggg gggcccatct   2760
ccctctcctg ttggctctcc tgtaggaagc aaccagtctc gatctggccc aatctctcct   2820
gcaagtatcc caggtagtca gatgcctccg cagccacccg ggagccagtc agaatccagt   2880
tcccatcccg ccttgagcca gtcaccaatg ccacaggaaa gaggttttat ggcaggcaca   2940
caaagaaacc ctcagatggc tcagtatgga cctcaacaga caggaccatc catgtcgcct   3000
catccttctc ctgggggcca gatgcatgct ggaatcagta gctttcagca gagtaactca   3060
agtgggactt acggtccaca gatgagccag tatggaccac aaggtaacta ctccagaccc   3120
ccagcgtata gtggggtgcc cagtgcaagc tacagcggcc cagggcccgg tatgggtatc   3180
agtgccaaca accagatgca tggacaaggg ccaagccagc catgtggtgc tgtgcccctg   3240
ggacgaatgc catcagctgg gatgcagaac agaccatttc ctggaaatat gagcagcatg   3300
acccccagtt ctcctggcat gtctcagcag ggagggccag gaatggggcc gccaatgcca   3360
actgtgaacc gtaaggcaca ggaggcagcc gcagcagtga tgcaggctgc tgcgaactca   3420
gcacaaagca ggcaaggcag tttccccggc atgaaccaga gtggacttat ggcttccagc   3480
tctccctaca gccagcccat gaacaacagc tctagcctga tgaacacgca ggcgccgccc   3540
tacagcatgg cgcccgccat ggtgaacagc tcggcagcat ctgtgggtct tgcagatatg   3600
atgtctcctg gtgaatccaa actgcccctg cctctcaaag cagacggcaa agaagaaggc   3660
actccacagc ccgagagcaa gtcaaagaag tccagctcct ccaccactac tggggagaag   3720
atcacgaagg tgtacgagct ggggaatgag ccagagagaa agctctgggt cgaccgatac   3780
ctcaccttca tggaagagag aggctctcct gtctcaagtc tgcctgccgt gggcaagaag   3840
cccctggacc tgttccgact ctacgtctgc gtcaaagaga tcgggggttt ggcccaggtt   3900
aataaaaaca agaagtggcg tgagctggca accaacctaa acgttggcac ctcaagcagt   3960
gcagcgagct ccctgaaaaa gcagtatatt cagtacctgt ttgcctttga gtgcaagatc   4020
```

-continued

```
gaacgtgggg aggagccccc gccggaagtc ttcagcaccg gggacaccaa aaagcagccc   4080
aagctccagc cgccatctcc tgctaactcg ggatccttgc aaggcccaca gacccccag   4140
tcaactggca gcaattccat ggcagaggtt ccaggtgacc tgaagccacc taccccagcc   4200
tccacccctc acggccagat gactccaatg caaggtggaa gaagcagtac aatcagtgtg   4260
cacgacccat tctcagatgt gagtgattca tccttcccga aacggaactc catgactcca   4320
aacgccccct accagcaggg catgagcatg cccgatgtga tgggcaggat gccctatgag   4380
cccaacaagg accccttgg  gggaatgaga aaagtgcctg gaagcagcga gccctttatg   4440
acgcaaggac agatgcccaa cagcagcatg caggacatgt acaaccaaag tccctccgga   4500
gcaatgtcta acctgggcat ggggcagcgc cagcagtttc cctatggagc cagttacgac   4560
cgaaggcatg aaccttatgg gcagcagtat ccaggccaag gccctccctc gggacagccg   4620
ccgtatggag ggcaccagcc cggcctgtac ccacagcagc cgaattacaa acgccatatg   4680
gacggcatgt acgggccccc agccaagcgc cacgagggcg acatgtacaa catgcagtac   4740
agcagccagc agcaggagat gtacaaccag tatggaggct cctactcggg cccggaccgc   4800
aggcccatcc agggccagta cccgtatccc tacagcaggg agaggatgca gggcccgggg   4860
cagatccaga cacacggaat cccgcctcag atgatgggcg gcccgctgca gtcgtcctcc   4920
agtgaggggc ctcagcagaa tatgtgggca gcacgcaatg atatgcctta tccctaccag   4980
aacaggcagg gccctggcgg ccctacacag gcgccccctt acccaggcat gaaccgcaca   5040
gacgatatga tggtacccga tcagaggata aatcatgaga gccagtggcc ttctcacgtc   5100
agccagcgtc agccttatat gtcgtcctca gcctccatgc agcccatcac acgcccacca   5160
cagccgtcct accagacgcc accgtcactg ccaaatcaca tctccagggc gcccagccca   5220
gcgtccttcc agcgctccct ggagaaccgc atgtctccaa gcaagtctcc ttttctgccg   5280
tctatgaaga tgcagaaggt catgcccacg gtccccacat cccaggtcac cgggccacca   5340
ccccaaccac cccaatcag  aagggagatc acctttcctc ctggctcagt agaagcatca   5400
caaccagtct tgaaacaaag gcgaaagatt acctccaaag atatcgttac tcctgaggcg   5460
tggcgtgtga tgatgtccct taaatcaggt cttttggctg agagtacgtg ggctttggac   5520
actattaata ttcttctgta tgatgacagc actgttgcta ctttcaatct ctcccagttg   5580
tctggatttc tcgaactttt agtcgagtac tttagaaaat gcctgattga catttttgga   5640
attcttatgg aatatgaagt gggagacccc agccaaaaag cacttgatca caacgcagca   5700
aggaaggatg acagccagtc cttggcagac gattctggga aagaggagga agatgctgaa   5760
tgtattgatg acgacgagga agacgaggag gatgaggagg aagacagcga gaagacagaa   5820
agcgatgaaa agagcagcat cgctctgact gccccggacg ccgctgcaga cccaaaggag   5880
aagcccaagc aagccagtaa gttcgacaag ctgccaataa agatagtcaa aaagaacaac   5940
ctgtttgttg ttgaccgatc tgacaagttg gggcgtgtgc aggagttcaa tagtggcctt   6000
ctgcactggc agctcggcgg gggtgacacc accgagcaca ttcagactca ctttgagagc   6060
aagatggaaa ttcctcctcg caggcgccca cctcccccct taagctccgc aggtagaaag   6120
aaagagcaag aaggcaaagg cgactctgaa gagcagcaag agaaaagcat catagcaacc   6180
atcgatgacg tcctctctgc tcggccaggg gcattgcctg aagacgcaaa ccctgggccc   6240
cagaccgaaa gcagtaagtt tccctttggt atccagcaag ccaaaagtca ccggaacatc   6300
aagctgctgg aggacgagcc caggagccga gacgagactc ctctgtgtac catcgcgcac   6360
tggcaggact cgctggctaa gcgatgcatc tgtgtgtcca atattgtccg tagcttgtca   6420
```

```
ttcgtgcctg gcaatgatgc cgaaatgtcc aaacatccag gcctggtgct gatcctgggg   6480
aagctgattc ttcttcacca cgagcatcca gagagaaagc gagcaccgca gacctatgag   6540
aaagaggagg atgaggacaa gggggtggcc tgcagcaaag atgagtggtg gtgggactgc   6600
ctcgaggtct tgagggataa cacgttggtc acgttggcca acatttccgg gcagctagac   6660
ttgtctgctt acacggaaag catctgcttg ccaattttgg atggcttgct gcactggatg   6720
gtgtgcccgt ctgcagaggc acaagatccc tttccaactg tgggacccaa ctcggtcctg   6780
tcgcctcaga gacttgtgct ggagaccctc tgtaaactca gtatccagga caataatgtg   6840
gacctgatct tggccactcc tccatttagt cgtcaggaga aattctatgc tacattagtt   6900
aggtacgttg gggatcgcaa aaacccagtc tgtcgagaaa tgtccatggc gcttttatcg   6960
aaccttgccc aaggggacgc actagcagca agggccatag ctgtgcagaa aggaagcatt   7020
ggaaacttga taagcttcct agaggatggg gtcacgatgg cccagtacca gcagagccag   7080
cacaacctca tgcacatgca gcccccgccc ctggaaccac ctagcgtaga catgatgtgc   7140
agggcggcca aggctttgct agccatggcc agagtggacg aaaaccgctc ggaattcctt   7200
ttgcacgagg gccggttgct ggatatctcg atatcagctg tcctgaactc tctggttgca   7260
tctgtcatct gtgatgtact gtttcagatt gggcagttat gacataagtg agaaggcaag   7320
catgtgtgag tgaagattag agggtcacat ataactggct gttttctgtt cttgtttatc   7380
cagcgtagga agaaggaaaa gaaaatcttt gctcctctgc cccattcact atttaccaat   7440
tgggaattaa agaaataatt aatttgaaca gttatgaaat taatatttgc tgtctgtgtg   7500
tataagtaca tcctttgggg tttttttttt ctctttttt taaccaaagt tgctgtctag   7560
tgcattcaaa ggtcactttt tgttcttcac agatcttttt aatgttcttt cccatgttgt   7620
attgcatttt tgggggaagc aaattgactt taaagaaaaa agttgtggca aaagatgcta   7680
agatgcgaaa atttcaccac actgagtcaa aaaggtgaaa aattatccat ttcctatgcg   7740
ttttactcct cagagaatga aaaaaactgc atcccatcac ccaaagttct gtgcaataga   7800
aatttctaca gatacaggta taggggctca aggaggtatg tcggtcagta gtcaaaacta   7860
tgaaatgata ctggtttctc cacaggaata tggttccatt aggctgggag caaaaacaat   7920
gtttttaag attgagaata catacctgac aacgatccgg aaactgctcc tcaccactcc   7980
cgtcatgcct gctgtcggcg tttgaccttc cacgtgacag ttcttcacaa ttcctttcat   8040
cattttttaa atattttttt tactgcctat gggctgtgat gtatatagaa gttgtacatt   8100
aaacataccc tcattttttt cttttctttt tttttttttt ttttagtaca aagttttagt   8160
ttctttttca tgatgtggta actacgaagt gatggtagat ttaaataatt ttttattttt   8220
attttatata ttttttcatt agggccatat ctccaaaaaa agaaagaaaa aatacaaaaa   8280
acaaaaacaa aaaaaaaaga gggtaatgta caagtttctg tatgtataaa gtcatgctcg   8340
atttcaggag agcagctgat cacaatttgc ttcatgaatc aaggtgtgga aatggttata   8400
tatggattga tttagaaaat ggttaccagt acagtcaaaa aagagaaaat gaaaaaaata   8460
caactaaaag gaagaaacac aacttcaaag atttttcagt gatgagaatc cacatttgta   8520
tttcaagata atgtagttta aaaaaaaaaa aaagaaaaaa acttgatgta aattcctcct   8580
tttcctctgg cttaatgaat atcatttatt cagtataaaa tctttatatg ttccacatgt   8640
taagaataaa tgtacattaa atcttgttaa gcactgtgat gggtgttctt gaatactgtt   8700
ctagtttcct taaagtggtt tcctagtaat caagttattt acaagaaata ggggaatgca   8760
```

```
gcagtgtatt cacattataa aaccctacat ttggaagaga cctttagggg ttacctactt   8820

tagagtgggg agcaacagtt tgattttctc aaattactta gctaattagt ctttctttga   8880

agcaattaac tctaacgaca ttgaggtatg atcattttca gtatttatgg gaggtggctg   8940

ctgacccact tgaggtgaga tctcagaagc ttaactggcc tgaaaatgta acattctgcc   9000

ttttactaac tccatcttag tttaatcaaa gttcaatcta ttccttgttt cttctgtgtg   9060

cctcagagtt attttgcatt tagtttactc caccgtgtat aatatttata ctgtgcaatg   9120

ttaaaaaaga atctgttata ttgtatgtgg tgtacatagt gcaaagtgat gatttctatt   9180

tcagggcata ttatggttct catattcctt cctacctggt gcacagtagc tttttaatac   9240

tagtcacttc taatttaaac tttctcttcc tgggtcattg actgttactg tgtaataatc   9300

gatttctttg aaactgctgc ataattatgc tgttagtgga cctctacctc ttctcttccc   9360

tctcccaatc acagtatact cagaatcccc agcccctcgc atacattgtg tcggttcaca   9420

ttactcacag taatatatgg aagagttaga caagaacatg cagttacagt cattgtgaga   9480

cgtgactctc cagtgtcacg aggaaaaaaa tcatcttttc tgcaaacagt ctctcatctg   9540

tcaactccca cattactgag tcaaacagtc ttcttacata acaatgcaac caaatatatg   9600

ttgaattaaa gacccattta taattctgct ttaaatacat ctgcttgcta agaacagatt   9660

tcagtgctcc aagcttcaaa tatggagatt tgtaagaggg aattcaatat tattctaatt   9720

tctctcttac agagtacaaa taaaaggtgt atacaaactc cgaacatatc cagtattcca   9780

attcctttgt caatcagaag agtaaaataa ttaacaaaag actgttgtta tggtttgcat   9840

tgtaaccgat acgcagagtc tgaccgttgg gcaacaagtt tttctatcct gatgcgcaac   9900

acagtctcta gagactaatc caggaagact ttagcctcct ttccatattc tcacccccga   9960

atcaagattt acagaagccc acgaagaatt tacagcctgc ttgagatcat cttgcctata  10020

aactgagtta ttgctttgtc ctaaaaatta gtcggttttt tttttctat gaggcttttc  10080

agaaatttac aggatgccca gactttacat gtgtaccaaa aaaaaaaaaa agataaaaaa  10140

taaaggtgca aagaaagttt agtattttgg aatggtgcta taaagttgaa             10190
```

```
<210> SEQ ID NO 16
<211> LENGTH: 2332
<212> TYPE: PRT
<213> ORGANISM: Homo sapiens

<400> SEQUENCE: 16

Met Ala Ala Arg Ala Ala Ala Ala Ala Ala Ala Ala Ala Ala Arg Ala
1               5                   10                  15

Arg Ala Arg Ala Gly Ser Gly Glu Arg Arg Ala Pro Pro Gly Pro Arg
            20                  25                  30

Pro Ala Pro Gly Ala Arg Asp Leu Glu Ala Gly Ala Arg Gly Ala Ala
        35                  40                  45

Ala Ala Ala Ala Ala Pro Gly Pro Met Leu Gly Gly Gly Gly Asp Gly
    50                  55                  60

Gly Gly Gly Leu Asn Ser Val His His His Pro Leu Leu Pro Arg His
65                  70                  75                  80

Glu Leu Asn Met Ala His Asn Ala Gly Ala Ala Ala Ala Ala Gly Thr
                85                  90                  95

His Ser Ala Lys Ser Gly Gly Ser Glu Ala Ala Leu Lys Glu Gly Gly
            100                 105                 110

Ser Ala Ala Ala Leu Ser Ser Ser Ser Ser Ser Ser Ala Ala Ala Ala
        115                 120                 125
```

-continued

```
Ala Ala Ser Ser Ser Ser Ser Ser Gly Pro Gly Ser Ala Met Glu Thr
    130                 135                 140

Gly Leu Leu Pro Asn His Lys Leu Lys Thr Val Gly Glu Ala Pro Ala
145                 150                 155                 160

Ala Pro Pro His Gln Gln His His His His His His Ala His His His
                165                 170                 175

His His His Ala His His Leu His His His His Ala Leu Gln Gln Gln
            180                 185                 190

Leu Asn Gln Phe Gln Gln Gln Gln Gln Gln Gln Gln Gln Gln Gln Gln
        195                 200                 205

Gln Gln Gln Gln Gln Gln His Pro Ile Ser Asn Asn Asn Ser Leu Gly
    210                 215                 220

Gly Ala Gly Gly Gly Ala Pro Gln Pro Gly Pro Asp Met Glu Gln Pro
225                 230                 235                 240

Gln His Gly Gly Ala Lys Asp Ser Ala Ala Gly Gly Gln Ala Asp Pro
                245                 250                 255

Pro Gly Pro Pro Leu Leu Ser Lys Pro Gly Asp Glu Asp Asp Ala Pro
            260                 265                 270

Pro Lys Met Gly Glu Pro Ala Gly Gly Arg Tyr Glu His Pro Gly Leu
        275                 280                 285

Gly Ala Leu Gly Thr Gln Gln Pro Pro Val Ala Val Pro Gly Gly Gly
    290                 295                 300

Gly Gly Pro Ala Ala Val Pro Glu Phe Asn Asn Tyr Tyr Gly Ser Ala
305                 310                 315                 320

Ala Pro Ala Ser Gly Gly Pro Gly Gly Arg Ala Gly Pro Cys Phe Asp
                325                 330                 335

Gln His Gly Gly Gln Gln Ser Pro Gly Met Gly Met Met His Ser Ala
            340                 345                 350

Ser Ala Ala Ala Ala Gly Ala Pro Gly Ser Met Asp Pro Leu Gln Asn
        355                 360                 365

Ser His Glu Gly Tyr Pro Asn Ser Gln Cys Asn His Tyr Pro Gly Tyr
    370                 375                 380

Ser Arg Pro Gly Ala Gly Gly Gly Gly Gly Gly Gly Gly Gly Gly Gly
385                 390                 395                 400

Gly Gly Ser Gly Gly Gly Gly Gly Gly Gly Gly Ala Gly Ala Gly Gly
                405                 410                 415

Ala Gly Ala Gly Ala Val Ala Ala Ala Ala Ala Ala Ala Ala Ala Ala
            420                 425                 430

Ala Gly Gly Gly Gly Gly Gly Gly Tyr Gly Gly Ser Ser Ala Gly Tyr
        435                 440                 445

Gly Val Leu Ser Ser Pro Arg Gln Gln Gly Gly Gly Met Met Met Gly
    450                 455                 460

Pro Gly Gly Gly Gly Ala Ala Ser Leu Ser Lys Ala Ala Ala Gly Ser
465                 470                 475                 480

Ala Ala Gly Gly Phe Gln Arg Phe Ala Gly Gln Asn Gln His Pro Ser
                485                 490                 495

Gly Ala Thr Pro Thr Leu Asn Gln Leu Leu Thr Ser Pro Ser Pro Met
            500                 505                 510

Met Arg Ser Tyr Gly Gly Ser Tyr Pro Glu Tyr Ser Ser Pro Ser Ala
        515                 520                 525

Pro Pro Pro Pro Pro Ser Gln Pro Gln Ser Gln Ala Ala Ala Ala Gly
    530                 535                 540
```

```
Ala Ala Ala Gly Gly Gln Gln Ala Ala Ala Gly Met Gly Leu Gly Lys
545                 550                 555                 560

Asp Met Gly Ala Gln Tyr Ala Ala Ala Ser Pro Ala Trp Ala Ala Ala
                565                 570                 575

Gln Gln Arg Ser His Pro Ala Met Ser Pro Gly Thr Pro Gly Pro Thr
            580                 585                 590

Met Gly Arg Ser Gln Gly Ser Pro Met Asp Pro Met Val Met Lys Arg
        595                 600                 605

Pro Gln Leu Tyr Gly Met Gly Ser Asn Pro His Ser Gln Pro Gln Gln
    610                 615                 620

Ser Ser Pro Tyr Pro Gly Gly Ser Tyr Gly Pro Pro Gly Pro Gln Arg
625                 630                 635                 640

Tyr Pro Ile Gly Ile Gln Gly Arg Thr Pro Gly Ala Met Ala Gly Met
                645                 650                 655

Gln Tyr Pro Gln Gln Gln Asp Ser Gly Asp Ala Thr Trp Lys Glu Thr
            660                 665                 670

Phe Trp Leu Met Pro Pro Gln Tyr Gly Gln Gln Gly Val Ser Gly Tyr
        675                 680                 685

Cys Gln Gln Gly Gln Gln Pro Tyr Tyr Ser Gln Gln Pro Gln Pro Pro
    690                 695                 700

His Leu Pro Pro Gln Ala Gln Tyr Leu Pro Ser Gln Ser Gln Gln Arg
705                 710                 715                 720

Tyr Gln Pro Gln Gln Asp Met Ser Gln Glu Gly Tyr Gly Thr Arg Ser
                725                 730                 735

Gln Pro Pro Leu Ala Pro Gly Lys Pro Asn His Glu Asp Leu Asn Leu
            740                 745                 750

Ile Gln Gln Glu Arg Pro Ser Ser Leu Pro Asp Leu Ser Gly Ser Ile
        755                 760                 765

Asp Asp Leu Pro Thr Gly Thr Glu Ala Thr Leu Ser Ser Ala Val Ser
    770                 775                 780

Ala Ser Gly Ser Thr Ser Ser Gln Gly Asp Gln Ser Asn Pro Ala Gln
785                 790                 795                 800

Ser Pro Phe Ser Pro His Ala Ser Pro His Leu Ser Ser Ile Pro Gly
                805                 810                 815

Gly Pro Ser Pro Ser Pro Val Gly Ser Pro Val Gly Ser Asn Gln Ser
            820                 825                 830

Arg Ser Gly Pro Ile Ser Pro Ala Ser Ile Pro Gly Ser Gln Met Pro
        835                 840                 845

Pro Gln Pro Pro Gly Ser Gln Ser Glu Ser Ser Ser His Pro Ala Leu
    850                 855                 860

Ser Gln Ser Pro Met Pro Gln Glu Arg Gly Phe Met Ala Gly Thr Gln
865                 870                 875                 880

Arg Asn Pro Gln Met Ala Gln Tyr Gly Pro Gln Gln Thr Gly Pro Ser
                885                 890                 895

Met Ser Pro His Pro Ser Pro Gly Gly Gln Met His Ala Gly Ile Ser
            900                 905                 910

Ser Phe Gln Gln Ser Asn Ser Ser Gly Thr Tyr Gly Pro Gln Met Ser
        915                 920                 925

Gln Tyr Gly Pro Gln Gly Asn Tyr Ser Arg Pro Pro Ala Tyr Ser Gly
    930                 935                 940

Val Pro Ser Ala Ser Tyr Ser Gly Pro Gly Pro Gly Met Gly Ile Ser
945                 950                 955                 960
```

-continued

```
Ala Asn Asn Gln Met His Gly Gln Gly Pro Ser Gln Pro Cys Gly Ala
                965                 970                 975

Val Pro Leu Gly Arg Met Pro Ser Ala Gly Met Gln Asn Arg Pro Phe
            980                 985                 990

Pro Gly Asn Met Ser Ser Met Thr  Pro Ser Ser Pro Gly  Met Ser Gln
        995                 1000                 1005

Gln Gly  Gly Pro Gly Met Gly  Pro Pro Met Pro Thr  Val Asn Arg
    1010                 1015                 1020

Lys Ala  Gln Glu Ala Ala Ala  Ala Val Met Gln Ala  Ala Ala Asn
    1025                 1030                 1035

Ser Ala  Gln Ser Arg Gln Gly  Ser Phe Pro Gly Met  Asn Gln Ser
    1040                 1045                 1050

Gly Leu  Met Ala Ser Ser Ser  Pro Tyr Ser Gln Pro  Met Asn Asn
    1055                 1060                 1065

Ser Ser  Ser Leu Met Asn Thr  Gln Ala Pro Pro Tyr  Ser Met Ala
    1070                 1075                 1080

Pro Ala  Met Val Asn Ser Ser  Ala Ala Ser Val Gly  Leu Ala Asp
    1085                 1090                 1095

Met Met  Ser Pro Gly Glu Ser  Lys Leu Pro Leu Pro  Leu Lys Ala
    1100                 1105                 1110

Asp Gly  Lys Glu Glu Gly Thr  Pro Gln Pro Glu Ser  Lys Ser Lys
    1115                 1120                 1125

Lys Ser  Ser Ser Ser Thr Thr  Thr Gly Glu Lys Ile  Thr Lys Val
    1130                 1135                 1140

Tyr Glu  Leu Gly Asn Glu Pro  Glu Arg Lys Leu Trp  Val Asp Arg
    1145                 1150                 1155

Tyr Leu  Thr Phe Met Glu Glu  Arg Gly Ser Pro Val  Ser Ser Leu
    1160                 1165                 1170

Pro Ala  Val Gly Lys Lys Pro  Leu Asp Leu Phe Arg  Leu Tyr Val
    1175                 1180                 1185

Cys Val  Lys Glu Ile Gly Gly  Leu Ala Gln Val Asn  Lys Asn Lys
    1190                 1195                 1200

Lys Trp  Arg Glu Leu Ala Thr  Asn Leu Asn Val Gly  Thr Ser Ser
    1205                 1210                 1215

Ser Ala  Ala Ser Ser Leu Lys  Lys Gln Tyr Ile Gln  Tyr Leu Phe
    1220                 1225                 1230

Ala Phe  Glu Cys Lys Ile Glu  Arg Gly Glu Glu Pro  Pro Pro Glu
    1235                 1240                 1245

Val Phe  Ser Thr Gly Asp Thr  Lys Lys Gln Pro Lys  Leu Gln Pro
    1250                 1255                 1260

Pro Ser  Pro Ala Asn Ser Gly  Ser Leu Gln Gly Pro  Gln Thr Pro
    1265                 1270                 1275

Gln Ser  Thr Gly Ser Asn Ser  Met Ala Glu Val Pro  Gly Asp Leu
    1280                 1285                 1290

Lys Pro  Pro Thr Pro Ala Ser  Thr Pro His Gly Gln  Met Thr Pro
    1295                 1300                 1305

Met Gln  Gly Gly Arg Ser Ser  Thr Ile Ser Val His  Asp Pro Phe
    1310                 1315                 1320

Ser Asp  Val Ser Asp Ser Ser  Phe Pro Lys Arg Asn  Ser Met Thr
    1325                 1330                 1335

Pro Asn  Ala Pro Tyr Gln Gln  Gly Met Ser Met Pro  Asp Val Met
    1340                 1345                 1350
```

-continued

Gly Arg Met Pro Tyr Glu Pro Asn Lys Asp Pro Phe Gly Gly Met
1355 1360 1365

Arg Lys Val Pro Gly Ser Ser Glu Pro Phe Met Thr Gln Gly Gln
1370 1375 1380

Met Pro Asn Ser Ser Met Gln Asp Met Tyr Asn Gln Ser Pro Ser
1385 1390 1395

Gly Ala Met Ser Asn Leu Gly Met Gly Gln Arg Gln Gln Phe Pro
1400 1405 1410

Tyr Gly Ala Ser Tyr Asp Arg Arg His Glu Pro Tyr Gly Gln Gln
1415 1420 1425

Tyr Pro Gly Gln Gly Pro Pro Ser Gly Gln Pro Pro Tyr Gly Gly
1430 1435 1440

His Gln Pro Gly Leu Tyr Pro Gln Gln Pro Asn Tyr Lys Arg His
1445 1450 1455

Met Asp Gly Met Tyr Gly Pro Pro Ala Lys Arg His Glu Gly Asp
1460 1465 1470

Met Tyr Asn Met Gln Tyr Ser Ser Gln Gln Gln Glu Met Tyr Asn
1475 1480 1485

Gln Tyr Gly Gly Ser Tyr Ser Gly Pro Asp Arg Arg Pro Ile Gln
1490 1495 1500

Gly Gln Tyr Pro Tyr Pro Tyr Ser Arg Glu Arg Met Gln Gly Pro
1505 1510 1515

Gly Gln Ile Gln Thr His Gly Ile Pro Pro Gln Met Met Gly Gly
1520 1525 1530

Pro Leu Gln Ser Ser Ser Ser Glu Gly Pro Gln Gln Asn Met Trp
1535 1540 1545

Ala Ala Arg Asn Asp Met Pro Tyr Pro Tyr Gln Asn Arg Gln Gly
1550 1555 1560

Pro Gly Gly Pro Thr Gln Ala Pro Pro Tyr Pro Gly Met Asn Arg
1565 1570 1575

Thr Asp Asp Met Met Val Pro Asp Gln Arg Ile Asn His Glu Ser
1580 1585 1590

Gln Trp Pro Ser His Val Ser Gln Arg Gln Pro Tyr Met Ser Ser
1595 1600 1605

Ser Ala Ser Met Gln Pro Ile Thr Arg Pro Pro Gln Pro Ser Tyr
1610 1615 1620

Gln Thr Pro Pro Ser Leu Pro Asn His Ile Ser Arg Ala Pro Ser
1625 1630 1635

Pro Ala Ser Phe Gln Arg Ser Leu Glu Asn Arg Met Ser Pro Ser
1640 1645 1650

Lys Ser Pro Phe Leu Pro Ser Met Lys Met Gln Lys Val Met Pro
1655 1660 1665

Thr Val Pro Thr Ser Gln Val Thr Gly Pro Pro Pro Gln Pro Pro
1670 1675 1680

Pro Ile Arg Arg Glu Ile Thr Phe Pro Pro Gly Ser Val Glu Ala
1685 1690 1695

Ser Gln Pro Val Leu Lys Gln Arg Arg Lys Ile Thr Ser Lys Asp
1700 1705 1710

Ile Val Thr Pro Glu Ala Trp Arg Val Met Met Ser Leu Lys Ser
1715 1720 1725

Gly Leu Leu Ala Glu Ser Thr Trp Ala Leu Asp Thr Ile Asn Ile
1730 1735 1740

```
Leu Leu  Tyr Asp Asp Ser Thr  Val Ala Thr Phe Asn  Leu Ser Gln
    1745                 1750                 1755

Leu Ser  Gly Phe Leu Glu Leu  Leu Val Glu Tyr Phe  Arg Lys Cys
    1760                 1765                 1770

Leu Ile  Asp Ile Phe Gly Ile  Leu Met Glu Tyr Glu  Val Gly Asp
    1775                 1780                 1785

Pro Ser  Gln Lys Ala Leu Asp  His Asn Ala Ala Arg  Lys Asp Asp
    1790                 1795                 1800

Ser Gln  Ser Leu Ala Asp Asp  Ser Gly Lys Glu Glu  Glu Asp Ala
    1805                 1810                 1815

Glu Cys  Ile Asp Asp Asp Glu  Glu Asp Glu Glu Asp  Glu Glu Glu
    1820                 1825                 1830

Asp Ser  Glu Lys Thr Glu Ser  Asp Glu Lys Ser Ser  Ile Ala Leu
    1835                 1840                 1845

Thr Ala  Pro Asp Ala Ala Ala  Asp Pro Lys Glu Lys  Pro Lys Gln
    1850                 1855                 1860

Ala Ser  Lys Phe Asp Lys Leu  Pro Ile Lys Ile Val  Lys Lys Asn
    1865                 1870                 1875

Asn Leu  Phe Val Val Asp Arg  Ser Asp Lys Leu Gly  Arg Val Gln
    1880                 1885                 1890

Glu Phe  Asn Ser Gly Leu Leu  His Trp Gln Leu Gly  Gly Gly Asp
    1895                 1900                 1905

Thr Thr  Glu His Ile Gln Thr  His Phe Glu Ser Lys  Met Glu Ile
    1910                 1915                 1920

Pro Pro  Arg Arg Arg Pro Pro  Pro Pro Leu Ser Ser  Ala Gly Arg
    1925                 1930                 1935

Lys Lys  Glu Gln Glu Gly Lys  Gly Asp Ser Glu Glu  Gln Gln Glu
    1940                 1945                 1950

Lys Ser  Ile Ile Ala Thr Ile  Asp Asp Val Leu Ser  Ala Arg Pro
    1955                 1960                 1965

Gly Ala  Leu Pro Glu Asp Ala  Asn Pro Gly Pro Gln  Thr Glu Ser
    1970                 1975                 1980

Ser Lys  Phe Pro Phe Gly Ile  Gln Gln Ala Lys Ser  His Arg Asn
    1985                 1990                 1995

Ile Lys  Leu Leu Glu Asp Glu  Pro Arg Ser Arg Asp  Glu Thr Pro
    2000                 2005                 2010

Leu Cys  Thr Ile Ala His Trp  Gln Asp Ser Leu Ala  Lys Arg Cys
    2015                 2020                 2025

Ile Cys  Val Ser Asn Ile Val  Arg Ser Leu Ser Phe  Val Pro Gly
    2030                 2035                 2040

Asn Asp  Ala Glu Met Ser Lys  His Pro Gly Leu Val  Leu Ile Leu
    2045                 2050                 2055

Gly Lys  Leu Ile Leu Leu His  His Glu His Pro Glu  Arg Lys Arg
    2060                 2065                 2070

Ala Pro  Gln Thr Tyr Glu Lys  Glu Glu Asp Glu Asp  Lys Gly Val
    2075                 2080                 2085

Ala Cys  Ser Lys Asp Glu Trp  Trp Trp Asp Cys Leu  Glu Val Leu
    2090                 2095                 2100

Arg Asp  Asn Thr Leu Val Thr  Leu Ala Asn Ile Ser  Gly Gln Leu
    2105                 2110                 2115

Asp Leu  Ser Ala Tyr Thr Glu  Ser Ile Cys Leu Pro  Ile Leu Asp
    2120                 2125                 2130
```

-continued

```
Gly Leu  Leu His Trp Met Val  Cys Pro Ser Ala Glu  Ala Gln Asp
    2135                 2140                 2145

Pro Phe  Pro Thr Val Gly Pro  Asn Ser Val Leu Ser  Pro Gln Arg
    2150                 2155                 2160

Leu Val  Leu Glu Thr Leu Cys  Lys Leu Ser Ile Gln  Asp Asn Asn
    2165                 2170                 2175

Val Asp  Leu Ile Leu Ala Thr  Pro Pro Phe Ser Arg  Gln Glu Lys
    2180                 2185                 2190

Phe Tyr  Ala Thr Leu Val Arg  Tyr Val Gly Asp Arg  Lys Asn Pro
    2195                 2200                 2205

Val Cys  Arg Glu Met Ser Met  Ala Leu Leu Ser Asn  Leu Ala Gln
    2210                 2215                 2220

Gly Asp  Ala Leu Ala Ala Arg  Ala Ile Ala Val Gln  Lys Gly Ser
    2225                 2230                 2235

Ile Gly  Asn Leu Ile Ser Phe  Leu Glu Asp Gly Val  Thr Met Ala
    2240                 2245                 2250

Gln Tyr  Gln Gln Ser Gln His  Asn Leu Met His Met  Gln Pro Pro
    2255                 2260                 2265

Pro Leu  Glu Pro Pro Ser Val  Asp Met Met Cys Arg  Ala Ala Lys
    2270                 2275                 2280

Ala Leu  Leu Ala Met Ala Arg  Val Asp Glu Asn Arg  Ser Glu Phe
    2285                 2290                 2295

Leu Leu  His Glu Gly Arg Leu  Leu Asp Ile Ser Ile  Ser Ala Val
    2300                 2305                 2310

Leu Asn  Ser Leu Val Ala Ser  Val Ile Cys Asp Val  Leu Phe Gln
    2315                 2320                 2325

Ile Gly  Gln Leu
    2330
```

<210> SEQ ID NO 17
<211> LENGTH: 3402
<212> TYPE: DNA
<213> ORGANISM: Homo sapiens

<400> SEQUENCE: 17

```
acccggagcg ctcgggactt gccgatagtg gtgacggcgg caacatgtct gtggctttcg     60

cggccccgag gcagcgaggc aagggggaga tcactcccgc tgcgattcag aagatgttgg    120

atgacaataa ccatcttatt cagtgtataa tggactctca gaataaagga aagacctcag    180

agtgttctca gtatcagcag atgttgcaca caaacttggt ataccttgct acaatagcag    240

attctaatca aaatatgcag tctcttttac cagcaccacc cacacagaat atgcctatgg    300

gtcctggagg gatgaatcag agcggccctc ccccacctcc acgctctcac aacatgcctt    360

cagatggaat ggtaggtggg ggtcctcctg caccgcacat gcagaaccag atgaacggcc    420

agatgcctgg gcctaaccat atgcctatgc agggacctgg acccaatcaa ctcaatatga    480

caaacagttc catgaatatg ccttcaagta gccatggatc catgggaggt tacaaccatt    540

ctgtgccatc atcacagagc atgccagtac agaatcagat gacaatgagt cagggacaac    600

caatgggaaa ctatggtccc agaccaaata tgagtatgca gccaaaccaa ggtccaatga    660

tgcatcagca gcctccttct cagcaataca atatgccaca gggaggcgga cagcattacc    720

aaggacagca gccacctatg ggaatgatgg gtcaagttaa ccaaggcaat catatgatgg    780

gtcagagaca gattcctccc tatagacctc ctcaacaggg cccaccacag cagtactcag    840

gccaggaaga ctattacggg gaccaataca gtcatggtgg acaaggtcct ccagaaggca    900
```

```
tgaaccagca atattaccct gatggtcata atgattacgg ttatcagcaa ccgtcgtatc    960
ctgaacaagg ctacgatagg ccttatgagg attcctcaca acattactac gaaggaggaa   1020
attcacagta tggccaacag caagatgcat accagggacc acctccacaa cagggatatc   1080
caccccagca gcagcagtac ccagggcagc aaggttaccc aggacagcag cagggctacg   1140
gtccttcaca gggtggtcca ggtcctcagt atcctaacta cccacaggga caaggtcagc   1200
agtatggagg atatagacca acacagcctg gaccaccaca gccaccccag cagaggcctt   1260
atggatatga ccagggacag tatggaaatt accagcagtg aaaaagtact tacattccag   1320
tagccagtat ctattagcag ccatattgtc acctcagcac tgtggacacc tccctgtgaa   1380
gagatccttc cattccatct agtttttgga aaaaccttgt ggataagtgg ctgtttcatc   1440
agtaagcagc ctttgtggtt tagttataaa aggctttagt agctcaaaaa tactcttgat   1500
ttcacatttc tactctagat ggcaacattg gacagaaaat gcaatgacat aaccaatttg   1560
taatgatttt ggaactgtgt ttcaaatgga ctgttacaga ctgaaaggtg tgaacagctt   1620
tgtatgttta tgaagggtaa gggaatttaa tacttttcca cagatttttt tgtaagggga   1680
agagggaaat gtacactttt tacagcagca atattttgta tattatgttt atttcatgtg   1740
gtgaatatgc aaggcggtac actacgcact ggacagcatc agaaatcctc tgttaatgtg   1800
gactggaaca tggtagatgc ttgattgttt tggtctcaaa atggtgtgct ataaagataa   1860
aggtgagggg aagacaaagc acaccatatg tccactgttc tgttctcata gaggaaattc   1920
aaatcccttt tatctattag ataatcaagg gcactgtgat acagttttga gtaaaaagac   1980
atttttaaa agccttccag ttttgtggat taaacctttt tataaagatc atttataata   2040
ctgttttaaa atgtgaggca ataagaatta ctttgtgttg gatctgagga ggctttggta   2100
aaacagtttc atctaaatga aagtggtaat cctcttctaa aatagcaata actgaaaatg   2160
aaagtgttaa ttttaccttg tttgagttat cagggaactt agtaagtaat atcaaagcat   2220
tttataaatg atatcaaaga agagtcaaca ttgatccagt cattttattt tgtaatattg   2280
agggataatt ggttattaaa ctgaatagtt caggagactt tacaaacctt tgtttcaact   2340
ttcttatctg gaaataatat catttataaa gggacacttt tatgtttttc ccttttttat   2400
gttggttgat ataacacaaa gagatattta ggaaaatgct tattgatgag gtttattcta   2460
tctgttttta aagcaccgag gttgcattct agataacctt gtttattagc atggcatatt   2520
ttaatcatta tttgagactg tcctgtgcct gattatttta gctaaattca gggagattgc   2580
gtggggcagg aaagcatgca ttgaaaaatt tctaaccacg gttatttaag cataatctga   2640
aaacatctag cccaaaggta agttgctatt ttcatcacag ttgcctatgc ccagggaata   2700
agatgtattc tttataattg aattggtttt tcccacgtct aactggaaac aaaacagaag   2760
gggcgtcata aatttgaata agcagaacat actgttctca acatactgta atcaaaagga   2820
ggaatttcag tgggtctctg tgtgtgtatg agagagagag tgtgtgtttg tgtgtttcaa   2880
ggtcagaaca ggtttttttg tttttgtttt ttgttctttg ttttttttt tgagatggag   2940
tcttgctctt gtcgcccagg ctggagtgca gtggcgcaat ctcagctcac tgcaacctcc   3000
gcctcccagg ttcaagcagt tctcctgcct cagcctcctg agtagctggg atgacaggca   3060
cccgccacca cacccagcta atttttgtac ttttagtaga gacgaggttt cgccatgttg   3120
gccaggctgg tctcgaactc ctgacctcag gtgatccacc cgcctcggcc ttccaaagtg   3180
ctgggattac aggcgtgagc caccgtgcct ggccagaata ggtttttct ttcaacttga   3240
```

```
tcagtagaaa atggacatca agtttgaaca gataaatcat ggacagcctt attgtgattg   3300

aaatgcttgt aggttctgtg ccaattttcc accactgtgt actttgttgc tatttaaaac   3360

tgtatcaact ctaacggaag aataaattat ttgtgatttt aa                      3402


<210> SEQ ID NO 18
<211> LENGTH: 418
<212> TYPE: PRT
<213> ORGANISM: Homo sapiens

<400> SEQUENCE: 18

Met Ser Val Ala Phe Ala Ala Pro Arg Gln Arg Gly Lys Gly Glu Ile
1               5                   10                  15

Thr Pro Ala Ala Ile Gln Lys Met Leu Asp Asp Asn Asn His Leu Ile
            20                  25                  30

Gln Cys Ile Met Asp Ser Gln Asn Lys Gly Lys Thr Ser Glu Cys Ser
        35                  40                  45

Gln Tyr Gln Gln Met Leu His Thr Asn Leu Val Tyr Leu Ala Thr Ile
    50                  55                  60

Ala Asp Ser Asn Gln Asn Met Gln Ser Leu Leu Pro Ala Pro Pro Thr
65                  70                  75                  80

Gln Asn Met Pro Met Gly Pro Gly Gly Met Asn Gln Ser Gly Pro Pro
                85                  90                  95

Pro Pro Pro Arg Ser His Asn Met Pro Ser Asp Gly Met Val Gly Gly
            100                 105                 110

Gly Pro Pro Ala Pro His Met Gln Asn Gln Met Asn Gly Gln Met Pro
        115                 120                 125

Gly Pro Asn His Met Pro Met Gln Gly Pro Gly Pro Asn Gln Leu Asn
    130                 135                 140

Met Thr Asn Ser Ser Met Asn Met Pro Ser Ser Ser His Gly Ser Met
145                 150                 155                 160

Gly Gly Tyr Asn His Ser Val Pro Ser Ser Gln Ser Met Pro Val Gln
                165                 170                 175

Asn Gln Met Thr Met Ser Gln Gly Gln Pro Met Gly Asn Tyr Gly Pro
            180                 185                 190

Arg Pro Asn Met Ser Met Gln Pro Asn Gln Gly Pro Met Met His Gln
        195                 200                 205

Gln Pro Pro Ser Gln Gln Tyr Asn Met Pro Gln Gly Gly Gly Gln His
    210                 215                 220

Tyr Gln Gly Gln Gln Pro Pro Met Gly Met Met Gly Gln Val Asn Gln
225                 230                 235                 240

Gly Asn His Met Met Gly Gln Arg Gln Ile Pro Pro Tyr Arg Pro Pro
                245                 250                 255

Gln Gln Gly Pro Pro Gln Gln Tyr Ser Gly Gln Glu Asp Tyr Tyr Gly
            260                 265                 270

Asp Gln Tyr Ser His Gly Gly Gln Gly Pro Pro Glu Gly Met Asn Gln
        275                 280                 285

Gln Tyr Tyr Pro Asp Gly His Asn Asp Tyr Gly Tyr Gln Gln Pro Ser
    290                 295                 300

Tyr Pro Glu Gln Gly Tyr Asp Arg Pro Tyr Glu Asp Ser Ser Gln His
305                 310                 315                 320

Tyr Tyr Glu Gly Gly Asn Ser Gln Tyr Gly Gln Gln Gln Asp Ala Tyr
                325                 330                 335

Gln Gly Pro Pro Pro Gln Gln Gly Tyr Pro Pro Gln Gln Gln Gln Tyr
            340                 345                 350
```

Pro Gly Gln Gln Gly Tyr Pro Gly Gln Gln Gln Gly Tyr Gly Pro Ser
355 360 365

Gln Gly Gly Pro Gly Pro Gln Tyr Pro Asn Tyr Pro Gln Gly Gln Gly
370 375 380

Gln Gln Tyr Gly Gly Tyr Arg Pro Thr Gln Pro Gly Pro Pro Gln Pro
385 390 395 400

Pro Gln Gln Arg Pro Tyr Gly Tyr Asp Gln Gly Gln Tyr Gly Asn Tyr
405 410 415

Gln Gln

<210> SEQ ID NO 19
<211> LENGTH: 8598
<212> TYPE: DNA
<213> ORGANISM: Homo sapiens

<400> SEQUENCE: 19
gccggcccat gactgagccc cgccgccgcc ggccgaggaa tgggctccgg gctctggtag 60
gaagcgctgg gagcgggggg cgcttttaaa acaccgatct gggtttttta aaaacctcct 120
ttgaaaaaat aatggcaaac tcgacgggga aggcgcctcc ggacgagcgg agaaagggac 180
tcgctttcct ggacgagctg cggcagttcc accacagcag agggtcgcct tttaaaaaaa 240
tccctgcggt gggtgggaag gagctggatc ttcacggtct ctacaccaga gtcactactt 300
taggcggatt cgcgaaggtt tctgagaaga atcagtgggg agaaattgtt gaagagttca 360
actttcccag aagttgttct aacgctgcct ttgctttaaa acagtattac ttgcgttacc 420
tagaaaagta cgagaaagtt catcattttg ggaggatgga tgatgaggta ccaccaggca 480
atccaaagcc acagcttcct attggtgcaa ttccatcttc ctacaattac cagcaacaca 540
gtgtgtcgga ttatctgcgt caaagttatg ggctgtccat ggactttaat tcgccaaatg 600
attataataa attggtgctt tcactgttat ctggactccc aaatgaagtg gactttgcta 660
ttaacgtatg cactctccta tcaaatgaaa gcaagcacgt catgcaactt gaaaaagatc 720
ctaaaatcat cactttacta cttgctaatg ccggggtgtt tgacgacact ttaggatcct 780
tttccactgt atttggagaa gaatggaaag agaagactga tagagacttc gttaagtttt 840
ggaaagacat cgttgatgat aatgaagttc gtgacctcat ttctgacaga aacaagtctc 900
atgaaggtac atcaggagaa tggatttggg agtctttatt tcatccacct cgaaagctgg 960
gcattaacga tattgaagga cagcgggtac ttcagattgc agtgattttg agaaatcttt 1020
cctttgagga gggcaatgtt aagctcttgg cagctaatcg tacctgtctt cgtttcctat 1080
tactttctgc acatagtcat tttatttctt taaggcaatt aggccttgac acattaggaa 1140
atattgcagc tgagctttta ctggaccctg ttgatttcaa aactactcat ctgatgtttc 1200
atactgttac aaaatgtcta atgtcaaggg atagattttt aaagatgaga ggcatggaaa 1260
ttttgggaaa tctttgcaaa gcagaagata atggtgtttt aatttgtgaa tatgtggatc 1320
aggattccta cagagagatc atttgtcatc tcactttacc tgatgtgctg cttgtaatct 1380
caacactcga ggtgctatac atgctcacgg aaatgggaga tgttgcttgc acaaaaattg 1440
caaaagtaga aaagagcata gacatgttag tgtgtctggt ttctatggat attcagatgt 1500
ttggccctga tgcactagct gcggtaaaac tcattgaaca cccaagttcc agtcatcaaa 1560
tgttatctga aattaggcca caagctatag agcaagtcca aacccagact catgtagcat 1620
ctgccccagc ttccagagca gttgtagcgc agcatgttgc tccacctcca ggaatagtgg 1680

-continued

```
aaatagatag tgagaagttt gcttgtcagt ggctaaatgc tcattttgaa gtaaatccag   1740
attgttctgt ttctcgagca gaaatgtatt ctgaatacct ctcgacttgc agtaaattag   1800
ctcgtggtgg aatcctaaca tcaactggat tttataaatg tcttagaacg gtctttccaa   1860
atcatacagt gaagagagtg gaggattcca gtagcaatgg gcaggcacat attcatgtgg   1920
taggagtaaa acggagggct ataccacttc ccattcagat gtactatcag cagcaaccag   1980
tttctacttc tgttgttcgt gttgattctg ttcctgatgt atctcctgct ccttcacctg   2040
caggaatccc tcatggatca caaaccatag gaaaccattt tcagaggact cctgttgcca   2100
accaatcttc aaatctgact gcaacacaaa tgtcttttcc tgtacaaggt gttcatactg   2160
tggcacaaac tgtttcaaga attccacaaa atccttcacc tcatacccac cagcaacaaa   2220
atgctccagt gactgtcatt caaagtaaag ctccaattcc ttgtgaagtt gttaaggcta   2280
cagttatcca gaattccata ccccagacag gagttcctgt tagtattgct gttggaggag   2340
gacctccaca gagttctgtt gttcagaatc atagtacagg gccacaacct gttacagttg   2400
tgaattctca gacattgctt caccatccat ctgtaattcc acagcagtct ccattacaca   2460
cagtggtacc aggacagatc ccttcaggca ctcctgttac agtaattcaa caagctgtcc   2520
cacagagtca tatgtttggc agagtacaga acataccagc atgtacttct acagtttcac   2580
agggtcaaca gttaatcacc acatcacccc aacctgtgca aacttcatct caacagacat   2640
cagctggtag ccagtcacaa gatactgtta tcatagcacc cccacagtat gtaacaactt   2700
ctgcatccaa tattgtctca gcaacttcag tacagaattt tcaggtagct acaggacaaa   2760
tggttactat tgctggtgtc ccaagtccac aagcctcaag ggtagggttt cagaacattg   2820
caccaaaacc tctcccttct cagcaagttt catctacagt ggtacagcag cctattcaac   2880
aaccacagca gccaacccaa caaagcgtag tgattgtaag ccagccagct caacaaggtc   2940
aaacttatgc accagccatt caccaaattg ttcttgctaa tccagcagct cttccagctg   3000
gtcagacagt tcagctaact ggacaaccta acataactcc atcttcttca ccatcacctg   3060
tcccagctac taataaccaa gtccctactg ccatgtcgtc gtcctctacc cctcaatcac   3120
agggaccacc tcctactgtc agtcaaatgt tatctgtgaa aaggcagcaa cagcagcaac   3180
attcaccagc acccccacca cagcaggtac aagtacaagt tcagcagccc caacaagtac   3240
agatgcaagt tcaacctcaa cagtcgaatg caggagttgg tcagcctgcc tctggtgagt   3300
cgagtctgat taaacagctt ctgcttccga aacgtggtcc ttcaacacca ggtggtaagc   3360
ttattctccc agctccacag attcctcccc ctaataatgc aagagctcct agccctcagg   3420
tggtctatca ggtggccagt aaccaagccg caggttttgg agtgcagggg caaactccag   3480
ctcagcagct attggttggg cagcaaaatg ttcagttggt cccaagtgca atgccaccct   3540
caggggggagt acaaactgtg cccatttcga acttacaaat attgccaggt ccactgatct   3600
caaatagccc agcaaccatt ttccaaggga cttctggcaa ccaggtaacc ataacagttg   3660
tgccaaatac gagttttgca cctgcaactg tgagtcaggg aaatgcaact cagctcattg   3720
ctccagcagg aattaccatg agcggaacgc agacaggagt tggacttcca gtacaaacgc   3780
ttccagccac tcaagcatct cctgctggac aatcatcatg tactactgct actcccccat   3840
tcaaaggtga taaaataatt tgccaaaagg aggaggaagc aaaggaagca acaggtttac   3900
atgttcatga acgtaaaatt gaagtcatgg agaacccgtc ctgccgacga ggagccacaa   3960
acaccagcaa tggggataca aaggaaaatg aaatgcatgt gggaagtctt ttaaatggga   4020
gaaagtacag tgactcaagt ctacctcctt caaactcagg gaaaattcaa agtgagacta   4080
```

-continued

```
atcagtgctc actaatcagt aatgggccat cattggaatt aggtgagaat ggagcatctg   4140
ggaaacagaa ctcagaacaa atagacatgc aagatatcaa aagtgatttg agaaaaccgc   4200
tagttaatgg aatctgtgat tttgataaag gagatggttc tcatttaagc aaaaacattc   4260
caaatcataa aacttccaat catgtaggaa atggtgagat atctccaatg gaaccacaag   4320
ggactttaga tatcactcag caagatactg ccaaaggtga tcaactagaa agaatttcta   4380
atggacctgt attaactttg ggtggttcat ctgtgagcag tatacaggag gcttcaaatg   4440
cggcaacaca gcaatttagt ggtactgatt tgcttaatgg acctctagct tcaagtttga   4500
attcagatgt gcctcagcaa cgcccaagtg tagttgtctc accacattct acaacctctg   4560
ttatacaggg acatcaaatc atagcagttc ccgactcagg atcaaaagta tcccattctc   4620
ctgccctatc atctgacgtt cggtctacaa atggcacagc agaatgcaaa actgtaaaga   4680
ggccagcaga ggatactgat agggaaacag tcgcaggaat tccaaataaa gtaggagtta   4740
gaattgttac aatcagtgac cccaacaatg ctggctgcag cgcaacaatg gttgctgtgc   4800
cagcaggagc agatccaagc actgtagcta aagtagcaat agaaagtgct gttcagcaaa   4860
agcaacagca tccaccaaca tatgtacaga atgtggtccc gcagaacact cctatgccac   4920
cttcaccagc tgtacaagtg cagggccagc ctaacagttc tcagccttct ccattcagtg   4980
gatccagtca gcctggagat ccaatgagaa aacctggaca gaacttcatg tgtctgtggc   5040
agtcttgtaa aaagtggttt cagacaccct cacaggtttt ctaccatgca gcaactgaac   5100
atggaggaaa agatgtatat ccagggcagt gtctttggga aggttgtgag ccttttcagc   5160
gacagcggtt ttcttttatt acccacttgc aggataagca ctgttcaaag gatgccctac   5220
ttgcaggatt aaaacaagat gaaccaggac aagcaggaag tcagaagtct tctaccaagc   5280
agccaactgt aggggggcaca agctcaactc ctagagcaca aaaggccatt gtgaatcatc   5340
ccagtgctgc acttatggct ctgaggagag gatcaagaaa ccttgtcttt cgagatttta   5400
cagatgaaaa agagggacca ataactaaac acatccgact aacagctgcc ttaatattaa   5460
aaaatattgg taaatattca gaatgtggtc gcagattgtt aaagagacat gaaaataact   5520
tatcagtgct agccattagt aacatggaag cttcctccac ccttgccaaa tgcctttatg   5580
aacttaattt tacagttcag agtaaggaac aagaaaaaga ctcagaaatg ctgcagtgaa   5640
aaataattcc acttacacag tgggggactc aaagtcagcc acatttcaca tactgttact   5700
gaagaaagca ccaagtctta atggaacaaa gaccatagaa tgaattattt tatctcctcc   5760
catgatgctg agaggaagct tcgtattctg atctctgagt gaatcccttt gttctctgtt   5820
taaaaaaatc taaaaagaaa aaggaaaaaa aaaaaagaac tgctgtggga ttgtcaacca   5880
gcttatctgc aggatgtttc agatctgata aatcctgatg gaaactggta tgatcagaat   5940
tcagtaccat ccacattgga atatacatgg aatattgtaa aacctacatg agcagatgaa   6000
atagaagcat taaatatttt tatctatatc caaaaaggag cacattttta tatttacaaa   6060
accgtttaag ctggtttgaa taatttaaaa aagtttcagc acacctatac ccccgatctc   6120
agagggggcc accaatatct agctatggat cgtgtgtttt gtttagaaat cagtagcttg   6180
gttttcttac ttgagccaat atattttcac ttatttatta tcataaaaat ttaccagtct   6240
gaatagatct tgtaaatatt tgtgaataga atgaatacct ttcatgccac tgcagccact   6300
ggaaatacat tctgtggtgt cctagaagca ttattggtag gttctaaagt tttctagact   6360
ttcctgtcaa ttgtaagtaa ttgtgatata ttctatgcag tggatgaatg ttctttaaat   6420
```

-continued

```
ttgtgtaaat acttctgcaa aggtactgat gctgtaaagt caaaacagtt ttgtggaact   6480
gtgatttttt tttcttttt ctttttttt ttctttttt ttttgtatta tacaccttgt   6540
agaactcatt ttgctggctg aaagagtatg gaataatata tctcatgtca ttttttagaa   6600
gaaaaactat ttgaaggtat tttttggttt tccttaacat gtatccactg taaacgtttg   6660
tcgtgtacaa gctcagagct tggacagaat tttttgtatt tgtaaattgg tttaaataca   6720
tggaatttta tacaggtttt ctcctgtgtt atatatgcat tatgtgcagg tatgatattt   6780
tcttcactac tttttctatc ttaatatagt gtggaatttt attgtattat tcttccattc   6840
ttaatactgt accacattcc tgctcagaaa ctgctcactt ccttaaattg tcttttttcc   6900
cccagcgtga aatgtatcca tttataactg cctattgcct gttctattag catccaaaaa   6960
tgtggaaggc ctcccaacca ccatttctgc tgtgtcctta ggatgtgcag taaaaaatat   7020
agacctaaca gtttatgtta tagaatggct ttatttactt tggtgactgt ttatagtttt   7080
taaataaaag actgaacatt ttcttgagtc cttcatttct gagtatgctt aagacatctt   7140
aaaaatatag agagaattct aaattcagct gaaggcaagg tataacggtc acctacctat   7200
ttgattatat gttgattgat aacatattaa atagagaaca aataagagag gtcctttaca   7260
tgacaaattt gcatgaaata agcagattaa ccaagtattt atttttcatc ttgttataat   7320
gcagagcaaa tgtagagaac agcaaatgat tgatgcagtt aaagctcaat atgccttttt   7380
ttactggata ctgtacattt ggctaaaagc ttttattgtt tgatgttgtg tttcttgact   7440
gtttattcag aatcacagtg tatccaaatc ttcagcttga atttggaggc agattcttag   7500
agtgaaaaag cctcagtttc catattaaaa atgttttaaa tattttgatt gaattagtac   7560
caatgtaaaa tctagtttct tcctgaagga ggatccctgg cgctgtcctg ccatgtctca   7620
aaggaatgtt tgagaaactt catctaatat tagttataag gttgtggaat ttatgcttgg   7680
cccaccttcc aagactggca ctgcccaaca gacaccgctg aaatcatgtg ggtatcccta   7740
ggatggcctt cagagccctc aaacttacaa gcacctggta gttgacatca tatggggaat   7800
tttctattca ccgtacttat ccaaaaatct cttttaaaaa gtaaatttgt gcaacaacgt   7860
ttatttgaaa gataatgtct tctcaaaatc agaaactgca gtggtaatta aattaataga   7920
aaagagaaca aactgcaggt ttagaaaaat ggttttcata ttcaccattc ttccacctca   7980
ttgaattgca tgctgtagtt ctagcttttc tgctataata tgtaaatatg actgtagcct   8040
tttaagcttc agtctcagca gagaatttcc taaatgcgtt tgacctaatg aaactgatca   8100
tggcttccca cttaggtttt tcttcttata gctttataga actatataat aatatggact   8160
tgctgtgtaa tggaattaaa gtgcttttgc acaataagtt ctgcaaaacc ctctcattca   8220
tgaaaaggtg ctccttgcta gacagaaact tgctgattta cagtattgtt atttttgtct   8280
aaagttctgt aaatacatgc tttaatgtta tctttgagaa atctatgtaa ataatatagt   8340
ctacaacata gagactgtat aattctgtgt tatatatgtg cctagtgctc tgttggcact   8400
caataaattt taagtaacaa aattgataat catatagcga aggcatattt ttcttccaag   8460
ctcaagtcag gattgtgact atatattaat gagactcagt aatccaaccc acacctgaga   8520
actcgtctca ttactttata gtcatgtcat gtatgttttt ttaaccatga aatgacaata   8580
aaatgatttt taaaatga                                                 8598
```

<210> SEQ ID NO 20
<211> LENGTH: 1835
<212> TYPE: PRT
<213> ORGANISM: Homo sapiens

<400> SEQUENCE: 20

Met Ala Asn Ser Thr Gly Lys Ala Pro Pro Asp Glu Arg Arg Lys Gly
1               5                   10                  15

Leu Ala Phe Leu Asp Glu Leu Arg Gln Phe His His Ser Arg Gly Ser
            20                  25                  30

Pro Phe Lys Lys Ile Pro Ala Val Gly Gly Lys Glu Leu Asp Leu His
        35                  40                  45

Gly Leu Tyr Thr Arg Val Thr Thr Leu Gly Gly Phe Ala Lys Val Ser
    50                  55                  60

Glu Lys Asn Gln Trp Gly Glu Ile Val Glu Glu Phe Asn Phe Pro Arg
65                  70                  75                  80

Ser Cys Ser Asn Ala Ala Phe Ala Leu Lys Gln Tyr Tyr Leu Arg Tyr
                85                  90                  95

Leu Glu Lys Tyr Glu Lys Val His His Phe Gly Glu Asp Asp Asp Glu
            100                 105                 110

Val Pro Pro Gly Asn Pro Lys Pro Gln Leu Pro Ile Gly Ala Ile Pro
        115                 120                 125

Ser Ser Tyr Asn Tyr Gln Gln His Ser Val Ser Asp Tyr Leu Arg Gln
    130                 135                 140

Ser Tyr Gly Leu Ser Met Asp Phe Asn Ser Pro Asn Asp Tyr Asn Lys
145                 150                 155                 160

Leu Val Leu Ser Leu Leu Ser Gly Leu Pro Asn Glu Val Asp Phe Ala
                165                 170                 175

Ile Asn Val Cys Thr Leu Leu Ser Asn Glu Ser Lys His Val Met Gln
            180                 185                 190

Leu Glu Lys Asp Pro Lys Ile Ile Thr Leu Leu Leu Ala Asn Ala Gly
        195                 200                 205

Val Phe Asp Asp Thr Leu Gly Ser Phe Ser Thr Val Phe Gly Glu Glu
    210                 215                 220

Trp Lys Glu Lys Thr Asp Arg Asp Phe Val Lys Phe Trp Lys Asp Ile
225                 230                 235                 240

Val Asp Asp Asn Glu Val Arg Asp Leu Ile Ser Asp Arg Asn Lys Ser
                245                 250                 255

His Glu Gly Thr Ser Gly Glu Trp Ile Trp Glu Ser Leu Phe His Pro
            260                 265                 270

Pro Arg Lys Leu Gly Ile Asn Asp Ile Glu Gly Gln Arg Val Leu Gln
        275                 280                 285

Ile Ala Val Ile Leu Arg Asn Leu Ser Phe Glu Glu Gly Asn Val Lys
    290                 295                 300

Leu Leu Ala Ala Asn Arg Thr Cys Leu Arg Phe Leu Leu Leu Ser Ala
305                 310                 315                 320

His Ser His Phe Ile Ser Leu Arg Gln Leu Gly Leu Asp Thr Leu Gly
                325                 330                 335

Asn Ile Ala Ala Glu Leu Leu Leu Asp Pro Val Asp Phe Lys Thr Thr
            340                 345                 350

His Leu Met Phe His Thr Val Thr Lys Cys Leu Met Ser Arg Asp Arg
        355                 360                 365

Phe Leu Lys Met Arg Gly Met Glu Ile Leu Gly Asn Leu Cys Lys Ala
    370                 375                 380

Glu Asp Asn Gly Val Leu Ile Cys Glu Tyr Val Asp Gln Asp Ser Tyr
385                 390                 395                 400

```
Arg Glu Ile Ile Cys His Leu Thr Leu Pro Asp Val Leu Leu Val Ile
                405                 410                 415

Ser Thr Leu Glu Val Leu Tyr Met Leu Thr Glu Met Gly Asp Val Ala
            420                 425                 430

Cys Thr Lys Ile Ala Lys Val Glu Lys Ser Ile Asp Met Leu Val Cys
        435                 440                 445

Leu Val Ser Met Asp Ile Gln Met Phe Gly Pro Asp Ala Leu Ala Ala
    450                 455                 460

Val Lys Leu Ile Glu His Pro Ser Ser Ser His Gln Met Leu Ser Glu
465                 470                 475                 480

Ile Arg Pro Gln Ala Ile Glu Gln Val Gln Thr Gln Thr His Val Ala
                485                 490                 495

Ser Ala Pro Ala Ser Arg Ala Val Val Ala Gln His Val Ala Pro Pro
            500                 505                 510

Pro Gly Ile Val Glu Ile Asp Ser Glu Lys Phe Ala Cys Gln Trp Leu
        515                 520                 525

Asn Ala His Phe Glu Val Asn Pro Asp Cys Ser Val Ser Arg Ala Glu
    530                 535                 540

Met Tyr Ser Glu Tyr Leu Ser Thr Cys Ser Lys Leu Ala Arg Gly Gly
545                 550                 555                 560

Ile Leu Thr Ser Thr Gly Phe Tyr Lys Cys Leu Arg Thr Val Phe Pro
                565                 570                 575

Asn His Thr Val Lys Arg Val Glu Asp Ser Ser Ser Asn Gly Gln Ala
            580                 585                 590

His Ile His Val Val Gly Val Lys Arg Arg Ala Ile Pro Leu Pro Ile
        595                 600                 605

Gln Met Tyr Tyr Gln Gln Gln Pro Val Ser Thr Ser Val Val Arg Val
    610                 615                 620

Asp Ser Val Pro Asp Val Ser Pro Ala Pro Ser Pro Ala Gly Ile Pro
625                 630                 635                 640

His Gly Ser Gln Thr Ile Gly Asn His Phe Gln Arg Thr Pro Val Ala
                645                 650                 655

Asn Gln Ser Ser Asn Leu Thr Ala Thr Gln Met Ser Phe Pro Val Gln
            660                 665                 670

Gly Val His Thr Val Ala Gln Thr Val Ser Arg Ile Pro Gln Asn Pro
        675                 680                 685

Ser Pro His Thr His Gln Gln Gln Asn Ala Pro Val Thr Val Ile Gln
    690                 695                 700

Ser Lys Ala Pro Ile Pro Cys Glu Val Val Lys Ala Thr Val Ile Gln
705                 710                 715                 720

Asn Ser Ile Pro Gln Thr Gly Val Pro Val Ser Ile Ala Val Gly Gly
                725                 730                 735

Gly Pro Pro Gln Ser Ser Val Val Gln Asn His Ser Thr Gly Pro Gln
            740                 745                 750

Pro Val Thr Val Val Asn Ser Gln Thr Leu Leu His His Pro Ser Val
        755                 760                 765

Ile Pro Gln Gln Ser Pro Leu His Thr Val Val Pro Gly Gln Ile Pro
    770                 775                 780

Ser Gly Thr Pro Val Thr Val Ile Gln Gln Ala Val Pro Gln Ser His
785                 790                 795                 800

Met Phe Gly Arg Val Gln Asn Ile Pro Ala Cys Thr Ser Thr Val Ser
                805                 810                 815
```

```
Gln Gly Gln Gln Leu Ile Thr Thr Ser Pro Gln Pro Val Gln Thr Ser
            820                 825                 830

Ser Gln Gln Thr Ser Ala Gly Ser Gln Ser Gln Asp Thr Val Ile Ile
        835                 840                 845

Ala Pro Pro Gln Tyr Val Thr Thr Ser Ala Ser Asn Ile Val Ser Ala
    850                 855                 860

Thr Ser Val Gln Asn Phe Gln Val Ala Thr Gly Gln Met Val Thr Ile
865                 870                 875                 880

Ala Gly Val Pro Ser Pro Gln Ala Ser Arg Val Gly Phe Gln Asn Ile
                885                 890                 895

Ala Pro Lys Pro Leu Pro Ser Gln Gln Val Ser Ser Thr Val Val Gln
            900                 905                 910

Gln Pro Ile Gln Gln Pro Gln Gln Pro Thr Gln Gln Ser Val Val Ile
        915                 920                 925

Val Ser Gln Pro Ala Gln Gln Gly Gln Thr Tyr Ala Pro Ala Ile His
    930                 935                 940

Gln Ile Val Leu Ala Asn Pro Ala Ala Leu Pro Ala Gly Gln Thr Val
945                 950                 955                 960

Gln Leu Thr Gly Gln Pro Asn Ile Thr Pro Ser Ser Ser Pro Ser Pro
                965                 970                 975

Val Pro Ala Thr Asn Asn Gln Val Pro Thr Ala Met Ser Ser Ser Ser
            980                 985                 990

Thr Pro Gln Ser Gln Gly Pro Pro  Pro Thr Val Ser Gln  Met Leu Ser
        995                 1000                 1005

Val Lys  Arg Gln Gln Gln Gln  Gln His Ser Pro Ala  Pro Pro Pro
    1010                 1015                 1020

Gln Gln  Val Gln Val Gln Val  Gln Gln Pro Gln Gln  Val Gln Met
    1025                 1030                 1035

Gln Val  Gln Pro Gln Gln Ser  Asn Ala Gly Val Gly  Gln Pro Ala
    1040                 1045                 1050

Ser Gly  Glu Ser Ser Leu Ile  Lys Gln Leu Leu Leu  Pro Lys Arg
    1055                 1060                 1065

Gly Pro  Ser Thr Pro Gly Gly  Lys Leu Ile Leu Pro  Ala Pro Gln
    1070                 1075                 1080

Ile Pro  Pro Pro Asn Asn Ala  Arg Ala Pro Ser Pro  Gln Val Val
    1085                 1090                 1095

Tyr Gln  Val Ala Ser Asn Gln  Ala Ala Gly Phe Gly  Val Gln Gly
    1100                 1105                 1110

Gln Thr  Pro Ala Gln Gln Leu  Leu Val Gly Gln Gln  Asn Val Gln
    1115                 1120                 1125

Leu Val  Pro Ser Ala Met Pro  Pro Ser Gly Gly Val  Gln Thr Val
    1130                 1135                 1140

Pro Ile  Ser Asn Leu Gln Ile  Leu Pro Gly Pro Leu  Ile Ser Asn
    1145                 1150                 1155

Ser Pro  Ala Thr Ile Phe Gln  Gly Thr Ser Gly Asn  Gln Val Thr
    1160                 1165                 1170

Ile Thr  Val Val Pro Asn Thr  Ser Phe Ala Pro Ala  Thr Val Ser
    1175                 1180                 1185

Gln Gly  Asn Ala Thr Gln Leu  Ile Ala Pro Ala Gly  Ile Thr Met
    1190                 1195                 1200

Ser Gly  Thr Gln Thr Gly Val  Gly Leu Pro Val Gln  Thr Leu Pro
    1205                 1210                 1215
```

-continued

```
Ala Thr  Gln Ala Ser Pro Ala  Gly Gln Ser Ser Cys  Thr Thr Ala
    1220                 1225                 1230

Thr Pro  Pro Phe Lys Gly Asp  Lys Ile Ile Cys Gln  Lys Glu Glu
    1235                 1240                 1245

Glu Ala  Lys Glu Ala Thr Gly  Leu His Val His Glu  Arg Lys Ile
    1250                 1255                 1260

Glu Val  Met Glu Asn Pro Ser  Cys Arg Arg Gly Ala  Thr Asn Thr
    1265                 1270                 1275

Ser Asn  Gly Asp Thr Lys Glu  Asn Glu Met His Val  Gly Ser Leu
    1280                 1285                 1290

Leu Asn  Gly Arg Lys Tyr Ser  Asp Ser Ser Leu Pro  Pro Ser Asn
    1295                 1300                 1305

Ser Gly  Lys Ile Gln Ser Glu  Thr Asn Gln Cys Ser  Leu Ile Ser
    1310                 1315                 1320

Asn Gly  Pro Ser Leu Glu Leu  Gly Glu Asn Gly Ala  Ser Gly Lys
    1325                 1330                 1335

Gln Asn  Ser Glu Gln Ile Asp  Met Gln Asp Ile Lys  Ser Asp Leu
    1340                 1345                 1350

Arg Lys  Pro Leu Val Asn Gly  Ile Cys Asp Phe Asp  Lys Gly Asp
    1355                 1360                 1365

Gly Ser  His Leu Ser Lys Asn  Ile Pro Asn His Lys  Thr Ser Asn
    1370                 1375                 1380

His Val  Gly Asn Gly Glu Ile  Ser Pro Met Glu Pro  Gln Gly Thr
    1385                 1390                 1395

Leu Asp  Ile Thr Gln Gln Asp  Thr Ala Lys Gly Asp  Gln Leu Glu
    1400                 1405                 1410

Arg Ile  Ser Asn Gly Pro Val  Leu Thr Leu Gly Gly  Ser Ser Val
    1415                 1420                 1425

Ser Ser  Ile Gln Glu Ala Ser  Asn Ala Ala Thr Gln  Gln Phe Ser
    1430                 1435                 1440

Gly Thr  Asp Leu Leu Asn Gly  Pro Leu Ala Ser Ser  Leu Asn Ser
    1445                 1450                 1455

Asp Val  Pro Gln Gln Arg Pro  Ser Val Val Val Ser  Pro His Ser
    1460                 1465                 1470

Thr Thr  Ser Val Ile Gln Gly  His Gln Ile Ile Ala  Val Pro Asp
    1475                 1480                 1485

Ser Gly  Ser Lys Val Ser His  Ser Pro Ala Leu Ser  Ser Asp Val
    1490                 1495                 1500

Arg Ser  Thr Asn Gly Thr Ala  Glu Cys Lys Thr Val  Lys Arg Pro
    1505                 1510                 1515

Ala Glu  Asp Thr Asp Arg Glu  Thr Val Ala Gly Ile  Pro Asn Lys
    1520                 1525                 1530

Val Gly  Val Arg Ile Val Thr  Ile Ser Asp Pro Asn  Asn Ala Gly
    1535                 1540                 1545

Cys Ser  Ala Thr Met Val Ala  Val Pro Ala Gly Ala  Asp Pro Ser
    1550                 1555                 1560

Thr Val  Ala Lys Val Ala Ile  Glu Ser Ala Val Gln  Gln Lys Gln
    1565                 1570                 1575

Gln His  Pro Pro Thr Tyr Val  Gln Asn Val Val Pro  Gln Asn Thr
    1580                 1585                 1590

Pro Met  Pro Pro Ser Pro Ala  Val Gln Val Gln Gly  Gln Pro Asn
    1595                 1600                 1605
```

```
Ser Ser Gln Pro Ser Pro Phe Ser Gly Ser Ser Gln Pro Gly Asp
    1610                1615                1620

Pro Met Arg Lys Pro Gly Gln Asn Phe Met Cys Leu Trp Gln Ser
    1625                1630                1635

Cys Lys Lys Trp Phe Gln Thr Pro Ser Gln Val Phe Tyr His Ala
    1640                1645                1650

Ala Thr Glu His Gly Gly Lys Asp Val Tyr Pro Gly Gln Cys Leu
    1655                1660                1665

Trp Glu Gly Cys Glu Pro Phe Gln Arg Gln Arg Phe Ser Phe Ile
    1670                1675                1680

Thr His Leu Gln Asp Lys His Cys Ser Lys Asp Ala Leu Leu Ala
    1685                1690                1695

Gly Leu Lys Gln Asp Glu Pro Gly Gln Ala Gly Ser Gln Lys Ser
    1700                1705                1710

Ser Thr Lys Gln Pro Thr Val Gly Gly Thr Ser Ser Thr Pro Arg
    1715                1720                1725

Ala Gln Lys Ala Ile Val Asn His Pro Ser Ala Ala Leu Met Ala
    1730                1735                1740

Leu Arg Arg Gly Ser Arg Asn Leu Val Phe Arg Asp Phe Thr Asp
    1745                1750                1755

Glu Lys Glu Gly Pro Ile Thr Lys His Ile Arg Leu Thr Ala Ala
    1760                1765                1770

Leu Ile Leu Lys Asn Ile Gly Lys Tyr Ser Glu Cys Gly Arg Arg
    1775                1780                1785

Leu Leu Lys Arg His Glu Asn Asn Leu Ser Val Leu Ala Ile Ser
    1790                1795                1800

Asn Met Glu Ala Ser Ser Thr Leu Ala Lys Cys Leu Tyr Glu Leu
    1805                1810                1815

Asn Phe Thr Val Gln Ser Lys Glu Gln Glu Lys Asp Ser Glu Met
    1820                1825                1830

Leu Gln
    1835
```

<210> SEQ ID NO 21
<211> LENGTH: 4549
<212> TYPE: DNA
<213> ORGANISM: Homo sapiens

<400> SEQUENCE: 21

```
gcagccggag tatccacctc gatgaccacg ggctgagccc cgcgccgcca ccatgtccgt     60

ggccttcgcg tctgcccggc caagaggcaa aggggaggtt acgcagcaaa ccatccagaa    120

gatgctggac gagaaccacc acctgatcca gtgcatcctg gagtaccaga gcaagggcaa    180

gacggccgag tgcacgcagt accagcagat cctgcaccgg aacctggtat acctggccac    240

gatcgcagac tccaaccaga acatgcagtc cctgcttcct gccccgccca cgcagaacat    300

gaacctgggc cctggagccc tgactcagag cggctccagc cagggcctgc actctcaggg    360

cagcctgagt gacgccatca gcacgggcct gccaccctcc tccctcctgc agggccagat    420

tggcaacggg ccgagccacg tgtccatgca gcagacggcg cctaacacgc tgcccaccac    480

ctccatgagc atctctgggc ccggctacag ccacgcggga cccgcctcgc agggcgtccc    540

catgcagggg caaggcacca tcggcaacta cgtgtctcgg accaacatca acatgcagtc    600

caacccagtc tccatgatgc agcagcaggc ggccacgtcg cactacagct cggcgcaggg    660

cggcagccag cactaccagg gccagtcgtc catcgccatg atggggcagg gcagccaggg    720
```

```
gagcagcatg atggggcagc ggcccatggc gccctaccgg ccctcccagc aaggctcttc    780
ccagcagtac ctgggccagg aggagtacta tggcgagcag tacagccaca gccagggcgc    840
cgcggagccc atgggccagc agtactaccc cgacggccat ggcgattacg cctaccagca    900
gtcatcctac acggagcaga gctacgaccg gtccttcgag gagtccacgc agcactacta    960
tgagggggga aactcccagt acagccagca gcaggccggg taccagcagg gtgccgcgca   1020
gcagcagacg tactcccagc agcagtaccc cagccagcag agctaccccg ggcagcagca   1080
gggctacggg tctgcccagg gagccccgtc acagtacccc ggctaccagc aaggccaagg   1140
ccagcagtac ggaagctacc gagcaccgca gacagcgccg tctgcccagc agcagcggcc   1200
ctacggctat gaacagggcc agtatggaaa ttaccagcag taagggacac acattctggc   1260
tggagccctt gtggtagcgt gttcatccag gggccggatg ggctggcggc agctctggtg   1320
aattgtgaca tgttggttac ctgttcgccc agtgccacgt ctgcatgtga agcgtgctca   1380
tttcatgctg ggtatgacgc cgagcgcaca ccactggcgt gagacagcgc ttggtggtgt   1440
gatacttttg gtgctgtgta tagtattgta tgtcggtaca cggagaggta tccttttttt   1500
gtcccccgcc cccttctcaa tgtttctagc tagctttggg ggtcattttg tcatcagagc   1560
attctgtgcc cagggacagg acagatctcg aggacaccac agtccacctg ttcccgtcaa   1620
cagacgttag gtctcatttt cctcctcatg cagtgttgta gtgtgggttg tcaacttttc   1680
tttaactggc tacgccacag ctggacacac atgcagcccc tggagggcag cctcttcctg   1740
tgcctcgatg ggtgggtgg gagggcatct tctgtgcgtt gggtcagttt ctgttacgta   1800
acgaaaagga taaacatctc ccacgggaga ggccacagat ggccacttcc agagcttgcc   1860
cattgcctgt ctctcgccaa ttccgtttat ccaaaaaggt acatgttttt gtattaaaaa   1920
gtaaacaggg atcagtgact gtattccaaa taaatatgaa tccctaaggg ccgtggacaa   1980
attgcctaac ccagggccag cggtattgct gaaggaaagg ggcagctctc tgggaagtgg   2040
gccctcagag attactctgg ctttgaccct tgtttagctg atggtcattt ctgggattgg   2100
aatatttaat aagcccaatt ctaagttgat aggtaatttt aaatattcaa accaaatctt   2160
cccaacagtt ggcaagttgt ttattttata ttatttcttc caggacctac ttgctcagat   2220
ctccaagcaa gcatttcttt tcttttaggg atgtctgaaa gtcacatcca gttacattac   2280
tgtgttcttt ctaatgaaaa gtaaaggttt tatatagaga aacttgagta atttttacat   2340
ttctaagaca ttaaatccca tttaaattct gtgtgaacat taaagacagc acacttgcaa   2400
aagtatggtc aaaggaaaaa aatcccacat ttcaattaac aagtagcatg gacatttgat   2460
caacctttag ttggaataat aatattcata tttgctatga atccttttaa aaaaatcttt   2520
ggataaatgc tgacagattt ccaagaacta ccaagaaaat acaagagata tccaatgctt   2580
gatatatgag gcctagtaat aacgatattt ctctttaatt gatgttttgt tttaaaagtt   2640
aaaagtaatt cttggcgtgg tggttcacgc ctgtaatccc agcactttgg gaggccgaag   2700
cgggcggatc acctgaggtc gggagttcga gaccagcctg accaacatgg agaaaccccg   2760
tccctactaa aaatacaaaa ttagccaggt atggtggtgc atacctgtaa tcccagctac   2820
tcgggaacct gaggcaggag aatggcttga acccaggaga cagaggttgt ggtggggcaa   2880
gatcgcacca ttgcacccga gcctaggcaa caagagtgaa attccgtctc aaaaaaataa   2940
ataaataaat aaataaataa gttaaaatta attctttatc cagagtcggg tgctttagaa   3000
tttataagtc acttatgtgt tttgcttgaa ttaattctga cagcccctat gaggaaatct   3060
```

-continued

```
ggaggcaggt aacagttccc attttagaga tgaagaactg aggcacagat taaaggactt   3120

gcctgtgttg aataccagtc ctgttctagg acattctccc ctctcctagg agacggatgt   3180

cacgcacaaa tggggagaga agtgtttatt ttgtaggcac taagggtttc taaaaccctt   3240

aacactggta agggctcaaa aataaacgta tgtgttcata ttcgatcacc gaaatgagag   3300

ttcttaattg ctaattgaca aacgcgttag caatttcagt tagggagtca tctcccttga   3360

ttgtgttctt ttcctgtcaa ttttcataga cctaatttgc aaactcaatc ggggactaaa   3420

atttcccact gaaaatgtta aacattttag ataactgtga agatagttta tttttattcc   3480

ttgccaatct gggaatatgc cttttttgtg tgtttgtgtg tttttttaag tgctgtatta   3540

ataatacttt ctgaaagaaa aggacactta ccccaaaact tcaatctgaa atgtcttaca   3600

ttaagaatat cttgaatgtt gtgtatatat tttaaaaagc actttgcaaa atagtttgta   3660

catttatttc ctaatttata catgattttt ggtgttaata tatttaatga ttaataacag   3720

aatgtttatt taatgtgctg tccattttta tgtaatatta tggggaaagt gatgccagca   3780

gttccttttc attattctat cttctgtcat atgaatgttg agcaaagctt aggccaacat   3840

gaattgtttg tgaagtgtgg ttgatggtgc tttgtttttt tctgactact tctatggaag   3900

gccagtgaag aagcaaagga agacatgaaa attgacgctc attcttcttc ctattgttcc   3960

ctgacatcca gcaaattgtg aatttgaaaa atgatggcca gttttcagaa gtgctgacaa   4020

attcatattg gtatgcaaaa gctcatcacc cattaaggtt tgttgttgaa tcaacagtac   4080

tcagcatatt aaaacagtac atcagaactc atgccaacag tctttatgat gggattaagg   4140

tggacaagat ctcctaagat ctgtgaatgg gattaaggtg gacaagatct cctaagatct   4200

gaaaagaaac cttaatacgc tcatatggtt ggagtgttaa gtgaacctct gatttgtca    4260

gggtttttct acgtgtaggc gtgaataggg ggcacccctt caaaactgta caaagaagac   4320

gactgttttc catttccatt taaacatttt tagccacttc atttctattt attgaacagg   4380

tcaaatttgt cttgttattt gtgagtacag tacatttaaa aaacatcctt atcggttatt   4440

tttttttcag tcggagtttg acgtataaat tgtttatgct tttggtgtaa tctcttaata   4500

aactggttct tcaaaaatca tcctataaag tgagttttca tgaagttaa               4549
```

```
<210> SEQ ID NO 22
<211> LENGTH: 396
<212> TYPE: PRT
<213> ORGANISM: Homo sapiens

<400> SEQUENCE: 22

Met Ser Val Ala Phe Ala Ser Ala Arg Pro Arg Gly Lys Gly Glu Val
1               5                   10                  15

Thr Gln Gln Thr Ile Gln Lys Met Leu Asp Glu Asn His His Leu Ile
            20                  25                  30

Gln Cys Ile Leu Glu Tyr Gln Ser Lys Gly Lys Thr Ala Glu Cys Thr
        35                  40                  45

Gln Tyr Gln Gln Ile Leu His Arg Asn Leu Val Tyr Leu Ala Thr Ile
    50                  55                  60

Ala Asp Ser Asn Gln Asn Met Gln Ser Leu Leu Pro Ala Pro Pro Thr
65                  70                  75                  80

Gln Asn Met Asn Leu Gly Pro Gly Ala Leu Thr Gln Ser Gly Ser Ser
                85                  90                  95

Gln Gly Leu His Ser Gln Gly Ser Leu Ser Asp Ala Ile Ser Thr Gly
            100                 105                 110
```

-continued

```
Leu Pro Pro Ser Ser Leu Leu Gln Gly Gln Ile Gly Asn Gly Pro Ser
        115                 120                 125

His Val Ser Met Gln Gln Thr Ala Pro Asn Thr Leu Pro Thr Thr Ser
    130                 135                 140

Met Ser Ile Ser Gly Pro Gly Tyr Ser His Ala Gly Pro Ala Ser Gln
145                 150                 155                 160

Gly Val Pro Met Gln Gly Gln Gly Thr Ile Gly Asn Tyr Val Ser Arg
                165                 170                 175

Thr Asn Ile Asn Met Gln Ser Asn Pro Val Ser Met Met Gln Gln Gln
            180                 185                 190

Ala Ala Thr Ser His Tyr Ser Ser Ala Gln Gly Gly Ser Gln His Tyr
        195                 200                 205

Gln Gly Gln Ser Ser Ile Ala Met Met Gly Gln Gly Ser Gln Gly Ser
    210                 215                 220

Ser Met Met Gly Gln Arg Pro Met Ala Pro Tyr Arg Pro Ser Gln Gln
225                 230                 235                 240

Gly Ser Ser Gln Gln Tyr Leu Gly Gln Glu Glu Tyr Tyr Gly Glu Gln
                245                 250                 255

Tyr Ser His Ser Gln Gly Ala Ala Glu Pro Met Gly Gln Gln Tyr Tyr
            260                 265                 270

Pro Asp Gly His Gly Asp Tyr Ala Tyr Gln Gln Ser Ser Tyr Thr Glu
        275                 280                 285

Gln Ser Tyr Asp Arg Ser Phe Glu Glu Ser Thr Gln His Tyr Tyr Glu
    290                 295                 300

Gly Gly Asn Ser Gln Tyr Ser Gln Gln Gln Ala Gly Tyr Gln Gln Gly
305                 310                 315                 320

Ala Ala Gln Gln Gln Thr Tyr Ser Gln Gln Gln Tyr Pro Ser Gln Gln
                325                 330                 335

Ser Tyr Pro Gly Gln Gln Gln Gly Tyr Gly Ser Ala Gln Gly Ala Pro
            340                 345                 350

Ser Gln Tyr Pro Gly Tyr Gln Gln Gly Gln Gly Gln Gln Tyr Gly Ser
        355                 360                 365

Tyr Arg Ala Pro Gln Thr Ala Pro Ser Ala Gln Gln Gln Arg Pro Tyr
    370                 375                 380

Gly Tyr Glu Gln Gly Gln Tyr Gly Asn Tyr Gln Gln
385                 390                 395
```

<210> SEQ ID NO 23
<211> LENGTH: 1854
<212> TYPE: DNA
<213> ORGANISM: Homo sapiens

<400> SEQUENCE: 23

```
aagtgtggct gagctccggg gtgtgtggac gccgctttgt tgcctgaggt gggtggcggt     60

ggaagttaag ggagtcaggg gctatcgctc ctcgagactc gcagtcgcgg ccactgcagt    120

cacttcgcca gttagccctt agggtaggag tcgcgccggc agcagccatg agcggcggcg    180

tgtacggggg agatgaagtt ggagcccttg tttttgacat tggatcctat actgtgagag    240

ctggttatgc tggtgaggac tgccccaagg tggattttcc tacagctatt ggtatggtgg    300

tagaaagaga tgacggaagc acattaatgg aaatagatgg cgataaaggc aaacaaggcg    360

gtcccaccta ctacatagat actaatgctc tgcgtgttcc gagggagaat atggaggcca    420

tttcacctct aaaaaatggg atggttgaag actgggatag tttccaagct attttggatc    480

atacctacaa aatgcatgtc aaatcagaag ccagtctcca tcctgttctc atgtcagagg    540
```

-continued

```
caccgtggaa tactagagca aagagagaga aactgacaga gttaatgttt gaacactaca    600

acatccctgc cttcttcctt tgcaaaactg cagttttgac agcatttgct aatggtcgtt    660

ctactgggct gattttggac agtggagcca ctcataccac tgcaattcca gtccacgatg    720

gctatgtcct tcaacaaggc attgtgaaat cccctcttgc tggagacttt attactatgc    780

agtgcagaga actcttccaa gaaatgaata ttgaattggt tcctccatat atgattgcat    840

caaaagaagc tgttcgtgaa ggatctccag caaactggaa aagaaaagag aagttgcctc    900

aggttacgag gtcttggcac aattatatgt gtaattgtgt tatccaggat tttcaagctt    960

cggtacttca agtgtcagat tcaacttatg atgaacaagt ggctgcacag atgccaactg   1020

ttcattatga attccccaat ggctacaatt gtgattttgg tgcagagcgg ctaaagattc   1080

cagaaggatt atttgaccct tccaatgtaa aggggttatc aggaaacaca atgttaggag   1140

tcagtcatgt tgtcaccaca agtgttggga tgtgtgatat tgacatcaga ccaggtctct   1200

atggcagtgt aatagtggca ggaggaaaca cactaataca gagttttact gacaggttga   1260

atagagagct gtctcagaaa actcctccaa gtatgcggtt gaaattgatt gcaaataata   1320

caacagtgga acggaggttt agctcatgga ttggcggctc cattctagcc tctttgggta   1380

cctttcaaca gatgtggatt tccaagcaag aatatgaaga aggagggaag cagtgtgtag   1440

aaagaaaatg cccttgagaa agagttccca agcttctacc ttccttttgt caccttacgt   1500

ttcatagctt tagtatactc aggaaaagaa tgaccatctt ttgtagaatg tttatacatt   1560

tttgcatatt tcaatttcca cttaaatttt ttaaagcttt aactggctct ataaattaag   1620

tttgtgcttt ccttgaaatg cacttattct tattacaagc attttataat tttgtataaa   1680

tgtctatttt ctctaaatat tttgctttca gtaaaatgct ttccaactct gtttagtgta   1740

ttaattacca gtggattggt agaactgctt tttattgact agtaaaagtt actgcctatg   1800

ctttttacct taggcttaca gaattaaata aaaattagcc attccagaaa tata         1854
```

<210> SEQ ID NO 24
<211> LENGTH: 429
<212> TYPE: PRT
<213> ORGANISM: Homo sapiens

<400> SEQUENCE: 24

```
Met Ser Gly Gly Val Tyr Gly Gly Asp Glu Val Gly Ala Leu Val Phe
1               5                   10                  15

Asp Ile Gly Ser Tyr Thr Val Arg Ala Gly Tyr Ala Gly Glu Asp Cys
            20                  25                  30

Pro Lys Val Asp Phe Pro Thr Ala Ile Gly Met Val Val Glu Arg Asp
        35                  40                  45

Asp Gly Ser Thr Leu Met Glu Ile Asp Gly Asp Lys Gly Lys Gln Gly
    50                  55                  60

Gly Pro Thr Tyr Tyr Ile Asp Thr Asn Ala Leu Arg Val Pro Arg Glu
65                  70                  75                  80

Asn Met Glu Ala Ile Ser Pro Leu Lys Asn Gly Met Val Glu Asp Trp
                85                  90                  95

Asp Ser Phe Gln Ala Ile Leu Asp His Thr Tyr Lys Met His Val Lys
            100                 105                 110

Ser Glu Ala Ser Leu His Pro Val Leu Met Ser Glu Ala Pro Trp Asn
        115                 120                 125

Thr Arg Ala Lys Arg Glu Lys Leu Thr Glu Leu Met Phe Glu His Tyr
    130                 135                 140
```

-continued

Asn Ile Pro Ala Phe Phe Leu Cys Lys Thr Ala Val Leu Thr Ala Phe
145 150 155 160

Ala Asn Gly Arg Ser Thr Gly Leu Ile Leu Asp Ser Gly Ala Thr His
165 170 175

Thr Thr Ala Ile Pro Val His Asp Gly Tyr Val Leu Gln Gln Gly Ile
180 185 190

Val Lys Ser Pro Leu Ala Gly Asp Phe Ile Thr Met Gln Cys Arg Glu
195 200 205

Leu Phe Gln Glu Met Asn Ile Glu Leu Val Pro Pro Tyr Met Ile Ala
210 215 220

Ser Lys Glu Ala Val Arg Glu Gly Ser Pro Ala Asn Trp Lys Arg Lys
225 230 235 240

Glu Lys Leu Pro Gln Val Thr Arg Ser Trp His Asn Tyr Met Cys Asn
245 250 255

Cys Val Ile Gln Asp Phe Gln Ala Ser Val Leu Gln Val Ser Asp Ser
260 265 270

Thr Tyr Asp Glu Gln Val Ala Ala Gln Met Pro Thr Val His Tyr Glu
275 280 285

Phe Pro Asn Gly Tyr Asn Cys Asp Phe Gly Ala Glu Arg Leu Lys Ile
290 295 300

Pro Glu Gly Leu Phe Asp Pro Ser Asn Val Lys Gly Leu Ser Gly Asn
305 310 315 320

Thr Met Leu Gly Val Ser His Val Val Thr Thr Ser Val Gly Met Cys
325 330 335

Asp Ile Asp Ile Arg Pro Gly Leu Tyr Gly Ser Val Ile Val Ala Gly
340 345 350

Gly Asn Thr Leu Ile Gln Ser Phe Thr Asp Arg Leu Asn Arg Glu Leu
355 360 365

Ser Gln Lys Thr Pro Pro Ser Met Arg Leu Lys Leu Ile Ala Asn Asn
370 375 380

Thr Thr Val Glu Arg Arg Phe Ser Ser Trp Ile Gly Gly Ser Ile Leu
385 390 395 400

Ala Ser Leu Gly Thr Phe Gln Gln Met Trp Ile Ser Lys Gln Glu Tyr
405 410 415

Glu Glu Gly Gly Lys Gln Cys Val Glu Arg Lys Cys Pro
420 425

<210> SEQ ID NO 25
<211> LENGTH: 3785
<212> TYPE: DNA
<213> ORGANISM: Homo sapiens

<400> SEQUENCE: 25
gcactgggcc aggcgcgcgg cggccccggg ctttgtgtgt gtgtgtatgt gtgtgtgtgt 60
gtgtgtgtgt gtgtgagtgt gtgcgtgtga gagtgcgagt gtctgtgcgc gagtgagtga 120
gcggcgggcg ggcgcgagtg tggccgccgc ggagcgcgag caggacccgg cgggcgcgct 180
ccccagcctc cgtctccccg ccggaaccat gtcgggcagg tcggttcgag ccgagacgag 240
gagccgggcc aaagatgata tcaagagggt catggcggcg atcgagaaag tgcgcaaatg 300
ggagaagaaa tgggtgaccg ttggtgacac atccctacga atctacaaat gggtccctgt 360
gacggagccc aaggttgatg acaaaaacaa gaataagaaa aaaggcaagg acgagaagtg 420
tggctcagag gtgaccactc cggagaacag ttcctcccca gggatgatgg acatgcatga 480

-continued

```
cgataacagc aaccagagct ccatcgcaga tgcctccccc atcaaacagg agaacagcag    540
caactccagc cccgctccag agcccaactc ggctgtgccc agcgacggca ccgaggccaa    600
ggtggatgag gcccaggctg atgggaagga gcacccagga gctgaagatg cttctgatga    660
gcagaattca cagtcctcga tggaacattc gatgaacagc tcagagaaag tagatcggca    720
gccgtctgga gactcgggtc tggccgcaga gacgtctgca atctctcagg tacctcgctc    780
gaggtctcag aggggcagcc agatcggccg ggagcccatt gggttgtcgg gggatttgga    840
aggagtgcca ccctctaaaa agatgaaact ggaggcctct caacaaaact ccgaagagat    900
gtagacgatg ctttaaagcc tccgatccat gttccatgga aggtacatca gcaattaatt    960
ctagagcaac tttgccccag cgattcctct tgggtgcgaa cagaactact aacgtttcaa   1020
gtttaccaag tgcaaatcca agaagaccca gaacggcgtc acttctcaga cactgaagaa   1080
ctctgctgtg aagcaaaaca ctcaaacctt taagggactg tccttgggga ggcaggcggg   1140
gctgacagct caggagtgtc tgcacactgt ctcggaagcc aggattccat ttgtgttgct   1200
gctgtatttt ccccccactt ctctatgtaa cgatataagc tatcggaggg tggtaccgat   1260
caggaacgct tttggcgggg gctttccact gttcaaccga ttccttccgc tttctttttt   1320
tgtgccttgt gcccttgagg tgacctctgg catgtatcct ggtggttctt acatccccct   1380
ctgcaaagtg ccctcttggt ttggttcggg cggcggctgc caccctactc accgctctcc   1440
tccctgcccc aggacttcat cggagcaggc agggtggagc gaaggagctc cttagcccac   1500
ctggtttgca ggtgcagggg gaccttaggc acgccccaag caccaggcac cagggcccaa   1560
ggacgcgcag gtgttggggc acagtcccca agggctcggc cccttggatc aggctgggca   1620
ctcgctgtgc tctcccctcc ttggggcgtt taggactggg cgtctccaag cccaccatgg   1680
cccagatgga cgtgcaaagc ccttggaatt ttctggcact tcctctctat tgccccccacc   1740
accaccaccc ccatcactgc tttctcccag acctccgaat acgaaatggc ttctctggct   1800
gactgcaagg ctgtctcctt aaggcactga gtgggccggg gaggctggga gccggcggca   1860
ggattagctg gtgctgaact ttctctcata ggacgtcgct tggatttcaa atccacggtc   1920
acctgctgcc ctttgcctcc cccgacgccc cagcctgtgc cccggagagg caggatcgca   1980
gtggtcagaa tccacgtgct ttcctattct caggctgttc tgactctgag ccaacagctg   2040
gaccgtgtct catccccaga acatgccgtc tgtccccacc ggggagtggg ccttgatggc   2100
cgggcctcga aggccacaaa caaggcgtcg aggaattgga aagatttgca caccctccag   2160
aaaggagaga cgcaatctcc cctccctccc atcccccacc ttcgctggaa cagcttcctc   2220
tcactgaacg gagacgcccc cttggacgaa ctgcctaatc gtttggttct gaggcctggt   2280
ttgctcttaa ttaatatatg aactcctcag accttaaacc ttttcctaag ctttctttac   2340
tgcactggag ttctgactcc ctttgagttg tgtgttactg gggtggggt ggggtcatgg   2400
gttttgttgt ttttgggggc taattggtgc atattcaggt accacctttg acgtgtggct   2460
ctttctcctg accatcatgg gaagtgtctg ctggattcca ttttctaaga gtttctgagg   2520
gtgaggctct tattttttt tttaagggat cctgtctatt tcctgcactt cgagaagaat   2580
caaaatgttc ctgaatttca aatacctcat gcaaaatgtc tcctgaaata agggaaaaaa   2640
aaaaaaccac aactttgaaa atcttaatgt tgaagttagc aatgccgaaa ggtttctgtc   2700
ttaaaaaaaa aaatccttgt acttatcaat tttgcccctt aggcagtcag ttttgttgag   2760
aactgtgtcc tgcatcctgg cgcagaacct acctgatgcg gttcctctcc acgcatctcg   2820
aggcggcgtt acctccagat tccgtagagt tagagtcaca tttttctttg cagcgaaact   2880
```

```
ccatcttggt gagagatgaa tttggatatt tatttccttc tctgtttttg ggaaacgaga   2940

ggctacaacc aagacagctg aaggagaatg aaacacacac atccacagaa acagagaggc   3000

gtaggtggcc ctgccgttga ccgcagcctc tctggacagg caaggggagt tggcgcaggt   3060

gaggactcag acgacgtcca ccgtcccaag gctgtcacta gtatttctct gaagtgcctg   3120

aaggtaggaa tgggccggcg attgggacca gctgggcccc accacggcca cgccaggcaa   3180

agcgccagca gccctgcact ccacgctggc caagaaggcc ttccacgcag aatgacaaga   3240

ctgcaaaaat ccgatgtgct tccttccctg gcgcagtcgc tcctcgagcc gctgcccccc   3300

acccaccctg cacccctcgc cctcccccca ccacagaatc taagaccttt cagcttcgag   3360

ccagggggcg ggggatcccg agcaaaagcc ttccgtggac atcaggcccc gtggcctcaa   3420

gggctcccag ggcaaaccta attcccccca aaacgtgaag tcggggaagc tgcggctaca   3480

cattccacaa agtgctggca cttacaccca caacccggaa ggctgtggac cgattcctct   3540

agggtggtga cctcccatta gcaaacggtg tcatggtttg gaatgttcat tatcgccaag   3600

aacctggtta gaggcataaa gaccttttt caccgttacc taattttttc ccctttcaag   3660

aatttttttt tttttggtg tgttgtacag cagtataatt tttcacttat ttattccatc   3720

agtagatatg gtttgtacaa tgtacaattg tttcatttca gaaaataaaa atttcaaatc   3780

atgaa                                                               3785
```

<210> SEQ ID NO 26
<211> LENGTH: 231
<212> TYPE: PRT
<213> ORGANISM: Homo sapiens

<400> SEQUENCE: 26

```
Met Ser Gly Arg Ser Val Arg Ala Glu Thr Arg Ser Arg Ala Lys Asp
1               5                   10                  15

Asp Ile Lys Arg Val Met Ala Ala Ile Glu Lys Val Arg Lys Trp Glu
            20                  25                  30

Lys Lys Trp Val Thr Val Gly Asp Thr Ser Leu Arg Ile Tyr Lys Trp
        35                  40                  45

Val Pro Val Thr Glu Pro Lys Val Asp Asp Lys Asn Lys Asn Lys Lys
    50                  55                  60

Lys Gly Lys Asp Glu Lys Cys Gly Ser Glu Val Thr Thr Pro Glu Asn
65                  70                  75                  80

Ser Ser Ser Pro Gly Met Met Asp Met His Asp Asp Asn Ser Asn Gln
                85                  90                  95

Ser Ser Ile Ala Asp Ala Ser Pro Ile Lys Gln Glu Asn Ser Ser Asn
            100                 105                 110

Ser Ser Pro Ala Pro Glu Pro Asn Ser Ala Val Pro Ser Asp Gly Thr
        115                 120                 125

Glu Ala Lys Val Asp Glu Ala Gln Ala Asp Gly Lys Glu His Pro Gly
    130                 135                 140

Ala Glu Asp Ala Ser Asp Glu Gln Asn Ser Gln Ser Ser Met Glu His
145                 150                 155                 160

Ser Met Asn Ser Ser Glu Lys Val Asp Arg Gln Pro Ser Gly Asp Ser
                165                 170                 175

Gly Leu Ala Ala Glu Thr Ser Ala Ile Ser Gln Val Pro Arg Ser Arg
            180                 185                 190

Ser Gln Arg Gly Ser Gln Ile Gly Arg Glu Pro Ile Gly Leu Ser Gly
        195                 200                 205
```

```
Asp Leu Glu Gly Val Pro Pro Ser Lys Lys Met Lys Leu Glu Ala Ser
    210                 215                 220

Gln Gln Asn Ser Glu Glu Met
225                 230


<210> SEQ ID NO 27
<211> LENGTH: 1524
<212> TYPE: DNA
<213> ORGANISM: Homo sapiens

<400> SEQUENCE: 27

gagtcccgcc ccgccaggga tcccgggagc tgtccggccg cctcggtgct gatcccgcca     60

ccgcccacgg gccgctagca gcgcagcggg cactatgagc gggggcgtct acggcggaga    120

tgaggtgggg gcgctggtct ttgacattgg ctccttctca gtccgcgctg ggtacgctgg    180

ggaggactgt cccaaggctg acttccccac cacagtgggg ctgctggccg cggaggaggg    240

gggcgggctg gagctggagg gggacaaaga gaagaaaggg aagatcttcc acatcgacac    300

caatgccctg cacgtgcctc gggatggagc ggaggtcatg tcgcccctca agaatggcat    360

gatcgaggac tgggagtgct tccgagccat cctggatcac acctacagca aacacgtcaa    420

gtctgagcca aacctgcacc cagtgctcat gtccgaggct ccgtggaaca cacgggccaa    480

gcgggagaag ctgacagagc tgatgttcga gcagtacaac attcctgcct tcttcttatg    540

caagacggct gtgctcaccg cctttgcaaa cgggcggtcc actggcctcg tgctggacag    600

tggagccacc cacaccacgg ccattccagt acatgacggc tacgttctgc agcaaggcat    660

cgtcaagtcc cctctggcag gggacttcat ctccatgcag tgccgggagc tgttccagga    720

gatggccatt gacatcatcc caccttacat gatcgcagcc aaggagcctg tccgggaggg    780

tgcccccca aactggaaga agaaggagaa gctaccccag gtctccaagt cctggcataa    840

ctacatgtgt aatgaggtga tccaggactt ccaggcctcc gtgctgcagg tctcagactc    900

cccctacgat gaacaggtgg ctgcacaaat gcccacagtg cactacgaga tgcccaatgg    960

ctacaataca gactacggcg ccgagcgact ccgcatccct gagggcctgt ttgatccctc   1020

gaacgtcaag ggcctgtcgg ggaacaccat gttgggtgtg ggccacgtgg tgaccaccag   1080

catcggcatg tgtgacattg atattcgccc gggcctgtac gggagtgtca ttgtcaccgg   1140

cgggaacaca ctgctgcagg gcttcactga caggctcaat cgagagcttt cccagaagac   1200

cccaccgagc atgcgactga aactcattgc cagcaacagc accatggagc gcaagttcag   1260

cccctggatc gggggttcca tcctggcctc actgggcact ttccagcaga tgtggatctc   1320

caagcaggaa tatgaggagg gcgggaagca gtgcgtggag cgaaagtgcc cctgatggca   1380

ctcctcccca cacacctgct cccaagctca gatggaagtc ccttaacccc catgccacat   1440

tgcccccctc ctcctttccc tcttgtcctc attaatggtg atgtttctgg gttgaaagaa   1500

gtaaaaatgt tttaagaaaa aaaa                                          1524


<210> SEQ ID NO 28
<211> LENGTH: 426
<212> TYPE: PRT
<213> ORGANISM: Homo sapiens

<400> SEQUENCE: 28

Met Ser Gly Gly Val Tyr Gly Gly Asp Glu Val Gly Ala Leu Val Phe
1               5                   10                  15
```

```
Asp Ile Gly Ser Phe Ser Val Arg Ala Gly Tyr Ala Gly Glu Asp Cys
            20                  25                  30

Pro Lys Ala Asp Phe Pro Thr Thr Val Gly Leu Leu Ala Ala Glu Glu
        35                  40                  45

Gly Gly Gly Leu Glu Leu Glu Gly Asp Lys Glu Lys Lys Gly Lys Ile
    50                  55                  60

Phe His Ile Asp Thr Asn Ala Leu His Val Pro Arg Asp Gly Ala Glu
65                  70                  75                  80

Val Met Ser Pro Leu Lys Asn Gly Met Ile Glu Asp Trp Glu Cys Phe
                85                  90                  95

Arg Ala Ile Leu Asp His Thr Tyr Ser Lys His Val Lys Ser Glu Pro
            100                 105                 110

Asn Leu His Pro Val Leu Met Ser Glu Ala Pro Trp Asn Thr Arg Ala
        115                 120                 125

Lys Arg Glu Lys Leu Thr Glu Leu Met Phe Glu Gln Tyr Asn Ile Pro
    130                 135                 140

Ala Phe Phe Leu Cys Lys Thr Ala Val Leu Thr Ala Phe Ala Asn Gly
145                 150                 155                 160

Arg Ser Thr Gly Leu Val Leu Asp Ser Gly Ala Thr His Thr Thr Ala
                165                 170                 175

Ile Pro Val His Asp Gly Tyr Val Leu Gln Gln Gly Ile Val Lys Ser
            180                 185                 190

Pro Leu Ala Gly Asp Phe Ile Ser Met Gln Cys Arg Glu Leu Phe Gln
        195                 200                 205

Glu Met Ala Ile Asp Ile Ile Pro Pro Tyr Met Ile Ala Ala Lys Glu
    210                 215                 220

Pro Val Arg Glu Gly Ala Pro Pro Asn Trp Lys Lys Lys Glu Lys Leu
225                 230                 235                 240

Pro Gln Val Ser Lys Ser Trp His Asn Tyr Met Cys Asn Glu Val Ile
                245                 250                 255

Gln Asp Phe Gln Ala Ser Val Leu Gln Val Ser Asp Ser Pro Tyr Asp
            260                 265                 270

Glu Gln Val Ala Ala Gln Met Pro Thr Val His Tyr Glu Met Pro Asn
        275                 280                 285

Gly Tyr Asn Thr Asp Tyr Gly Ala Glu Arg Leu Arg Ile Pro Glu Gly
    290                 295                 300

Leu Phe Asp Pro Ser Asn Val Lys Gly Leu Ser Gly Asn Thr Met Leu
305                 310                 315                 320

Gly Val Gly His Val Val Thr Thr Ser Ile Gly Met Cys Asp Ile Asp
                325                 330                 335

Ile Arg Pro Gly Leu Tyr Gly Ser Val Ile Val Thr Gly Gly Asn Thr
            340                 345                 350

Leu Leu Gln Gly Phe Thr Asp Arg Leu Asn Arg Glu Leu Ser Gln Lys
        355                 360                 365

Thr Pro Pro Ser Met Arg Leu Lys Leu Ile Ala Ser Asn Ser Thr Met
    370                 375                 380

Glu Arg Lys Phe Ser Pro Trp Ile Gly Gly Ser Ile Leu Ala Ser Leu
385                 390                 395                 400

Gly Thr Phe Gln Gln Met Trp Ile Ser Lys Gln Glu Tyr Glu Glu Gly
                405                 410                 415

Gly Lys Gln Cys Val Glu Arg Lys Cys Pro
            420                 425
```

<210> SEQ ID NO 29
<211> LENGTH: 1663
<212> TYPE: DNA
<213> ORGANISM: Homo sapiens

<400> SEQUENCE: 29

```
gcgacggccg ctgtgacgct gcggcggcgg cgggcgggcg gcggcgcgtg aggcgcgcga      60
tccccggtgt cttgggagca gtgccccggc ccccgccgct cccgccgccg ccatgtcggg     120
ccggtcggtc cgggcggaga cccgcagccg ggccaaggac gacatcaaga aggtgatggc     180
ggccatcgag aaagtgcgga aatgggagaa gaagtgggtg actgtgggtg acacgtccct     240
gaggatattt aagtgggttc ctgtgacaga cagcaaggag aaagaaaagt caaaatcgaa     300
cagttcagca gcccgagaac ctaatggctt tccttctgat gcctcagcca attcctctct     360
ccttcttgaa ttccaggacg aaaacagcaa ccagagttcc gtgtctgacg tctatcagct     420
taaggtggac agcagcacca actcaagccc cagcccccag cagagtgagt ccctgagccc     480
agcacacacc tccgacttcc gcacggatga ctcccagccc ccaacgctgg gccaggagat     540
cctggaggag ccctccctgc cctcctcgga agttgctgat gaacctccta ccctcaccaa     600
ggaagaacca gttccactag agacacaggt cgttgaggaa gaggaagact caggtgcccc     660
gcccctgaag cgcttctgtg tggaccaacc cacagtgccg cagacggcgt cagaaagcta     720
gcaccatccc ggccctccgc ctcctggccc tgcctctatt tattgcattc tggttctggc     780
cgcgccgcgt tgctggggta agggcaagca ctggggtcaa gagcctgcac acatgagcct     840
tccgggctgg aaggctggcg taggacttgg ggctgtagca tcatcttcct gaccctggca     900
cctgtgtcta cttgctcccg agaagaggag cgctcatgtc ttttttgcac cccaagttgg     960
ctggagcatc ggccacccca agattcatct gtgacctcca ggcagcagtc tctgctccag    1020
aatctctgga cggagctgct ggcagcttct gcgagaagag agagatgtgg aaggcacctt    1080
ctagaagaga gcgtgcctca ggttacttga acttgaacgg agactgtaga ctcccggact    1140
ttcccctagg actgggggcc ctgtaggctg ctgttggagg actgggtaga gacattggag    1200
ggaagggaag ggcttttctc cacacaaggg cagagagtcc gtctagattt cttgctgtcc    1260
tgccagctct gcccatgcct gaggtggtcc tacctctcac gggcacccta gctgctgaca    1320
gccctttgtg gccgccgtcc ccatcccctg ccctcagcac acacatctgc acacacgcag    1380
ctttgttctc acctctacct gtcattccag catccctgcc tcttgtcaca aactgcccca    1440
gcaagaattt gaggttctga caacagtacc catcccccac agtacccctt cagctcagtt    1500
tctagaaagc tccctttttct ttgaaatctg catgttgaat tgaactttgt gattttattt    1560
tttgtttcaa aaaagtttaa gaaaatggaa atgggcaaca gtgagtgaag acatatttta    1620
gcactgaata gaatattttt aaaattaaac tatttgaaat atg                      1663
```

<210> SEQ ID NO 30
<211> LENGTH: 202
<212> TYPE: PRT
<213> ORGANISM: Homo sapiens

<400> SEQUENCE: 30

```
Met Ser Gly Arg Ser Val Arg Ala Glu Thr Arg Ser Arg Ala Lys Asp
1               5                   10                  15

Asp Ile Lys Lys Val Met Ala Ala Ile Glu Lys Val Arg Lys Trp Glu
            20                  25                  30
```

-continued

```
Lys Lys Trp Val Thr Val Gly Asp Thr Ser Leu Arg Ile Phe Lys Trp
        35                  40                  45

Val Pro Val Thr Asp Ser Lys Glu Lys Glu Lys Ser Lys Ser Asn Ser
    50                  55                  60

Ser Ala Ala Arg Glu Pro Asn Gly Phe Pro Ser Asp Ala Ser Ala Asn
65                  70                  75                  80

Ser Ser Leu Leu Leu Glu Phe Gln Asp Glu Asn Ser Asn Gln Ser Ser
                85                  90                  95

Val Ser Asp Val Tyr Gln Leu Lys Val Asp Ser Ser Thr Asn Ser Ser
            100                 105                 110

Pro Ser Pro Gln Gln Ser Glu Ser Leu Ser Pro Ala His Thr Ser Asp
        115                 120                 125

Phe Arg Thr Asp Asp Ser Gln Pro Pro Thr Leu Gly Gln Glu Ile Leu
    130                 135                 140

Glu Glu Pro Ser Leu Pro Ser Ser Glu Val Ala Asp Glu Pro Pro Thr
145                 150                 155                 160

Leu Thr Lys Glu Glu Pro Val Pro Leu Glu Thr Gln Val Val Glu Glu
                165                 170                 175

Glu Glu Asp Ser Gly Ala Pro Pro Leu Lys Arg Phe Cys Val Asp Gln
            180                 185                 190

Pro Thr Val Pro Gln Thr Ala Ser Glu Ser
        195                 200


<210> SEQ ID NO 31
<211> LENGTH: 2348
<212> TYPE: DNA
<213> ORGANISM: Homo sapiens

<400> SEQUENCE: 31

gtgctcccgc cccccgggaa tgaatggatg ggcggcctca gcgcccgccc gaccgctggg      60

aggaccgacc cggcggggac ctgctggggg caggacccgg ggagcaagat ggccactgtc     120

atccctggcc ccctgagcct aggcgaggac ttctaccgcg aggccatcga gcactgccgc     180

agttacaacg cgcgcctgtg cgccgagcgc agcctgcgac tgcccttcct cgactcgcag     240

accggcgtgg cccagaacaa ctgctacatc tggatggaga agacccaccg cgggccgggt     300

ttggccccgg gacagattta cacgtacccc gcccgctgtt ggaggaagaa acggagactc     360

aacatcctgg aggaccccag actcaggccc tgcgagtaca agatcgactg tgaagcaccc     420

ctgaagaagg agggtggcct cccggaaggg ccggtcctcg aggctctact gtgtgcagag     480

acgggggaga agaagattga gctgaaggag gaggagacca ttatggactg tcagaaacag     540

cagttgctgg agtttccgca tgacctcgag gtggaagact tggaggatga cattcccagg     600

aggaagaaca gggccaaagg aaaggcatat ggcatcgggg gtctccggaa acgccaggac     660

accgcttccc tggaggaccg agacaagccg tatgtctgtg atatctgtgg gaaacggtat     720

aagaaccggc cggggctcag ctaccactac acccacaccc acctggccga ggaggagggg     780

gaggagaacg ccgaacgcca cgccctgccc ttccaccgga aaaacaacca taaacagttt     840

tacaaagaat tggcctgggt ccctgaggca caaaggaaac acacagccaa gaaggcgccc     900

gacggcactg tcatccccaa cggctactgt gacttctgcc tgggggctc caagaagacg      960

gggtgtcccg aggacctcat ctcctgtgcg gactgtgggc gatcaggaca cccctcgtgt    1020

ttacaattca cggtgaacat gacggcagcc gtgcggacct accgctggca gtgcatcgag    1080

tgcaaatcct gcagcctgtg cggaacctcc gagaacgacg accagctgct gttttgtgat    1140
```

```
gactgcgatc ggggttacca catgtactgc ctgagtcccc ccatggcgga gcccccggaa   1200

gggagctgga gctgtcacct ctgtctccgg cacctgaagg aaaaggcttc tgcttacatc   1260

accctcacct aggccggctc ggctcgccgc gactctgggg tggtgctcgc ctacctgcct   1320

ctccgagctc ctcaattctc ccccaccctg aacatcccgc agggggaggg ggagaggggg   1380

aagccgagag ggggctgggc cacccccctcc cctctgtgca agtggaatgt ctgccctgtg   1440

ggtgggtggg cccggccagg gcctctccct ccctccctcc ctctctgtcc cttggcaaat   1500

ggacaccagg ggcttctccc ctcaaagcca taccccgcct ctgggcgggc atggggggtg   1560

gtgggtgcca gccaggggca tggacagagc ctttttctaa agaaaaagac aaaaagttaa   1620

aaaaaaaaaa aagaagaaaa gaaaagaagt taatatatac aaagagtcct ccaaggcctg   1680

gctgggtgga ggggcgctgc tgagagtgtc caccgggcac ccgcctctgc cggccccccg   1740

ccgggcgccc caaccccaat ttctggagct gcagccgtcc cgcgccccac ccaaggtggg   1800

cgccttcccc tcttgtgccc agggcggtgg gcgtggtgtc cacccgcccc tcctggtgcc   1860

cacggtggat actgcatgat gtgaaccttg gttttgaact ctgttcctgc ccctccccga   1920

ccgccccagc ctgtgcccgc cccgtgcctg ccgtggctgg tgggtggcgg tggtggggcc   1980

gggtgggccc ccgcccagcg cctgctggaa tgagaagcac agactccgcc acggactcct   2040

tttctctccc tcctcccgcc ccgccaggcc tggcggcccc cgcccccctc gctggccatt   2100

ttgggggagt gagggggcgt ggttgtttct tgtggttgtg tgtgtttgtt gttcgggttt   2160

taaaaaaggg aaactgagac tgcaggtggg ggaggtggtg ggttttgggg ggatgtcccc   2220

taatccagga gtgcccccctc acttgtcacc gagtctcctc tattgcctgc ctctgctgtg   2280

aattaacttg ttctgtgtat taaactgggc ctgacccctc tgcccacgaa aaaaaaaaaa   2340

aaaaaaaa                                                            2348
```

```
<210> SEQ ID NO 32
<211> LENGTH: 414
<212> TYPE: PRT
<213> ORGANISM: Homo sapiens

<400> SEQUENCE: 32

Met Gly Gly Leu Ser Ala Arg Pro Thr Ala Gly Arg Thr Asp Pro Ala
1               5                   10                  15

Gly Thr Cys Trp Gly Gln Asp Pro Gly Ser Lys Met Ala Thr Val Ile
            20                  25                  30

Pro Gly Pro Leu Ser Leu Gly Glu Asp Phe Tyr Arg Glu Ala Ile Glu
        35                  40                  45

His Cys Arg Ser Tyr Asn Ala Arg Leu Cys Ala Glu Arg Ser Leu Arg
    50                  55                  60

Leu Pro Phe Leu Asp Ser Gln Thr Gly Val Ala Gln Asn Asn Cys Tyr
65                  70                  75                  80

Ile Trp Met Glu Lys Thr His Arg Gly Pro Gly Leu Ala Pro Gly Gln
                85                  90                  95

Ile Tyr Thr Tyr Pro Ala Arg Cys Trp Arg Lys Lys Arg Arg Leu Asn
            100                 105                 110

Ile Leu Glu Asp Pro Arg Leu Arg Pro Cys Glu Tyr Lys Ile Asp Cys
        115                 120                 125

Glu Ala Pro Leu Lys Lys Glu Gly Gly Leu Pro Glu Gly Pro Val Leu
    130                 135                 140
```

-continued

```
Glu Ala Leu Leu Cys Ala Glu Thr Gly Glu Lys Lys Ile Glu Leu Lys
145                 150                 155                 160

Glu Glu Glu Thr Ile Met Asp Cys Gln Lys Gln Gln Leu Leu Glu Phe
                165                 170                 175

Pro His Asp Leu Glu Val Glu Asp Leu Glu Asp Asp Ile Pro Arg Arg
            180                 185                 190

Lys Asn Arg Ala Lys Gly Lys Ala Tyr Gly Ile Gly Gly Leu Arg Lys
        195                 200                 205

Arg Gln Asp Thr Ala Ser Leu Glu Asp Arg Asp Lys Pro Tyr Val Cys
    210                 215                 220

Asp Ile Cys Gly Lys Arg Tyr Lys Asn Arg Pro Gly Leu Ser Tyr His
225                 230                 235                 240

Tyr Thr His Thr His Leu Ala Glu Glu Glu Gly Glu Glu Asn Ala Glu
                245                 250                 255

Arg His Ala Leu Pro Phe His Arg Lys Asn Asn His Lys Gln Phe Tyr
            260                 265                 270

Lys Glu Leu Ala Trp Val Pro Glu Ala Gln Arg Lys His Thr Ala Lys
        275                 280                 285

Lys Ala Pro Asp Gly Thr Val Ile Pro Asn Gly Tyr Cys Asp Phe Cys
    290                 295                 300

Leu Gly Gly Ser Lys Lys Thr Gly Cys Pro Glu Asp Leu Ile Ser Cys
305                 310                 315                 320

Ala Asp Cys Gly Arg Ser Gly His Pro Ser Cys Leu Gln Phe Thr Val
                325                 330                 335

Asn Met Thr Ala Ala Val Arg Thr Tyr Arg Trp Gln Cys Ile Glu Cys
            340                 345                 350

Lys Ser Cys Ser Leu Cys Gly Thr Ser Glu Asn Asp Asp Gln Leu Leu
        355                 360                 365

Phe Cys Asp Asp Cys Asp Arg Gly Tyr His Met Tyr Cys Leu Ser Pro
    370                 375                 380

Pro Met Ala Glu Pro Pro Glu Gly Ser Trp Ser Cys His Leu Cys Leu
385                 390                 395                 400

Arg His Leu Lys Glu Lys Ala Ser Ala Tyr Ile Thr Leu Thr
                405                 410
```

<210> SEQ ID NO 33
<211> LENGTH: 857
<212> TYPE: DNA
<213> ORGANISM: Homo sapiens

<400> SEQUENCE: 33

```
gagagagggc gcggccaact ccaggggggga cggcaggccg agagcgcggc gcccgggcct      60

ggcgcggagc ctgagcccgc cggacgggag gcggccccgc cgcgggctcg gccccggccc     120

cagccccgcc agcatggccg gccggactgt acgggccgag acccggagcc gggccaagga     180

tgacatcaag aaggtgatgg cgaccatcga gaaggtccgg agatgggaga agcgatgggt     240

gactgtgggc gacacttccc ttcgtatctt caagtgggtg ccagtggtgg atccccagga     300

ggaggagcga aggcgggcag gtggcggggc agagagatcc cgtggccggg aacgtcgggg     360

caggggcgcc agtccccgag ggggtggccc tctcatcctg ctggatctta atgatgagaa     420

cagcaaccag agtttccatt cggaaggttc cctgcaaaag ggcacagagc ccagtcctgg     480

gggcaccccc cagcccagcc gccctgtgtc acctgccgga cccccagaag ggtccctga      540

ggaggctcag cccccacggc tggccaaga gagagatccc gggggcataa ctgctggcag      600
```

caccgacgaa cccccaatgc tgaccaagga ggagcctgtt ccagaactgc tggaagctga 660
ggcccccgaa gcttaccctg tctttgagcc agtgccacct gtccctgagg cagcccaggg 720
tgacacagag gactcggagg gtgccccccc actcaagcgc atctgcccaa atgcccctga 780
cccctgagaa gccggcctgc ctgtcctgtt gccccagggg cccctttggc tttttacaaa 840
taaagaccct tttgtaa 857

<210> SEQ ID NO 34
<211> LENGTH: 217
<212> TYPE: PRT
<213> ORGANISM: Homo sapiens

<400> SEQUENCE: 34

Met Ala Gly Arg Thr Val Arg Ala Glu Thr Arg Ser Arg Ala Lys Asp
1 5 10 15

Asp Ile Lys Lys Val Met Ala Thr Ile Glu Lys Val Arg Arg Trp Glu
20 25 30

Lys Arg Trp Val Thr Val Gly Asp Thr Ser Leu Arg Ile Phe Lys Trp
35 40 45

Val Pro Val Val Asp Pro Gln Glu Glu Glu Arg Arg Arg Ala Gly Gly
50 55 60

Gly Ala Glu Arg Ser Arg Gly Arg Glu Arg Arg Gly Arg Gly Ala Ser
65 70 75 80

Pro Arg Gly Gly Gly Pro Leu Ile Leu Leu Asp Leu Asn Asp Glu Asn
85 90 95

Ser Asn Gln Ser Phe His Ser Glu Gly Ser Leu Gln Lys Gly Thr Glu
100 105 110

Pro Ser Pro Gly Gly Thr Pro Gln Pro Ser Arg Pro Val Ser Pro Ala
115 120 125

Gly Pro Pro Glu Gly Val Pro Glu Glu Ala Gln Pro Pro Arg Leu Gly
130 135 140

Gln Glu Arg Asp Pro Gly Gly Ile Thr Ala Gly Ser Thr Asp Glu Pro
145 150 155 160

Pro Met Leu Thr Lys Glu Glu Pro Val Pro Glu Leu Leu Glu Ala Glu
165 170 175

Ala Pro Glu Ala Tyr Pro Val Phe Glu Pro Val Pro Pro Val Pro Glu
180 185 190

Ala Ala Gln Gly Asp Thr Glu Asp Ser Glu Gly Ala Pro Pro Leu Lys
195 200 205

Arg Ile Cys Pro Asn Ala Pro Asp Pro
210 215

<210> SEQ ID NO 35
<211> LENGTH: 3714
<212> TYPE: DNA
<213> ORGANISM: Homo sapiens

<400> SEQUENCE: 35
ggggcttctc ggcccgaggc agaggaacag ggaagatggc ggctgtggtg gagaatgtag 60
tgaagctcct tggggagcag tactacaaag atgccatgga gcagtgccac aattacaatg 120
ctcgcctctg tgctgagcgc agcgtgcgcc tgcctttctt ggactcacag accggagtag 180
cccagagcaa ttgttacatc tggatggaaa agcgacaccg gggtccagga ttggcctccg 240
gacagctgta ctcctaccct gcccggcgct ggcggaaaaa gcggcgagcc catcccccctg 300

-continued

```
aggatccacg actttccttc ccatctatta agccagacac agaccagacc ctgaagaagg    360
aggggctgat ctctcaggat ggcagtagtt tagaggctct gttgcgcact gaccccctgg    420
agaagcgagg tgccccggat ccccgagttg atgatgacag cctgggcgag tttcctgtga    480
ccaacagtcg agcgcgaaag cggatcctag aaccagatga cttcctggat gacctcgatg    540
atgaagacta tgaagaagat actcccaagc gtcggggaaa ggggaaatcc aagggtaagg    600
gtgtgggcag tgcccgtaag aagctggatg cttccatcct ggaggaccgg gataagccct    660
atgcctgtga catttgtgga aaacgttaca agaaccgacc aggcctcagt taccactatg    720
cccactccca cttggctgag gaggagggcg aggacaagga agactctcaa ccacccactc    780
ctgtttccca gaggtctgag gagcagaaat ccaaaaaggg tcctgatgga ttggccttgc    840
ccaacaacta ctgtgacttc tgcctggggg actcaaagat taacaagaag acgggacaac    900
ccgaggagct ggtgtcctgt tctgactgtg gccgctcagg gcatccatct tgcctccaat    960
ttacccccgt gatgatggcg gcagtgaaga cataccgctg gcagtgcatc gagtgcaaat   1020
gttgcaatat ctgcggcacc tccgagaatg acgaccagtt gctcttctgt gatgactgcg   1080
atcgtggcta ccacatgtac tgtctcaccc cgtccatgtc tgagcccccct gaaggaagtt  1140
ggagctgcca cctgtgtctg gacctgttga aagagaaagc ttccatctac cagaaccaga   1200
actcctcttg atgtggccac ccacctgctc cccgacatat ctaaggctgt ttctctcctc   1260
cacttcatat ttcataccca tctttccctt cttcctcctc tccttcacaa atccagagaa   1320
ccttggggtg gttgtgccag cctgcctttg gcagctgcaa gctgaggtgg cagctctgac   1380
cacctctggc cccaggccct cagggagaaa ggagcaacac actgccccta ggcgtgcgtg   1440
tggcccagtt tctctctgct ctccattaag tgcattcact ctgcttgcct tgggcccagc   1500
ccctggtgat cacagggttc aaacagtgtc ctcctagaaa gagtgggaga gcagctcact   1560
tctctgtgtt ctgcctcccc tctggtctcc agagttttcc tgtcctctag aggcaagcca   1620
ggccagggag ctgggagcga gcaagctgag gccacgtcca caaggagctt ttcatgcccc   1680
tgtgccgcat agcctcacct ctttcctcca gagtggctct ctgcggccct gtgttcctgc   1740
tacagagtgt tcttttctgg agtcaggatg ttctcggtca ccctcctggt tctgccctgt   1800
cccattccac cccaccccag ggggaacagt agcttcacct tgttattccc attgctctcc   1860
tggctcactc ttacggtcgg tctccagtga ctgaagcatt ccccaccctt ggaatttctc   1920
atcttctgcc tcccttccta ctccttttgg ttttgtgggg agaggggaag gatcaggggg   1980
ccaggccagc agctcggggg ccacaaggag atggataatg tgcctgtttt ttaacacaac   2040
aaaaaagcct acctccaaaa tccccttttt gttcttcctg gacctgggca ttcagcctcc   2100
tgctcttaac tgaattggga gcctctgcca cctgccccgt gtatcctggc tctcagctca   2160
tggggaagcc acatagacat ccctttcttc ccttgcacgc tcgctagcag ctggtaaggt   2220
cttcacaccc tgattcctca agttttctgc ttagtggcac tgacattaag tagtgggggg   2280
acagtccatg ccaggacacc ctggagtagc cttccccctt ggccgtgggc aggccctaac   2340
tcactgtcgc tttggagttg aggtgtcttt tttttttctt tctttagttc ctgtattcta   2400
aacattagta aaaataaatg tttttacaca gagccctctg ctggatggtt tatctcctgc   2460
ctttctccat taagaaggcc atttcatcct aagatttcca tgatggtggt tttttttttt   2520
aatgttttga aatacagctt ttttcccccc aaattaaaat ttttttgtgg aaccccaata   2580
tgtaaagcga atataaaatt ggttattttg ttttgttaca taaattcaag tttataacaa   2640
ttctttgtta taaagaacaa tgaagctgtt ttgatcaata caaaatttgg gttaaaatca   2700
```

-continued

```
actttaacat ctatttttat gtttcagttg atttggagaa ttctcctagt cttggataca   2760

tagatggaag tgatgacagg tttataacag ttgaccttgc aatctcagac atttaaaaca   2820

ggaccagaag tttatataaa tataattaat aagcaaacta atgacatcac catgggacac   2880

acacaaaagt tcttgcagga gcagggtctg tgtggcttca gttgcctgca gcgctcccag   2940

gccagagcaa gtgctctagg atctgaactg cccgcagtgc agccctgcag cctttcccag   3000

ggcacgttga tgtgcacaca gtttccctga aggcaaagtg aacatgtgga gagcttacgt   3060

ggcagcgcgt atgtcttcag tgtgtgtttt agaagtccaa ctgttgtttt tatgttttta   3120

aaggaaagat ttgaatcaag cagttatggg ccccctgaag tatccttttt tctagaacat   3180

tctgaaagtc atccttgcct atgggaagcc taggccggcc tgcactgtta tgttcaataa   3240

ataagcaggg tgctctgggc tggggattgt gtgaggagca gagcgcagcc cgtcctcatg   3300

cttttccact gaagtaggcc aggcagagag ggagtacagc aatggatgcg ctttggcagc   3360

tgagtagtcc gagagccaga aaagaaatgt ggaaaataag aacgctgtag caggcctagg   3420

tgaggaaatt taggaagggt ttgcgggagg taggatttga gatgggtctt ggagagttgg   3480

acagtgtcag ccggtaggac gggggtgcgg acggaagcct gtgaggaagg cagaggatgc   3540

ggagctgtga gcggagggag cagcgaggct ggagagcagc tgggctgcgg gtcaagacgt   3600

ctgcgtttaa ttcgggactg aaggttagca gggaagggaa cgatgccaga tcttgagttt   3660

aagaacttga atcttgtaaa gtaccaaatc taataaaata ctcgtcctaa atca         3714
```

<210> SEQ ID NO 36
<211> LENGTH: 391
<212> TYPE: PRT
<213> ORGANISM: Homo sapiens

<400> SEQUENCE: 36

```
Met Ala Ala Val Val Glu Asn Val Val Lys Leu Leu Gly Glu Gln Tyr
1               5                   10                  15

Tyr Lys Asp Ala Met Glu Gln Cys His Asn Tyr Asn Ala Arg Leu Cys
            20                  25                  30

Ala Glu Arg Ser Val Arg Leu Pro Phe Leu Asp Ser Gln Thr Gly Val
        35                  40                  45

Ala Gln Ser Asn Cys Tyr Ile Trp Met Glu Lys Arg His Arg Gly Pro
    50                  55                  60

Gly Leu Ala Ser Gly Gln Leu Tyr Ser Tyr Pro Ala Arg Arg Trp Arg
65                  70                  75                  80

Lys Lys Arg Arg Ala His Pro Pro Glu Asp Pro Arg Leu Ser Phe Pro
                85                  90                  95

Ser Ile Lys Pro Asp Thr Asp Gln Thr Leu Lys Lys Glu Gly Leu Ile
            100                 105                 110

Ser Gln Asp Gly Ser Ser Leu Glu Ala Leu Leu Arg Thr Asp Pro Leu
        115                 120                 125

Glu Lys Arg Gly Ala Pro Asp Pro Arg Val Asp Asp Asp Ser Leu Gly
    130                 135                 140

Glu Phe Pro Val Thr Asn Ser Arg Ala Arg Lys Arg Ile Leu Glu Pro
145                 150                 155                 160

Asp Asp Phe Leu Asp Asp Leu Asp Asp Glu Asp Tyr Glu Glu Asp Thr
                165                 170                 175

Pro Lys Arg Arg Gly Lys Gly Lys Ser Lys Gly Lys Gly Val Gly Ser
            180                 185                 190
```

-continued

```
Ala Arg Lys Lys Leu Asp Ala Ser Ile Leu Glu Asp Arg Asp Lys Pro
        195                 200                 205

Tyr Ala Cys Asp Ile Cys Gly Lys Arg Tyr Lys Asn Arg Pro Gly Leu
    210                 215                 220

Ser Tyr His Tyr Ala His Ser His Leu Ala Glu Glu Glu Gly Glu Asp
225                 230                 235                 240

Lys Glu Asp Ser Gln Pro Pro Thr Pro Val Ser Gln Arg Ser Glu Glu
                245                 250                 255

Gln Lys Ser Lys Lys Gly Pro Asp Gly Leu Ala Leu Pro Asn Asn Tyr
            260                 265                 270

Cys Asp Phe Cys Leu Gly Asp Ser Lys Ile Asn Lys Lys Thr Gly Gln
        275                 280                 285

Pro Glu Glu Leu Val Ser Cys Ser Asp Cys Gly Arg Ser Gly His Pro
    290                 295                 300

Ser Cys Leu Gln Phe Thr Pro Val Met Met Ala Ala Val Lys Thr Tyr
305                 310                 315                 320

Arg Trp Gln Cys Ile Glu Cys Lys Cys Cys Asn Ile Cys Gly Thr Ser
                325                 330                 335

Glu Asn Asp Asp Gln Leu Leu Phe Cys Asp Asp Cys Asp Arg Gly Tyr
            340                 345                 350

His Met Tyr Cys Leu Thr Pro Ser Met Ser Glu Pro Pro Glu Gly Ser
        355                 360                 365

Trp Ser Cys His Leu Cys Leu Asp Leu Leu Lys Glu Lys Ala Ser Ile
    370                 375                 380

Tyr Gln Asn Gln Asn Ser Ser
385                 390
```

<210> SEQ ID NO 37
<211> LENGTH: 6102
<212> TYPE: DNA
<213> ORGANISM: Homo sapiens

<400> SEQUENCE: 37

```
gtctctgtcc atccagactc ctgacgttca agttcgcagg gacgtcacgt ccgcacttga      60

acttgcagct caggggggct tttgccattt ttttcatctc tctctctctc tctccctcta     120

tctctcttct ctctctctcc ctcttttttt tttttttttt tttttttttt ttgcttaaaa     180

aaaagccatg acggctctcc cacaattcat cttccctgcg ccatctttgt attatttcta     240

atttattttg gatgtcaaaa ggcactgatg aagatatttt ctctggagtc tccttctttc     300

taacccggct ctcccgatgt gaaccgagcc gtcgtccgcc cgccgccgcc gccgccgccg     360

ccgccgcccg ccccgcagcc caccatgtct cgccgcaagc aaggcaaacc ccagcactta     420

agcaaacggg aattctcgcc cgagcctctt gaagccattc ttacagatga tgaaccagac     480

cacggcccgt tgggagctcc agaaggggat catgacctcc tcacctgtgg gcagtgccag     540

atgaacttcc cattggggga cattcttatt tttatcgagc acaaacggaa acaatgcaat     600

ggcagcctct gcttagaaaa agctgtggat aagccacctt ccccttcacc aatcgagatg     660

aaaaaagcat ccaatcccgt ggaggttggc atccaggtca cgccagagga tgacgattgt     720

ttatcaacgt catctagagg aatttgcccc aaacaggaac acatagcaga taaacttctg     780

cactggaggg gcctctcctc ccctcgttct gcacatggag ctctaatccc cacgcctggg     840

atgagtgcag aatatgcccc gcagggtatt tgtaaagatg agcccagcag ctacacatgt     900

acaacttgca aacagccatt caccagtgca tggtttctct tgcaacacgc acagaacact     960
```

-continued

```
catggattaa gaatctactt agaaagcgaa cacggaagtc ccctgacccc gcgggttggt   1020
atcccttcag gactaggtgc agaatgtcct tcccagccac ctctccatgg gattcatatt   1080
gcagacaata accccttaa cctgctaaga ataccaggat cagtatcgag agaggcttcc    1140
ggcctggcag aagggcgctt tccacccact ccccccctgt ttagtccacc accgagacat   1200
cacttggacc cccaccgcat agagcgcctg ggggcggaag agatggccct ggccacccat   1260
cacccgagtg cctttgacag ggtgctgcgg ttgaatccaa tggctatgga gcctcccgcc   1320
atggatttct ctaggagact tagagagctg gcagggaaca cgtctagccc accgctgtcc   1380
ccaggccggc ccagccctat gcaaaggtta ctgcaaccat tccagccagg tagcaagccg   1440
cccttcctgg cgacgccccc cctccctcct ctgcaatccg cccctcctcc ctcccagccc   1500
ccggtcaagt ccaagtcatg cgagttctgc ggcaagacgt tcaaatttca gagcaacctg   1560
gtggtgcacc ggcgcagcca cacgggcgag aagccctaca agtgcaacct gtgcgaccac   1620
gcgtgcaccc aggccagcaa gctgaagcgc cacatgaaga cgcacatgca caaatcgtcc   1680
cccatgacgg tcaagtccga cgacggtctc tccaccgcca gctccccgga acccggcacc   1740
agcgacttgg tgggcagcgc cagcagcgcg ctcaagtccg tggtggccaa gttcaagagc   1800
gagaacgacc ccaacctgat cccggagaac ggggacgagg aggaagagga ggacgacgag   1860
gaagaggaag aagaggagga agaggaggag gaggagctga cggagagcga gagggtggac   1920
tacggcttcg ggctgagcct ggaggcggcg cgccaccacg agaacagctc gcggggcgcg   1980
gtcgtgggcg tgggcgacga gagccgcgcc ctgcccgacg tcatgcaggg catggtgctc   2040
agctccatgc agcacttcag cgaggccttc caccaggtcc tgggcgagaa gcataagcgc   2100
ggccacctgg ccgaggccga gggccacagg gacacttgcg acgaagactc ggtggccggc   2160
gagtcggacc gcatagacga tggcactgtt aatggccgcg gctgctcccc gggcgagtcg   2220
gcctcggggg gcctgtccaa aaagctgctg ctgggcagcc ccagctcgct gagccccttc   2280
tctaagcgca tcaagctcga gaaggagttc gacctgcccc cggccgcgat gcccaacacg   2340
gagaacgtgt actcgcagtg gctcgccggc tacgcggcct ccaggcagct caaagatccc   2400
ttccttagct tcggagactc cagacaatcg ccttttgcct cctcgtcgga gcactcctcg   2460
gagaacggga gtttgcgctt ctccacaccg cccggggagc tggacggagg gatctcgggg   2520
cgcagcggca cgggaagtgg agggagcacg ccccatatta gtggtccggg cccgggcagg   2580
cccagctcaa aagagggcag acgcagcgac acttgtgagt actgtgggaa agtcttcaag   2640
aactgtagca atctcactgt ccacaggaga agccacacgg gcgaaaggcc ttataaatgc   2700
gagctgtgca actatgcctg tgcccagagt agcaagctca ccaggcacat gaaaacgcat   2760
ggccaggtgg ggaaggacgt ttacaaatgt gaaatttgta agatgccttt tagcgtgtac   2820
agtaccctgg agaaacacat gaaaaaatgg cacagtgatc gagtgttgaa taatgatata   2880
aaaactgaat agaggtatat taatacccct ccctcactcc cacctgacac cccctttttc   2940
accactcccc ttccccatcg ccctccagcc ccactccctg taggattttt ttctagtccc   3000
atgtgattta aacaaacaaa caaacaaaca gaagtaacga agctaagaat atgagagtgc   3060
ttgtcaccag cacacctgtt ttttttcttt ttctttttct tttttctttt tccttttttt   3120
tttttttcct ttatgttctc accgtttgaa tgcatgatct gtatggggca atactattgc   3180
attttacgca aactttgagc ctttctcttg tgcaataatt tacatgttgt gtatgttttt   3240
ttttaaactt agacagcatg tatggtatgt tatggctatt ttaaattgtc cctaattcgt   3300
tgctgagcaa acatgttgct gtttccagtt ccgttctgag agaaaaagag agagagagag   3360
```

-continued

```
aaaaagacca tgctgcatac attctgtaat acatatcatg tacagtttta ttttataacg   3420
tgaggaggaa aaacagtctt tggattaacc ctctatagac agaatagata gcactgaaaa   3480
aaaatctcta tgagctaaat gtctgtctct aaagggttaa atgtatcaat tggaaaggaa   3540
gaaaaaaggc cttgaattga caaattaaca gaaaaacaga acaagtttat tctatcattt   3600
ggttttaaaa tatgagtgcc ttggatctat taaaaccaca tcgatggttc tttctacttg   3660
ttataaactt gtagcttaat tcagcattgg gtgaggtaat aaaccttagg aactagcata   3720
taattctata ttgtatttct cacaacaatg gctacctaaa aagatgaccc attatgtcct   3780
agttaatcat catttttcct ttagtttaat tttataaaca aaactgatta taccagtata   3840
aaagctactt tgctcctggt gagagcttaa aagaaatggg ctgttttgcc caaagtttta   3900
ttttttttaa acaatgatta aattgaatgt gtaatgtgca aaagccctgg aacgcaatta   3960
aatacactag taaggagttc attttatgaa gatatttgct ttaataatgt ctttttaaaa   4020
atactggcac caaaagaaat agatccagat ctacttggtt gtcaagtgga caatcaaatg   4080
ataaacttta agaccttgta taccatattg aaaggaagag gctgacaata aggtttgaca   4140
gaggggaaca gaagaaaata atatgattta ttagcacaac gtggtactat ttgccattta   4200
aaactagaac aggtatataa gctaatattg atacaatgat gattaactat gaattcttaa   4260
gacttgcatt taaatgtgac attcttaaaa aaagaagaga aagaatttta agagtagcag   4320
tatatatgtc tgtgctccct aaaagttgta cttcatttct tttccataca ctgtgtgcta   4380
tttgtgttaa catggaagag gattcattgt ttttattttt atttttttaa ttttttcttt   4440
tttattaagc tagcatctgc cccagttggt gttcaaatag cacttgactc tgcctgtgat   4500
atctgtatct tttctctaat cagagataca gaggttgagt ataaaataaa cctgctcaga   4560
taggacaatt aagtgcactg tacaattttc ccagtttaca ggtctatact taagggaaaa   4620
gttgcaagaa tgctgaaaaa aaattgaaca caatctcatt gaggagcatt ttttaaaaac   4680
taaaaaaaaa aaaactttgc cagccattta cttgactatt gagcttactt acttggacgc   4740
aacattgcaa gcgctgtgaa tggaaacaga atacacttaa catagaaatg aatgattgct   4800
ttcgcttcta cagtgcaagg atttttttgt acaaaacttt tttaaatata aatgttaaga   4860
aaaatttttt ttaaaaaaca cttcattatg tttagggggg aactgcattt tagggttcca   4920
ttgtcttggt ggtgttacaa gacttgttat ccatttaaaa atggtagtgg aaattctatg   4980
ccttggatac acaccgctct tcaggttgta aaaaaaaaaa acatacattg gggaaaggtt   5040
taagattata tagtacttaa atataggaaa atgcacactc atgttgattc ctatgctaaa   5100
atacatttat ggtctttttt ctgtatttct agaatggtat ttgaattaaa tgttcatcta   5160
gtgttaggca ctatagtatt tatattgaag cttgtatttt taactgttgc ttgttctctt   5220
aaaaggtatc aatgtacctt ttttggtagt ggaaaaaaaa aagacaggct gccacagtat   5280
attttttttaa tttggcagga taatatagtg caaattattt gtatgcttca aaaaaaaaaa   5340
aaagagagaa acaaaaaagt gtgacattac agatgagaag ccatataatg gcggtttggg   5400
ggagcctgct agaatgtcac atggatggct gtcatagggg ttgtacatat cctttttttgt   5460
tcctttttcc tgctgccata ctgtatgcag tactgcaagc taataacgtt ggtttgttat   5520
gtagtgtgct ttttgtccct ttccttctat caccctacat tccagcatct taccttcata   5580
tgcagtaaaa gaaagaaaga aaaaaaaagg aaaaaaaaaa aaaaaccaat gttttgcagt   5640
tttttttcatt gccaaaaact aaatggtgct ttatatttag attggaaaga atttcatatg   5700
```

```
caaagcatat taaagagaaa gcccgcttta gtcaatactt ttttgtaaat ggcaatgcag   5760

aatattttgt tattggcctt ttctattcct gtaatgaaag ctgtttgtcg taacttgaaa   5820

ttttatcttt tactatggga gtcactattt attattgctt atgtgccctg ttcaaaacag   5880

aggcacttaa tttgatcttt tatttttctt tgtttttatt ttttttttta tttagatgac   5940

caaaggtcat tacaacctgg ctttttattg tatttgtttc tggtctttgt taagttctat   6000

tggaaaaacc actgtctgtg tttttttggc agttgtctgc attaacctgt tcatacaccc   6060

attttgtccc tttattgaaa aaataaaaaa aattaaagta ca                      6102


<210> SEQ ID NO 38
<211> LENGTH: 835
<212> TYPE: PRT
<213> ORGANISM: Homo sapiens

<400> SEQUENCE: 38

Met Ser Arg Arg Lys Gln Gly Lys Pro Gln His Leu Ser Lys Arg Glu
1               5                   10                  15

Phe Ser Pro Glu Pro Leu Glu Ala Ile Leu Thr Asp Asp Glu Pro Asp
            20                  25                  30

His Gly Pro Leu Gly Ala Pro Glu Gly Asp His Asp Leu Leu Thr Cys
        35                  40                  45

Gly Gln Cys Gln Met Asn Phe Pro Leu Gly Asp Ile Leu Ile Phe Ile
    50                  55                  60

Glu His Lys Arg Lys Gln Cys Asn Gly Ser Leu Cys Leu Glu Lys Ala
65                  70                  75                  80

Val Asp Lys Pro Pro Ser Pro Ser Pro Ile Glu Met Lys Lys Ala Ser
                85                  90                  95

Asn Pro Val Glu Val Gly Ile Gln Val Thr Pro Glu Asp Asp Asp Cys
            100                 105                 110

Leu Ser Thr Ser Ser Arg Gly Ile Cys Pro Lys Gln Glu His Ile Ala
        115                 120                 125

Asp Lys Leu Leu His Trp Arg Gly Leu Ser Ser Pro Arg Ser Ala His
    130                 135                 140

Gly Ala Leu Ile Pro Thr Pro Gly Met Ser Ala Glu Tyr Ala Pro Gln
145                 150                 155                 160

Gly Ile Cys Lys Asp Glu Pro Ser Ser Tyr Thr Cys Thr Thr Cys Lys
                165                 170                 175

Gln Pro Phe Thr Ser Ala Trp Phe Leu Leu Gln His Ala Gln Asn Thr
            180                 185                 190

His Gly Leu Arg Ile Tyr Leu Glu Ser Glu His Gly Ser Pro Leu Thr
        195                 200                 205

Pro Arg Val Gly Ile Pro Ser Gly Leu Gly Ala Glu Cys Pro Ser Gln
    210                 215                 220

Pro Pro Leu His Gly Ile His Ile Ala Asp Asn Asn Pro Phe Asn Leu
225                 230                 235                 240

Leu Arg Ile Pro Gly Ser Val Ser Arg Glu Ala Ser Gly Leu Ala Glu
                245                 250                 255

Gly Arg Phe Pro Pro Thr Pro Pro Leu Phe Ser Pro Pro Pro Arg His
            260                 265                 270

His Leu Asp Pro His Arg Ile Glu Arg Leu Gly Ala Glu Glu Met Ala
        275                 280                 285

Leu Ala Thr His His Pro Ser Ala Phe Asp Arg Val Leu Arg Leu Asn
    290                 295                 300
```

-continued

```
Pro Met Ala Met Glu Pro Pro Ala Met Asp Phe Ser Arg Arg Leu Arg
305                 310                 315                 320

Glu Leu Ala Gly Asn Thr Ser Ser Pro Pro Leu Ser Pro Gly Arg Pro
                325                 330                 335

Ser Pro Met Gln Arg Leu Leu Gln Pro Phe Gln Pro Gly Ser Lys Pro
            340                 345                 350

Pro Phe Leu Ala Thr Pro Pro Leu Pro Pro Leu Gln Ser Ala Pro Pro
        355                 360                 365

Pro Ser Gln Pro Pro Val Lys Ser Lys Ser Cys Glu Phe Cys Gly Lys
    370                 375                 380

Thr Phe Lys Phe Gln Ser Asn Leu Val Val His Arg Arg Ser His Thr
385                 390                 395                 400

Gly Glu Lys Pro Tyr Lys Cys Asn Leu Cys Asp His Ala Cys Thr Gln
                405                 410                 415

Ala Ser Lys Leu Lys Arg His Met Lys Thr His Met His Lys Ser Ser
            420                 425                 430

Pro Met Thr Val Lys Ser Asp Asp Gly Leu Ser Thr Ala Ser Ser Pro
        435                 440                 445

Glu Pro Gly Thr Ser Asp Leu Val Gly Ser Ala Ser Ser Ala Leu Lys
    450                 455                 460

Ser Val Val Ala Lys Phe Lys Ser Glu Asn Asp Pro Asn Leu Ile Pro
465                 470                 475                 480

Glu Asn Gly Asp Glu Glu Glu Glu Glu Asp Asp Glu Glu Glu Glu Glu
                485                 490                 495

Glu Glu Glu Glu Glu Glu Glu Glu Leu Thr Glu Ser Glu Arg Val Asp
            500                 505                 510

Tyr Gly Phe Gly Leu Ser Leu Glu Ala Ala Arg His His Glu Asn Ser
        515                 520                 525

Ser Arg Gly Ala Val Val Gly Val Gly Asp Glu Ser Arg Ala Leu Pro
    530                 535                 540

Asp Val Met Gln Gly Met Val Leu Ser Ser Met Gln His Phe Ser Glu
545                 550                 555                 560

Ala Phe His Gln Val Leu Gly Glu Lys His Lys Arg Gly His Leu Ala
                565                 570                 575

Glu Ala Glu Gly His Arg Asp Thr Cys Asp Glu Asp Ser Val Ala Gly
            580                 585                 590

Glu Ser Asp Arg Ile Asp Asp Gly Thr Val Asn Gly Arg Gly Cys Ser
        595                 600                 605

Pro Gly Glu Ser Ala Ser Gly Gly Leu Ser Lys Lys Leu Leu Leu Gly
    610                 615                 620

Ser Pro Ser Ser Leu Ser Pro Phe Ser Lys Arg Ile Lys Leu Glu Lys
625                 630                 635                 640

Glu Phe Asp Leu Pro Pro Ala Ala Met Pro Asn Thr Glu Asn Val Tyr
                645                 650                 655

Ser Gln Trp Leu Ala Gly Tyr Ala Ala Ser Arg Gln Leu Lys Asp Pro
            660                 665                 670

Phe Leu Ser Phe Gly Asp Ser Arg Gln Ser Pro Phe Ala Ser Ser Ser
        675                 680                 685

Glu His Ser Ser Glu Asn Gly Ser Leu Arg Phe Ser Thr Pro Pro Gly
    690                 695                 700

Glu Leu Asp Gly Gly Ile Ser Gly Arg Ser Gly Thr Gly Ser Gly Gly
705                 710                 715                 720
```

```
Ser Thr Pro His Ile Ser Gly Pro Gly Pro Gly Arg Pro Ser Ser Lys
                725                 730                 735

Glu Gly Arg Arg Ser Asp Thr Cys Glu Tyr Cys Gly Lys Val Phe Lys
            740                 745                 750

Asn Cys Ser Asn Leu Thr Val His Arg Arg Ser His Thr Gly Glu Arg
        755                 760                 765

Pro Tyr Lys Cys Glu Leu Cys Asn Tyr Ala Cys Ala Gln Ser Ser Lys
    770                 775                 780

Leu Thr Arg His Met Lys Thr His Gly Gln Val Gly Lys Asp Val Tyr
785                 790                 795                 800

Lys Cys Glu Ile Cys Lys Met Pro Phe Ser Val Tyr Ser Thr Leu Glu
                805                 810                 815

Lys His Met Lys Lys Trp His Ser Asp Arg Val Leu Asn Asn Asp Ile
            820                 825                 830

Lys Thr Glu
        835
```

<210> SEQ ID NO 39
<211> LENGTH: 1166
<212> TYPE: DNA
<213> ORGANISM: Homo sapiens

<400> SEQUENCE: 39

```
agacaatatt ctgttacatt gtagcaaaat ggcgactgtc attcacaacc ccctgaaagc     60

gctcggggac cagttctaca aggaagccat tgagcactgc cggagttaca actcacggct    120

gtgtgcagag cgcagcgtgc gtcttccctt cctggactca cagactgggg tggcccagaa    180

caactgctac atctggatgg agaagaggca ccgaggccca ggccttgccc cgggccagct    240

gtatacatac cctgcccgct gctggcgcaa gaagagacga ttgcacccac ctgaagatcc    300

aaaactgcgg ctgctggaga taaaacctga agtggagctt cccctgaaga aggatgggtt    360

cacctcagag agcaccacgc tggaagcctt gctccgtggc gaggggggttg agaagaaggt   420

ggatgccagg gaggaggaaa gcatccagga aatacagagg gttttggaaa atgatgaaaa    480

tgtagaagaa gggaatgaag aagaggattt ggaagaggat attcccaagc gaaagaacag    540

gactagagga cgggctcgcg gctctgcagg gggcaggagg aggcacgacg ccgcctctca    600

ggaagaccac gacaaacctt acgtctgtga catctgtggc aagcgctaca agaaccgacc    660

ggggctcagc taccactatg ctcacactca cctggccagc gaggaggggg atgaagctca    720

agaccaggag actcggtccc cacccaacca cagaaatgag aaccacaggc cccagaaagg    780

accggatgga acagtcattc ccaataacta ctgtgacttc tgcttggggg gctccaacat    840

gaacaagaag agtgggcggc ctgaagagct ggtgtcctgc gcagactgtg gacgctctgg    900

tcacccaacc tgcctgcagt ttaccctgaa catgaccgag gctgtcaaga cctacaagtg    960

gcagtgcata gagtgcaaat cctgtatcct ctgtgggacc tcagagaatg atgaccagct   1020

actcttctgc gatgactgtg accgaggcta tcacatgtac tgtttaaatc cccggtggc    1080

tgagccccca gaaggaagct ggagctgcca cttatgctgg gaactgctca aagagaaagc   1140

ctcagccttt ggctgccagg cctagg                                        1166
```

<210> SEQ ID NO 40
<211> LENGTH: 378
<212> TYPE: PRT
<213> ORGANISM: Homo sapiens

<400> SEQUENCE: 40

```
Met Ala Thr Val Ile His Asn Pro Leu Lys Ala Leu Gly Asp Gln Phe
1               5                   10                  15

Tyr Lys Glu Ala Ile Glu His Cys Arg Ser Tyr Asn Ser Arg Leu Cys
            20                  25                  30

Ala Glu Arg Ser Val Arg Leu Pro Phe Leu Asp Ser Gln Thr Gly Val
        35                  40                  45

Ala Gln Asn Asn Cys Tyr Ile Trp Met Glu Lys Arg His Arg Gly Pro
    50                  55                  60

Gly Leu Ala Pro Gly Gln Leu Tyr Thr Tyr Pro Ala Arg Cys Trp Arg
65                  70                  75                  80

Lys Lys Arg Arg Leu His Pro Pro Glu Asp Pro Lys Leu Arg Leu Leu
                85                  90                  95

Glu Ile Lys Pro Glu Val Glu Leu Pro Leu Lys Lys Asp Gly Phe Thr
            100                 105                 110

Ser Glu Ser Thr Thr Leu Glu Ala Leu Leu Arg Gly Glu Gly Val Glu
        115                 120                 125

Lys Lys Val Asp Ala Arg Glu Glu Glu Ser Ile Gln Glu Ile Gln Arg
    130                 135                 140

Val Leu Glu Asn Asp Glu Asn Val Glu Glu Gly Asn Glu Glu Glu Asp
145                 150                 155                 160

Leu Glu Glu Asp Ile Pro Lys Arg Lys Asn Arg Thr Arg Gly Arg Ala
                165                 170                 175

Arg Gly Ser Ala Gly Gly Arg Arg Arg His Asp Ala Ala Ser Gln Glu
            180                 185                 190

Asp His Asp Lys Pro Tyr Val Cys Asp Ile Cys Gly Lys Arg Tyr Lys
        195                 200                 205

Asn Arg Pro Gly Leu Ser Tyr His Tyr Ala His Thr His Leu Ala Ser
    210                 215                 220

Glu Glu Gly Asp Glu Ala Gln Asp Gln Glu Thr Arg Ser Pro Pro Asn
225                 230                 235                 240

His Arg Asn Glu Asn His Arg Pro Gln Lys Gly Pro Asp Gly Thr Val
                245                 250                 255

Ile Pro Asn Asn Tyr Cys Asp Phe Cys Leu Gly Gly Ser Asn Met Asn
            260                 265                 270

Lys Lys Ser Gly Arg Pro Glu Glu Leu Val Ser Cys Ala Asp Cys Gly
        275                 280                 285

Arg Ser Gly His Pro Thr Cys Leu Gln Phe Thr Leu Asn Met Thr Glu
    290                 295                 300

Ala Val Lys Thr Tyr Lys Trp Gln Cys Ile Glu Cys Lys Ser Cys Ile
305                 310                 315                 320

Leu Cys Gly Thr Ser Glu Asn Asp Asp Gln Leu Leu Phe Cys Asp Asp
                325                 330                 335

Cys Asp Arg Gly Tyr His Met Tyr Cys Leu Asn Pro Pro Val Ala Glu
            340                 345                 350

Pro Pro Glu Gly Ser Trp Ser Cys His Leu Cys Trp Glu Leu Leu Lys
        355                 360                 365

Glu Lys Ala Ser Ala Phe Gly Cys Gln Ala
    370                 375
```

<210> SEQ ID NO 41
<211> LENGTH: 8528
<212> TYPE: DNA
<213> ORGANISM: Homo sapiens

<400> SEQUENCE: 41
agccatagag agaccgagag ctcccagaga acccggactc cgccatcttc acgttgcaat 60
ctatagctcc cagtctgcgc ccgcaccgac ccaggcgcac tgggcgagcc gcccctccgc 120
cccgctcccc ccgggcccgc ggcgccaggg gagcgctggg gagcgctcgc ggggactcgg 180
cagcccctcc ggccggcgcc agcctgccag gtgaactggg aaggagcctc tcctggtgtc 240
cccccagagc ctcggaaggg tcagtctccg agaaaaaaca aaaacaaaaa caaaaacagg 300
cagcccgcag aaaacccaga aacaaccgaa ccggggcagt tttacattgc tttgggtttt 360
ttgagggggc ggggtgaggg ggtacgagac aagtccccaa gttttctttg cttttttttt 420
tcctttgctt tttcttcttt tatttttta tttgtttgca tttttttcc cctcctggta 480
gaagtgcgct ttccacctac cagaccctga aagaaagtgt caggagccgg tgcaaaaccc 540
agtttaagtt caagaagaca tttgcaagtg caagaggcca agcagtttga agaagtgtaa 600
gagatttttt ttccttcgaa agaatatatt tttaaagaaa ccagccagtc cgcggaaagc 660
aacagcagtt tttttttttt ttgcctcttt ttcttatttt agatcgagag gtttttcttg 720
cttttcttcc cttttttttc tttttgcaaa caaaacaaaa aacagcatag aagaaagagc 780
aaaataaaga agaagaagag gaggaagaga gggaaagaga ggaagggaaa aaaaacacca 840
acccgggcag aggaggaggt gcggcggcgg cggcggcggc ggcagcggcg gcagcggcgc 900
ggcggcggct cggacccccct cccccggctc cccccatcag tgcagctctc cgggcgatgc 960
cagaatagat gccggggcaa tgtcccgccg caaacagggc aacccgcagc acttgtccca 1020
gagggagctc atcaccccag aggctgacca tgtggaggcc gccatcctcg aagaagacga 1080
gggtctggag atagaggagc caagtggcct ggggctgatg gtgggtggcc ccgaccctga 1140
cctgctcacc tgtggccagt gtcaaatgaa cttccccttg gggacatcc tggtttttat 1200
agagcacaaa aggaagcagt gtggcggcag cttgggtgcc tgctatgaca aggccctgga 1260
caaggacagc ccgccaccct cctcacgctc cgagctcagg aaagtgtccg agccggtgga 1320
gatcgggatc caagtcaccc ccgacgaaga tgaccacctg ctctcaccca cgaaaggcat 1380
ctgtcccaag caggagaaca ttgcagggcc gtgcaggcct gcccagctgc cagcggtggc 1440
ccccatagct gcctcctccc accctcactc atccgtgatc acttcacctc tgcgtgccct 1500
gggcgctctc ccgccctgcc tccccctgcc gtgctgcagc gcgcgcccgg tctcgggtga 1560
cgggactcag ggtgagggtc agacggaggc tccctttgga tgccagtgtc agttgtcagg 1620
taaagatgag ccttccagct acatttgcac aacatgcaag cagcccttca acagcgcgtg 1680
gttcctgctg cagcacgcgc agaacacgca cggcttccgc atctacctgg agcccgggcc 1740
ggccagcagc tcgctcacgc cgcggctcac catcccgccg ccgctcgggc cggaggccgt 1800
ggcgcagtcc ccgctcatga atttcctggg cgacagcaac cccttcaacc tgctgcgcat 1860
gacgggcccc atcctgcggg accacccggg cttcggcgag ggccgcctgc cgggcacgcc 1920
gcctctcttc agtcccccgc cgcgccacca cctggacccg caccgcctca gtgccgagga 1980
gatggggctc gtcgcccagc accccagtgc cttcgaccga gtcatgcgcc tgaaccccat 2040
ggccatcgac tcgcccgcca tggacttctc gcggcggctc cgcgagctgg cgggcaacag 2100
ctccacgccg ccgcccgtgt ccccgggccg cggcaaccct atgcaccggc tcctgaaccc 2160
cttccagccc agccccaagt ccccgttcct gagcacgccg ccgctgccgc ccatgccccc 2220
tggcggcacg ccgcccccgc agccgccagc caagagcaag tcgtgcgagt tctgcggcaa 2280
gaccttcaag ttccagagca atctcatcgt gcaccggcgc agtcacacgg gcgagaagcc 2340
ctacaagtgc cagctgtgcg accacgcgtg ctcgcaggcc agcaagctca agcgccacat 2400
gaagacgcac atgcacaagg ccggctcgct ggccggccgc tccgacgacg ggctctcggc 2460
cgccagctcc cccgagcccg gcaccagcga gctggcgggc gagggcctca aggcggccga 2520
cggtgacttc cgccaccacg agagcgaccc gtcgctgggc cacgagccgg aggaggagga 2580
cgaggaggag gaggaggagg aggaggagct gctactggag aacgagagcc ggcccgagtc 2640
gagcttcagc atggactcgg agctgagccg caaccgcgag aacggcggtg gtggggtgcc 2700
cggggtcccg ggcgcggggg gcggcgcggc caaggcgctg gctgacgaga aggcgctggt 2760
gctgggcaag gtcatggaga acgtgggcct aggcgcactg ccgcagtacg gcgagctcct 2820
ggccgacaag cagaagcgcg gcgccttcct gaagcgtgcg gcgggcggcg gggacgcggg 2880
cgacgacgac gacgcgggcg gctgcgggga cgcgggcgcg ggcggcgcgg tcaacgggcg 2940
cgggggcggc ttcgcgccag gcaccgagcc cttccccggg ctcttcccgc gcaagcccgc 3000
gccgctgccc agccccgggc tcaacagcgc cgccaagcgc atcaaggtgg agaaggacct 3060
ggagctgccg cccgccgcgc tcatcccgtc cgagaacgtg tactcgcagt ggctggtggg 3120
ctacgcggcg tcgcggcact tcatgaagga ccccttcctg ggcttcacgg acgcacgaca 3180
gtcgcccttc gccacgtcgt ccgagcactc gtccgagaac ggcagcctgc gcttctccac 3240
gccgcccggg gacctgctgg acggcggcct ctcgggccgc agcggcacgg ccagcggagg 3300
cagcaccccg cacctgggcg gcccgggccc cgggcggccc agctccaagg agggccgccg 3360
cagcgacacg tgcgagtact gcggcaaggt gttcaagaac tgcagcaact tgacggtgca 3420
ccggcggagc cacaccggcg agcggcctta caagtgcgag ctgtgcaact acgcgtgcgc 3480
gcagagcagc aagctcacgc gccacatgaa gacgcacggg cagatcggca aggaggtgta 3540
ccgctgcgac atctgccaga tgcccttcag cgtctacagc accctggaga aacacatgaa 3600
aaagtggcac ggcgagcact tgctgactaa cgacgtcaaa atcgagcagg ccgagaggag 3660
ctaagcgcgc gggccccggc gccccgcacc tgtacagtgg aaccgttgcc aaccgagaga 3720
atgctgacct gacttgcctc cgtgtcaccg ccaccccgca ccccgcgtgt ccccggggcc 3780
caggggaggc ggcactccaa cctaacctgt gtctgcgaag tcctatggaa acccgagggt 3840
tgattaaggc agtacaaatt gtggagcctt ttaactgtgc aataatttct gtatttattg 3900
ggttttgtaa tttttttggc atgtgcaggt actttttatt attatttttt ctgtttgaat 3960
tcctttaaga gattttgttg ggtatccatc ccttctttgt ttttttttta acccggtagt 4020
agcctgagca atgactcgca agcaatgtta gaggggaagc atatctttta aattataatt 4080
tggggggagg ggtggtgctg ctttttttgaa atttaagcta agcatgtgta atttcttgtg 4140
aagaagccaa cactcaaatg acttttaaag ttgtttactt tttcattcct tccttttttt 4200
tgtcctgaaa taaaaagtgg catgcagttt ttttttttaat tatttttttaa ttttttttttt 4260
ggtttttgtt tttggggtgg ggggtgtgga tgtacagcgg ataacaatct ttcaagtcgt 4320
agcactttgt ttcagaactg gaatggagat gtagcactca tgtcgtcccg agtcaagcgg 4380
ccttttctgt gttgatttcg gctttcatat tacataaggg aaaccttgag tggtggtgct 4440
gggggaggca ccccacagac tcagcgccgc cagagatagg gtttttggag ggctcctctg 4500
ggaaatggcc cgacagcatt ctgaggttgt gcatgaccag cagatactat cctgttggtg 4560
tgccctgggg tgccatggct gctattcgct gtagattagg ctacataaaa tgggctgagg 4620
gtaccttttt ggggagatgg ggtggcctgc agtgacacag aaaggaagaa actagcggtg 4680

-continued

```
ttcttttagg cgttttctgg cttgacggct tctctctttt tttaaatcac ccccaccaca   4740
taaatctcaa atcctatgtt gctacaaggg gtcatccatc atttcccaag cagacgaatg   4800
ccctaattaa ttgaagttag tgttctctca tttaatgcac actgatgata ttgtagggat   4860
gggtggggtg gggatcttgc aaatttctat tctcttttac tgaaaaagca ggggatgagt   4920
tccatcagaa ggtgcccagc gctacttccc aggtttttat ttttttttc ctatctcatt   4980
aggttggaag gtactaaata ttgaactgtt aagattagac atttgaattc tgttgacccg   5040
cactttaaag cttttgtttg catttaaatt aaatggcttc taaacaagaa attgcagcat   5100
attcttctct ttggcccaga ggtgggttaa actgtaaggg acagctgaga ttgagtgtca   5160
gtattgctaa gcgtggcatt cacaatactg gcactataaa gaacaaaata aaataataat   5220
ttataggaca gtttttctac tgccattcaa tttgatgtga gtgccttgaa aactgatctt   5280
cctatttgag tctcttgaga caaatgcaaa actttttttt tgaaatgaaa agacttttta   5340
aaaaagtaaa acaagaaaag tacattcttt agaaactaac aaagccacat ttactttaag   5400
taaaaaaaaa aaaaattctg gttgaagata gaggatatga aatgccataa gacccaatca   5460
aatgaagaaa taaacccagc acaaccttgg acatccatta gctgaattat cctcagcccc   5520
ttttgttttt gggacaacgc tgcttagata tggagtggag gtgatttact gctgaattaa   5580
aactcaagtg acacaagtta caagttgata tcgttgaatg aaaagcaaaa caaaaacaat   5640
tcaggaacaa cggctaattt tttctaaagt taaatttagt gcactctgtc ttaaaaatac   5700
gtttacagta ttgggtacat acaagggtaa aaaaaaaatt gtgtgtatgt gtgttggagc   5760
gatctttttt tttcaaagtt tgcttaatag gttatacaaa aatgccacag tggccgcgtg   5820
tatattgttt tcttttggtg acggggtttt agtatatatt atatatatta aaatttcttg   5880
attactgtaa aagtggacca gtatttgtaa taatcgagaa tgcctgggca ttttacaaaa   5940
caagaaaaaa aataccctt tcttttcctt gaaaatgttg cagtaaaatt taaatggtgg   6000
gtctataaat ttgttcttgt tacagtaact gtaaagtcgg agttttagta aattttttc   6060
tgccttgggt gttgaatttt tatttcaaaa aaaatgtata gaaacttgta tttggggatt   6120
caaaggggat tgctacacca tgtagaaaaa gtatgtagaa aaaaagtgct taatattgtt   6180
attgctttgc agaaaaaaaa aaaatcacat ttctgacctg tacttatttt tctcttcccg   6240
cctccctctg gaatggatat attggttggt tcatatgatg taggcacttg ctgtattttt   6300
actggagctc gtaatttttt aactgtaagc ttgtcctttt aaagggattt aatgtacctt   6360
tttgttagtg aatttggaaa taaaaagaaa aaaaaaacaa aaacaaacag gctgccataa   6420
tatatttttt taatttggca ggataaaata ttgcaaaaaa aacacatttg tatgttaagt   6480
cctattgtac aggagaaaaa gggttgtttg acaacctttg agaaaaagaa acaaaaggaa   6540
gtagttaaat gctttggttc acaaatcatt tagttgtata tattttttgt cggaattggc   6600
ctacacagag aaccgttcgt gttgggcttc tctctgaacg ccccgaacct tgcatcaagg   6660
ctccttggtg tggccacagc agaccagatg ggaaattatt tgtgttgagt ggaaaaaaat   6720
cagtttttgt aaagatgtca gtaacattcc acatcgtcct ccctttctct aagaggccat   6780
ctctaagatg tcagatgtag aggagagaga gcgagagaac atcttccttc tctaccatca   6840
ctcctgtggc ggtcaccacc accacctctc ccgcccttac cagcagaaag caatgcaaac   6900
tgagctgctt tagtccttga gaaattgtga aacaaacaca aatatcataa aaggagctgg   6960
tgattcagct gggtccaggt gaagtgacct gctgttgaga ccggtacaaa ttggatttca   7020
```

-continued

```
ggaaggagac tccatcacag ccaggacctt tcgtgccatg gagagtgttg gcctcttgtc   7080
tttcttccct gctttgctgc tttgctctct gaaacctaca ttccgtcagt ttccgaatgc   7140
gagggcctgg gatgaatttg gtgcctttcc atatctcgtt ctctctcctt cccctgcgtt   7200
tcctctccat ccttcatcct ccattggtcc tttttttttc tttcattttt tatttaattt   7260
cttttcttcc tgtctgttcc tcccctaatc ctctatttta tttttatttt ttgtaaagcc   7320
aagtagcttt aagataaagt ggtggtcttt tggatgaggg aataatgcat ttttaaataa   7380
aataccaata tcaggaagcc attttttatt tcaggaaatg taagaaacca ttatttcagg   7440
ttatgaaagt ataaccaagc atccttttgg gcaattcctt accaaatgca gaagcttttc   7500
tgttcgatgc actctttcct ccttgccact tacctttgca aagttaaaaa aaaggggggga  7560
gggaatggga gagaaagctg agatttcagt ttcctactgc agtttcctac ctgcagatcc   7620
aggggctgct gttgcctttg gatgccccac tgaggtccta gagtgcctcc agggtggtct   7680
tcctgtagtc ataacagcta gccagtgctc accagcttac cagattgcca ggactaagcc   7740
atcccaaagc acaagcattg tgtgtctctg tgactgcaga gaagagagaa ttttgcttct   7800
gttttgtgtt taaaaaacca acacggaagc agatgatccc gagagagagg cctctagcat   7860
gggtgaccca gccgacctca ggccggtttc cgcactgcca caactttgtt caaagttgcc   7920
cccaattgga acctgccact tggcattaga gggtctttca tggggagaga aggagactga   7980
attactctaa gcaaaatgtg aaaagtaagg aaatcagcct ttcatcccgg tcctaagtaa   8040
ccgtcagccg aaggtctcgt ggaacacagg caaacccgtg attttggtgc tccttgtaac   8100
tcagccctgc aaagcaaagt cccattgatt taagttgttt gcatttgtac tggcaaggca   8160
aaatattttt attacctttt ctattactta ttgtatgagc ttttgttgtt tacttggagg   8220
ttttgtcttt tactacaagt ttggaactat ttattattgc ttggtatttg tgctctgttt   8280
aagaaacagg cacttttttt tattatggat aaaatgttga gatgacagga ggtcatttca   8340
atatggctta gtaaaatatt tattgttcct ttattctctg tacaagattt tgggcctctt   8400
tttttcctta atgtcacaat gttgagttca gcatgtgtct gccatttcat ttgtacgctt   8460
gttcaaaacc aagtttgttc tggtttcaag ttataaaaat aaattggaca tttaacttga   8520
tctccaaa                                                            8528
```

<210> SEQ ID NO 42
<211> LENGTH: 894
<212> TYPE: PRT
<213> ORGANISM: Homo sapiens

<400> SEQUENCE: 42

```
Met Ser Arg Arg Lys Gln Gly Asn Pro Gln His Leu Ser Gln Arg Glu
1               5                   10                  15

Leu Ile Thr Pro Glu Ala Asp His Val Glu Ala Ala Ile Leu Glu Glu
            20                  25                  30

Asp Glu Gly Leu Glu Ile Glu Glu Pro Ser Gly Leu Gly Leu Met Val
        35                  40                  45

Gly Gly Pro Asp Pro Asp Leu Leu Thr Cys Gly Gln Cys Gln Met Asn
    50                  55                  60

Phe Pro Leu Gly Asp Ile Leu Val Phe Ile Glu His Lys Arg Lys Gln
65                  70                  75                  80

Cys Gly Gly Ser Leu Gly Ala Cys Tyr Asp Lys Ala Leu Asp Lys Asp
                85                  90                  95
```

```
Ser Pro Pro Pro Ser Ser Arg Ser Glu Leu Arg Lys Val Ser Glu Pro
            100                 105                 110

Val Glu Ile Gly Ile Gln Val Thr Pro Asp Glu Asp Asp His Leu Leu
        115                 120                 125

Ser Pro Thr Lys Gly Ile Cys Pro Lys Gln Glu Asn Ile Ala Gly Pro
    130                 135                 140

Cys Arg Pro Ala Gln Leu Pro Ala Val Ala Pro Ile Ala Ala Ser Ser
145                 150                 155                 160

His Pro His Ser Ser Val Ile Thr Ser Pro Leu Arg Ala Leu Gly Ala
                165                 170                 175

Leu Pro Pro Cys Leu Pro Leu Pro Cys Cys Ser Ala Arg Pro Val Ser
            180                 185                 190

Gly Asp Gly Thr Gln Gly Glu Gly Gln Thr Glu Ala Pro Phe Gly Cys
        195                 200                 205

Gln Cys Gln Leu Ser Gly Lys Asp Glu Pro Ser Ser Tyr Ile Cys Thr
    210                 215                 220

Thr Cys Lys Gln Pro Phe Asn Ser Ala Trp Phe Leu Leu Gln His Ala
225                 230                 235                 240

Gln Asn Thr His Gly Phe Arg Ile Tyr Leu Glu Pro Gly Pro Ala Ser
                245                 250                 255

Ser Ser Leu Thr Pro Arg Leu Thr Ile Pro Pro Pro Leu Gly Pro Glu
            260                 265                 270

Ala Val Ala Gln Ser Pro Leu Met Asn Phe Leu Gly Asp Ser Asn Pro
        275                 280                 285

Phe Asn Leu Leu Arg Met Thr Gly Pro Ile Leu Arg Asp His Pro Gly
    290                 295                 300

Phe Gly Glu Gly Arg Leu Pro Gly Thr Pro Pro Leu Phe Ser Pro Pro
305                 310                 315                 320

Pro Arg His His Leu Asp Pro His Arg Leu Ser Ala Glu Glu Met Gly
                325                 330                 335

Leu Val Ala Gln His Pro Ser Ala Phe Asp Arg Val Met Arg Leu Asn
            340                 345                 350

Pro Met Ala Ile Asp Ser Pro Ala Met Asp Phe Ser Arg Arg Leu Arg
        355                 360                 365

Glu Leu Ala Gly Asn Ser Ser Thr Pro Pro Pro Val Ser Pro Gly Arg
    370                 375                 380

Gly Asn Pro Met His Arg Leu Leu Asn Pro Phe Gln Pro Ser Pro Lys
385                 390                 395                 400

Ser Pro Phe Leu Ser Thr Pro Pro Leu Pro Pro Met Pro Pro Gly Gly
                405                 410                 415

Thr Pro Pro Pro Gln Pro Pro Ala Lys Ser Lys Ser Cys Glu Phe Cys
            420                 425                 430

Gly Lys Thr Phe Lys Phe Gln Ser Asn Leu Ile Val His Arg Arg Ser
        435                 440                 445

His Thr Gly Glu Lys Pro Tyr Lys Cys Gln Leu Cys Asp His Ala Cys
    450                 455                 460

Ser Gln Ala Ser Lys Leu Lys Arg His Met Lys Thr His Met His Lys
465                 470                 475                 480

Ala Gly Ser Leu Ala Gly Arg Ser Asp Asp Gly Leu Ser Ala Ala Ser
                485                 490                 495

Ser Pro Glu Pro Gly Thr Ser Glu Leu Ala Gly Glu Gly Leu Lys Ala
            500                 505                 510
```

-continued

```
Ala Asp Gly Asp Phe Arg His His Glu Ser Asp Pro Ser Leu Gly His
        515                 520                 525

Glu Pro Glu Glu Glu Asp Glu Glu Glu Glu Glu Glu Glu Glu Glu Leu
    530                 535                 540

Leu Leu Glu Asn Glu Ser Arg Pro Glu Ser Ser Phe Ser Met Asp Ser
545                 550                 555                 560

Glu Leu Ser Arg Asn Arg Glu Asn Gly Gly Gly Gly Val Pro Gly Val
                565                 570                 575

Pro Gly Ala Gly Gly Gly Ala Ala Lys Ala Leu Ala Asp Glu Lys Ala
            580                 585                 590

Leu Val Leu Gly Lys Val Met Glu Asn Val Gly Leu Gly Ala Leu Pro
        595                 600                 605

Gln Tyr Gly Glu Leu Leu Ala Asp Lys Gln Lys Arg Gly Ala Phe Leu
    610                 615                 620

Lys Arg Ala Ala Gly Gly Gly Asp Ala Gly Asp Asp Asp Asp Ala Gly
625                 630                 635                 640

Gly Cys Gly Asp Ala Gly Ala Gly Gly Ala Val Asn Gly Arg Gly Gly
                645                 650                 655

Gly Phe Ala Pro Gly Thr Glu Pro Phe Pro Gly Leu Phe Pro Arg Lys
            660                 665                 670

Pro Ala Pro Leu Pro Ser Pro Gly Leu Asn Ser Ala Ala Lys Arg Ile
        675                 680                 685

Lys Val Glu Lys Asp Leu Glu Leu Pro Pro Ala Ala Leu Ile Pro Ser
    690                 695                 700

Glu Asn Val Tyr Ser Gln Trp Leu Val Gly Tyr Ala Ala Ser Arg His
705                 710                 715                 720

Phe Met Lys Asp Pro Phe Leu Gly Phe Thr Asp Ala Arg Gln Ser Pro
                725                 730                 735

Phe Ala Thr Ser Ser Glu His Ser Ser Glu Asn Gly Ser Leu Arg Phe
            740                 745                 750

Ser Thr Pro Pro Gly Asp Leu Leu Asp Gly Gly Leu Ser Gly Arg Ser
        755                 760                 765

Gly Thr Ala Ser Gly Gly Ser Thr Pro His Leu Gly Gly Pro Gly Pro
    770                 775                 780

Gly Arg Pro Ser Ser Lys Glu Gly Arg Arg Ser Asp Thr Cys Glu Tyr
785                 790                 795                 800

Cys Gly Lys Val Phe Lys Asn Cys Ser Asn Leu Thr Val His Arg Arg
                805                 810                 815

Ser His Thr Gly Glu Arg Pro Tyr Lys Cys Glu Leu Cys Asn Tyr Ala
            820                 825                 830

Cys Ala Gln Ser Ser Lys Leu Thr Arg His Met Lys Thr His Gly Gln
        835                 840                 845

Ile Gly Lys Glu Val Tyr Arg Cys Asp Ile Cys Gln Met Pro Phe Ser
    850                 855                 860

Val Tyr Ser Thr Leu Glu Lys His Met Lys Lys Trp His Gly Glu His
865                 870                 875                 880

Leu Leu Thr Asn Asp Val Lys Ile Glu Gln Ala Glu Arg Ser
                885                 890
```

<210> SEQ ID NO 43
<211> LENGTH: 5191
<212> TYPE: DNA
<213> ORGANISM: Homo sapiens

<400> SEQUENCE: 43

```
gccagcgcct gcgcactgag ggcggcctgg tcgtcgtctg cggcggcggc ggcggctgag     60
gagcccggct gaggcgccag tacccggccc ggtccgcatt tcgccttccg gcttcggttt    120
ccctcggccc agcacgcccc ggccccgccc cagccctcct gatccctcgc agcccggctc    180
cggccgcccg cctctgccgc cgcaatgatg atgatggcgc tgagcaagac cttcgggcag    240
aagcccgtga agttccagct ggaggacgac ggcgagttct acatgatcgg ctccgaggtg    300
ggaaactacc tccgtatgtt ccgaggttct ctgtacaaga gataccccctc actctggagg    360
cgactagcca ctgtggaaga gaggaagaaa atagttgcat cgtcacatgg taaaaaaaca    420
aaacctaaca ctaaggatca cggatacacg actctagcca ccagtgtgac cctgttaaaa    480
gcctcggaag tggaagagat tctggatggc aacgatgaga agtacaaggc tgtgtccatc    540
agcacagagc cccccaccta cctcagggaa cagaaggcca agaggaacag ccagtgggta    600
cccaccctgc ccaacagctc ccaccactta gatgccgtgc catgctccac aaccatcaac    660
aggaaccgca tgggccgaga caagaagaga accttccccc tttgctttga tgaccatgac    720
ccagctgtga tccatgagaa cgcatctcag cccgaggtgc tggtccccat ccggctggac    780
atggagatcg atgggcagaa gctgcgagac gccttcacct ggaacatgaa tgagaagttg    840
atgacgcctg agatgttttc agaaatcctc tgtgacgatc tggatttgaa cccgctgacg    900
tttgtgccag ccatcgcctc tgccatcaga cagcagatcg agtcctaccc cacggacagc    960
atcctggagg accagtcaga ccagcgcgtc atcatcaagc tgaacatcca tgtgggaaac   1020
atttccctgg tggaccagtt tgagtgggac atgtcagaga aggagaactc accagagaag   1080
tttgccctga agctgtgctc ggagctgggg ttgggcgggg agtttgtcac caccatcgca   1140
tacagcatcc ggggacagct gagctggcat cagaagacct acgccttcag cgagaaccct   1200
ctgcccacag tggagattgc catccggaac acgggcgatg cggaccagtg gtgcccactg   1260
ctggagactc tgacagacgc tgagatggag aagaagatcc gcgaccagga caggaacacg   1320
aggcggatga ggcgtcttgc caacacggcc ccggcctggt aaccagccca tcagcacacg   1380
gctcccacgg agcatctcag aagattgggc cgcctctcct ccatcttctg gcaaggacag   1440
aggcgagggg acagcccagc gccatcctga ggatcgggtg ggggtggagt gggggcttcc   1500
aggtggccct tcccggcaca cattccattt gttgagcccc agtcctgccc cccaccccac   1560
cctccctacc cctccccagt ctctggggtc aggaagaaac cttattttag gttgtgtttt   1620
gtttttgtat aggagcccca ggcagggcta gtaacagttt ttaaataaaa ggcaacaggt   1680
catgttcaat ttcttcaaca ggtcatgttc aatttcttca aagttttaac ataaaaataa   1740
tgagagccag gagtggggcc ggggcctggg gggacgaagg tggtatgtga acaaggttgg   1800
cacacaggcc tcaccctcct ctgcctcaga ttcccaagtg ggcaggtggg ggtgaatggg   1860
gctccgggta gcacctcagc tcctctcagc tcccctcagc ctgttctcct tccagaccca   1920
gagagctgag aagagtagct gtgaggctca gggcaagagg ctctctgcct ttcaggaaca   1980
gccctaaccc tgctcccctt gcttggcctc aggaaggtgc cgcgagctct cctgccgtcc   2040
ctgggccgcc ctggctctgc tgtgtccaga tggtcaggct actgccagct ggggccttgc   2100
tgctctgaag tcccctgcgg agggcccagt cctgtgtggg cactgctggg ctgtcgccag   2160
cctgggtgca ggagggctgt tctagctcca gtggcaccca tagccaggtc agctggggcc   2220
ctttcccacc ccagcaggtg ctgtggcctg ggccagctcc tgccttacaa gccagctgtg   2280
```

-continued

```
aggaatatgg gaatagccct cccggcctgg tgccagctct tggagttgac acggtacagg   2340
gaggagacac agcccagggt cccttcccag ccctgcctcc aaggagttca tgtcccctct   2400
gttctcatct gtaataggga ggtgtcccca ttcttcagaa tggacacagg atctgggagg   2460
gcagcaaact ggctcgcagc tccagcctta ctgaagagaa tgggcacaga tccgggcaca   2520
gatcccagca cagactgctg ccaccctcag ctgttggcag gtcccatgct gccagggcag   2580
ggctagggtc agaggctgct gtgctccctg gaagtggggt agggccccat gtggggcaga   2640
ggcagagctc tgattaggga ttggggttct tggtcgctga gatgtgagag gagggctcct   2700
ttgagcacat gttagcatgg gactcttccc agggagtttg cactcagggc ctctgccctc   2760
catcaaagag tggaactccc cagagcccca tgcacagcaa ggggacagct gggccttact   2820
ggaaggcctt gaacaaaggg gaagattccc agcccagctg ctcttagaca tgaacaggtt   2880
tcattgctga ggtgtttgtt ctgtccatga ggtaggaacc tcggcaatga aagggtgagg   2940
cagccctgtg tctccacaac tgggggggatg gaaggaacct tggctgcctc accccacagg   3000
tcgggcaggg ccacctggct gggaggtgcc gggaaggctg ggccctcact cctgaccgcc   3060
agctcacacc gccgcaaagc catctccaca aggtctggct acaacacgga gggcagactc   3120
aacagagaac agtgttgtta ccatgaaaat gacaacctgt ctttggagga ggccccgtgc   3180
cactgagcat ccagaaataa accacaacat ggacaggctt agaacaacaa ggaaagctgc   3240
caggtcagaa gagaaaaatg agccacaggg gtcggataag gctcacacac gtcctcagct   3300
aaaaagggca ggaacagaac cttccagaag tccctgcctc acccagtctc agaactctgc   3360
taaggtgaaa acttaggctc tgaggtcata gaaagggcag aagacctagt cctggccctc   3420
ttctgcacct gaatccatgg ggctttggca tcaccagatg aaaaatgagg catacgccca   3480
cctgtcaggg tggctgatga gagacaggag aggctagatt ggcatcagcc tgaaggcacc   3540
actggcagga acatctgtag gctggtttgg cacaacctag gagacgcctg tcctggcccc   3600
agcagccgaa atctggtgaa cttccccgct gactggcagg tagcagaggc ctatggtggg   3660
caggacttgc ccaaggccct ggtggggcca ggatgagaac cctgagcctg tcacctgtga   3720
gctcaaaagc tctgcctggc aacctgtgag ctcaaagctc tgccaggcaa ccatgggcag   3780
tttctttgcc ctctgtgggc accoctatcc taccacctgc agttgggctg agaggccaca   3840
ctgagtgagg acggggcagg catagaagga tgtggccagg tgagatgggg aagccagtgc   3900
tgtgggccaa gagactgcag ctcattctgt ttattcaggt gggcccttgc atgggcccag   3960
cctttaggat gggtttttc tgccccaagt aggggtcatg ggtaggatgg aagctgccag   4020
aagcctctta ggcctggccc tgggtggggg tcactgctgc gggggtggca gatggggtcc   4080
tggctgttcc tcagggaggg gcaggtaatt ggggtcttct gcaggggcat ccaggagcag   4140
ctttctgtgg ggaggggccc gtgttgagca caggccagca caggtcccca tcggtgggga   4200
tccttctgag ggtggggaga gggagggagg gctctcaaca ctcacaggaa gccaggggtc   4260
tgcaggagcc tcttgcctcc aggctggttg gggaagacgt cctccaggaa gtagtagata   4320
tggcccaccg caatccctgt gagacagcca cggactgtgg ggtcaccctc cacagcccag   4380
agtcctagac cagcagagcc tgccccaggc ccccatccac agcctggtgg ccctgcaggc   4440
cccacagcat gagtgcccca aagccttgca cagagtgcca gccccgggtt ggccgtgaag   4500
gacaagctta aaaggcccag aagcaggcag gacccaggga ggggagggcc tgagaatagt   4560
ggaggagtgg gagccatggg gcaggaaccc tgaccctccc atcctcactc ccatcaggac   4620
cgtgcaagca tcagtagatc cgtcctgacg atgcaaatta tgtgggccgg ctggcttgag   4680
```

```
gggctgtaag agcacagcag ctgggagggc aggaagatgg ggatggagcc aggtgtgagg   4740

agaactccag caaggatggg agaggggccc cagggcataa gcagcgtgtc ctgaggggag   4800

tggccagcct ggggcggact agatgtaccg ggaggctcac ccagcaggtc cacgaggatg   4860

gagttgccca gcagcagcga gaagcccatg agcgcccaag gcaggaacgg tgcctggaaa   4920

gtgagcaggc cgaagaagtt gaccctcacc cgagggctgc ggcggctcca cacgtacacc   4980

agcatggcca tgagggcctg gcccaggaag aacaggctgc ccaggagtcc cagcagctgg   5040

gccagagtca aggtgctccg gtgcaggcct cagcccaagc ccagggcccc tctgacttcc   5100

caagaccctg gaattcttcc cctcatctcc cctatgtgct attccctcat caagatgagc   5160

cagtccaata aaggcgacac actccacggg c                                  5191
```

<210> SEQ ID NO 44
<211> LENGTH: 385
<212> TYPE: PRT
<213> ORGANISM: Homo sapiens

<400> SEQUENCE: 44

```
Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Pro Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270
```

```
Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Arg Leu Ala Asn Thr Ala Pro Ala
    370                 375                 380

Trp
385


<210> SEQ ID NO 45
<211> LENGTH: 5427
<212> TYPE: DNA
<213> ORGANISM: Homo sapiens

<400> SEQUENCE: 45

gccccccccg ccgccgctct cgggctccgg ccgggtctcg cgcgccgtct tctcgagagg     60

ggcatcgcgc cgcccggcgc gcgccgcccc cctgcctcgc ggcgcggggt ctcgcgggcc    120

ccgctcccgc cctccgctcg cctggcccgg accggaagcg gcgccgcacg gcctgggcct    180

ggcgcggggg gcgggcaccg gggcccggtc ggacatgggc aagaagcaca agaagcacaa    240

gtcggacaaa cacctctacg aggagtatgt agagaagccc ttgaagctgg tcctcaaagt    300

aggagggaac gaagtcaccg aactctccac gggcagctcg gggcacgact ccagcctctt    360

cgaagacaaa aacgatcatg acaaacacaa ggacagaaag cggaaaaaga gaaagaaagg    420

agagaagcag attccagggg aagaaaaggg gagaaaacgg agaagagtta aggaggataa    480

aaagaagcga gatcgagacc gggtggagaa tgaggcagaa aaagatctcc agtgtcacgc    540

ccctgtgaga ttagacttgc ctcctgagaa gcctctcaca agctctttag ccaaacaaga    600

agaagtagaa cagacacccc ttcaagaagc tttgaatcaa ctgatgagac aattgcagag    660

aaaagatcca agtgctttct tttcatttcc tgtgactgat tttattgctc ctggctactc    720

catgatcatt aaacacccaa tggattttag taccatgaaa gaaaagatca agaacaatga    780

ctatcagtcc atagaagaac taaaggataa cttcaaacta atgtgtacta atgccatgat    840

ttacaataaa ccagagacca tttattataa agctgcaaag aagctgttgc actcaggaat    900

gaaaattctt agccaggaaa gaattcagag cctgaagcag agcatagact tcatggctga    960

cttgcagaaa actcgaaagc agaaagatgg aacagacacc tcacagagtg gggaggacgg   1020

aggctgctgg cagagagaga gagaggactc tggagatgcc gaagcacacg ccttcaagag   1080

tcccagcaaa gaaaataaaa agaaagacaa agatatgctt gaagataagt ttaaaagcaa   1140

taatttagag agagagcagg agcagcttga ccgcatcgtg aaggaatctg gaggaaagct   1200

gaccaggcgg cttgtgaaca gtcagtgcga atttgaaaga agaaaaccag atggaacaac   1260

gacgttggga cttctccatc ctgtggatcc cattgtagga gagccaggct actgccctgt   1320

gagactggga atgacaactg gaagacttca gtctggagtg aatactttgc aggggttcaa   1380
```

-continued

```
agaggataaa aggaacaaag tcactccagt gttatatttg aattatgggc cctacagttc   1440
ttatgcaccg cattatgact ccacatttgc aaatatcagc aaggatgatt ctgatttaat   1500
ctattcaacc tatggggaag actctgatct tccaagtgat ttcagcatcc atgagttttt   1560
ggccacgtgc caagattatc cgtatgtcat ggcagatagt ttactggatg ttttaacaaa   1620
aggagggcat tccaggaccc tacaagagat ggagatgtca ttgcctgaag atgaaggcca   1680
tactaggaca cttgacacag caaaagaaat ggagcagatt acagaagtag agccaccagg   1740
gcgtttggac tccagtactc aagacaggct catagcgctg aaagcagtaa caaattttgg   1800
cgttccagtt gaagtttttg actctgaaga agctgaaata ttccagaaga aacttgatga   1860
gaccaccaga ttgctcaggg aactccagga agcccagaat gaacgtttga gcaccagacc   1920
ccctccgaac atgatctgtc tcttgggtcc ctcatacaga gaaatgcatc ttgctgaaca   1980
agtgaccaat aatcttaaag aacttgcaca gcaagtaact ccaggtgata tcgtaagcac   2040
gtatggagtt cgaaaagcaa tggggatttc cattccttcc cccgtcatgg aaaacaactt   2100
tgtggatttg acagaagaca ctgaagaacc taaaaagacg gatgttgctg agtgtggacc   2160
tggtggaagt tgaggctgcc tggtatttga ttatatatta tgtacatact ttttcattct   2220
taacttagaa atgcttttca gaagatatta aatatttgta aattgtgttt ttaattaaac   2280
tttggaacag cgaatttgga tgttccagag gttggacttg tattaggtaa taaagctgga   2340
cctgggactc gtgaggaagg aatgtgcttg gggctgttgc catacctgtg cagcattctt   2400
tcaaaatagt gccttccaat gcttcttcct tatgtcccac agacaggatc atcactaaga   2460
agcgttctta aaacggcccc atccagtgag attttccgtt atacgaacat acttgaaata   2520
attttagaat ttactactgt ggttctgccc ctgcataccc agtgggaatg atgcccttgt   2580
atgggtaatt aggcacctcc cacccacccc tgacaaaagc acactgggag ttttatagca   2640
ctgtcacatg gctagtgttc tttttggtt ttttccgttt tttaaagaaa gaggagttac   2700
ttagtactat agcaaagtaa taagccaaat aagataaact aagtcatcct tgaatagatc   2760
agggaattac cagattacca aaaggtgaca tttctacttt acttactgtt tatctgaaat   2820
acaaaggtca agtacccaag gagttgaact ctaagtagga gaccacaaga ttcatggccc   2880
ccttttatca gcaagctgag ataaatggtg attttgctga atcggtatag aacctgttat   2940
acacaaggga aaaaaatcag gatggagata gatagataga tagccttgtt cagtgaacaa   3000
attaagtttg aaggccctta tacaatcctt ctataaatca cccaggcagg aagccatttg   3060
atttctatta ttttcctgac tttgaaaatt aattagtatt taggaagaac aaatagggta   3120
aaggaaaatt aattccctca aaagacttaa aatcttatgc taaaagagtc aaattttcaa   3180
gttgtttgag tctactttta atctctagtg agttcatgag gaccacgaaa ataaaatacc   3240
ttcagatatt tgagtttttc aaattgctaa tttaatgtat aaaaagcagc taaacactgg   3300
tactttataa aaatgaaaca gcattttgaa acaaatgtta cagatctata aatattcatt   3360
atatagaata aaccctagtt acttgcatgc accacctcaa atcatatttc tttacactga   3420
cctattatat acacaaagta tacagtggtt aatgatcttc tcttctgttt gtttgtttgt   3480
ttgtttgtta ggaaatttcc tcaataagcc agaaaacctt aggtattatt ttcacaaaag   3540
ttaactcagg agaaattgta aggaagtcct tgacccatgg agaaggtcac tgtttgtttg   3600
tttgttagat acgtgtgtct gtcataaaac aaaatgacac cagtaattac ttggtaattt   3660
aaaaacaagt tcataaaaag aaaatacctg caggtaattt ttatggtcag ttatattcta   3720
taacctgaac actgaaaact aaaaactttt acttacaaac tattattatc tgagcacagc   3780
```

```
acagtgcttt gctttaattg gaaataaaaa tgcatgagtg agtggtagtc agttatttgt   3840

taaactccca actggggttt ctgttgttac tgaagaaaaa aacaaatatt ccaagagtac   3900

aaatatgctg acctcagaga ggcccagtgc actaatgtgt ttctatgtta tattagcaac   3960

agaaaccttc ctgacttgcc aggagagccc ccgccgggca gccctggtca ctgctagatc   4020

ttgagagcac agatttcagt atagtattca tgtgaaacca gcccttcatg taaaaagttt   4080

tggtgtgtaa aaaaggcaac ttaagcgagg ctaattgccc ttaccagcat tgttgccatg   4140

aaattccttt atacagcaag ttcttctatt catactgatt ccacttatgt gcagcacatg   4200

agagctgcca ctagtctacc cagcaccttt gtgcaaatta gaatacacct gcccttcctc   4260

gggctgataa agccacacga cacagcacag gcagacaggt tcaattttcg ttccctccac   4320

cgccaccccc gcacttagct gtactcttaa tttgcagccc ggggcaactc atcccaggac   4380

cccaacaagt ctggtcagtc acccaatctg caaccctgta taatcatctt gtaaaggctc   4440

ctgtatgcaa gactttgtgt agaactttac ggggttcatg gggacaccta gctaagaatc   4500

cctgctatgt agggaaactg agtgcattag aaatcctggc gatgctctgg tgatgaggcc   4560

accggttaag tcttccggtt atgaagtcca ttcagaaaaa gtcacgggca gtttggtcat   4620

ttctcaccct gttgttacag ttaggttgac tttcaattcc ttgggaagtt gaagcacagt   4680

aagacacatc cccaaaacct ggctttttgc atttgccttg actcacgcag tttcagagca   4740

agaacggctc agcatttgtg agggggcggg cttcccagat ccaggagcct ctgcatgcac   4800

ccatgcggag tagatccttc tagttttgaa gctctccaga gttagctgtg aagactaaag   4860

gaaagaagag atgcactcac aggttgtcca agttgtctct aaacagactc cattcctttc   4920

tggtaagaaa agtaagatac agttgaagga cggcagggga gaacgcaaag atgtgtgagt   4980

aatcaaggaa gaggtgaaag gccgcacctt actttcaaag cacctctctc cagaatgctt   5040

gcctcacaag ctgcctcatt caaaggcaag gctctgctgc tccccgcctt cttgctgtga   5100

ccacattcct caggactcta tccccacagc cagctgaccc cataagctga tgctagacag   5160

tagtcctcct tacatgtcag tggttaaaaa ggcagagcat acactggagg gaagagattt   5220

atgtctagtg tctgaaaagt cattcaaaag gataaaaacc ccattaatgt attcatttaa   5280

aacaaacatg ccagacaagg caaaaagtaa cagtgttaat tgtggtgttt ttctctctac   5340

ctgtttgaaa ccgtttacag atgtaaaaca cccctttcag cttcatttac cagaatgcct   5400

ctgtgagaaa tgctgtcatt gccaggc                                       5427
```

<210> SEQ ID NO 46
<211> LENGTH: 652
<212> TYPE: PRT
<213> ORGANISM: Homo sapiens

<400> SEQUENCE: 46

```
Met Gly Lys Lys His Lys Lys His Lys Ser Asp Lys His Leu Tyr Glu
1               5                   10                  15

Glu Tyr Val Glu Lys Pro Leu Lys Leu Val Leu Lys Val Gly Gly Asn
            20                  25                  30

Glu Val Thr Glu Leu Ser Thr Gly Ser Ser Gly His Asp Ser Ser Leu
        35                  40                  45

Phe Glu Asp Lys Asn Asp His Asp Lys His Lys Asp Arg Lys Arg Lys
    50                  55                  60

Lys Arg Lys Lys Gly Glu Lys Gln Ile Pro Gly Glu Glu Lys Gly Arg
65                  70                  75                  80
```

-continued

```
Lys Arg Arg Arg Val Lys Glu Asp Lys Lys Lys Arg Asp Arg Asp Arg
                85                  90                  95

Val Glu Asn Glu Ala Glu Lys Asp Leu Gln Cys His Ala Pro Val Arg
            100                 105                 110

Leu Asp Leu Pro Pro Glu Lys Pro Leu Thr Ser Ser Leu Ala Lys Gln
        115                 120                 125

Glu Glu Val Glu Gln Thr Pro Leu Gln Glu Ala Leu Asn Gln Leu Met
    130                 135                 140

Arg Gln Leu Gln Arg Lys Asp Pro Ser Ala Phe Phe Ser Phe Pro Val
145                 150                 155                 160

Thr Asp Phe Ile Ala Pro Gly Tyr Ser Met Ile Ile Lys His Pro Met
                165                 170                 175

Asp Phe Ser Thr Met Lys Glu Lys Ile Lys Asn Asn Asp Tyr Gln Ser
            180                 185                 190

Ile Glu Glu Leu Lys Asp Asn Phe Lys Leu Met Cys Thr Asn Ala Met
        195                 200                 205

Ile Tyr Asn Lys Pro Glu Thr Ile Tyr Tyr Lys Ala Ala Lys Lys Leu
    210                 215                 220

Leu His Ser Gly Met Lys Ile Leu Ser Gln Glu Arg Ile Gln Ser Leu
225                 230                 235                 240

Lys Gln Ser Ile Asp Phe Met Ala Asp Leu Gln Lys Thr Arg Lys Gln
                245                 250                 255

Lys Asp Gly Thr Asp Thr Ser Gln Ser Gly Glu Asp Gly Gly Cys Trp
            260                 265                 270

Gln Arg Glu Arg Glu Asp Ser Gly Asp Ala Glu Ala His Ala Phe Lys
        275                 280                 285

Ser Pro Ser Lys Glu Asn Lys Lys Lys Asp Lys Asp Met Leu Glu Asp
    290                 295                 300

Lys Phe Lys Ser Asn Asn Leu Glu Arg Glu Gln Glu Gln Leu Asp Arg
305                 310                 315                 320

Ile Val Lys Glu Ser Gly Gly Lys Leu Thr Arg Arg Leu Val Asn Ser
                325                 330                 335

Gln Cys Glu Phe Glu Arg Arg Lys Pro Asp Gly Thr Thr Thr Leu Gly
            340                 345                 350

Leu Leu His Pro Val Asp Pro Ile Val Gly Glu Pro Gly Tyr Cys Pro
        355                 360                 365

Val Arg Leu Gly Met Thr Thr Gly Arg Leu Gln Ser Gly Val Asn Thr
    370                 375                 380

Leu Gln Gly Phe Lys Glu Asp Lys Arg Asn Lys Val Thr Pro Val Leu
385                 390                 395                 400

Tyr Leu Asn Tyr Gly Pro Tyr Ser Ser Tyr Ala Pro His Tyr Asp Ser
                405                 410                 415

Thr Phe Ala Asn Ile Ser Lys Asp Asp Ser Asp Leu Ile Tyr Ser Thr
            420                 425                 430

Tyr Gly Glu Asp Ser Asp Leu Pro Ser Asp Phe Ser Ile His Glu Phe
        435                 440                 445

Leu Ala Thr Cys Gln Asp Tyr Pro Tyr Val Met Ala Asp Ser Leu Leu
    450                 455                 460

Asp Val Leu Thr Lys Gly Gly His Ser Arg Thr Leu Gln Glu Met Glu
465                 470                 475                 480

Met Ser Leu Pro Glu Asp Glu Gly His Thr Arg Thr Leu Asp Thr Ala
                485                 490                 495
```

```
Lys Glu Met Glu Gln Ile Thr Glu Val Glu Pro Pro Gly Arg Leu Asp
            500                 505                 510

Ser Ser Thr Gln Asp Arg Leu Ile Ala Leu Lys Ala Val Thr Asn Phe
        515                 520                 525

Gly Val Pro Val Glu Val Phe Asp Ser Glu Glu Ala Glu Ile Phe Gln
    530                 535                 540

Lys Lys Leu Asp Glu Thr Thr Arg Leu Leu Arg Glu Leu Gln Glu Ala
545                 550                 555                 560

Gln Asn Glu Arg Leu Ser Thr Arg Pro Pro Pro Asn Met Ile Cys Leu
                565                 570                 575

Leu Gly Pro Ser Tyr Arg Glu Met His Leu Ala Glu Gln Val Thr Asn
            580                 585                 590

Asn Leu Lys Glu Leu Ala Gln Gln Val Thr Pro Gly Asp Ile Val Ser
        595                 600                 605

Thr Tyr Gly Val Arg Lys Ala Met Gly Ile Ser Ile Pro Ser Pro Val
    610                 615                 620

Met Glu Asn Asn Phe Val Asp Leu Thr Glu Asp Thr Glu Glu Pro Lys
625                 630                 635                 640

Lys Thr Asp Val Ala Glu Cys Gly Pro Gly Gly Ser
                645                 650


<210> SEQ ID NO 47
<211> LENGTH: 6354
<212> TYPE: DNA
<213> ORGANISM: Homo sapiens

<400> SEQUENCE: 47

agtggcggct acgcgcgcgg gggtgcgcgc gggaacgacc gggaaacacc gcgagggccg      60

gggtgggcca ggctgtgggg acgacgggct gcgacgatgg ccgcagcggc gggcggcggc     120

gggccgggga cagcggtagg cgccacgggc tcggggattg cggcggcagc cgcaggccta     180

gctgtttatc gacggaagga tgggggcccg gccaccaagt tttgggagag cccggagacg     240

gtgtcccagc tggattcggt gcgggtctgg ctgggcaagc actacaagaa gtatgttcat     300

gcggatgctc ctaccaataa aacactggct gggctggtgg tgcagcttct tcagttccag     360

gaagatgcct ttgggaagca tgtcaccaac ccggccttca ccaaactccc tgcaaagtgt     420

ttcatggatt tcaaagctgg aggcgcctta tgtcacattc ttggggctgc ttacaagtat     480

aaaaatgaac agggatggcg gaggtttgac ctacagaacc catctcgaat ggatcgtaat     540

gtggaaatgt ttatgaacat tgaaaaaaca ttggtgcaga acaattgttt gaccagaccc     600

aacatctacc tcattccaga cattgatctg aagttggcta acaaattgaa agatatcatc     660

aaacgacatc agggaacatt tacggatgag aagtcaaaag cttcccacca catttaccca     720

tattcttcct cacaagacga tgaagaatgg ttgagaccgg tgatgagaaa agagaagcaa     780

gtgttagtgc attggggctt ttacccagac agctatgata cttgggtcca tagtaatgat     840

gttgatgctg aaattgaaga tccaccaatt ccagaaaaac catggaaggt tcatgtgaaa     900

tggattttgg acactgatat tttcaatgaa tggatgaatg aggaggatta tgaggtggat     960

gaaaatagga agcctgtgag ttttcgtcag cggatttcaa ccaagaatga agagccagtc    1020

agaagtccag aaagaagaga tagaaaagca tcagctaatg ctcgaaagag gaaacattcg    1080

ccttcgcctc cccctccgac accaacagaa tcacggaaga agagtgggaa gaaaggccaa    1140

gctagccttt atgggaagcg cagaagtcag aaagaggaag atgagcaaga agatctaacc    1200

aaggatatgg aagacccaac acctgtaccc aatatagaag aagtagtact tcccaaaaat    1260
```

```
gtgaacctaa agaaagatag tgaaaataca cctgttaaag gaggaactgt agcggatcta   1320
gatgagcagg atgaagaaac agtcacagca ggaggaaagg aagatgaaga tcctgccaaa   1380
ggtgatcaga gtcgatcagt tgaccttggg gaagataatg tgacagagca gaccaatcac   1440
attattattc ctagttatgc atcatggttt gattataact gtattcatgt gattgaacgg   1500
cgtgctcttc ctgagttctt caatggaaaa aacaaatcca agactccaga aatatacttg   1560
gcatatcgaa attttatgat tgacacgtat cgtctaaacc cccaagagta tttaactagc   1620
actgcttgtc ggaggaactt gactggagat gtgtgtgctg tgatgagggt ccatgccttt   1680
ttagagcagt ggggactcgt taattaccaa gttgacccgg aaagtagacc catggcaatg   1740
ggacctcctc ctactcctca ttttaatgta ttagctgata ccccctctgg gcttgtgcct   1800
ctgcatcttc gatcacctca ggttcctgct gctcaacaga tgctaaattt tcctgagaaa   1860
aacaaggaaa aaccagttga tttgcagaac tttggtctcc gtactgacat ttactccaag   1920
aaaacattag caaagagtaa aggtgctagt gctggaagag aatggactga acaggagacc   1980
cttctactcc tggaggccct ggagatgtac aaggatgatt ggaacaaagt gtcggaacat   2040
gttggaagtc gtactcagga tgaatgcatc ctccactttt tgagacttcc cattgaggac   2100
ccataccttg agaattcaga tgcttccctt gggcctttgg cctaccagcc tgtccccttc   2160
agtcagtcag gaaatccagt tatgagtact gttgcttttt tggcatctgt ggtggaccct   2220
cgcgtggcat ctgctgcagc aaaagcggct ttggaggagt tttctcgggt ccgggaggag   2280
gtaccactgg aattggttga agctcatgtc aagaaagtac aagaagcagc acgagcctct   2340
gggaaagtgg atcccaccta cggtctggag agcagctgca ttgcaggcac agggcccgat   2400
gagccagaga agcttgaagg agctgaagag gaaaaaatgg aagccgaccc tgatggtcag   2460
cagcctgaaa aggcagaaaa taaagtggaa aatgaaacgg atgaaggtga taaagcacaa   2520
gatggagaaa atgaaaaaaa tagtgaaaag gaacaggata gtgaagtgag tgaggatacc   2580
aaatcagaag aaaaggagac tgaagagaac aaagaactca ctgatacatg taaagaaaga   2640
gaaagtgata ctgggaagaa gaaagtagaa catgaaattt ccgaaggaaa tgttgccaca   2700
gccgcagcag ctgctcttgc ctcagcggct accaaagcca agcacctggc tgcagtggaa   2760
gaaagaaaga tcaagtccct ggtagctctc ttggttgaga cacaaatgaa gaaactagag   2820
atcaaacttc gacattttga agagctggaa actatcatgg acagagagaa agaagctcta   2880
gaacaacaga ggcagcagtt gcttactgaa cgccaaaact tccacatgga acagctgaag   2940
tatgctgaat tacgagcacg acagcaaatg gaacagcagc agcatggcca gaaccctcaa   3000
caggcacacc agcactcagg aggacctggc ctggccccac ttggagcagc agggcaccct   3060
ggcatgatgc ctcatcaaca gcccccctccc taccctctga tgcaccacca gatgccacca   3120
cctcatccac cccagccagg tcagatacca ggcccaggtt ccatgatgcc cgggcagcac   3180
atgccaggcc gcatgattcc cactgttgca gccaacatcc acccctctgg gagtggccct   3240
acccctcctg gcatgccacc aatgccagga aacatcttag gaccccgggt accccctgaca   3300
gcacctaacg gcatgtatcc ccctccacca cagcagcagc caccgccacc accacctgca   3360
gatggggtcc ctccgcctcc tgctcctggc ccgccagcct cagctgctcc ttagcctgga   3420
agatgcaggg aacctccacg cccaccacca tgagctggag tggggatgac aagacttgtg   3480
ttcctcaact ttcttgggtt tctttcagga tttttcttct cacagctcca agcacgtgtc   3540
ccgtgcctcc ccactcctct taccaccccct ctctctgaca ctttttgtgt tgggtcctca   3600
```

-continued

```
gccaacactc aaggggaaac ctgtagtgac agtgtgccct ggtcatcctt aaaataacct   3660
gcatctcccc tgtcctggtg tgggagtaag ctgacagttt ctctgcaggt cctgtcaact   3720
ttagcatgct atgtctttac catttttgct ctcttgcagt tttttgcttt gtcttatgct   3780
tctatggata atgctatata atcattatct ttttatcttt ctgttattat tgttttaaag   3840
gagagcatcc taagttaata ggaaccaaaa aataatgatg ggcagaaggg ggggaatagc   3900
cacaggggac aaaccttaag gcattataag tgaccttatt tctgcttttc tgagctaaga   3960
atggtgctga tggtaaagtt tgagactttt gccacacaca aatttgtgaa aattaaacga   4020
gatgtggaag gagaacctca gtgattttat tccctagtga ggcctctgag ggcctccaca   4080
ctgcctggca gaacatacca ctgaactagt atgtgctaga ggagggcaca aacatccgct   4140
ccttccctag gcctgctggc tctggttttc tatgcagatg attcattgga ttgggggtga   4200
gtgttttgtt tttctggggg cagtgtgagc tttgagggtt ggaatattgg gaggcattcc   4260
ttagtttcct caactagcct ggaaagttag gagtctaggg taattacccc caatgagtct   4320
agcctactat tcactgcttt gtgtgcattt ttttctccct ctttaaaaaa ccctttaaaa   4380
gaaaaaaaaa agtagatagt gctaaatatt ttagctcatg aaacttggtt aggatggctg   4440
ggggtacaag tccccaaact acctcttgtt acagtagcca gggagtggaa tttcgtcaac   4500
cggtactttt aaggttagga tgggacggga aaagtgaagc aggatattag ctccttatac   4560
cttctccctt ccatttctga gatctcacat tccatctatc acagggtttt caaagagatg   4620
ctgagggtaa caaggaactc acttggcagt cagagcatca tgctttgagg tttggggtgc   4680
tcaggctggg agggtagaat gccattccag aggacaagcc acaaaaatgc cttaatttga   4740
gctcgtattt acccctgctg ataagtgact tgagagttcc cggttttttc ctcttgtcct   4800
tccctccctt ctgtccttcc atgtgtgggg aaagggtgtt tttggtagag cttggtttcc   4860
aaagcgcctg gctttctcac ttcacattct caagtggcag tttcattatt tagaatgcaa   4920
ggtggacatc ttttggatat ctttttctat atattttcta aagctttaca tatgagaggg   4980
tatagggagg tgtttataaa acacttgaga actttttttcc ttaatatcag aaagcaaaaa   5040
aataaaacca caattgagat ttgcctttca aaccctcagg tttgcctcta accaggtgtc   5100
cctggtcacc atcagagtac tggaatacgg gaaccgagga gaccttggtc cttttgtttt   5160
tgttctggac tcttgggagt ggaaatgaga atgagtttat tcctactgga gcttagttcc   5220
aatgcatttg gctccagaaa gaccccagtg ccttttgaca atggccaggg ttttacctac   5280
ttcctgccag tctttcccaa aggaaactca ttccaaatac ttcttttttc ccctggagtc   5340
cgagaaggaa aatggaattc tggttcatac tgtggtccct tgtaacctca ggtctttaat   5400
gtgatcactt tcaaatttaa aagatccagg tggaaatatt tttactatag taataattct   5460
acaaaatacc tgaattctta acactgttat atttcagtat aagtggtggc tttttctttt   5520
catgtctttg atctggtttt attcctgtaa ttcagccacc tgattttgtg agggggggga   5580
ataatatgtg gtttttgtac aaacatgttt ctcagtgtgt tgttattttg gaaaaaatga   5640
ggggagggag tttggcaaga atggagaaaa tgaatgaaga aggcctaatc tctctctttt   5700
tcagtgaata aatggaacac catttctgga ttctagtccc attctctgca ttcatacacc   5760
agtttcttca tatatcctat gaagaaccta aacatttggc cccacctggt cttggtttga   5820
tcagcagtta aaattctgtg actcgggctt ccttcccgac tgcccacctt catgatgtgt   5880
aaggaacata cattttgagg gtacctcacc cactgttcat ttgcatggtc aaagtgaaaa   5940
tgagtggaag ttctccaaaa atgatggcca acatcctggc acctccaggt gtgagaaata   6000
```

-continued gctttgcttg gtgaatggga taatgtttgt caggatgcag tttagacagt cccaagttgg 6060
aggcaggcct tgagggcaga agattctgtg aaccttgggg gacagctttt gggtactcac 6120
agatataaac cctgtgcaga aaaaaagaag tgattgtttt caggatgctt ataaatcgag 6180
tgaagcaaaa gaagaggatt ctgtgtctgc catgagatga acgccctgct cttcacgaag 6240
gtgtgcctct aataaagaga gccaaagcca gctgggtctc accagattcc tatactttct 6300
caaggatgtt gggggaggtt aatcctttat cgaaactaaa gactggttta taaa 6354

<210> SEQ ID NO 48
<211> LENGTH: 1105
<212> TYPE: PRT
<213> ORGANISM: Homo sapiens

<400> SEQUENCE: 48

Met Ala Ala Ala Ala Gly Gly Gly Gly Pro Gly Thr Ala Val Gly Ala
1 5 10 15

Thr Gly Ser Gly Ile Ala Ala Ala Ala Ala Gly Leu Ala Val Tyr Arg
20 25 30

Arg Lys Asp Gly Gly Pro Ala Thr Lys Phe Trp Glu Ser Pro Glu Thr
35 40 45

Val Ser Gln Leu Asp Ser Val Arg Val Trp Leu Gly Lys His Tyr Lys
50 55 60

Lys Tyr Val His Ala Asp Ala Pro Thr Asn Lys Thr Leu Ala Gly Leu
65 70 75 80

Val Val Gln Leu Leu Gln Phe Gln Glu Asp Ala Phe Gly Lys His Val
85 90 95

Thr Asn Pro Ala Phe Thr Lys Leu Pro Ala Lys Cys Phe Met Asp Phe
100 105 110

Lys Ala Gly Gly Ala Leu Cys His Ile Leu Gly Ala Ala Tyr Lys Tyr
115 120 125

Lys Asn Glu Gln Gly Trp Arg Arg Phe Asp Leu Gln Asn Pro Ser Arg
130 135 140

Met Asp Arg Asn Val Glu Met Phe Met Asn Ile Glu Lys Thr Leu Val
145 150 155 160

Gln Asn Asn Cys Leu Thr Arg Pro Asn Ile Tyr Leu Ile Pro Asp Ile
165 170 175

Asp Leu Lys Leu Ala Asn Lys Leu Lys Asp Ile Ile Lys Arg His Gln
180 185 190

Gly Thr Phe Thr Asp Glu Lys Ser Lys Ala Ser His His Ile Tyr Pro
195 200 205

Tyr Ser Ser Ser Gln Asp Asp Glu Glu Trp Leu Arg Pro Val Met Arg
210 215 220

Lys Glu Lys Gln Val Leu Val His Trp Gly Phe Tyr Pro Asp Ser Tyr
225 230 235 240

Asp Thr Trp Val His Ser Asn Asp Val Asp Ala Glu Ile Glu Asp Pro
245 250 255

Pro Ile Pro Glu Lys Pro Trp Lys Val His Val Lys Trp Ile Leu Asp
260 265 270

Thr Asp Ile Phe Asn Glu Trp Met Asn Glu Glu Asp Tyr Glu Val Asp
275 280 285

Glu Asn Arg Lys Pro Val Ser Phe Arg Gln Arg Ile Ser Thr Lys Asn
290 295 300

-continued

```
Glu Glu Pro Val Arg Ser Pro Glu Arg Arg Asp Arg Lys Ala Ser Ala
305                 310                 315                 320

Asn Ala Arg Lys Arg Lys His Ser Pro Ser Pro Pro Pro Pro Thr Pro
                325                 330                 335

Thr Glu Ser Arg Lys Lys Ser Gly Lys Lys Gly Gln Ala Ser Leu Tyr
            340                 345                 350

Gly Lys Arg Arg Ser Gln Lys Glu Glu Asp Glu Gln Glu Asp Leu Thr
        355                 360                 365

Lys Asp Met Glu Asp Pro Thr Pro Val Pro Asn Ile Glu Glu Val Val
    370                 375                 380

Leu Pro Lys Asn Val Asn Leu Lys Lys Asp Ser Glu Asn Thr Pro Val
385                 390                 395                 400

Lys Gly Gly Thr Val Ala Asp Leu Asp Glu Gln Asp Glu Glu Thr Val
                405                 410                 415

Thr Ala Gly Gly Lys Glu Asp Glu Asp Pro Ala Lys Gly Asp Gln Ser
            420                 425                 430

Arg Ser Val Asp Leu Gly Glu Asp Asn Val Thr Glu Gln Thr Asn His
        435                 440                 445

Ile Ile Ile Pro Ser Tyr Ala Ser Trp Phe Asp Tyr Asn Cys Ile His
    450                 455                 460

Val Ile Glu Arg Arg Ala Leu Pro Glu Phe Phe Asn Gly Lys Asn Lys
465                 470                 475                 480

Ser Lys Thr Pro Glu Ile Tyr Leu Ala Tyr Arg Asn Phe Met Ile Asp
                485                 490                 495

Thr Tyr Arg Leu Asn Pro Gln Glu Tyr Leu Thr Ser Thr Ala Cys Arg
            500                 505                 510

Arg Asn Leu Thr Gly Asp Val Cys Ala Val Met Arg Val His Ala Phe
        515                 520                 525

Leu Glu Gln Trp Gly Leu Val Asn Tyr Gln Val Asp Pro Glu Ser Arg
    530                 535                 540

Pro Met Ala Met Gly Pro Pro Pro Thr Pro His Phe Asn Val Leu Ala
545                 550                 555                 560

Asp Thr Pro Ser Gly Leu Val Pro Leu His Leu Arg Ser Pro Gln Val
                565                 570                 575

Pro Ala Ala Gln Gln Met Leu Asn Phe Pro Glu Lys Asn Lys Glu Lys
            580                 585                 590

Pro Val Asp Leu Gln Asn Phe Gly Leu Arg Thr Asp Ile Tyr Ser Lys
        595                 600                 605

Lys Thr Leu Ala Lys Ser Lys Gly Ala Ser Ala Gly Arg Glu Trp Thr
    610                 615                 620

Glu Gln Glu Thr Leu Leu Leu Leu Glu Ala Leu Glu Met Tyr Lys Asp
625                 630                 635                 640

Asp Trp Asn Lys Val Ser Glu His Val Gly Ser Arg Thr Gln Asp Glu
                645                 650                 655

Cys Ile Leu His Phe Leu Arg Leu Pro Ile Glu Asp Pro Tyr Leu Glu
            660                 665                 670

Asn Ser Asp Ala Ser Leu Gly Pro Leu Ala Tyr Gln Pro Val Pro Phe
        675                 680                 685

Ser Gln Ser Gly Asn Pro Val Met Ser Thr Val Ala Phe Leu Ala Ser
    690                 695                 700

Val Val Asp Pro Arg Val Ala Ser Ala Ala Ala Lys Ala Ala Leu Glu
705                 710                 715                 720
```

-continued

```
Glu Phe Ser Arg Val Arg Glu Glu Val Pro Leu Glu Leu Val Glu Ala
            725                 730                 735

His Val Lys Lys Val Gln Glu Ala Ala Arg Ala Ser Gly Lys Val Asp
            740                 745                 750

Pro Thr Tyr Gly Leu Glu Ser Ser Cys Ile Ala Gly Thr Gly Pro Asp
        755                 760                 765

Glu Pro Glu Lys Leu Glu Gly Ala Glu Glu Glu Lys Met Glu Ala Asp
    770                 775                 780

Pro Asp Gly Gln Gln Pro Glu Lys Ala Glu Asn Lys Val Glu Asn Glu
785                 790                 795                 800

Thr Asp Glu Gly Asp Lys Ala Gln Asp Gly Glu Asn Glu Lys Asn Ser
                805                 810                 815

Glu Lys Glu Gln Asp Ser Glu Val Ser Glu Asp Thr Lys Ser Glu Glu
            820                 825                 830

Lys Glu Thr Glu Glu Asn Lys Glu Leu Thr Asp Thr Cys Lys Glu Arg
        835                 840                 845

Glu Ser Asp Thr Gly Lys Lys Lys Val Glu His Glu Ile Ser Glu Gly
    850                 855                 860

Asn Val Ala Thr Ala Ala Ala Ala Ala Leu Ala Ser Ala Ala Thr Lys
865                 870                 875                 880

Ala Lys His Leu Ala Ala Val Glu Glu Arg Lys Ile Lys Ser Leu Val
                885                 890                 895

Ala Leu Leu Val Glu Thr Gln Met Lys Lys Leu Glu Ile Lys Leu Arg
            900                 905                 910

His Phe Glu Glu Leu Glu Thr Ile Met Asp Arg Glu Lys Glu Ala Leu
        915                 920                 925

Glu Gln Gln Arg Gln Gln Leu Leu Thr Glu Arg Gln Asn Phe His Met
    930                 935                 940

Glu Gln Leu Lys Tyr Ala Glu Leu Arg Ala Arg Gln Gln Met Glu Gln
945                 950                 955                 960

Gln Gln His Gly Gln Asn Pro Gln Gln Ala His Gln His Ser Gly Gly
                965                 970                 975

Pro Gly Leu Ala Pro Leu Gly Ala Ala Gly His Pro Gly Met Met Pro
            980                 985                 990

His Gln Gln Pro Pro Pro Tyr Pro  Leu Met His His Gln  Met Pro Pro
        995                 1000                 1005

Pro His  Pro Pro Gln Pro Gly  Gln Ile Pro Gly Pro  Gly Ser Met
    1010                 1015                 1020

Met Pro  Gly Gln His Met Pro  Gly Arg Met Ile Pro  Thr Val Ala
    1025                 1030                 1035

Ala Asn  Ile His Pro Ser Gly  Ser Gly Pro Thr Pro  Pro Gly Met
    1040                 1045                 1050

Pro Pro  Met Pro Gly Asn Ile  Leu Gly Pro Arg Val  Pro Leu Thr
    1055                 1060                 1065

Ala Pro  Asn Gly Met Tyr Pro  Pro Pro Pro Gln Gln  Gln Pro Pro
    1070                 1075                 1080

Pro Pro  Pro Pro Ala Asp Gly  Val Pro Pro Pro Pro  Ala Pro Gly
    1085                 1090                 1095

Pro Pro  Ala Ser Ala Ala Pro
    1100                 1105
```

<210> SEQ ID NO 49
<211> LENGTH: 2665
<212> TYPE: DNA

<213> ORGANISM: Homo sapiens

<400> SEQUENCE: 49
gtttccggcg cggcccagcg agctcggcaa cctcggcgca gcgagcgcgg gcggccagcc 60
agggccaggg ggcggtggcg gccaaggtcc gaccgggtgc cagctgttcc cagccccccgc 120
ctcgggcccg ccgccggcgc cgccatgggc aagaagcaca agaagcacaa ggccgagtgg 180
cgctcgtcct acgaggatta tgccgacaag cccctggaga agcctctaaa gctagtcctg 240
aaggtcggag gaagtgaagt gactgaactc tcaggatccg gccacgactc cagttactat 300
gatgacaggt cagaccatga gcgagagagg cacaaagaaa agaaaaagaa gaagaagaag 360
aagtccgaga aggagaagca tctggacgat gaggaaagaa ggaagcgaaa ggaagagaag 420
aagcggaagc gagagaggga gcactgtgac acggagggag aggctgacga ctttgatcct 480
gggaagaagg tggaggtgga gccgcccccca gatcggccag tccgagcgtg ccggacacag 540
ccagccgaaa atgagagcac acctattcag caactcctgg aacacttcct ccgccagctt 600
cagagaaaag atccccatgg attttttgct tttcctgtca cggatgcaat tgctcctgga 660
tattcaatga taataaaaca tcccatggat tttggcacca tgaaagacaa aattgtagct 720
aatgaataca agtcagttac ggaatttaag gcagatttca agctgatgtg tgataatgca 780
atgacataca ataggccaga taccgtgtac tacaagttgg cgaagaagat ccttcacgca 840
ggctttaaga tgatgagcaa acaggcagct cttttgggca atgaagatac agctgttgag 900
gaacctgtcc ctgaagttgt accagtacaa gtagaaactg ccaagaaatc caaaaagccg 960
agtagagaag ttatcagctg catgtttgag cctgaaggga atgcctgcag cttgacggac 1020
agtaccgcag aggagcacgt gctggcgctg gtggagcacg cagctgacga agctcgggac 1080
aggatcaacc ggttcctccc aggcggcaag atgggctatc tgaagaggaa cggggacggg 1140
agcctgctct acagcgtggt caacacggcc gagccggacg ctgatgagga ggagacccac 1200
ccggtggact tgagctcgct ctccagtaag ctactcccag gcttcaccac gctgggcttc 1260
aaagacgaga gaagaaacaa agtcaccttt ctctccagtg ccactactgc gctttcgatg 1320
cagaataatt cagtatttgg cgacttgaag tcggacgaga tggagctgct ctactcagcc 1380
tacggagatg agacaggcgt gcagtgtgcg ctgagcctgc aggagtttgt gaaggatgct 1440
gggagctaca gcaagaaagt ggtggacgac ctcctggacc agatcacagg cggagaccac 1500
tctaggacgc tcttccagct gaagcagaga agaaatgttc ccatgaagcc tccagatgaa 1560
gccaaggttg gggacaccct aggagacagc agcagctctg ttctggagtt catgtcgatg 1620
aagtcctatc ccgacgtttc tgtggatatc tccatgctca gctctctggg gaaggtgaag 1680
aaggagctgg accctgacga cagccatttg aacttggatg agacgacgaa gctcctgcag 1740
gacctgcacg aagcacaggc ggagcgcggc ggctctcggc cgtcgtccaa cctcagctcc 1800
ctgtccaacg cctccgagag ggaccagcac cacctgggaa gcccttctcg cctgagtgtc 1860
ggggagcagc cagacgtcac ccacgacccc tatgagtttc ttcagtctcc agagcctgcg 1920
gcctctgcca agacctaact ctagaccacc ttcagctctt ttattttatt tttttagttt 1980
tattttgcac gtgtagagtt tttgtcatca gacaaggact ttgatcctgt cccctttggc 2040
atgcgggaag cagccgcggg gaggtaatga attgtctgtg gtatcatgtc agcagagtct 2100
ccaagcccca cgaaccctga ggagtggagt catacgcgaa ggccatatgg ccatcgtgtc 2160
agcagagaga gtctctgtac acagccccgt gaaccctgag gagtggagtc atacacgaag 2220
ggcgtgtggc catcgtgtca gcagagagag tctctgtaca cagccccgtg aaccctgagg 2280

```
agtggagtca tacgcgaagg gtgtgtggcc aggctgcaga gctgcgtgcc gtttgtgtcc   2340

gagcatcacg tgtggctcca gcccttgttt ctgccagtgt agacacctct gtctgcccca   2400

ctgtcctggg gtcgctcttg ggaggcacag gcatgggtgt gtctggcctc attctgtatc   2460

agtccagtgt gttcctgtca tagtttgtgt ctcccaggca ggccatggta ggggcctcgc   2520

aggggccatt ggggagcaca gggccaggct ggggtgagga gagctcccct gttttctgtt   2580

taattgatga gcctgggaaa ggagtgtgtt ctgcctgccc gttacagtgg agcgttccgt   2640

gtccataaaa cgttttctaa ctggg                                          2665


<210> SEQ ID NO 50
<211> LENGTH: 597
<212> TYPE: PRT
<213> ORGANISM: Homo sapiens

<400> SEQUENCE: 50

Met Gly Lys Lys His Lys Lys His Lys Ala Glu Trp Arg Ser Ser Tyr
1               5                   10                  15

Glu Asp Tyr Ala Asp Lys Pro Leu Glu Lys Pro Leu Lys Leu Val Leu
            20                  25                  30

Lys Val Gly Gly Ser Glu Val Thr Glu Leu Ser Gly Ser Gly His Asp
        35                  40                  45

Ser Ser Tyr Tyr Asp Asp Arg Ser Asp His Glu Arg Glu Arg His Lys
    50                  55                  60

Glu Lys Lys Lys Lys Lys Lys Lys Lys Ser Glu Lys Glu Lys His Leu
65                  70                  75                  80

Asp Asp Glu Glu Arg Arg Lys Arg Lys Glu Glu Lys Lys Arg Lys Arg
                85                  90                  95

Glu Arg Glu His Cys Asp Thr Glu Gly Glu Ala Asp Asp Phe Asp Pro
            100                 105                 110

Gly Lys Lys Val Glu Val Glu Pro Pro Pro Asp Arg Pro Val Arg Ala
        115                 120                 125

Cys Arg Thr Gln Pro Ala Glu Asn Glu Ser Thr Pro Ile Gln Gln Leu
    130                 135                 140

Leu Glu His Phe Leu Arg Gln Leu Gln Arg Lys Asp Pro His Gly Phe
145                 150                 155                 160

Phe Ala Phe Pro Val Thr Asp Ala Ile Ala Pro Gly Tyr Ser Met Ile
                165                 170                 175

Ile Lys His Pro Met Asp Phe Gly Thr Met Lys Asp Lys Ile Val Ala
            180                 185                 190

Asn Glu Tyr Lys Ser Val Thr Glu Phe Lys Ala Asp Phe Lys Leu Met
        195                 200                 205

Cys Asp Asn Ala Met Thr Tyr Asn Arg Pro Asp Thr Val Tyr Tyr Lys
    210                 215                 220

Leu Ala Lys Lys Ile Leu His Ala Gly Phe Lys Met Met Ser Lys Gln
225                 230                 235                 240

Ala Ala Leu Leu Gly Asn Glu Asp Thr Ala Val Glu Glu Pro Val Pro
                245                 250                 255

Glu Val Val Pro Val Gln Val Glu Thr Ala Lys Lys Ser Lys Lys Pro
            260                 265                 270

Ser Arg Glu Val Ile Ser Cys Met Phe Glu Pro Glu Gly Asn Ala Cys
        275                 280                 285

Ser Leu Thr Asp Ser Thr Ala Glu Glu His Val Leu Ala Leu Val Glu
    290                 295                 300
```

His Ala Ala Asp Glu Ala Arg Asp Arg Ile Asn Arg Phe Leu Pro Gly
305 310 315 320

Gly Lys Met Gly Tyr Leu Lys Arg Asn Gly Asp Gly Ser Leu Leu Tyr
325 330 335

Ser Val Val Asn Thr Ala Glu Pro Asp Ala Asp Glu Glu Glu Thr His
340 345 350

Pro Val Asp Leu Ser Ser Leu Ser Ser Lys Leu Leu Pro Gly Phe Thr
355 360 365

Thr Leu Gly Phe Lys Asp Glu Arg Arg Asn Lys Val Thr Phe Leu Ser
370 375 380

Ser Ala Thr Thr Ala Leu Ser Met Gln Asn Asn Ser Val Phe Gly Asp
385 390 395 400

Leu Lys Ser Asp Glu Met Glu Leu Leu Tyr Ser Ala Tyr Gly Asp Glu
405 410 415

Thr Gly Val Gln Cys Ala Leu Ser Leu Gln Glu Phe Val Lys Asp Ala
420 425 430

Gly Ser Tyr Ser Lys Lys Val Val Asp Asp Leu Leu Asp Gln Ile Thr
435 440 445

Gly Gly Asp His Ser Arg Thr Leu Phe Gln Leu Lys Gln Arg Arg Asn
450 455 460

Val Pro Met Lys Pro Pro Asp Glu Ala Lys Val Gly Asp Thr Leu Gly
465 470 475 480

Asp Ser Ser Ser Ser Val Leu Glu Phe Met Ser Met Lys Ser Tyr Pro
485 490 495

Asp Val Ser Val Asp Ile Ser Met Leu Ser Ser Leu Gly Lys Val Lys
500 505 510

Lys Glu Leu Asp Pro Asp Asp Ser His Leu Asn Leu Asp Glu Thr Thr
515 520 525

Lys Leu Leu Gln Asp Leu His Glu Ala Gln Ala Glu Arg Gly Gly Ser
530 535 540

Arg Pro Ser Ser Asn Leu Ser Ser Leu Ser Asn Ala Ser Glu Arg Asp
545 550 555 560

Gln His His Leu Gly Ser Pro Ser Arg Leu Ser Val Gly Glu Gln Pro
565 570 575

Asp Val Thr His Asp Pro Tyr Glu Phe Leu Gln Ser Pro Glu Pro Ala
580 585 590

Ala Ser Ala Lys Thr
595

<210> SEQ ID NO 51
<211> LENGTH: 4811
<212> TYPE: DNA
<213> ORGANISM: Homo sapiens

<400> SEQUENCE: 51
ggcggggccc gagccggaga agatggcggt gcggaagaag gacggcggcc ccaacgtgaa 60
gtactacgag gccgcggaca ccgtgaccca gttcgacaac gtgcggctgt ggctcggcaa 120
gaactacaag aagtatatac aagctgaacc acccaccaac aagtccctgt ctagcctggt 180
tgtacagttg ctacaatttc aggaagaagt ttttggcaaa catgtcagca atgcaccgct 240
cactaaactg ccgatcaaat gtttcctaga tttcaaagcg ggaggctcct tgtgccacat 300
tcttgcagct gcctacaaat tcaagagtga ccagggatgg cggcgttacg atttccagaa 360
tccatcacgc atggaccgca atgtggaaat gtttatgacc attgagaagt ccttggtgca 420

-continued

```
gaataattgc ctgtctcgac ctaacatttt tctgtgccca gaaattgagc ccaaactact    480
agggaaatta aaggacatta tcaagagaca ccagggaaca gtcactgagg ataagaacaa    540
tgcctcccat gttgtgtatc ctgtcccggg gaatctagaa gaagaggaat gggtacgacc    600
agtcatgaag agggataagc aggttcttct gcactggggc tactatcctg acagttacga    660
cacgtggatc ccagcgagtg aaattgaggc atctgtggaa gatgctccaa ctcctgagaa    720
acctaggaag gttcatgcaa agtggatcct ggacaccgac accttcaatg aatggatgaa    780
tgaggaagac tatgaagtaa atgatgacaa aaaccctgtc tcccgccgaa agaagatttc    840
agccaagaca ctgacagatg aggtgaacag cccagattca gatcgacggg acaagaaggg    900
gggaaactat aagaagagga agcgctcccc ctctccttca ccaaccccag aagcaaagaa    960
gaaaaatgct aagaaaggtc cctcaacacc ttacactaag tcaaagcgtg gccacagaga   1020
agaggagcaa gaagacctga caaaggacat ggacgagccc tcaccagtcc ccaatgtaga   1080
agaggtgaca cttcccaaaa cagtcaacac aaagaaagac tcagagtcgg ccccagtcaa   1140
aggcggcacc atgaccgacc tggatgaaca ggaagatgaa agcatggaga cgacgggcaa   1200
ggatgaggat gagaacagta cggggaacaa gggagagcag accaagaatc cagacctgca   1260
tgaggacaat gtgactgaac agacccacca catcatcatt cccagctacg ctgcctggtt   1320
tgactacaat agtgttcatg ccattgagcg gagggctctc cccgagttct tcaacggcaa   1380
gaacaagtcc aagactccag agatctacct ggcctatcga aactttatga ttgacactta   1440
ccgactgaac ccccaagagt atcttacctc taccgcctgc cgccgaaacc tagcgggtga   1500
tgtctgtgcc atcatgaggg tccatgcctt cctagaacag tggggtctta ttaactacca   1560
ggtggatgct gagagtcgac caaccccaat ggggcctccg cctacctctc acttccatgt   1620
cttggctgac acaccatcag ggctggtgcc tctgcagccc aagacacctc agggccgcca   1680
ggttgatgct gataccaagg ctgggcgaaa gggcaaagag ctggatgacc tggtgccaga   1740
gacggctaag ggcaagccag agctgcagac ctctgcttcc caacaaatgc tcaactttcc   1800
tgacaaaggc aaagagaaac caacagacat gcaaaacttt gggctgcgca cagacatgta   1860
cacaaaaaag aatgttccct ccaagagcaa ggctgcagcc agtgccactc gtgagtggac   1920
agaacaggaa accctgcttc tcctggaggc actggaaatg tacaaagatg actggaacaa   1980
agtgtccgag catgtgggaa gccgcacaca ggacgagtgc atcttgcatt ttcttcgtct   2040
tcccattgaa gacccatacc tggaggactc agaggcctcc ctaggccccc tggcctacca   2100
acccatcccc ttcagtcagt cgggcaaccc tgttatgagc actgttgcct tcctggcctc   2160
tgtcgtcgat ccccgagtcg cctctgctgc tgcaaagtca gccctagagg agttctccaa   2220
aatgaaggaa gaggtaccca cggccttggt ggaggcccat gttcgaaaag tggaagaagc   2280
agccaaagta acaggcaagg cggaccctgc cttcggtctg gaaagcagtg gcattgcagg   2340
aaccacctct gatgagcctg agcggattga ggagagcggg aatgacgagg ctcgggtgga   2400
aggccaggcc acagatgaga agaaggagcc caaggaaccc cgagaaggag gggtgctat    2460
agaggaggaa gcaaaagaga aaaccagcga ggctcccaag aaggatgagg agaaagggaa   2520
agaaggcgac agtgagaagg agtccgagaa gagtgatgga gacccaatag tcgatcctga   2580
gaaggagaag gagccaaagg aagggcagga ggaagtgctg aaggaagtgg tggagtctga   2640
gggggaaagg aagacaaagg tggagcggga cattggcgag ggcaacctct ccaccgctgc   2700
tgccgccgcc ctggccgccg ccgcagtgaa agctaagcac ttggctgctg ttgaggaaag   2760
```

```
gaagatcaaa tctttggtgg ccctgctggt ggagacccag atgaaaaagt tggagatcaa   2820
acttcggcac tttgaggagc tggagactat catggaccgg gagcgagaag cactggagta   2880
tcagaggcag cagctcctgg ccgacagaca agccttccac atggagcagc tgaagtatgc   2940
ggagatgagg gctcggcagc agcacttcca acagatgcac caacagcagc agcagccacc   3000
accagccctg cccccaggct cccagcctat ccccccaaca ggggctgctg ggccacccgc   3060
agtccatggc ttggctgtgg ctccagcctc tgtagtccct gctcctgctg gcagtggggc   3120
ccctccagga agtttgggcc cttctgaaca gattgggcag gcagggtcaa ctgcagggcc   3180
acagcagcag caaccagctg gagcccccca gcctggggca gtcccaccag ggttcccccc   3240
ccctggaccc catggcccct caccgttccc caaccaacaa actcctccct caatgatgcc   3300
aggggcagtg ccaggcagcg ggcacccagg cgtggcggcc caaagccctg ccattgtggc   3360
agctgttcag ggcaacctcc tgcccagtgc cagcccactg ccagacccag gcaccccccct  3420
gcctccagac cccacagccc cgagcccagg cacggtcacc cctgtgccac ctccacagtg   3480
aggagccagc cagacatctc tccccctcac cccctgtgga catcacggtt ccaggaacag   3540
cccttccccc accactggga ccctccccag cctggagagt tcatcactac gtaaggaaag   3600
ctccttccgc ccctccaaag ccctcaccat gcctaacaga ggcatgcatt tttatatcag   3660
attattcaag gacttctgtt taaaagatgt ttataatgtc tgggagagag gataggatgg   3720
gaatgctgcc ctaaaggaag ggctggtgaa aggtgtttat acaaggttct attaaccact   3780
tctaagggta cacctccctc caaactactg cattttctat ggattaaaaa aaaaaaaaaa   3840
aagtagattt taaaaagcca cattggagct cccttctacc cactaaaaaa taaccaattt   3900
ttacattttt tgagggggag tgagttttag gaaaggggaa ttaagattcc agggagagct   3960
ctggggatag aacagggcgc agattccatc tctccccaag cccctttta gtgactaagt    4020
caaggcccca actcccctcc cccaccctac gctgagctta ttcgagttca ttcgtactaa   4080
taatccctcc tgcggcttcc tcattgttgc tgttttaggc caccccagct cagccaatga   4140
ttcctttccc tctgaatgtc agttttgttt ttaaaagtca cttgcttagt tgatgtcagc   4200
gtatgtgtat ttggtgggga aaacctaatt tcggggattt ctgtggtagg taataggaga   4260
agaaagggca ctgggggctg ttctccttcc ttccctgggc tgtatccatg gactcctgga   4320
aggcacagag aagggagcta taagaggatg tgaagtttta aaacctgaaa ttgtttttta   4380
aagcacttaa gcacctccat attatgactt ggtgggtcac cccttagctt cctccctctc   4440
ccaccaagac tatgagaact tcagctgata gctgggggct ccccagatga ggatgcaggg   4500
atttgggagc agtggaagag ggtgcccaac cttgggttgg accaaccctt ggctcgcagc   4560
tcaactctgc ttcccgcatt cctgctccac gtgtcccagc ttctcccctg tgacgggaag   4620
gcaggtgtga ctccaggctc tgcactggtt cttcttggtt cctcccacca ggccctttgt   4680
tcctcatgtc cccatgtttc tctccctctg cgtcttagca cctttcttct gttcaaagtt   4740
ttctgtaaat tttctctttt tttctttctt tcttttttt tttttataa attaatttgc     4800
tttcagttcc a                                                         4811
```

<210> SEQ ID NO 52
<211> LENGTH: 1152
<212> TYPE: PRT
<213> ORGANISM: Homo sapiens

<400> SEQUENCE: 52

Met Ala Val Arg Lys Lys Asp Gly Gly Pro Asn Val Lys Tyr Tyr Glu
1 5 10 15

Ala Ala Asp Thr Val Thr Gln Phe Asp Asn Val Arg Leu Trp Leu Gly
20 25 30

Lys Asn Tyr Lys Lys Tyr Ile Gln Ala Glu Pro Pro Thr Asn Lys Ser
35 40 45

Leu Ser Ser Leu Val Val Gln Leu Leu Gln Phe Gln Glu Glu Val Phe
50 55 60

Gly Lys His Val Ser Asn Ala Pro Leu Thr Lys Leu Pro Ile Lys Cys
65 70 75 80

Phe Leu Asp Phe Lys Ala Gly Gly Ser Leu Cys His Ile Leu Ala Ala
85 90 95

Ala Tyr Lys Phe Lys Ser Asp Gln Gly Trp Arg Arg Tyr Asp Phe Gln
100 105 110

Asn Pro Ser Arg Met Asp Arg Asn Val Glu Met Phe Met Thr Ile Glu
115 120 125

Lys Ser Leu Val Gln Asn Asn Cys Leu Ser Arg Pro Asn Ile Phe Leu
130 135 140

Cys Pro Glu Ile Glu Pro Lys Leu Leu Gly Lys Leu Lys Asp Ile Ile
145 150 155 160

Lys Arg His Gln Gly Thr Val Thr Glu Asp Lys Asn Asn Ala Ser His
165 170 175

Val Val Tyr Pro Val Pro Gly Asn Leu Glu Glu Glu Glu Trp Val Arg
180 185 190

Pro Val Met Lys Arg Asp Lys Gln Val Leu Leu His Trp Gly Tyr Tyr
195 200 205

Pro Asp Ser Tyr Asp Thr Trp Ile Pro Ala Ser Glu Ile Glu Ala Ser
210 215 220

Val Glu Asp Ala Pro Thr Pro Glu Lys Pro Arg Lys Val His Ala Lys
225 230 235 240

Trp Ile Leu Asp Thr Asp Thr Phe Asn Glu Trp Met Asn Glu Glu Asp
245 250 255

Tyr Glu Val Asn Asp Asp Lys Asn Pro Val Ser Arg Arg Lys Lys Ile
260 265 270

Ser Ala Lys Thr Leu Thr Asp Glu Val Asn Ser Pro Asp Ser Asp Arg
275 280 285

Arg Asp Lys Lys Gly Gly Asn Tyr Lys Lys Arg Lys Arg Ser Pro Ser
290 295 300

Pro Ser Pro Thr Pro Glu Ala Lys Lys Lys Asn Ala Lys Lys Gly Pro
305 310 315 320

Ser Thr Pro Tyr Thr Lys Ser Lys Arg Gly His Arg Glu Glu Glu Gln
325 330 335

Glu Asp Leu Thr Lys Asp Met Asp Glu Pro Ser Pro Val Pro Asn Val
340 345 350

Glu Glu Val Thr Leu Pro Lys Thr Val Asn Thr Lys Lys Asp Ser Glu
355 360 365

Ser Ala Pro Val Lys Gly Gly Thr Met Thr Asp Leu Asp Glu Gln Glu
370 375 380

Asp Glu Ser Met Glu Thr Thr Gly Lys Asp Glu Asp Glu Asn Ser Thr
385 390 395 400

```
Gly Asn Lys Gly Glu Gln Thr Lys Asn Pro Asp Leu His Glu Asp Asn
                405                 410                 415

Val Thr Glu Gln Thr His His Ile Ile Ile Pro Ser Tyr Ala Ala Trp
            420                 425                 430

Phe Asp Tyr Asn Ser Val His Ala Ile Glu Arg Arg Ala Leu Pro Glu
        435                 440                 445

Phe Phe Asn Gly Lys Asn Lys Ser Lys Thr Pro Glu Ile Tyr Leu Ala
    450                 455                 460

Tyr Arg Asn Phe Met Ile Asp Thr Tyr Arg Leu Asn Pro Gln Glu Tyr
465                 470                 475                 480

Leu Thr Ser Thr Ala Cys Arg Arg Asn Leu Ala Gly Asp Val Cys Ala
                485                 490                 495

Ile Met Arg Val His Ala Phe Leu Glu Gln Trp Gly Leu Ile Asn Tyr
            500                 505                 510

Gln Val Asp Ala Glu Ser Arg Pro Thr Pro Met Gly Pro Pro Pro Thr
        515                 520                 525

Ser His Phe His Val Leu Ala Asp Thr Pro Ser Gly Leu Val Pro Leu
    530                 535                 540

Gln Pro Lys Thr Pro Gln Gly Arg Gln Val Asp Ala Asp Thr Lys Ala
545                 550                 555                 560

Gly Arg Lys Gly Lys Glu Leu Asp Asp Leu Val Pro Glu Thr Ala Lys
                565                 570                 575

Gly Lys Pro Glu Leu Gln Thr Ser Ala Ser Gln Gln Met Leu Asn Phe
            580                 585                 590

Pro Asp Lys Gly Lys Glu Lys Pro Thr Asp Met Gln Asn Phe Gly Leu
        595                 600                 605

Arg Thr Asp Met Tyr Thr Lys Lys Asn Val Pro Ser Lys Ser Lys Ala
    610                 615                 620

Ala Ala Ser Ala Thr Arg Glu Trp Thr Glu Gln Glu Thr Leu Leu Leu
625                 630                 635                 640

Leu Glu Ala Leu Glu Met Tyr Lys Asp Asp Trp Asn Lys Val Ser Glu
                645                 650                 655

His Val Gly Ser Arg Thr Gln Asp Glu Cys Ile Leu His Phe Leu Arg
            660                 665                 670

Leu Pro Ile Glu Asp Pro Tyr Leu Glu Asp Ser Glu Ala Ser Leu Gly
        675                 680                 685

Pro Leu Ala Tyr Gln Pro Ile Pro Phe Ser Gln Ser Gly Asn Pro Val
    690                 695                 700

Met Ser Thr Val Ala Phe Leu Ala Ser Val Val Asp Pro Arg Val Ala
705                 710                 715                 720

Ser Ala Ala Ala Lys Ser Ala Leu Glu Glu Phe Ser Lys Met Lys Glu
                725                 730                 735

Glu Val Pro Thr Ala Leu Val Glu Ala His Val Arg Lys Val Glu Glu
            740                 745                 750

Ala Ala Lys Val Thr Gly Lys Ala Asp Pro Ala Phe Gly Leu Glu Ser
        755                 760                 765

Ser Gly Ile Ala Gly Thr Thr Ser Asp Glu Pro Glu Arg Ile Glu Glu
    770                 775                 780

Ser Gly Asn Asp Glu Ala Arg Val Glu Gly Gln Ala Thr Asp Glu Lys
785                 790                 795                 800

Lys Glu Pro Lys Glu Pro Arg Glu Gly Gly Gly Ala Ile Glu Glu Glu
                805                 810                 815
```

-continued

```
Ala Lys Glu Lys Thr Ser Glu Ala Pro Lys Lys Asp Glu Glu Lys Gly
            820                 825                 830

Lys Glu Gly Asp Ser Glu Lys Glu Ser Glu Lys Ser Asp Gly Asp Pro
        835                 840                 845

Ile Val Asp Pro Glu Lys Glu Lys Glu Pro Lys Glu Gly Gln Glu Glu
    850                 855                 860

Val Leu Lys Glu Val Val Glu Ser Glu Gly Glu Arg Lys Thr Lys Val
865                 870                 875                 880

Glu Arg Asp Ile Gly Glu Gly Asn Leu Ser Thr Ala Ala Ala Ala Ala
                885                 890                 895

Leu Ala Ala Ala Ala Val Lys Ala Lys His Leu Ala Ala Val Glu Glu
            900                 905                 910

Arg Lys Ile Lys Ser Leu Val Ala Leu Leu Val Glu Thr Gln Met Lys
        915                 920                 925

Lys Leu Glu Ile Lys Leu Arg His Phe Glu Glu Leu Glu Thr Ile Met
    930                 935                 940

Asp Arg Glu Arg Glu Ala Leu Glu Tyr Gln Arg Gln Gln Leu Leu Ala
945                 950                 955                 960

Asp Arg Gln Ala Phe His Met Glu Gln Leu Lys Tyr Ala Glu Met Arg
                965                 970                 975

Ala Arg Gln Gln His Phe Gln Gln Met His Gln Gln Gln Gln Gln Pro
            980                 985                 990

Pro Pro Ala Leu Pro Pro Gly Ser  Gln Pro Ile Pro Pro  Thr Gly Ala
        995                 1000                1005

Ala Gly  Pro Pro Ala Val His  Gly Leu Ala Val Ala  Pro Ala Ser
    1010                 1015                1020

Val Val  Pro Ala Pro Ala Gly  Ser Gly Ala Pro Pro  Gly Ser Leu
    1025                 1030                1035

Gly Pro  Ser Glu Gln Ile Gly  Gln Ala Gly Ser Thr  Ala Gly Pro
    1040                 1045                1050

Gln Gln  Gln Gln Pro Ala Gly  Ala Pro Gln Pro Gly  Ala Val Pro
    1055                 1060                1065

Pro Gly  Val Pro Pro Pro Gly  Pro His Gly Pro Ser  Pro Phe Pro
    1070                 1075                1080

Asn Gln  Gln Thr Pro Pro Ser  Met Met Pro Gly Ala  Val Pro Gly
    1085                 1090                1095

Ser Gly  His Pro Gly Val Ala  Ala Gln Ser Pro Ala  Ile Val Ala
    1100                 1105                1110

Ala Val  Gln Gly Asn Leu Leu  Pro Ser Ala Ser Pro  Leu Pro Asp
    1115                 1120                1125

Pro Gly  Thr Pro Leu Pro Pro  Asp Pro Thr Ala Pro  Ser Pro Gly
    1130                 1135                1140

Thr Val  Thr Pro Val Pro Pro  Pro Gln
    1145                 1150
```

<210> SEQ ID NO 53
<211> LENGTH: 7622
<212> TYPE: DNA
<213> ORGANISM: Homo sapiens

<400> SEQUENCE: 53

```
ggttttgcgg cggcaccggg aggggtaagg gaggtgaggg cggcgggtgc cgaagcgacg      60

gcagcggccg cggccggagg agcaatagca gcagccgtgg cggccacggg gcggggcgcg     120

gcggtcggtg accgcggccg gggctgcagg cggcggagcg gctggaagtt ggattccatg     180
```

-continued

```
ggttccaaga gaagaagagc tacctcccct tccagcagtg tcagcgggga ctttgatgat    240
gggcaccatt ctgtgtcaac accaggccca agcaggaaaa ggaggagact ttccaatctt    300
ccaactgtag atcctattgc cgtgtgccat gaactctata ataccatccg agactataag    360
gatgaacagg gcagacttct ctgtgagctc ttcattaggg caccaaagcg aagaaatcaa    420
ccagactatt atgaagtggt ttctcagccc attgacttga tgaaaatcca acagaaacta    480
aaaatggaag agtatgatga tgttaatttg ctgactgctg acttccagct tctttttaac    540
aatgcaaagt cctattataa gccagattct cctgaatata aagccgcttg caaactctgg    600
gatttgtacc ttcgaacaag aaatgagttt gttcagaaag gagaagcaga tgacgaagat    660
gatgatgaag atgggcaaga caatcagggc acagtgactg aaggatcttc tccagcttac    720
ttgaaggaga tcctggagca gcttcttgaa gccatagttg tagctacaaa tccatcagga    780
cgtctcatta gcgaactttt tcagaaactg ccttctaaag tgcaatatcc agattattat    840
gcaataatta aggagcctat agatctcaag accattgccc agaggataca gaatggaagc    900
tacaaaagta ttcatgcaat ggccaaagat atagatctcc tcgcaaaaaa tgccaaaact    960
tataatgagc ctggctctca agtattcaag gatgcaaatt caattaaaaa aatattttat   1020
atgaaaaagg ctgaaattga acatcatgaa atggctaagt caagtcttcg aatgaggact   1080
ccatccaact tggctgcagc cagactgaca ggtccttcac acagtaaagg cagccttggt   1140
gaagagagaa atcccactag caagtattac cgtaataaaa gagcagtaca aggaggtcgt   1200
ttatcagcaa ttacaatggc acttcaatat ggctcagaaa gtgaagaaga tgctgcttta   1260
gctgctgcac gctatgaaga gggagagtca gaagcagaaa gcatcacttc ctttatggat   1320
gtttcaaatc ctttttatca gctttatgac acagttagga gttgtcggaa taaccaaggg   1380
cagctaatag ctgaaccttt ttaccatttg ccttcaaaga aaaaataccc tgattattac   1440
cagcaaatta aaatgcccat atcactacaa cagatccgaa caaaactgaa gaatcaagaa   1500
tatgaaactt tagatcattt ggagtgtgat ctgaatttaa tgtttgaaaa tgccaaacgc   1560
tataatgtgc ccaattcagc catctacaag cgagttctaa aattgcagca agttatgcag   1620
gcaaagaaga aagagcttgc caggagagac gatatcgagg acggagacag catgatctct   1680
tcagccacct ctgatactgg tagtgccaaa agaaaaagta aaaagaacat aagaaagcag   1740
cgaatgaaaa tcttattcaa tgttgttctt gaagctcgag agccaggttc aggcagaaga   1800
ctttgtgacc tatttatggt taaaccatcc aaaaaggact atcctgatta ttataaaatc   1860
atcttggagc caatggactt gaaaataatt gagcataaca tccgcaatga caaatatgct   1920
ggtgaagagg gaatgataga agacatgaag ctgatgttcc ggaatgccag gcactataat   1980
gaggagggct cccaggttta taatgatgca catatcctgg agaagttact caaggagaaa   2040
aggaaagagc tgggcccact gcctgatgat gatgacatgg cttctcccaa actcaagctg   2100
agtaggaaga gtggcatttc tcctaaaaaa tcaaaataca tgactccaat gcagcagaaa   2160
ctaaatgagg tctatgaagc tgtaaagaac tatactgata agaggggtcg ccgcctcagt   2220
gccatatttc tgaggcttcc ctctagatct gagttgcctg actactatct gactattaaa   2280
aagcccatgg acatggaaaa aattcgaagt cacatgatgg ccaacaagta ccaagatatt   2340
gactctatgg ttgaggactt tgtcatgatg tttaataatg cctgtacata caatgagccg   2400
gagtctttga tctacaaaga tgctcttgtt ctacacaaag tcctgcttga aacacgcaga   2460
gacctggagg gagatgagga ctctcatgtc ccaaatgtga ctttgctgat tcaagagctt   2520
```

-continued

```
atccacaatc tttttgtgtc agtcatgagt catcaggatg atgagggaag atgctacagc   2580
gattctttag cagaaattcc tgctgtggat cccaactttc ctaacaaacc accccttaca   2640
tttgacataa ttaggaagaa tgttgaaaat aatcgctacc gtcggcttga tttatttcaa   2700
gagcatatgt ttgaagtatt ggaacgagca agaaggatga atcggacaga ttcagaaata   2760
tatgaagatg cagtagaact tcagcagttt tttattaaaa ttcgtgatga actctgcaaa   2820
aatggagaga ttcttctttc accggcactc agctatacca caaaacattt gcataatgat   2880
gtggagaaag agagaaagga aaaattgcca aaagaaatag aggaagataa actaaaacga   2940
gaagaagaaa aaagagaagc tgaaaagagt gaagattcct ctggtgctgc aggcctctca   3000
ggcttacatc gcacatacag ccaggactgt agctttaaaa acagcatgta ccatgttgga   3060
gattacgtct atgtggaacc tgcagaggcc aacctacaac cacatatcgt ctgtattgaa   3120
agactgtggg aggattcagc tgaaaaagaa gtttttaaga gtgactatta caacaaagtt   3180
ccagttagta aaattctagg caagtgtgtg gtcatgtttg tcaaggaata ctttaagtta   3240
tgcccagaaa acttccgaga tgaggatgtt tttgtctgtg aatcacggta ttctgccaaa   3300
accaaatctt ttaagaaaat taaactgtgg accatgccca tcagctcagt caggtttgtc   3360
cctcgggatg tgcctctgcc tgtggttcgc gtggcctctg tatttgcaaa tgcagataaa   3420
ggtgatgatg agaagaatac agacaactca gaggacagtc gagctgaaga caattttaac   3480
ttggaaaagg aaaaagaaga tgtccctgtg gaaatgtcca atggtgaacc aggttgccac   3540
tactttgagc agctccatta caatgacatg tggctgaagg ttggcgactg tgtcttcatc   3600
aagtcccatg gcctggtgcg tcctcgtgtg ggcagaattg aaaaagtatg ggttcgagat   3660
ggagctgcat atttttatgg ccccatcttc attcacccag aagaaacaga gcatgagccc   3720
acaaaaatgt tctacaaaaa agaagtattt ctgagtaatc tggaagaaac ctgccccatg   3780
acatgtattc tcggaaagtg tgctgtgttg tcattcaagg acttcctctc ctgcaggcca   3840
actgaaatac cagaaaatga cattctgctt tgtgagagcc gctacaatga gagcgacaag   3900
cagatgaaga aattcaaagg attgaagagg ttttcactct ctgctaaagt ggtagatgat   3960
gaaatttact acttcagaaa accaattgtt cctcagaagg agccatcacc tttgctggaa   4020
aagaagatcc agttgctaga agctaaattt gccgagttag aaggtggaga tgatgatatt   4080
gaagagatgg gagaagaaga tagtgagtct accccaaagt ctgccaaagg cagtgcaaag   4140
aaggaaggct ccaaacggaa aatcaacatg agtggctaca tcctgttcag cagtgagatg   4200
agggctgtga ttaaggccca acacccagac tactctttcg gggagctcag ccgcctggtg   4260
gggacagaat ggagaaatct tgagacagcc aagaaagcag aatatgaagg catgatgggt   4320
ggctatccgc caggccttcc acctttgcag ggcccagttg atggccttgt tagcatgggc   4380
agcatgcagc cacttcaccc tggggggcct ccaccccacc atcttccgcc aggtgtgcct   4440
ggcctcccgg gcatcccacc accgggtgtg atgaaccaag gagtggcccc tatggtaggg   4500
actccagcac caggtggaag tccatatgga caacaggtgg gagttttggg gcctccaggg   4560
cagcaggcac cacctccata tcccggccca catccagctg gaccccctgt catacagcag   4620
ccaacaacac ccatgtttgt agctccccca ccaaagaccc agcggcttct tcactcagag   4680
gcctacctga aatacattga aggactcagt gcggagtcca acagcattag caagtgggat   4740
cagacactgg cagctcgaag acgcgacgtc catttgtcga aagaacagga gagccgccta   4800
ccctctcact ggctgaaaag caaaggggcc cacaccacca tggcagatgc cctctggcgc   4860
cttcgagatt tgatgctccg ggacaccctc aacattcgcc aagcatacaa cctagaaaat   4920
```

gtttaatcac atcattacgt ttcttttata tagaagcata aagagttgtg gatcagtagc 4980
cattttagtt actgggggtg gggggaagga acaaaggagg ataattttta ttgcatttta 5040
ctgtacatca caaggccatt tttatatacg gacactttta ataagctatt tcaatttgtt 5100
tgttatatta agttgacttt atcaaataca caaagatttt tttgcatatg tttccttcgt 5160
ttaaaaccag tttcataatt ggttgtatat gtagacttgg agttttatct ttttacttgt 5220
tgccatggaa ctgaaaccat tagaggtttt tgtcttggct tggggttttt gttttcttgg 5280
ttttgggttt ttttatatat atatataaaa gaacaaaatg aaaaaaaaca cacacacaca 5340
agagtttaca gattagttta aattgataat gaaatgtgaa gtttgtccta gtttacatct 5400
tagagagggg agtatacttg tgtttgtttc atgtgcctga atatcttaag ccactttctg 5460
caaaagctgt ttcttacaga tgaagtgctt tctttgaaag gtggttattt aggttttaga 5520
tgtttaatag acacagcaca tttgctctat taactcagag gctcactaca gaaatatgta 5580
atcagtgctg tgcatctgtc tgcagctaat gtacctcctg gacaccagga ggggaaaaag 5640
cactttttca attgtgctga gttagacatc tgtgagttag actatggtgt cagtgatttt 5700
tgcagaacac gtgcacaacc ctgaggtatg tttaatctag gcaggtacgt ttaaggatat 5760
tttgatctat ttataatgaa ttcacaattt atgcctataa atttcagatg atttaaaatt 5820
ttaaacctgt tacattgaaa aacattgaag ttcgtcttga agaaagcatt aaggtatgca 5880
tggaggtgat ttatttttaa acataacacc taacctaaca tgggtaagag agtatggaac 5940
tagatatgag ctgtataaga agcataattg tgaacaagta gattgattgc cttcatatac 6000
aagtatgttt tagtattcct tatttcctta ttatcagatg tattttttct tttaagtttc 6060
aatgttgtta taattctcaa ccagaaattt aatactttct aaaatatttt ttaaatttag 6120
cttgtgcttt tgaattacag gagaagggaa tcataattta ataaaacgct tactagaaag 6180
accattacag atcccaaaca cttgggtttg gtgaccctgt ctttcttata tgaccctaca 6240
ataaacattt gaaggcagca taggatggca gacagtagga acattgtttc acttggcggc 6300
atgtttttga aacctgcttt atagtaactg ggtgattgcc attgtggtag agcttccact 6360
gctgtttata atctgagaga gttaatctca gaggatgctt ttttcctttt aatctgctat 6420
gaatcagtac ccagatgttt aattactgta cttattaaat catgagggca aaagagtgta 6480
gaatggaaaa aagtctcttg tatctagata ctttaaatat gggaggccct ttaacttaat 6540
tgcctttagt caaccactgg atttgaattt gcatcaagta ttttaaataa tattgaattt 6600
aaaaaaatgt attgcagtag tgtgtcagta ccttattgtt aaagtgagtc agataaatct 6660
tcaattcctg gctatttggg caattgaatc atcatggact gtataatgca atcagattat 6720
tttgtttcta gacatccttg aattacacca aagaacatga aatttagttg tggttaaatt 6780
atttatttat ttcatgcatt cattttattt cccttaaggt ctggatgaga cttctttggg 6840
gagcctctaa aaaaattttt cactgggggc cacgtgggtc attagaagcc agagctctcc 6900
tccaggctcc ttcccagtgc ctagaggtgc tataggaaac atagatccag ccaggggctt 6960
ccctaaagca gtgcagcacc ggcccagggc atcactagac aggccctaat taagtttttt 7020
ttaaaaagcc tgtgtattta ttttagaatc atgtttttct gtatattaac ttgggggata 7080
tcgttaatat ttaggatata agatttgagg tcagccatct tcaaaaaaga aaaaaaaatt 7140
gactcaagaa agtacaagta aactatacac cttttttttca taagttttag gaactgtagt 7200
aatgtggctt agaaagtata atggcctaaa tgttttcaaa atgtaagttc ctgtggagaa 7260

```
gaattgttta tattgcaaac ggggggactg aggggaacct gtaggtttaa aacagtatgt   7320

ttgtcagcca actgatttaa aaggccttta actgttttgg ttgttgtttt ttttttaagc   7380

cactctcccc ttcctatgag gaagaattga gaggggcacc tatttctgta aaatccccaa   7440

attggtgttg atgattttga gcttgaatgt tttcatacct gattaaaact tggtttattc   7500

taatttctgt atcatatcat ctgaggttta cgtggtaact agtcttataa catgtatgta   7560

tctttttttt gttgttcatc taaagctttt taatccaaat aaatacagag tttgcaaagt   7620

ga                                                                  7622


<210> SEQ ID NO 54
<211> LENGTH: 1582
<212> TYPE: PRT
<213> ORGANISM: Homo sapiens

<400> SEQUENCE: 54

Met Gly Ser Lys Arg Arg Arg Ala Thr Ser Pro Ser Ser Ser Val Ser
1               5                   10                  15

Gly Asp Phe Asp Asp Gly His His Ser Val Ser Thr Pro Gly Pro Ser
            20                  25                  30

Arg Lys Arg Arg Arg Leu Ser Asn Leu Pro Thr Val Asp Pro Ile Ala
        35                  40                  45

Val Cys His Glu Leu Tyr Asn Thr Ile Arg Asp Tyr Lys Asp Glu Gln
    50                  55                  60

Gly Arg Leu Leu Cys Glu Leu Phe Ile Arg Ala Pro Lys Arg Arg Asn
65                  70                  75                  80

Gln Pro Asp Tyr Tyr Glu Val Val Ser Gln Pro Ile Asp Leu Met Lys
                85                  90                  95

Ile Gln Gln Lys Leu Lys Met Glu Glu Tyr Asp Asp Val Asn Leu Leu
            100                 105                 110

Thr Ala Asp Phe Gln Leu Leu Phe Asn Asn Ala Lys Ser Tyr Tyr Lys
        115                 120                 125

Pro Asp Ser Pro Glu Tyr Lys Ala Ala Cys Lys Leu Trp Asp Leu Tyr
    130                 135                 140

Leu Arg Thr Arg Asn Glu Phe Val Gln Lys Gly Glu Ala Asp Asp Glu
145                 150                 155                 160

Asp Asp Asp Glu Asp Gly Gln Asp Asn Gln Gly Thr Val Thr Glu Gly
                165                 170                 175

Ser Ser Pro Ala Tyr Leu Lys Glu Ile Leu Glu Gln Leu Leu Glu Ala
            180                 185                 190

Ile Val Val Ala Thr Asn Pro Ser Gly Arg Leu Ile Ser Glu Leu Phe
        195                 200                 205

Gln Lys Leu Pro Ser Lys Val Gln Tyr Pro Asp Tyr Tyr Ala Ile Ile
    210                 215                 220

Lys Glu Pro Ile Asp Leu Lys Thr Ile Ala Gln Arg Ile Gln Asn Gly
225                 230                 235                 240

Ser Tyr Lys Ser Ile His Ala Met Ala Lys Asp Ile Asp Leu Leu Ala
                245                 250                 255

Lys Asn Ala Lys Thr Tyr Asn Glu Pro Gly Ser Gln Val Phe Lys Asp
            260                 265                 270

Ala Asn Ser Ile Lys Lys Ile Phe Tyr Met Lys Lys Ala Glu Ile Glu
        275                 280                 285

His His Glu Met Ala Lys Ser Ser Leu Arg Met Arg Thr Pro Ser Asn
    290                 295                 300
```

```
Leu Ala Ala Ala Arg Leu Thr Gly Pro Ser His Ser Lys Gly Ser Leu
305                 310                 315                 320

Gly Glu Glu Arg Asn Pro Thr Ser Lys Tyr Tyr Arg Asn Lys Arg Ala
                325                 330                 335

Val Gln Gly Gly Arg Leu Ser Ala Ile Thr Met Ala Leu Gln Tyr Gly
            340                 345                 350

Ser Glu Ser Glu Glu Asp Ala Ala Leu Ala Ala Ala Arg Tyr Glu Glu
        355                 360                 365

Gly Glu Ser Glu Ala Glu Ser Ile Thr Ser Phe Met Asp Val Ser Asn
    370                 375                 380

Pro Phe Tyr Gln Leu Tyr Asp Thr Val Arg Ser Cys Arg Asn Asn Gln
385                 390                 395                 400

Gly Gln Leu Ile Ala Glu Pro Phe Tyr His Leu Pro Ser Lys Lys Lys
                405                 410                 415

Tyr Pro Asp Tyr Tyr Gln Gln Ile Lys Met Pro Ile Ser Leu Gln Gln
            420                 425                 430

Ile Arg Thr Lys Leu Lys Asn Gln Glu Tyr Glu Thr Leu Asp His Leu
        435                 440                 445

Glu Cys Asp Leu Asn Leu Met Phe Glu Asn Ala Lys Arg Tyr Asn Val
    450                 455                 460

Pro Asn Ser Ala Ile Tyr Lys Arg Val Leu Lys Leu Gln Gln Val Met
465                 470                 475                 480

Gln Ala Lys Lys Lys Glu Leu Ala Arg Arg Asp Asp Ile Glu Asp Gly
                485                 490                 495

Asp Ser Met Ile Ser Ser Ala Thr Ser Asp Thr Gly Ser Ala Lys Arg
            500                 505                 510

Lys Ser Lys Lys Asn Ile Arg Lys Gln Arg Met Lys Ile Leu Phe Asn
        515                 520                 525

Val Val Leu Glu Ala Arg Glu Pro Gly Ser Gly Arg Arg Leu Cys Asp
    530                 535                 540

Leu Phe Met Val Lys Pro Ser Lys Lys Asp Tyr Pro Asp Tyr Tyr Lys
545                 550                 555                 560

Ile Ile Leu Glu Pro Met Asp Leu Lys Ile Ile Glu His Asn Ile Arg
                565                 570                 575

Asn Asp Lys Tyr Ala Gly Glu Glu Gly Met Ile Glu Asp Met Lys Leu
            580                 585                 590

Met Phe Arg Asn Ala Arg His Tyr Asn Glu Glu Gly Ser Gln Val Tyr
        595                 600                 605

Asn Asp Ala His Ile Leu Glu Lys Leu Leu Lys Glu Lys Arg Lys Glu
    610                 615                 620

Leu Gly Pro Leu Pro Asp Asp Asp Met Ala Ser Pro Lys Leu Lys
625                 630                 635                 640

Leu Ser Arg Lys Ser Gly Ile Ser Pro Lys Lys Ser Lys Tyr Met Thr
                645                 650                 655

Pro Met Gln Gln Lys Leu Asn Glu Val Tyr Glu Ala Val Lys Asn Tyr
            660                 665                 670

Thr Asp Lys Arg Gly Arg Arg Leu Ser Ala Ile Phe Leu Arg Leu Pro
        675                 680                 685

Ser Arg Ser Glu Leu Pro Asp Tyr Tyr Leu Thr Ile Lys Lys Pro Met
    690                 695                 700

Asp Met Glu Lys Ile Arg Ser His Met Met Ala Asn Lys Tyr Gln Asp
705                 710                 715                 720
```

```
Ile Asp Ser Met Val Glu Asp Phe Val Met Met Phe Asn Asn Ala Cys
                725                 730                 735

Thr Tyr Asn Glu Pro Glu Ser Leu Ile Tyr Lys Asp Ala Leu Val Leu
            740                 745                 750

His Lys Val Leu Leu Glu Thr Arg Arg Asp Leu Glu Gly Asp Glu Asp
        755                 760                 765

Ser His Val Pro Asn Val Thr Leu Leu Ile Gln Glu Leu Ile His Asn
    770                 775                 780

Leu Phe Val Ser Val Met Ser His Gln Asp Asp Glu Gly Arg Cys Tyr
785                 790                 795                 800

Ser Asp Ser Leu Ala Glu Ile Pro Ala Val Asp Pro Asn Phe Pro Asn
                805                 810                 815

Lys Pro Pro Leu Thr Phe Asp Ile Ile Arg Lys Asn Val Glu Asn Asn
            820                 825                 830

Arg Tyr Arg Arg Leu Asp Leu Phe Gln Glu His Met Phe Glu Val Leu
        835                 840                 845

Glu Arg Ala Arg Arg Met Asn Arg Thr Asp Ser Glu Ile Tyr Glu Asp
    850                 855                 860

Ala Val Glu Leu Gln Gln Phe Phe Ile Lys Ile Arg Asp Glu Leu Cys
865                 870                 875                 880

Lys Asn Gly Glu Ile Leu Leu Ser Pro Ala Leu Ser Tyr Thr Thr Lys
                885                 890                 895

His Leu His Asn Asp Val Glu Lys Glu Arg Lys Glu Lys Leu Pro Lys
            900                 905                 910

Glu Ile Glu Glu Asp Lys Leu Lys Arg Glu Glu Glu Lys Arg Glu Ala
        915                 920                 925

Glu Lys Ser Glu Asp Ser Ser Gly Ala Ala Gly Leu Ser Gly Leu His
    930                 935                 940

Arg Thr Tyr Ser Gln Asp Cys Ser Phe Lys Asn Ser Met Tyr His Val
945                 950                 955                 960

Gly Asp Tyr Val Tyr Val Glu Pro Ala Glu Ala Asn Leu Gln Pro His
                965                 970                 975

Ile Val Cys Ile Glu Arg Leu Trp Glu Asp Ser Ala Glu Lys Glu Val
            980                 985                 990

Phe Lys Ser Asp Tyr Tyr Asn Lys  Val Pro Val Ser Lys  Ile Leu Gly
        995                 1000                1005

Lys Cys  Val Val Met Phe Val  Lys Glu Tyr Phe Lys  Leu Cys Pro
    1010                1015                1020

Glu Asn  Phe Arg Asp Glu Asp  Val Phe Val Cys Glu  Ser Arg Tyr
    1025                1030                1035

Ser Ala  Lys Thr Lys Ser Phe  Lys Lys Ile Lys Leu  Trp Thr Met
    1040                1045                1050

Pro Ile  Ser Ser Val Arg Phe  Val Pro Arg Asp Val  Pro Leu Pro
    1055                1060                1065

Val Val  Arg Val Ala Ser Val  Phe Ala Asn Ala Asp  Lys Gly Asp
    1070                1075                1080

Asp Glu  Lys Asn Thr Asp Asn  Ser Glu Asp Ser Arg  Ala Glu Asp
    1085                1090                1095

Asn Phe  Asn Leu Glu Lys Glu  Lys Glu Asp Val Pro  Val Glu Met
    1100                1105                1110

Ser Asn  Gly Glu Pro Gly Cys  His Tyr Phe Glu Gln  Leu His Tyr
    1115                1120                1125
```

-continued

```
Asn Asp Met Trp Leu Lys Val Gly Asp Cys Val Phe Ile Lys Ser
    1130                1135                1140

His Gly Leu Val Arg Pro Arg Val Gly Arg Ile Glu Lys Val Trp
    1145                1150                1155

Val Arg Asp Gly Ala Ala Tyr Phe Tyr Gly Pro Ile Phe Ile His
    1160                1165                1170

Pro Glu Glu Thr Glu His Glu Pro Thr Lys Met Phe Tyr Lys Lys
    1175                1180                1185

Glu Val Phe Leu Ser Asn Leu Glu Glu Thr Cys Pro Met Thr Cys
    1190                1195                1200

Ile Leu Gly Lys Cys Ala Val Leu Ser Phe Lys Asp Phe Leu Ser
    1205                1210                1215

Cys Arg Pro Thr Glu Ile Pro Glu Asn Asp Ile Leu Leu Cys Glu
    1220                1225                1230

Ser Arg Tyr Asn Glu Ser Asp Lys Gln Met Lys Lys Phe Lys Gly
    1235                1240                1245

Leu Lys Arg Phe Ser Leu Ser Ala Lys Val Val Asp Asp Glu Ile
    1250                1255                1260

Tyr Tyr Phe Arg Lys Pro Ile Val Pro Gln Lys Glu Pro Ser Pro
    1265                1270                1275

Leu Leu Glu Lys Lys Ile Gln Leu Leu Glu Ala Lys Phe Ala Glu
    1280                1285                1290

Leu Glu Gly Gly Asp Asp Asp Ile Glu Glu Met Gly Glu Glu Asp
    1295                1300                1305

Ser Glu Ser Thr Pro Lys Ser Ala Lys Gly Ser Ala Lys Lys Glu
    1310                1315                1320

Gly Ser Lys Arg Lys Ile Asn Met Ser Gly Tyr Ile Leu Phe Ser
    1325                1330                1335

Ser Glu Met Arg Ala Val Ile Lys Ala Gln His Pro Asp Tyr Ser
    1340                1345                1350

Phe Gly Glu Leu Ser Arg Leu Val Gly Thr Glu Trp Arg Asn Leu
    1355                1360                1365

Glu Thr Ala Lys Lys Ala Glu Tyr Glu Gly Met Met Gly Gly Tyr
    1370                1375                1380

Pro Pro Gly Leu Pro Pro Leu Gln Gly Pro Val Asp Gly Leu Val
    1385                1390                1395

Ser Met Gly Ser Met Gln Pro Leu His Pro Gly Gly Pro Pro Pro
    1400                1405                1410

His His Leu Pro Pro Gly Val Pro Gly Leu Pro Gly Ile Pro Pro
    1415                1420                1425

Pro Gly Val Met Asn Gln Gly Val Ala Pro Met Val Gly Thr Pro
    1430                1435                1440

Ala Pro Gly Gly Ser Pro Tyr Gly Gln Gln Val Gly Val Leu Gly
    1445                1450                1455

Pro Pro Gly Gln Gln Ala Pro Pro Pro Tyr Pro Gly Pro His Pro
    1460                1465                1470

Ala Gly Pro Pro Val Ile Gln Gln Pro Thr Thr Pro Met Phe Val
    1475                1480                1485

Ala Pro Pro Pro Lys Thr Gln Arg Leu Leu His Ser Glu Ala Tyr
    1490                1495                1500

Leu Lys Tyr Ile Glu Gly Leu Ser Ala Glu Ser Asn Ser Ile Ser
    1505                1510                1515
```

Lys Trp Asp Gln Thr Leu Ala Ala Arg Arg Arg Asp Val His Leu
1520 1525 1530

Ser Lys Glu Gln Glu Ser Arg Leu Pro Ser His Trp Leu Lys Ser
1535 1540 1545

Lys Gly Ala His Thr Thr Met Ala Asp Ala Leu Trp Arg Leu Arg
1550 1555 1560

Asp Leu Met Leu Arg Asp Thr Leu Asn Ile Arg Gln Ala Tyr Asn
1565 1570 1575

Leu Glu Asn Val
1580

<210> SEQ ID NO 55
<211> LENGTH: 3283
<212> TYPE: DNA
<213> ORGANISM: Homo sapiens

<400> SEQUENCE: 55
gtgcggctgc atcggcggct ccgggaagat ggcggcccgg gcgggtttcc agtctgtggc 60
tccaagcggc ggcgccggag cctcaggagg ggcgggcgcg gctgctgcct tgggcccggg 120
cggaactccg gggcctcctg tgcgaatggg cccggctccg ggtcaagggc tgtaccgctc 180
cccgatgccc ggagcggcct atccgagacc aggtatgttg ccaggcagcc gaatgacacc 240
tcagggacct tccatgggac cccctggcta tgggggggaac ccttcagtcc gacctggcct 300
ggcccagtca gggatggatc agtcccgcaa gagacctgcc cctcagcaga tccagcaggt 360
ccagcagcag gcggtccaaa atcgaaacca caatgcaaag aaaaagaaga tggctgacaa 420
aattctacct caaaggattc gtgaactggt accagaatcc caggcctata tggatctctt 480
ggcttttgaa aggaaactgg accagactat catgaggaaa cggctagata tccaagaggc 540
cttgaaacgt cccatcaagc aaaaacggaa gctgcgaatt ttcatttcta acactttcaa 600
tccggctaag tcagatgccg aggatgggga agggacggtg gcttcctggg agcttcgggt 660
agaaggacgg ctcctggagg attcagcctt gtccaaatat gatgccacta aacaaaagag 720
gaagttctct tcctttttta agtccttggt gattgaactg gacaaagacc tgtatgggcc 780
agacaaccat ctggtagaat ggcacaggac cgccactacc caggagaccg atggctttca 840
ggtgaagcgg ccgggagacg tgaatgtacg gtgtactgtc ctactgatgc tggattacca 900
gcctccccag tttaaattag acccccgcct agctcgactc ctgggcatcc atacccagac 960
tcgtccagtg atcatccaag cactgtggca atatattaag acacataagc tccaggaccc 1020
tcacgagcgg gagtttgtca tctgtgacaa gtacctgcag cagatctttg agtctcaacg 1080
tatgaagttt tcagagatcc ctcagcggct ccatgccttg cttatgccac cagaacctat 1140
catcattaat catgtcatca gtgttgaccc gaatgatcag aaaaagacag cttgttatga 1200
cattgatgtt gaagtggatg acaccttgaa gacccagatg aattcttttc tgctgtccac 1260
tgccagccaa caggagattg ctactctaga caacaagatc catgagacaa tagaaaccat 1320
caaccagctg aagactcagc gggagttcat gctgagcttt gccagagacc ctcagggttt 1380
catcaatgac tggcttcagt cccagtgcag ggacctcaag acaatgactg atgtggtggg 1440
taacccagag gaggagcgcc gagctgagtt ctacttccag ccctgggctc aggaggctgt 1500
gtgccgatac ttctactcca aggtgcagca gagacgacaa gaattagagc aagccctggg 1560
aatccggaat acatagggcc tctcccacag ccctgattcg actgcaccaa ttcttgattt 1620
gggccctgtg ctgcctgcct catagtatct gccttggtct tgcttggggc gttccagggg 1680

```
atgctgttgg ttcaaggaca acaccagaat gaagagggtc tcacaagaca cctgttatcc   1740

tcttctttca ccctatctct tcccacccc agcttccctt tgccccacaa agttcccatg    1800

tgcctgtacc ctcccctggt ctacatagga cctctagata gtgttagaga gagaacatgt   1860

agtggtaatg agtgcttgga atggattggg cctcaggcca ggtggtcttc aaggggacca   1920

gctaactgat cctgcccttc agagacccag gagttgggag ctttcgctcc ttctccaaga   1980

ctcaggcctg tgggcactct ataagctagt tgatcttggc tctcctgata acagaatcca   2040

atttccttcc ttccctccac aggtttggaa caaactctcc cttcacttgt tgccctgtag   2100

cactacagaa accctggttc ttgggctcca ctgagcccca ggtcagtccc cagccctctg   2160

ggttggcctg ctgtcagtgc ttctctcact ccttagttgg ggtccacatc agtattggag   2220

ttttgttctt tattgctccc tcccagacac tccctgtggc tgccctttgt gattccctca   2280

gatctgccct aatcccgggc atttgggtgg gggaatcttg cctttccctt tcagagcccc   2340

agggatctca tctggggaac tgtcattgcc agcagaggct gttccttcct gctgtttgga   2400

gatgtgactc attcattcac tcactccacc ctgcctctgc atcccttaat ggagaaacgg   2460

gcctaaaacc aaacgggtaa aaagccctgg gccatccctg tcttcctgtc ccttgtctgc   2520

ccagttgaca cctactggtg acttctaggg cactgaggag tgaaagcgcc tagggctgga   2580

gaatagcgct gagttgggtt tgtgactctt ccctctccct gcctcacagg attgtgactc   2640

cccagcccct gccctcaaag cttcagaccc ctcaggtagc agcaggacct tgtgatcttg   2700

gccccttgga tctgagatgg tttttgcatc tttccaggag agcctcacat tcttcttcca   2760

ggttgtatca cccccgagtt agcatatccc aggctcgcag actcaacaca gcaagggtgg   2820

gagacagctg ggcacaaagg gggaattccg ttcagcatgg gctctaaacc cacagaactg   2880

acaaagcccc tgcttcccca ccccctcctc aggctcctgc gagcacaccc ccaccccccaa   2940

atccctccct gttctacact ggggacagca gaattttctc cccgtcttcc ccttcctgcc   3000

attttccctc ccttgaaagg ttgacactgg acaaccttgg ggcagctgag ccctggccgc   3060

ctcctggctg gaaccatgag aaggaagctc agtacttccc acagtgtccc tgttgataac   3120

tgtttttatt aactgaattg ttttttcat ggaccaaact ttttttgta ctgtcccctt     3180

attgatgtta cccagtttta ataaaagaat cttctgaagg atgggtcctc ctacctactg   3240

tgagagagct cttccctgag ctcttcttcc ttcaatacca tta                     3283
```

```
<210> SEQ ID NO 56
<211> LENGTH: 515
<212> TYPE: PRT
<213> ORGANISM: Homo sapiens

<400> SEQUENCE: 56

Met Ala Ala Arg Ala Gly Phe Gln Ser Val Ala Pro Ser Gly Gly Ala
1               5                   10                  15

Gly Ala Ser Gly Gly Ala Gly Ala Ala Ala Ala Leu Gly Pro Gly Gly
            20                  25                  30

Thr Pro Gly Pro Pro Val Arg Met Gly Pro Ala Pro Gly Gln Gly Leu
        35                  40                  45

Tyr Arg Ser Pro Met Pro Gly Ala Ala Tyr Pro Arg Pro Gly Met Leu
    50                  55                  60

Pro Gly Ser Arg Met Thr Pro Gln Gly Pro Ser Met Gly Pro Pro Gly
65                  70                  75                  80
```

-continued

```
Tyr Gly Gly Asn Pro Ser Val Arg Pro Gly Leu Ala Gln Ser Gly Met
                85                  90                  95

Asp Gln Ser Arg Lys Arg Pro Ala Pro Gln Gln Ile Gln Gln Val Gln
            100                 105                 110

Gln Gln Ala Val Gln Asn Arg Asn His Asn Ala Lys Lys Lys Lys Met
        115                 120                 125

Ala Asp Lys Ile Leu Pro Gln Arg Ile Arg Glu Leu Val Pro Glu Ser
    130                 135                 140

Gln Ala Tyr Met Asp Leu Leu Ala Phe Glu Arg Lys Leu Asp Gln Thr
145                 150                 155                 160

Ile Met Arg Lys Arg Leu Asp Ile Gln Glu Ala Leu Lys Arg Pro Ile
                165                 170                 175

Lys Gln Lys Arg Lys Leu Arg Ile Phe Ile Ser Asn Thr Phe Asn Pro
            180                 185                 190

Ala Lys Ser Asp Ala Glu Asp Gly Glu Gly Thr Val Ala Ser Trp Glu
        195                 200                 205

Leu Arg Val Glu Gly Arg Leu Leu Glu Asp Ser Ala Leu Ser Lys Tyr
    210                 215                 220

Asp Ala Thr Lys Gln Lys Arg Lys Phe Ser Ser Phe Phe Lys Ser Leu
225                 230                 235                 240

Val Ile Glu Leu Asp Lys Asp Leu Tyr Gly Pro Asp Asn His Leu Val
                245                 250                 255

Glu Trp His Arg Thr Ala Thr Thr Gln Glu Thr Asp Gly Phe Gln Val
            260                 265                 270

Lys Arg Pro Gly Asp Val Asn Val Arg Cys Thr Val Leu Leu Met Leu
        275                 280                 285

Asp Tyr Gln Pro Pro Gln Phe Lys Leu Asp Pro Arg Leu Ala Arg Leu
    290                 295                 300

Leu Gly Ile His Thr Gln Thr Arg Pro Val Ile Ile Gln Ala Leu Trp
305                 310                 315                 320

Gln Tyr Ile Lys Thr His Lys Leu Gln Asp Pro His Glu Arg Glu Phe
                325                 330                 335

Val Ile Cys Asp Lys Tyr Leu Gln Gln Ile Phe Glu Ser Gln Arg Met
            340                 345                 350

Lys Phe Ser Glu Ile Pro Gln Arg Leu His Ala Leu Leu Met Pro Pro
        355                 360                 365

Glu Pro Ile Ile Ile Asn His Val Ile Ser Val Asp Pro Asn Asp Gln
    370                 375                 380

Lys Lys Thr Ala Cys Tyr Asp Ile Asp Val Glu Val Asp Asp Thr Leu
385                 390                 395                 400

Lys Thr Gln Met Asn Ser Phe Leu Leu Ser Thr Ala Ser Gln Gln Glu
                405                 410                 415

Ile Ala Thr Leu Asp Asn Lys Ile His Glu Thr Ile Glu Thr Ile Asn
            420                 425                 430

Gln Leu Lys Thr Gln Arg Glu Phe Met Leu Ser Phe Ala Arg Asp Pro
        435                 440                 445

Gln Gly Phe Ile Asn Asp Trp Leu Gln Ser Gln Cys Arg Asp Leu Lys
    450                 455                 460

Thr Met Thr Asp Val Val Gly Asn Pro Glu Glu Glu Arg Arg Ala Glu
465                 470                 475                 480

Phe Tyr Phe Gln Pro Trp Ala Gln Glu Ala Val Cys Arg Tyr Phe Tyr
                485                 490                 495
```

```
Ser Lys Val Gln Gln Arg Arg Gln Glu Leu Glu Gln Ala Leu Gly Ile
            500                 505                 510

Arg Asn Thr
        515


<210> SEQ ID NO 57
<211> LENGTH: 2167
<212> TYPE: DNA
<213> ORGANISM: Homo sapiens

<400> SEQUENCE: 57

gagtacaacg ccgggccgtg gggagccagg cggcggcggg gctgaggcgg ccgcggggct      60

gaggggagcg gcggggctga ggcgagcggc ggggctgagg cgagcggcgg ggctgaggcg     120

gccgcggggc tgaggcgagc gagcggcggg gctgaggcga gcgagtggcg gggctgaagg     180

gagtcgcggc ggcgctgagg ccagcggcgg agctgtgggg ggcaacggtg ctgaggcggt     240

ggccgcggcc gggcgggttg ggctgacgtg agaagcgccg ccgccgctgg gcctcctcca     300

ttccggcccg cagccccgcg ccctcccagc ctttggcgcc ctcccgcgcg ggcggcgcgc     360

tggcgacggc catggcggtg gcggcggcgc tggcgggccg cggggcgcgc ggcggcaggg     420

gccggccccc gggcgggcgg gcggaggggg cggggccggg gcggcggggg gcccgcgcgg     480

cggcggcggc ggcggcggcg gcagcggcgg cggcggccgg gacaaggcgg aggcgacggc     540

ggcggcggcg gcgcggggcg ctcgggctga tggcggcggc ggccgggccc ggggctgcgc     600

tgtccccgcg gccgtgcgac agcgacccag ccacccccgg agcgcagtcc ccgaaggatg     660

ataatgaaga taattcaaat gatgggaccc agccatccaa aaggaggcga atgggctcag     720

gagatagttc taggagttgt gaaacttcaa gtcaagatct tggttttagt tactatccag     780

cagaaaactt gatagagtac aaatggccac ctgatgaaac aggagaatac tatatgcttc     840

aagaacaagt cagtgaatat ttgggtgtga cctcctttaa aaggaaatat ccagatttag     900

agcgacgaga tttgtctcac aaggagaaac tctacctgag agagctaaat gtcattactg     960

aaactcagtg cactctaggc ttaacagcat tgcgcagtga tgaagtgatt gatttaatga    1020

taaaagaata tccagccaaa catgctgagt attctgttat tctacaagaa aaagaacgtc    1080

aacgaattac agaccattat aaagagtatt cccaaatgca acaacagaat actcagaaag    1140

ttgaagccag taaagtgcct gagtatatta agaaagctgc caaaaaagca gcagaattta    1200

atagcaactt aaaccgggaa cgcatggaag aaagaagagc ttattttgac ttgcagacac    1260

atgttatcca ggtacctcaa gggaagtaca aagttttgcc aacagagcga acaaaggtca    1320

gttcttaccc agtggctctc atccccggac agttccagga atattataag aggtactcac    1380

cagatgagct gcggtatctg ccattaaaca cagccctgta tgagcccccct ctggatcctg    1440

agctccctgc tctagacagt gatggtgatt cagatgatgg cgaagatggt cgaggtgatg    1500

agaaacggaa aaataaaggc acttcggaca gctcctctgg caatgtatct gaagggggaaa   1560

gccctcctga cagccaggag gactctttcc agggaagaca gaaatcaaaa gacaaagctg    1620

ccactccaag aaaagatggt cccaaacgtt ctgtactgtc caagtcagtt cctgggtaca    1680

agccaaaggt cattccaaat gctatatgtg gaatttgtct gaagggtaag gagtccaaca    1740

agaaaggaaa ggctgaatca cttatacact gctcccaatg tgagaatagt ggccatcctt    1800

cttgcctgga tatgacaatg gagcttgttt ctatgattaa gacctaccca tggcagtgta    1860

tggaatgtaa aacatgcatt atatgtggac aaccccacca tgaagaagaa atgatgttct    1920

gtgatatgtg tgacagaggt tatcatactt tttgtgtggg ccttggtgct attccatcag    1980
```

gtcgctggat ttgtgactgt tgtcagcggg cccccccaac acccaggaaa gtgggcagaa 2040
gggggaaaaa cagcaaagag ggataaaata gtttttgact ctaatactgt atatgcattt 2100
aagtggaata tttggtgcca tttacaacat tattttcatg ccaataaaag attttttttg 2160
caaatta 2167

<210> SEQ ID NO 58
<211> LENGTH: 498
<212> TYPE: PRT
<213> ORGANISM: Homo sapiens

<400> SEQUENCE: 58

Met Ala Ala Ala Ala Gly Pro Gly Ala Ala Leu Ser Pro Arg Pro Cys
1 5 10 15

Asp Ser Asp Pro Ala Thr Pro Gly Ala Gln Ser Pro Lys Asp Asp Asn
20 25 30

Glu Asp Asn Ser Asn Asp Gly Thr Gln Pro Ser Lys Arg Arg Arg Met
35 40 45

Gly Ser Gly Asp Ser Ser Arg Ser Cys Glu Thr Ser Ser Gln Asp Leu
50 55 60

Gly Phe Ser Tyr Tyr Pro Ala Glu Asn Leu Ile Glu Tyr Lys Trp Pro
65 70 75 80

Pro Asp Glu Thr Gly Glu Tyr Tyr Met Leu Gln Glu Gln Val Ser Glu
85 90 95

Tyr Leu Gly Val Thr Ser Phe Lys Arg Lys Tyr Pro Asp Leu Glu Arg
100 105 110

Arg Asp Leu Ser His Lys Glu Lys Leu Tyr Leu Arg Glu Leu Asn Val
115 120 125

Ile Thr Glu Thr Gln Cys Thr Leu Gly Leu Thr Ala Leu Arg Ser Asp
130 135 140

Glu Val Ile Asp Leu Met Ile Lys Glu Tyr Pro Ala Lys His Ala Glu
145 150 155 160

Tyr Ser Val Ile Leu Gln Glu Lys Glu Arg Gln Arg Ile Thr Asp His
165 170 175

Tyr Lys Glu Tyr Ser Gln Met Gln Gln Gln Asn Thr Gln Lys Val Glu
180 185 190

Ala Ser Lys Val Pro Glu Tyr Ile Lys Lys Ala Ala Lys Lys Ala Ala
195 200 205

Glu Phe Asn Ser Asn Leu Asn Arg Glu Arg Met Glu Glu Arg Arg Ala
210 215 220

Tyr Phe Asp Leu Gln Thr His Val Ile Gln Val Pro Gln Gly Lys Tyr
225 230 235 240

Lys Val Leu Pro Thr Glu Arg Thr Lys Val Ser Ser Tyr Pro Val Ala
245 250 255

Leu Ile Pro Gly Gln Phe Gln Glu Tyr Tyr Lys Arg Tyr Ser Pro Asp
260 265 270

Glu Leu Arg Tyr Leu Pro Leu Asn Thr Ala Leu Tyr Glu Pro Pro Leu
275 280 285

Asp Pro Glu Leu Pro Ala Leu Asp Ser Asp Gly Asp Ser Asp Asp Gly
290 295 300

Glu Asp Gly Arg Gly Asp Glu Lys Arg Lys Asn Lys Gly Thr Ser Asp
305 310 315 320

Ser Ser Ser Gly Asn Val Ser Glu Gly Glu Ser Pro Pro Asp Ser Gln
325 330 335

```
Glu Asp Ser Phe Gln Gly Arg Gln Lys Ser Lys Asp Lys Ala Ala Thr
            340                 345                 350

Pro Arg Lys Asp Gly Pro Lys Arg Ser Val Leu Ser Lys Ser Val Pro
        355                 360                 365

Gly Tyr Lys Pro Lys Val Ile Pro Asn Ala Ile Cys Gly Ile Cys Leu
    370                 375                 380

Lys Gly Lys Glu Ser Asn Lys Lys Gly Lys Ala Glu Ser Leu Ile His
385                 390                 395                 400

Cys Ser Gln Cys Glu Asn Ser Gly His Pro Ser Cys Leu Asp Met Thr
                405                 410                 415

Met Glu Leu Val Ser Met Ile Lys Thr Tyr Pro Trp Gln Cys Met Glu
            420                 425                 430

Cys Lys Thr Cys Ile Ile Cys Gly Gln Pro His His Glu Glu Glu Met
        435                 440                 445

Met Phe Cys Asp Met Cys Asp Arg Gly Tyr His Thr Phe Cys Val Gly
    450                 455                 460

Leu Gly Ala Ile Pro Ser Gly Arg Trp Ile Cys Asp Cys Cys Gln Arg
465                 470                 475                 480

Ala Pro Pro Thr Pro Arg Lys Val Gly Arg Arg Gly Lys Asn Ser Lys
                485                 490                 495

Glu Gly
```

<210> SEQ ID NO 59
<211> LENGTH: 19
<212> TYPE: RNA
<213> ORGANISM: Artificial Sequence
<220> FEATURE:
<223> OTHER INFORMATION: PLK1

<400> SEQUENCE: 59
gcacauaccg ccugagucu 19

<210> SEQ ID NO 60
<211> LENGTH: 19
<212> TYPE: RNA
<213> ORGANISM: Artificial Sequence
<220> FEATURE:
<223> OTHER INFORMATION: ON-TARGETplus Non-targeting Control

<400> SEQUENCE: 60
ugguuuacau gucgacuaa 19

<210> SEQ ID NO 61
<211> LENGTH: 19
<212> TYPE: RNA
<213> ORGANISM: Artificial Sequence
<220> FEATURE:
<223> OTHER INFORMATION: GPX1 siRNA #1

<400> SEQUENCE: 61
gcaagguacu acuuaucga 19

<210> SEQ ID NO 62
<211> LENGTH: 19
<212> TYPE: RNA
<213> ORGANISM: Artificial Sequence
<220> FEATURE:
<223> OTHER INFORMATION: GPX1 siRNA #2

<400> SEQUENCE: 62
cgccaagaac gaagagauu 19

<210> SEQ ID NO 63
<211> LENGTH: 19
<212> TYPE: RNA
<213> ORGANISM: Artificial Sequence
<220> FEATURE:
<223> OTHER INFORMATION: GPX2 siRNA #1

<400> SEQUENCE: 63
gacaucaagc gccuccuua 19

<210> SEQ ID NO 64
<211> LENGTH: 19
<212> TYPE: RNA
<213> ORGANISM: Artificial Sequence
<220> FEATURE:
<223> OTHER INFORMATION: GPX2 siRNA #2

<400> SEQUENCE: 64
gggccgugcu gauugagaa 19

<210> SEQ ID NO 65
<211> LENGTH: 19
<212> TYPE: RNA
<213> ORGANISM: Artificial Sequence
<220> FEATURE:
<223> OTHER INFORMATION: GPX3 siRNA #1

<400> SEQUENCE: 65
guacggagcc cucaccauu 19

<210> SEQ ID NO 66
<211> LENGTH: 19
<212> TYPE: RNA
<213> ORGANISM: Artificial Sequence
<220> FEATURE:
<223> OTHER INFORMATION: GPX3 siRNA #2

<400> SEQUENCE: 66
ggucagcaac gucaagaug 19

<210> SEQ ID NO 67
<211> LENGTH: 19
<212> TYPE: RNA
<213> ORGANISM: Artificial Sequence
<220> FEATURE:
<223> OTHER INFORMATION: GPX4 siRNA #1

<400> SEQUENCE: 67
gcugcguggu gaagcgcua 19

<210> SEQ ID NO 68
<211> LENGTH: 19
<212> TYPE: RNA
<213> ORGANISM: Artificial Sequence
<220> FEATURE:
<223> OTHER INFORMATION: GPX4 siRNA #2

<400> SEQUENCE: 68
acgaagagau caaagaguu 19

<210> SEQ ID NO 69

<211> LENGTH: 19
<212> TYPE: RNA
<213> ORGANISM: Artificial Sequence
<220> FEATURE:
<223> OTHER INFORMATION: GPX5 siRNA #1

<400> SEQUENCE: 69
uggcguacuu gaagcaauu 19

<210> SEQ ID NO 70
<211> LENGTH: 19
<212> TYPE: RNA
<213> ORGANISM: Artificial Sequence
<220> FEATURE:
<223> OTHER INFORMATION: GPX5 siRNA #2

<400> SEQUENCE: 70
aaucauccuu ccacgacaa 19

<210> SEQ ID NO 71
<211> LENGTH: 19
<212> TYPE: RNA
<213> ORGANISM: Artificial Sequence
<220> FEATURE:
<223> OTHER INFORMATION: GPX6 siRNA #1

<400> SEQUENCE: 71
ccgcaagacu cuaggccuc 19

<210> SEQ ID NO 72
<211> LENGTH: 19
<212> TYPE: RNA
<213> ORGANISM: Artificial Sequence
<220> FEATURE:
<223> OTHER INFORMATION: GPX6 siRNA #2

<400> SEQUENCE: 72
guguauggau auguagaau 19

<210> SEQ ID NO 73
<211> LENGTH: 19
<212> TYPE: RNA
<213> ORGANISM: Artificial Sequence
<220> FEATURE:
<223> OTHER INFORMATION: GPX7 siRNA #1

<400> SEQUENCE: 73
cuggagaagu accgcggau 19

<210> SEQ ID NO 74
<211> LENGTH: 19
<212> TYPE: RNA
<213> ORGANISM: Artificial Sequence
<220> FEATURE:
<223> OTHER INFORMATION: GPX7 siRNA #2

<400> SEQUENCE: 74
aacaauaccu cacgauaua 19

<210> SEQ ID NO 75
<211> LENGTH: 19
<212> TYPE: RNA
<213> ORGANISM: Artificial Sequence
<220> FEATURE:
<223> OTHER INFORMATION: GPX8 siRNA #1

<400> SEQUENCE: 75
agaaauuacu uagggcuga 19

<210> SEQ ID NO 76
<211> LENGTH: 19
<212> TYPE: RNA
<213> ORGANISM: Artificial Sequence
<220> FEATURE:
<223> OTHER INFORMATION: GPX8 siRNA #2

<400> SEQUENCE: 76
cuaaaauucc ucaaaccua 19

<210> SEQ ID NO 77
<211> LENGTH: 19
<212> TYPE: RNA
<213> ORGANISM: Artificial Sequence
<220> FEATURE:
<223> OTHER INFORMATION: GCLC siRNA #1

<400> SEQUENCE: 77
uggcagacaa ugagauuua 19

<210> SEQ ID NO 78
<211> LENGTH: 19
<212> TYPE: RNA
<213> ORGANISM: Artificial Sequence
<220> FEATURE:
<223> OTHER INFORMATION: GCLC siRNA #2

<400> SEQUENCE: 78
ccaucuccau uuauagaaa 19

<210> SEQ ID NO 79
<211> LENGTH: 19
<212> TYPE: RNA
<213> ORGANISM: Artificial Sequence
<220> FEATURE:
<223> OTHER INFORMATION: GCLM siRNA #1

<400> SEQUENCE: 79
cagauauucu uucgucaua 19

<210> SEQ ID NO 80
<211> LENGTH: 19
<212> TYPE: RNA
<213> ORGANISM: Artificial Sequence
<220> FEATURE:
<223> OTHER INFORMATION: GCLM siRNA #2

<400> SEQUENCE: 80
gguauucggu cauugugaa 19

<210> SEQ ID NO 81
<211> LENGTH: 19
<212> TYPE: RNA
<213> ORGANISM: Artificial Sequence
<220> FEATURE:
<223> OTHER INFORMATION: GSS siRNA #1

<400> SEQUENCE: 81
cgacgaacau uugaagaua 19

<210> SEQ ID NO 82

<211> LENGTH: 19
<212> TYPE: RNA
<213> ORGANISM: Artificial Sequence
<220> FEATURE:
<223> OTHER INFORMATION: GSS siRNA #2

<400> SEQUENCE: 82
aaacauauuu gaccagcgu 19

<210> SEQ ID NO 83
<211> LENGTH: 19
<212> TYPE: RNA
<213> ORGANISM: Artificial Sequence
<220> FEATURE:
<223> OTHER INFORMATION: MGST1 siRNA #1

<400> SEQUENCE: 83
aaaugaugcu uaugaguac 19

<210> SEQ ID NO 84
<211> LENGTH: 19
<212> TYPE: RNA
<213> ORGANISM: Artificial Sequence
<220> FEATURE:
<223> OTHER INFORMATION: MGST1 siRNA #2

<400> SEQUENCE: 84
ggaauuggcc uccuguauu 19

<210> SEQ ID NO 85
<211> LENGTH: 19
<212> TYPE: RNA
<213> ORGANISM: Artificial Sequence
<220> FEATURE:
<223> OTHER INFORMATION: MGST3 siRNA #1

<400> SEQUENCE: 85
guguuuacca cccgcguau 19

<210> SEQ ID NO 86
<211> LENGTH: 19
<212> TYPE: RNA
<213> ORGANISM: Artificial Sequence
<220> FEATURE:
<223> OTHER INFORMATION: MGST3 siRNA #2

<400> SEQUENCE: 86
cuggauuguu ggacgaguu 19

<210> SEQ ID NO 87
<211> LENGTH: 19
<212> TYPE: RNA
<213> ORGANISM: Artificial Sequence
<220> FEATURE:
<223> OTHER INFORMATION: GSR siRNA #1

<400> SEQUENCE: 87
ggucugugcu aacaaggaa 19

<210> SEQ ID NO 88
<211> LENGTH: 19
<212> TYPE: RNA
<213> ORGANISM: Artificial Sequence
<220> FEATURE:
<223> OTHER INFORMATION: GSR siRNA #2

-continued

<400> SEQUENCE: 88
aaacuugccc aucgacuuu 19

<210> SEQ ID NO 89
<211> LENGTH: 19
<212> TYPE: RNA
<213> ORGANISM: Artificial Sequence
<220> FEATURE:
<223> OTHER INFORMATION: G6PD siRNA #1

<400> SEQUENCE: 89
acagauacaa gaacgugaa 19

<210> SEQ ID NO 90
<211> LENGTH: 19
<212> TYPE: RNA
<213> ORGANISM: Artificial Sequence
<220> FEATURE:
<223> OTHER INFORMATION: G6PD siRNA #2

<400> SEQUENCE: 90
ccguguacac caagaugau 19

<210> SEQ ID NO 91
<211> LENGTH: 19
<212> TYPE: RNA
<213> ORGANISM: Artificial Sequence
<220> FEATURE:
<223> OTHER INFORMATION: GPX4 siRNA #3

<400> SEQUENCE: 91
acgucaaauu cgauauguu 19

METHOD FOR PREDICTING SENSITIVITY OF CANCER CELL TO GPX4 INHIBITOR

CROSS-REFERENCE TO RELATED APPLICATIONS

This application is the National Stage of International Application No. PCT/JP2020/048811, filed Dec. 25, 2020, which claims the benefit of Japanese Application No. JP2019-236516, filed Dec. 26, 2019.

SEQUENCE LISTING

This application contains a Sequence Listing that has been submitted electronically as an ASCII text file named SequenceListing.txt. The ASCII text file, created on Jun. 13, 2022, is 365 kilobytes in size. The material in the ASCII text file is hereby incorporated by reference in its entirety.

TECHNICAL FIELD

The present invention relates to a method for predicting sensitivity of a cancer cell to a GPX4 inhibitor. The present invention also relates to a method for predicting sensitivity of a cancer patient to treatment with a GPX4 inhibitor, a method for selecting a cancer patient for cancer treatment with a GPX4 inhibitor, a method for suppressing growth of cancer cells, a method for treating cancer, a method for screening compounds to be used for cancer treatment, and a cancer therapeutic drug.

BACKGROUND ART

In recent years, due to rapid advancement of genome sequence techniques, it has been possible to analyze the genome information including unique gene mutations in cancer cells. For development of anticancer drugs, inhibitors have been discovered which inhibit the functions specifically of a cancer cell having a gain-of-function gene mutation typified by EGFR gene mutation, BRAF gene mutation, an ALK fusion gene, a ROSI fusion gene or the like (Non Patent Literatures 1 to 3 etc.). Treatment methods which target a cancer cell having such a gene mutation and are specific to the cancer cell are expected as treatment methods with high cancer selectivity and a high efficacy.

On the other hand, gene mutations found in human cancer cells include not only the gain-of-function gene mutations but also the loss-of-function gene mutations. For a loss-of-function gene mutation, it is difficult to discover a drug specific to the gene mutation, and a treatment strategy different from treatment targeting a cancer cell having a gain-of-function gene mutation is required.

The SWI/SNF complex is a chromatin remodeling factor including 12 to 15 subunits (complex factors). In recent years, suppressed functions such as loss-of-function gene mutations and suppressed expression of SWI/SNF complex factors have been reported to be observed in many human cancers, and have been pointed as being involved in tumor development and advancement. Since these mutations are thought to suppress important functions of the SWI/SNF complex such as dissociation of DNA stored in nucleosome and recruiting of transcription factors and transcription modulating factors such as histone deacetylases in DNA, there may be an important relationship between such a suppressed function and cancer development and advancement, and studies have been conducted.

For Example, Non Patent Literature 4 describes that in non-small cell lung cancer, deficiency of SMARCA4 which is a SWI/SNF complex factor is in a synthetic lethal relationship with a CDK 4/6 inhibitor, Non Patent Literature 5 describes that lung cancer deficient in SMARCA4 had increased sensitivity to an OXPHOS (mitochondrial oxidative phosphorylation) inhibitor, Non Patent Literature 6 describes that the mutation of a gene for SMARCA4 in non-small cell lung cancer had increased sensitivity to an Aurora kinase inhibitor, and Non Patent Literature 7 describes that the mutation of a gene for ARID1A which is likewise a SWI/SNF complex factor is in a synthetic lethal relationship with a GSH synthesis inhibitor.

However, the treatment strategy specifically targeting a cancer cell having a suppressed function of a SWI/SNF complex has not been sufficient yet.

CITATION LIST

Non Patent Literature

[Non Patent Literature 1] Makoto Maemondo et al., NEJM 2010 Jun. 24; 362 (25), p. 2380-2388

[Non Patent Literature 2] Paul B. Chapman et al., NEJM 2011 Jun. 30; 364 (26), p. 2507-2516

[Non Patent Literature 3] D. Ross Camidge et al., J Thorac Oncol. 2019 July; 14 (7), p. 1233-1243

[Non Patent Literature 4] Yibo Xue et al., Nat. Commun. 10:557, 2019

[Non Patent Literature 5] Yonathan Lissanu Deribe et al., Nat. Med. Vol 24, July 2018, p. 1047-1057

[Non Patent Literature 6] Vural Tagal et al., Nat. Commun. 8:14098, 2017

[Non Patent Literature 7] Hideaki Ogiwara et al., 2019, Cancer Cell 35, p. 177-190

SUMMARY OF INVENTION

Technical Problem

The present invention has been made in view of the circumstances described above. An object of the present invention is to develop a treatment strategy capable of specifically targeting a cancer cell having a suppressed function of a SWI/SNF complex. More specifically, the object of the present invention is to develop a treatment strategy specifically targeting a cancer cell having a suppressed function of a SWI/SNF complex factor detected.

Solution to Problem

The present inventors have extensively conducted studies for solving the above-described problems, and resultantly found that when expression of GPX4 is suppressed or the function of GPX4 is inhibited in a cancer cell having a suppressed function of a SWI/SNF complex factor detected, growth of the cancer cells is markedly suppressed and/or cell death is induced, whereas such suppression of growth and/or cell death do not occur in a cell which does not have a suppressed function of a SWI/SNF complex factor.

More specifically, the present inventors have conducted exhaustive knockdown experiments on human cancer cell lines, to extensively investigate which drug suppressing a function of a protein leads to antitumor activity against a human cancer cell having a suppressed function of a SWI/SNF complex factor. As a result, it has been found that when expression of GPX4 is suppressed in a cancer cell line having a deficiency type mutation in a gene for SMARCA4 that is a core component of a SWI/SNF complex and/or having no expressed SMARCA4 protein detected, cell death of the cancer cell is induced to markedly suppress cell growth.

The present inventors have found that even when the activity of GPX4 is inhibited using a compound reported to inhibit the enzymatic activity of GPX4 (e.g. ML210 or RSL3), cell death of a cancer cell having a suppressed function of SMARCA4 is induced to markedly suppress cell growth as in the case where expression of GPX4 is suppressed.

Further, as molecules belonging to a GPX family in a human, eight types of molecules of GPX1, GPX2, GPX3, GPX4, GPX5, GPX6, GPX7 and GPX8 have been reported, and the present inventors have found that in particular, inhibition of GPX4, among the molecules, specifically exhibits antitumor activity against a cancer cell having a suppressed function of SMARCA4.

On the other hand, since SMARCA4 is a protein forming a SWI/SNF complex, it has been thought that GPX4 may also be effective on a cell having a suppressed function of another protein forming a SWI/SNF complex. Thus, antitumor activity by suppression of expression and/or inhibition of activity of GPX4 has been evaluated using a cancer cell line having a suppressed function in other SWI/SNF complex factors in addition to SMARCA4 (e.g. SMARCA2, ARID1A, ARID1B, ARID2 and BCL11B), and resultantly, it has been found that even in a cancer cell line having a suppressed function in other SWI/SNF complex factors, suppression of cell growth and cell death are markedly induced by inhibition of GPX4 as in a cancer cell line having a suppressed function of SMARCA4.

Since GPX4 is an enzyme which consumes glutathione in cells to perform hydrolysis, it has been thought that inhibition of a group of other factors (proteins) involved in glutathione synthesis may exhibit antitumor activity against a cancer cell having a suppressed function of a SWI/SNF complex factor. However, it has been revealed that even when a group of other factors related to glutathione synthesis (e.g. gamma-glutamylcysteine synthetase (GCLC), glutathione synthetase (GSS), Glutamate-Cysteine Ligase Modifier Subunit (GCLM), Microsomal Glutathione S-Transferase 1 (MGST1), Microsomal Glutathione S-Transferase 3 (MGST3), Glutathione-Disulfide Reductase (GSR) and glucose-6-phosphate dehydrogenase (G6PD)) are inhibited, sufficient antitumor activity cannot be obtained as compared to inhibition of GPX4, and it is particularly important to inhibit GPX4 for obtaining antitumor activity targeting a cancer cell having a suppressed function of a SWI/SNF complex factor.

Further, the present inventors have demonstrated that in a tumor-bearing mouse into which a cancer cell having a suppressed function of SWI/SNF complex factor is transplanted, an increase in tumor volume is markedly suppressed by administration of a compound (GPX4 inhibitor) reported to inhibit enzymatic activity of GPX4, and inhibition of GPX4 reliably exhibits an antitumor effect even in vivo.

Thus, the present inventors have found that treatment for inhibiting GPX4 (suppression of expression or inhibition of activity) is a promising approach for treatment targeting a cancer cell having a suppressed function of a SWI/SNF complex factor. It has also been revealed that in this treatment strategy, it is possible to select a cancer patient using a suppressed function of a SWI/SNF complex factor as an indicator, followed by administering a GPX4 inhibitor, so that efficient treatment based on companion diagnosis is possible.

Further, the present inventors have also found that screening of drugs useful for treatment of cancer having a suppressed function of a SWI/SNF complex factor can be performed on the basis of whether GPX4 is inhibited or not, leading to completion of the present invention.

Accordingly, the present invention relates to a treatment method specifically targeting a cancer cell having a suppressed function of a SWI/SNF complex factor, and companion diagnosis for the treatment method. More specifically, the present invention provides the following.

[1]

A cancer therapeutic drug comprising a compound which inhibits GPX4 as an active ingredient, the cancer therapeutic drug being a therapeutic drug for cancer containing a cancer cell having a suppressed function of a SWI/SNF complex factor detected.

[2]

A cancer therapeutic drug comprising a compound which inhibits GPX4 as an active ingredient, the cancer therapeutic drug being a therapeutic drug for treating a cancer patient having a suppressed function of a SWI/SNF complex factor detected in a cancer cell contained in a cancer patient-derived sample.

[3]

A cancer therapeutic drug comprising a compound, which inhibits GPX4, as an active ingredient, the cancer therapeutic drug being a therapeutic drug to be administered to a cancer patient having a suppressed function of a SWI/SNF complex factor detected in a cancer cell contained in a cancer patient-derived sample.

[4]

A method for predicting sensitivity of a cancer cell to a GPX4 inhibitor, the method comprising the step of:

predicting a cancer cell having a suppressed function of a SWI/SNF complex factor detected in the cancer cell, as having sensitivity to a GPX4 inhibitor.

[5]

A method for predicting sensitivity of a cancer cell to a GPX4 inhibitor, the method comprising the steps of:

(a) detecting the presence or absence of a suppressed function of a SWI/SNF complex factor in the cancer cell; and (b) predicting a cancer cell having the suppressed function of a SWI/SNF complex factor, as having sensitivity to a GPX4 inhibitor.

[6]

A method for predicting sensitivity of a cancer patient to treatment with a GPX4 inhibitor, the method comprising the step of:

predicting a cancer patient having a suppressed function of a SWI/SNF complex factor detected in a cancer cell contained in a cancer patient-derived sample, as having sensitivity to treatment with a GPX4 inhibitor.

[7]

A method for predicting sensitivity of a cancer patient to treatment with a GPX4 inhibitor, the method comprising the steps of:

(a) detecting the presence or absence of a suppressed function of a SWI/SNF complex factor in a cancer cell contained in a cancer patient-derived sample; and (b) predicting a cancer patient having the suppressed function of a SWI/SNF complex factor detected in the cancer cell, as having sensitivity to treatment with a GPX4 inhibitor.

[8]

A method for selecting a cancer patient for cancer treatment with a GPX4 inhibitor, the method comprising the step of:

selecting a cancer patient having a suppressed function of a SWI/SNF complex factor detected in a cancer cell contained in a cancer patient-derived sample, for cancer treatment with a GPX4 inhibitor.

[9]

A method for selecting a cancer patient for cancer treatment with a GPX4 inhibitor, the method comprising the steps of:

(a) detecting the presence or absence of a suppressed function of a SWI/SNF complex factor in a cancer cell contained in a cancer patient-derived sample; and (b) selecting a cancer patient having the suppressed function of a SWI/SNF complex factor detected in the cancer cell, for cancer treatment with a GPX4 inhibitor.

[10]

A method for suppressing growth of cancer cells having a suppressed function of a SWI/SNF complex factor detected, the method comprising the step of:

contacting a GPX4 inhibitor with a cancer cell having the suppressed function of a SWI/SNF complex factor detected.

[11]

A method for treating cancer, the method comprising the step of:

administering a GPX4 inhibitor to a cancer patient having a suppressed function of a SWI/SNF complex factor detected in a cancer cell contained in a cancer patient-derived sample.

[12]

A method for treating cancer, the method comprising the steps of:

(a) detecting the presence or absence of a suppressed function of a SWI/SNF complex factor in a cancer cell contained in a cancer patient-derived sample; and (b) administering a GPX4 inhibitor to a cancer patient having the suppressed function of a SWI/SNF complex factor detected in the cancer cell.

[13]

A method for screening compounds to be used for treatment of cancer containing a cancer cell having a suppressed function of a SWI/SNF complex factor detected, the method comprising the step of:

selecting a compound on the basis of whether GPX4 is inhibited or not.

[14]

The cancer therapeutic drug according to any one of [1] to [3], wherein the SWI/SNF complex factor is a BAF complex factor.

[15]

The method according to any one of [4] to [13], wherein the SWI/SNF complex factor is a BAF complex factor.

[16]

The cancer therapeutic drug according to any one of [1] to [3], wherein the SWI/SNF complex factor is at least one selected from the group consisting of SMARCA2, SMARCA4, ARID1A, ARID1B, ARID2 and BCL11B.

[17]

The method according to any one of [4] to [13], wherein the SWI/SNF complex factor is at least one selected from the group consisting of SMARCA2, SMARCA4, ARID1A, ARID1B, ARID2 and BCL11B.

[18]

The cancer therapeutic drug according to any one of [1] to [3], wherein the suppressed function of a SWI/SNF complex factor is a decrease in activity of a SWI/SNF complex having the SWI/SNF complex factor as a constituent factor and/or a decrease in expression of the SWI/SNF complex factor.

[19]

The method according to any one of [4] to [13], wherein the suppressed function of a SWI/SNF complex factor is a decrease in activity of a SWI/SNF complex having the SWI/SNF complex factor as a constituent factor and/or a decrease in expression of the SWI/SNF complex factor.

[20]

The cancer therapeutic drug according to any one of [1] to [3], wherein the suppressed function of a SWI/SNF complex factor is a loss-of-function mutation of a gene for the SWI/SNF complex factor.

[21]

The method according to any one of [4] to [13], wherein the suppressed function of a SWI/SNF complex factor is a loss-of-function mutation of a gene for the SWI/SNF complex factor.

[22]

A cancer therapeutic drug comprising a compound, which inhibits GPX4, as an active ingredient, the cancer therapeutic drug being a therapeutic drug for cancer containing a cancer cell having a loss-of-function mutation of a gene for a SWI/SNF complex factor detected.

[23]

A cancer therapeutic drug comprising a compound, which inhibits GPX4, as an active ingredient, the cancer therapeutic drug being a therapeutic drug for treating a cancer patient having a loss-of-function mutation of a gene for a SWI/SNF complex factor detected in a cancer cell contained in a cancer patient-derived sample.

[24]

A cancer therapeutic drug comprising a compound which inhibits GPX4 as an active ingredient, the cancer therapeutic drug being a therapeutic drug to be administered to a cancer patient having a loss-of-function mutation of a gene for a SWI/SNF complex factor detected in a cancer cell contained in a cancer patient-derived sample.

[25]

A method for predicting sensitivity of a cancer cell to a GPX4 inhibitor, the method comprising the steps of:

predicting a cancer cell having a loss-of-function mutation of a gene for a SWI/SNF complex factor detected in the cancer cell, as having sensitivity to a GPX4 inhibitor.

[26]

A method for predicting sensitivity of a cancer cell to a GPX4 inhibitor, the method comprising the steps of:

(a) detecting the presence or absence of a loss-of-function mutation of a gene for a SWI/SNF complex factor in the cancer cell; and (b) predicting a cancer cell having the loss-of-function mutation of a gene for a SWI/SNF complex factor detected, as having sensitivity to a GPX4 inhibitor.

[27]

A method for predicting sensitivity of a cancer patient to treatment with a GPX4 inhibitor, the method comprising the step of:

predicting a cancer patient having a loss-of-function mutation of a gene for a SWI/SNF complex factor detected in a cancer cell contained in a cancer patient-derived sample, as having sensitivity to treatment with a GPX4 inhibitor.

[28]

A method for predicting sensitivity of a cancer patient to treatment with a GPX4 inhibitor, the method comprising the steps of:

(a) detecting the presence or absence of a loss-of-function mutation of a gene for a SWI/SNF complex factor in a cancer cell contained in a cancer patient-derived sample; and (b) predicting a cancer patient having the loss-of-function mutation of a gene for a SWI/SNF complex factor detected in the cancer cell, as having sensitivity to treatment with a GPX4 inhibitor.

[29]

A method for selecting a cancer patient for cancer treatment with a GPX4 inhibitor, the method comprising the step of:

selecting a cancer patient having a loss-of-function mutation of a gene for a SWI/SNF complex factor detected in a cancer cell contained in a cancer patient-derived sample, for cancer treatment with a GPX4 inhibitor.

[30]

A method for selecting a cancer patient for cancer treatment with a GPX4 inhibitor, the method comprising the steps of:

(a) detecting the presence or absence of a loss-of-function mutation of a gene for a SWI/SNF complex factor in a cancer cell contained in a cancer patient-derived sample; and (b) selecting a cancer patient having the loss-of-function mutation of a gene for a SWI/SNF complex factor detected in the cancer cell, for cancer treatment with a GPX4 inhibitor.

[31]

A method for suppressing growth of cancer cells having a loss-of-function mutation of a gene for a SWI/SNF complex factor detected, the method comprising the step of: contacting a GPX4 inhibitor with a cancer cell having the loss-of-function mutation of a gene for a SWI/SNF complex factor detected.

[32]

A method for treating cancer, the method comprising the step of:

administering a GPX4 inhibitor to a cancer patient having a loss-of-function mutation of a gene for a SWI/SNF complex factor detected in a cancer cell contained in a cancer patient-derived sample.

[33]

A method for treating cancer, the method comprising the steps of:

(a) detecting the presence or absence of a loss-of-function mutation of a gene for a SWI/SNF complex factor in a cancer cell contained in a cancer patient-derived sample; and (b) administering a GPX4 inhibitor to a cancer patient having the loss-of-function mutation of a gene for a SWI/SNF complex factor detected in the cancer cell.

[34]

A method for screening compounds to be used for treatment of cancer containing a cancer cell having a loss-of-function mutation of a gene for a SWI/SNF complex factor detected, the method comprising the step of:

selecting a compound on the basis of whether GPX4 is inhibited or not.

[35]

The cancer therapeutic drug according to any one of to [24], wherein the SWI/SNF complex factor is a BAF complex factor.

The cancer therapeutic drug according to any one of to [34], wherein the SWI/SNF complex factor is a BAF complex factor.

The cancer therapeutic drug according to any one of to [24], wherein the SWI/SNF complex factor is at least one selected from the group consisting of SMARCA2, SMARCA4, ARID1A, ARID1B, ARID2 and BCL11B.

[38]

The method according to any one of to [34], wherein the SWI/SNF complex factor is at least one selected from the group consisting of SMARCA2, SMARCA4, ARID1A, ARID1B, ARID2 and BCL11B.

Advantageous Effects of Invention

According to the present invention, it is possible to efficiently predict sensitivity to cancer treatment with a GPX4 inhibitor using a suppressed function of a SWI/SNF complex factor (e.g. gene mutation or a decrease in expression of protein in SWI/SNF complex factors typified by SMARCA4 and ARID1A) as an indicator. In addition, according to the present invention, it is possible to detect the presence or absence of a suppressed function of a SWI/SNF complex factor in a cancer patient-derived sample and select a patient having the mutation detected, followed by subjecting the patient to treatment of cancer with a GPX4 inhibitor. This enables significant improvement of cancer treatment outcomes. By using a probe or a primer against a gene for a SWI/SNF complex factor and an antibody against a SWI/SNF complex factor, companion diagnosis can be efficiently performed by detection of the presence or absence of such a suppressed function of the SWI/SNF complex factor.

DESCRIPTION OF EMBODIMENTS

Figure 1:
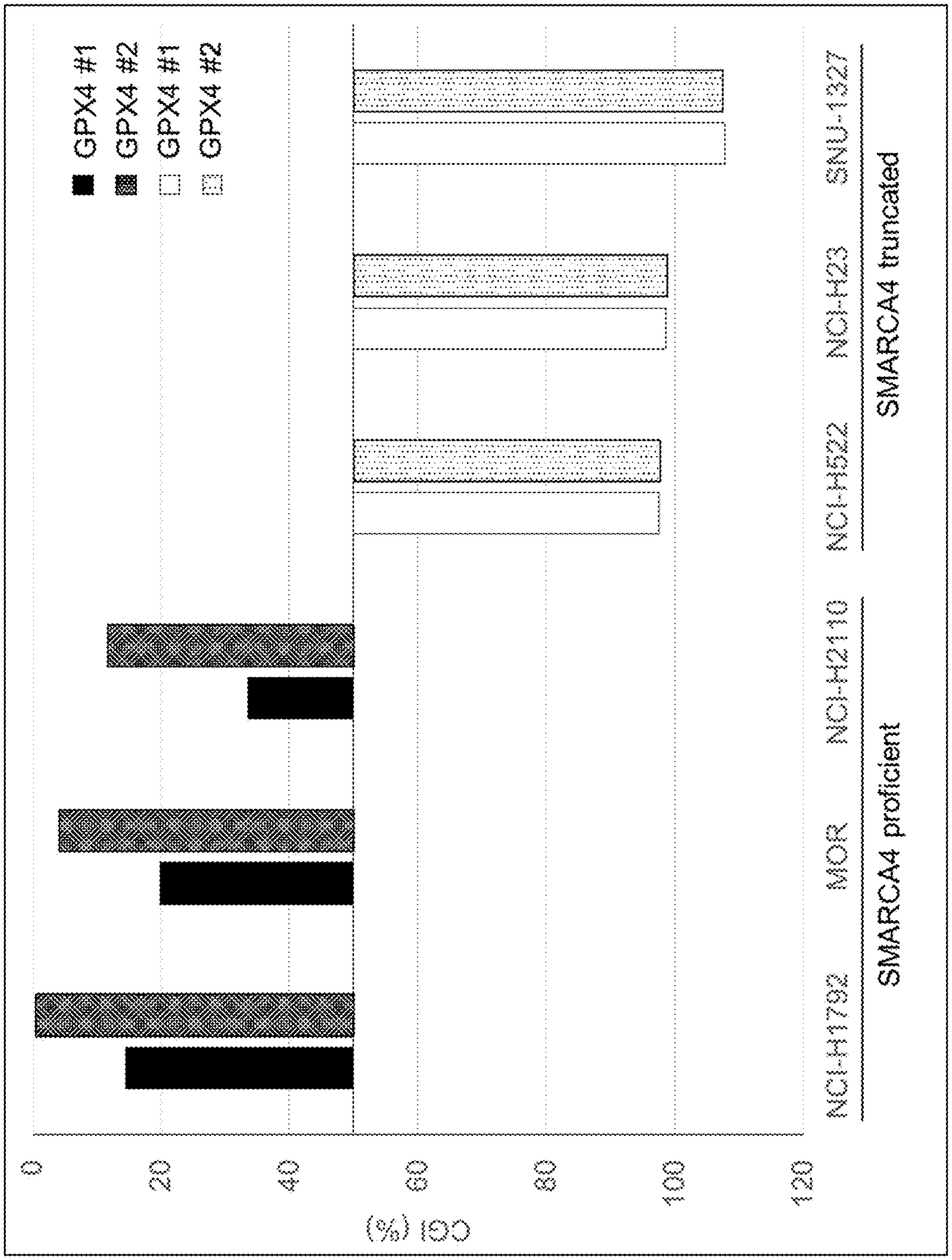
FIG. 1 is a graph showing cell growth inhibition ratios (CGI (%)) in suppression of expression of GPX4 (#1 and #2) in the cell lines of NCI-H1792, MOR, NCI-H2110, NCI-H522, NCI-H23 and SNU-1327.

Hereinafter, the present invention will be described in detail along preferred embodiments thereof.

<Method for Predicting Sensitivity of Cancer Cell to GPX4 Inhibitor, Method for Predicting Sensitivity of Patient to Treatment with GPX4 Inhibitor, and Method for Selecting a Cancer Patient for Cancer Treatment with GPX4 Inhibitor>

In the present invention, it has been found that when GPX4 is inhibited in a cancer cell having a suppressed function of a SWI/SNF complex factor, growth of the cancer cell can be suppressed. According to this finding, sensitivity of a cancer cell to a GPX4 inhibitor can be predicted using a suppressed function of a SWI/SNF complex factor as an indicator. Accordingly, the present invention provides:

a method for predicting sensitivity of a cancer cell to a GPX4 inhibitor, the method comprising:

(a) detecting the presence or absence of a suppressed function of a SWI/SNF complex factor in a cancer cell; and (b) predicting a cancer cell having the suppressed function of a SWI/SNF complex factor detected, as having sensitivity to a GPX4 inhibitor.

(Hereinafter, the method is sometimes referred to as a "cancer cell sensitivity prediction method".)

According to the above-described finding, sensitivity to treatment with a GPX4 inhibitor can be predicted using a suppressed function of a SWI/SNF complex factor as an indicator. Accordingly, the present invention provides:

a method for predicting sensitivity of a cancer patient to treatment with a GPX4 inhibitor, the method comprising:

(a) detecting the presence or absence of a suppressed function of a SWI/SNF complex factor in a cancer cell contained in a cancer patient-derived sample; and (b) predicting a cancer patient having the suppressed function of a SWI/SNF complex factor detected in the cancer cell, as having sensitivity to treatment with a GPX4 inhibitor.

(Hereinafter, the method is sometimes referred to as a "cancer patient sensitivity prediction method".)

Further, a patient having a suppressed function of a SWI/SNF complex factor detected in this way can be suitable for cancer treatment with a GPX4 inhibitor, and therefore using the suppressed function of a SWI/SNF complex factor as an indicator, a patient who benefits from cancer treatment with a GPX4 inhibitor and a patient who does not benefit from the cancer treatment can be discriminated from each other to perform efficient treatment. Accordingly, the present invention provides:

a method for selecting a cancer patient for cancer treatment with GPX4 inhibitor, the method comprising:

(a) detecting the presence or absence of a suppressed function of a SWI/SNF complex factor in a cancer cell contained in a cancer patient-derived sample; and (b) selecting a cancer patient having the suppressed function of a SWI/SNF complex factor detected in the cancer cell, for cancer treatment with a GPX4 inhibitor.

(Hereinafter, the method is sometimes referred to as a "cancer patient selection method".)

(Samples)

In the present invention, malignant neoplasms such as carcinomas (epithelial tumors), leukemia, malignant lymphomas, myelomas, sarcomas and carcinosarcomas, are referred to collectively as "cancer" or "tumor", and a cell forming the cancer is referred to as a "cancer cell". The cancer containing a cancer cell in which the presence or absence of a suppressed function of a SWI/SNF complex factor can be detected is not particularly limited, and examples thereof include lung cancer, ovary cancer, uterus cancer, liver cancer, stomach cancer, esophagus cancer, bowel cancer, pancreas cancer, prostate cancer, bladder cancer and kidney cancer.

In the present invention, the "cancer patient" may be not only a human affected with the cancer, but also a human possibly affected with the cancer. In the method of the present invention, the cancer patient to be subjected to detection of a suppressed function of a SWI/SNF complex factor is not particularly limited, and may include all cancer patients.

The "cancer patient-derived sample" for use in the present invention is not particularly limited as long as it is a biological sample allowing the presence or absence of suppressed function of a SWI/SNF complex factor to be detected, and a specimen material such as a cancer biopsy specimen material, blood, urine, body cavity fluid or tumor cell-derived circulating DNA (ctDNA). The cancer patient-derived sample may be a protein extract or a nucleic acid extract obtained from the specimen material (e.g. a mRNA extract, or a cDNA preparation or a cRNA preparation prepared from a mRNA extract). In the present description, the "biological sample" includes cancer patient-derived samples and cancer cell culture-derived samples.

(GPX4 Inhibitor)

The "GPX4 inhibitor" in the present invention means a composition containing at least one compound which inhibits GPX4 (glutathione peroxidase 4). The GPX4 inhibitor may be one including only the compounds or a combination thereof, or one further containing additive ingredients described below. The "compound which inhibits GPX4" in the present invention includes compounds which inhibit at least one of the activity of GPX4 and the expression of GPX4.

The "GPX4 (herein, sometimes referred to as "GPX4 protein") targeted by the GPX4 inhibitor in the present invention is one of isozymes of glutathione peroxidase having peroxidase activity in which the peroxide structure of glutathione is oxidized and cleaved to be broken down into two hydroxy groups (eight types: GPX 1 to GPX 8 are currently known). GPXs other than GPX4 can reduce hydrogen peroxide and peroxidized fatty acids as substrates, whereas GPX4 is an enzyme which also has a function of directly reducing peroxidized phospholipid. A nucleotide sequence of human-derived typical DNA (cDNA) encoding GPX4 is set forth as SEQ ID NO: 1 (NCBI reference number: NM_002085.5), and a typical amino acid sequence of human-derived GPX4 protein is set forth as SEQ ID NO: 2 (NCBI reference number: NP_002076.2). Even among DNAs encoding GPX4 which does not have a mutation associated with substitution, deletion, insertion, addition and the like of amino acid sequences, there may be an interindividual difference in sequence due to polymorphism or the like.

Inhibition of the activity of GPX4 by the compound can be confirmed by, for example, adding phosphatidylcholine hydroperoxide, which is a substrate of GPX4, to a lysate of a cell treated with a test compound, and using reduction thereof as an indicator (e.g. Viswanathan et al., Nature. 2017 Jul. 27; 547 (7664): 453-457, Dependency of a therapy-resistant state of cancer cells on a lipid peroxidase pathway, and Yang et al., Cell. 2014 Jan. 16 156 (0): 317-331, Regulation of Ferroptotic Cancer Cell Death by GPX4). When the activity of GPX4 is inhibited by the test compound, reduction of the substrate does not occur, or hardly occurs (the amount of reduction decreases).

Inhibition of the activity of GPX4 by the compound can also be confirmed by, for example, treating a purified GPX4 preparation with a test compound, adding GSH and a peroxide which are substrates of GPX4, glutathione reductase and NADPH, and measuring activity by an enzyme recycling method (e.g. Shinome et al., Antioxid. Redox Signal. 22 (4), 281-293, Expression of Inactive Glutathione Peroxidase 4 Leads to Embryonic Lethality, and Inactivation of the Alox15 Gene Does Not Rescue Such Knock-In Mice). When the activity of GPX4 is inhibited by the test compound, the amount of GSH or NADPH consumed decreases.

Inhibition of the expression of GPX4 by the compound can be confirmed by, for example, detecting a decrease in expression of GPX4 in a cell treated with the test compound. Examples of the method for detecting a decrease in expression of GPX4 include a method in which normally, the expression level of GPX4 is detected at a transcriptional level or a translational level, and compared to a control (e.g. expression level of a cell which is not treated with the test compound) to confirm that the expression level is lower than the control.

In the method for detecting the expression level of GPX4 at a transcriptional level, first, RNA or cDNA is prepared from a cell treated with the test compound. The method for extracting RNA from the cell is not particularly limited, and a known method can be appropriately selected and used. Examples thereof include extraction methods using phenol and a chaotropic salt (more specifically, extraction methods using a commercially available kit such as TRIzol (manufactured by Invitrogen Corporation) or ISOGEN (manufactured by Wako Pure Chemical Industries, Ltd.)), and methods using another commercially available kit (e.g. RNAPrep Total RNA Extraction Kit (manufactured by Beckman Coulter Inc.), RNeasy Mini (manufactured by QIAGEN N.V.) or RNA Extraction Kit (manufactured by Pharmacia Biotech, Inc.)). Further, the reverse transcriptase used for preparation of cDNA from extracted RNA is not particularly limited, and examples thereof include reverse transcriptases derived from retroviruses such as RAV (Rous associated virus) and AMV (Avian myeloblastosis virus), and reverse transcriptases derived from mouse retroviruses such as MMLV (Moloney murine leukemia virus).

Subsequently, an oligonucleotide primer or an oligonucleotide probe is used for an amplification reaction or a hybridization reaction, and an amplified product or a hybrid product thereof is detected. As such a method, for example, a RT-PCR method, a Northern blot method, a dot blot method, a DNA array method, an in situ hybridization method, a RNase protection assay method, mRNA-seq or the like can be used. Those skilled in the art can design an oligonucleotide primer or an oligonucleotide probe suitable for each method in a conventional manner on the basis of a nucleotide sequence of cDNA encoding GPX4.

In the method for detecting the expression level of GPX4 at a translational level, first, a protein sample is prepared from a cell treated with the test compound. Subsequently, using an antibody specific to GPX4 protein, an antigen-antibody reaction is carried out, and GPX4 protein is detected. In such a method for detecting protein using an antibody, for example, an antibody specific to GPX4 protein is added to the protein sample to carry out an antigen-antibody reaction, and binding of the antibody to GPX4 protein is detected. When the sample is labeled with antibody specific to GPX4 protein, GPX4 protein can be directly detected, and when the sample is not labeled, a labeled molecule which recognizes the antibody (e.g. secondary antibody or protein A) can be further applied to indirectly detect GPX4 protein using the label of the molecule. As such a method, for example, an immunohistochemistry (immunostaining) method, a Western blotting method, an ELISA method, flow cytometry, imaging cytometry, radioimmunoassay, an immunoprecipitation method, or an analysis method using an antibody array can be used.

The type, the origin and the like of an antibody used are not particularly limited, and a monoclonal antibody is preferable. An oligoclonal antibody (mixture of several antibodies or dozens of antibodies) or a polyclonal antibody can also be used as long as it is possible to detect GPX4 protein with sufficient specificity. Functional fractions of antibodies such as Fab, Fab', $F(ab')_2$, Fv, scFv, sc $(Fv)_2$, dsFv and diabodies, and multimers (e.g. dimers, trimers, tetramers and polymers) thereof can also be used. Such an anti-GPX4 protein antibody may be a marketed product.

The GPX4 protein can also be detected by mass spectrometry (MS). In particular, analysis by a mass spectrometer coupled with liquid chromatography (LC/MS) is sensitive, and therefore advantageous. Detection by mass spectrometry can be performed by, for example, labeling the protein sample with the protein, fractionating the labeled protein, subjecting the fractionated protein to mass analysis, and identifying GPX4 protein from the mass analysis value. As the label, an isotopic labeling reagent known in the art can be used, and an appropriate labeling reagent can be obtained as a marketed product. The fractionation can be performed by a method known in the art, and for example, a commercially available ion-exchange column or the like can be used.

The "compound which inhibits GPX4" in the present invention is not particularly limited, may be a known compound, or a compound identified by screening described later, and is preferably at least one selected from the group consisting of an organic or inorganic compound molecule, a polypeptide and a polynucleotide.

Examples of the compound molecule include low-molecular compounds (molecular weight: less than 800) and middle-molecular compounds (molecular weight: 800 to 2,000). The polypeptide includes full-length polypeptides encoded by a gene, fractions thereof, synthesized polypeptides, cyclic polypeptides and glycopeptides. The polypeptide includes antibodies and antigen peptides, and the antibody may be a polyclonal antibody or a monoclonal antibody. The antibody includes complete antibodies, antibody fractions (e.g. Fab, Fab', $F(ab')_2$, Fv, scFv, sc $(Fv)_2$, dsFv and diabodies), multimers thereof, and low-molecular antibodies in which variable regions of antibodies are bound. Examples of the polynucleotide include DNA, RNA and SiRNA, including full-length polynucleotides, fractions thereof and synthesized polynucleotides.

The "GPX4 inhibitor" in the present invention can be used as various dosage forms such as tablets, pills, powders, granules, capsules and solutions depending on the properties thereof, may further contain pharmacologically acceptable additive ingredients such as sterilized water, physiological saline, vegetable oil, solvents, bases, emulsifiers, suspension agents, surfactants, stabilizers, flavoring agents, fragrances, excipients, vehicles, preservatives, binders, diluents, tonicity agents, soothing agents, extenders, disintegrants, buffering agents, coating agents, lubricants, colorants, sweeteners, viscous agents, taste and odor improvers and solubilizers depending on the dosage form, and can be produced by a known pharmaceutical method using these components.

In the GPX4 inhibitor according to the present invention, the content of the compound which inhibits the GPX4 (the total content of the compounds if there are the two or more compounds) can be appropriately adjusted according to the dosage form or the use purpose of the GPX4 inhibitor.

(Suppressed Function of SWI/SNF Complex Factor)

[SWI/SNF Complex Factor]

The "SWI/SNF complex" in the present invention, which is one of chromatin modeling factors, is a complex having mainly a function of converting a chromatin structure by moving and removing nucleosome with the utilization of energy from ATP hydrolysis, and includes a plurality of subunits.

The "SWI/SNF complex factor (herein, sometimes referred to as "SWI/SNF complex factor protein")" in the present invention is a subunit forming the SWI/SNF complex, and examples thereof include SMARCA2 (herein, sometimes referred to as "SMARCA2 protein"; hereinafter, the same applies to subsequent factors), SMARCA4, ARID1A, ARID1B, ARID2, ACTL6A, ACTL6B, DPF1, DPF2, DPF3, SMARCB1, SMARCC1, SMARCC2, SMARCD1, SMARCD2, SMARCD3, SMARCE1, SS18, SS18L1, BCL7A, BCL7B, BCL7C, BCL11A, BCL11B, BRD7, BRD9, PBRM1 and PHF10. The SWI/SNF complex factor in which a suppressed function is detected may be one of the above-mentioned factors alone, or a combination of two or more of the above-mentioned factors.

Among the SWI/SNF complex factors, SMARCA2, SMARCA4, SMARCC1, SMARCC2, SMARCB1, ARID1A, ARID1B, SMARCD1, SMARCD2, SMARCD3, BCL11B, SMARCE1, PHF10, DPF1, DPF3, ACTL6A and ACTL6B are BAF complex factors forming the BAF complex, and SMARCA4, SMARCC1, SMARCC2, SMARCB1, ARID2, PBRM1, BRD7, BCL11B, SMARCE1, PHF10, DPF1, DPF3, ACTL6A and ACTL6B are PBAF complex factors forming the PBAF complex. The SWI/SNF complex factor according to the present invention is preferably at least one selected from the group consisting of SMARCA2, SMARCA4, ARID1A, ARID1B, ARID2 and BCL11B, more preferably at least one selected from the group consisting of BAF complex factors, still more preferably at least one selected from the group consisting of SMARCA2, SMARCA4, ARID1A, ARID1B and BCL11B, among the above-mentioned factors.

For the above-described SWI/SNF complex factors, Tables 1 to 3 show the sequence numbers of nucleotide sequences of human-derived typical DNAs (cDNAs) encoding the SWI/SNF complex factors, and the sequence numbers of typical amino acid sequences of the human-derived SWI/SNF complex factor proteins, but the sequence numbers are not limited thereto. Tables 1 to 3 also show names and reference IDs in NCBI RefSeq Database (National Center for Biotechnology Information Reference Sequence Database) for the SWI/SNF complex factors. Even among DNAs encoding a SWI/SNF complex factor which does not have a mutation associated with substitution, deletion, insertion, addition and the like of amino acid sequences, there may be an interindividual difference in sequence due to polymorphism or the like.

TABLE 1

| SEQ ID NO: | Nucleotide sequence/amino acid sequence | Name (SWI/SNF complex factor) | Name (NCBI) | NCBI Reference ID |
|---|---|---|---|---|
| 3 | Nucleotide sequence (cDNA) | SMARCA2 | *Homo sapiens* SWI/SNF related, matrix associated, actin dependent regulator of chromatin, subfamily a, member 2 (SMARCA2), transcript variant 3, mRNA | NM_001289396.1 |
| 4 | Amino acid sequence | SMARCA2 | probable global transcription activator SNF2L2 isoform a | NP_001276325.1 |
| 5 | Nucleotide sequence (cDNA) | SMARCD2 | *Homo sapiens* SWI/SNF related, matrix associated, actin dependent regulator of chromatin, subfamily d, member 2 (SMARCD2), transcript variant 1, mRNA | NM_001098426.2 |
| 6 | Amino acid sequence | SMARCD2 | SWI/SNF-related matrix-associated actin-dependent regulator of chromatin subfamily D member 2 isoform 1 | NP_001091896.1 |
| 7 | Nucleotide sequence (cDNA) | SMARCA4 | *Homo sapiens* SWI/SNF related, matrix associated, actin dependent regulator of chromatin, subfamily a, member 4 (SMARCA4), transcript variant 1, mRNA | NM_ 001128849.3 |
| 8 | Amino acid sequence | SMARCA4 | transcription activator BRG1 isoform A [*Homo sapiens*] | NP_001122321.1 |
| 9 | Nucleotide sequence (cDNA) | SMARCD3 | *Homo sapiens* SWI/SNF related, matrix associated, actin dependent regulator of chromatin, subfamily d, member 3 (SMARCD3), transcript variant 3, mRNA | NM_001003801.2 |
| 10 | Amino acid sequence | SMARCD3 | SWI/SNF-related matrix-associated actin-dependent regulator of chromatin subfamily D member 3 isoform 2 | NP_001003801.1 |
| 11 | Nucleotide sequence (cDNA) | ARID1A | *Homo sapiens* AT-rich interaction domain 1A (ARID1A), transcript variant 1, mRNA | NM_006015.6 |
| 12 | Amino acid sequence | ARID1A | AT-rich interactive domain-containing protein 1A isoform a | NP_006006.3 |
| 13 | Nucleotide sequence (cDNA) | SMARCE1 | *Homo sapiens* SWI/SNF related, matrix associated, actin dependent regulator of chromatin, subfamily e, member 1 (SMARCE1), mRNA | NM_003079.5 |
| 14 | Amino acid sequence | SMARCE1 | SWI/SNF-related matrix-associated actin-dependent regulator of chromatin subfamily E member 1 | NP_003070.3 |
| 15 | Nucleotide sequence (cDNA) | ARID1B | *Homo sapiens* AT-rich interaction domain 1B (ARID1B), transcript variant 2, mRNA | NM_001374820.1 |

TABLE 1-continued

| SEQ ID NO: | Nucleotide sequence/amino acid sequence | Name (SWI/SNF complex factor) | Name (NCBI) | NCBI Reference ID |
|---|---|---|---|---|
| 16 | Amino acid sequence | ARID1B | AT-rich interactive domain-containing protein 1B isoform 2 | NP_001361749.1 |
| 17 | Nucleotide sequence (cDNA) | SS18 | *Homo sapiens* SS18 subunit of BAF chromatin remodeling complex (SS18), transcript variant 1, mRNA | NM_001007559.3 |
| 18 | Amino acid sequence | SS18 | protein SSXT isoform 1 | NP_001007560.1 |
| 19 | Nucleotide sequence (cDNA) | ARID2 | *Homo sapiens* AT-rich interaction domain 2 (ARID2), transcript variant 1, mRNA | NM_152641.4 |
| 20 | Amino acid sequence | ARID2 | AT-rich interactive domain-containing protein 2 isoform 1 | NP_689854.2 |

TABLE 2

| SEQ ID NO: | Nucleotide sequence/amino acid sequence | Name (SWI/SNF complex factor) | Name (NCBI) | NCBI Reference ID |
|---|---|---|---|---|
| 21 | Nucleotide sequence (cDNA) | SS18L1 | *Homo sapiens* SS18L1 subunit of BAF chromatin remodeling complex (SS18L1), transcript variant 1, mRNA | NM_198935.3 |
| 22 | Amino acid sequence | SS18L1 | calcium-responsive transactivator isoform 1 | NP_945173.1 |
| 23 | Nucleotide sequence (cDNA) | ACTL6A | *Homo sapiens* actin like 6A (ACTL6A), transcript variant 1, mRNA | NM_004301.5 |
| 24 | Amino acid sequence | ACTL6A | actin-like protein 6A isoform 1 | NP_004292.1 |
| 25 | Nucleotide sequence (cDNA) | BCL7A | *Homo sapiens* BAF chromatin remodeling complex subunit BCL7A (BCL7A), transcript variant 1, mRNA | NM_020993.5 |
| 26 | Amino acid sequence | BCL7A | B-cell CLL/lymphoma 7 protein family member A isoform a | NP_066273.1 |
| 27 | Nucleotide sequence (cDNA) | ACTL6B | *Homo sapiens* actin like 6B (ACTL6B), transcript variant 1, mRNA | NM_016188.5 |
| 28 | Amino acid sequence | ACTL6B | actin-like protein 6B | NP_057272.1 |
| 29 | Nucleotide sequence (cDNA) | BCL7B | *Homo sapiens* BAF chromatin remodeling complex subunit BCL7B (BCL7B), transcript variant 1, mRNA | NM_001707.4 |
| 30 | Amino acid sequence | BCL7B | B-cell CLL/lymphoma 7 protein family member B isoform 1 | NP_001698.2 |
| 31 | Nucleotide sequence (cDNA) | DPF1 | *Homo sapiens* double PHD fingers 1 (DPF1), transcript variant 1, mRNA | NM_001135155.2 |
| 32 | Amino acid sequence | DPF1 | zinc finger protein neuro-d4 isoform a | NP_001128627.1 |
| 33 | Nucleotide sequence (CDNA) | BCL7C | *Homo sapiens* BAF chromatin remodeling complex subunit BCL7C (BCL7C), transcript variant 2, mRNA | NM_004765.4 |
| 34 | Amino acid sequence | BCL7C | B-cell CLL/lymphoma 7 protein family member C isoform 2 | NP_004756.2 |
| 35 | Nucleotide sequence (cDNA) | DPF2 | *Homo sapiens* double PHD fingers 2 (DPF2), transcript variant 1, mRNA | NM_006268.5 |
| 36 | Amino acid sequence | DPF2 | zinc finger protein ubi-d4 isoform 1 | NP_006259.1 |
| 37 | Nucleotide sequence (CDNA) | BCL11A | *Homo sapiens* BAF chromatin remodeling complex subunit BCL11A (BCL11A), transcript variant 1, mRNA | NM_022893.4 |
| 38 | Amino acid sequence | BCL11A | B-cell lymphoma/leukemia 11A isoform 1 | NP_075044.2 |
| 39 | Nucleotide sequence (cDNA) | DPF3 | *Homo sapiens* double PHD fingers 3 (DPF3), transcript variant 2, mRNA | NM_001280542.1 |
| 40 | Amino acid sequence | DPF3 | zinc finger protein DPF3 isoform 2 | NP_001267471.1 |

TABLE 3

| SEQ ID NO: | Nucleotide sequence/amino acid sequence | Name (SWI/SNF complex factor) | Name (NCBI) | NCBI Reference ID |
|---|---|---|---|---|
| 41 | Nucleotide sequence (CDNA) | BCL11B | *Homo sapiens* BAF chromatin remodeling complex subunit BCL11B (BCL11B), transcript variant 1, mRNA | NM_138576.4 |
| 42 | Amino acid sequence | BCL11B | B-cell lymphoma/leukemia 11B isoform 1 | NP_612808.1 |

TABLE 3-continued

| SEQ ID NO: | Nucleotide sequence/amino acid sequence | Name (SWI/SNF complex factor) | Name (NCBI) | NCBI Reference ID |
|---|---|---|---|---|
| 43 | Nucleotide sequence (cDNA) | SMARCB1 | *Homo sapiens* SWI/SNF related, matrix associated, actin dependent regulator of chromatin, subfamily b, member 1 (SMARCB1), transcript variant 1, mRNA | NM_003073.5 |
| 44 | Amino acid sequence | SMARCB1 | SWI/SNF-related matrix-associated actin-dependent regulator of chromatin subfamily B member 1 isoform a | NP_003064.2 |
| 45 | Nucleotide sequence (cDNA) | BRD7 | *Homo sapiens* bromodomain containing 7 (BRD7), transcript variant 1, mRNA | NM_001173984.3 |
| 46 | Amino acid sequence | BRD7 | bromodomain-containing protein 7 isoform 1 | NP_001167455.1 |
| 47 | Nucleotide sequence (cDNA) | SMARCC1 | *Homo sapiens* SWI/SNF related, matrix associated, actin dependent regulator of chromatin subfamily c member 1 (SMARCC1), mRNA | NM_003074.4 |
| 48 | Amino acid sequence | SMARCC1 | SWI/SNF complex subunit SMARCC1 | NP_003065.3 |
| 49 | Nucleotide sequence (cDNA) | BRD9 | *Homo sapiens* bromodomain containing 9 (BRD9), transcript variant 1, mRNA | NM_023924.5 |
| 50 | Amino acid sequence | BRD9 | bromodomain-containing protein 9 isoform 1 | NP_076413.3 |
| 51 | Nucleotide sequence (cDNA) | SMARCC2 | *Homo sapiens* SWI/SNF related, matrix associated, actin dependent regulator of chromatin subfamily c member 2 (SMARCC2), transcript variant 3, mRNA | NM_001130420.3 |
| 52 | Amino acid sequence | SMARCC2 | SWI/SNF complex subunit SMARCC2 isoform c | NP_001123892.1 |
| 53 | Nucleotide sequence (cDNA) | PBRM1 | *Homo sapiens* polybromo 1 (PBRM1), transcript variant 2, mRNA | NM_018313.5 |
| 54 | Amino acid sequence | PBRM1 | protein polybromo-1 isoform 2 | NP_060783.3 |
| 55 | Nucleotide sequence (cDNA) | SMARCD1 | *Homo sapiens* SWI/SNF related, matrix associated, actin dependent regulator of chromatin, subfamily d, member 1 (SMARCD1), transcript variant 1, mRNA | NM_003076.5 |
| 56 | Amino acid sequence | SMARCD1 | SWI/SNF-related matrix-associated actin-dependent regulator of chromatin subfamily D member 1 isoform a | NP_003067.3 |
| 57 | Nucleotide sequence (cDNA) | PHF10 | *Homo sapiens* PHD finger protein 10 (PHF10), transcript variant 1, mRNA | NM_018288.4 |
| 58 | Amino acid sequence | PHF10 | PHD finger protein 10 isoform a | NP_060758.2 |

The "suppressed function of a SWI/SNF complex factor" in the present invention includes a decrease in activity, including inactivation of a SWI/SNF complex containing the factor (having the factor as a constituent factor), and a decrease in expression of a SWI/SNF complex factor.

[Detection of Decrease in Activity of SWI/SNF Complex]

The "decrease in activity of a SWI/SNF complex" means that the intrinsic activity of the SWI/SNF complex decreases, and normally means that the activity level is lower than a control (e.g. activity level in a healthy subject or a non-cancer tissue of the same patient). The "decrease in activity of a SWI/SNF complex" includes both inactivation and a decrease in activity of all or part of the SWI/SNF complex.

[Direct Detection of Decrease in Activity of SWI/SNF Complex]

The method for "direct detection of a decrease in activity of a SWI/SNF complex" in the present invention is not particularly limited, and a decrease in activity of a SWI/SNF complex can be confirmed by, for example, purifying a SWI/SNF complex from a biological sample by a method such as immunoprecipitation and measuring chromatin remodeling activity (e.g. Michael L. Phelan et al., Molecular Cell, Vol. 3, p. 247-253, February 1999, Reconstitution of a Core Chromatin Remodeling Complex from SWI/SNF Subunits). When the activity is lower than a control, it can be determined that a decrease in activity of the SWI/SNF complex is detected.

As a method for directly detecting a decrease in activity of the SWI/SNF complex, for example, the decrease in activity can also be confirmed by measuring ATPase activity. For example, a SWI/SNF complex is purified from a biological sample by a method such as immunoprecipitation, and using a marketed product such as ADP-glo (manufactured by Promega Corporation), the amount of ATP consumed by the complex is detected. When the result of the detection shows that the amount of ATP consumed is lower than a control, it can be determined a decrease in activity of the SWI/SNF complex is detected.

<Detection of Mutation of Gene for SWI/SNF Complex Factor>

The decrease in activity of a SWI/SNF complex is typically caused by a loss-of-function mutation in a gene for a SWI/SNF complex factor forming the complex (DNA encoding a SWI/SNF complex factor). Thus, a mutation of a gene for a SWI/SNF complex factor can be detected as a decrease in activity of the SWI/SNF complex.

The loss-of-function mutation can be caused by, for example, a missense mutation in a gene for a SWI/SNF complex factor, a nonsense mutation over the entire region, a frameshift mutation, total or partial deletion of a gene, or the like, but is not limited thereto as long as the activity of the SWI/SNF complex is decreased. Table 4 below shows examples of a mutation of a gene for a SWI/SNF complex factor in main cancer cells. Table 4 also shows examples of the presence or absence of a SWI/SNF complex factor in main cancer cells.

TABLE 4

| | | | Status of SWI/SNF component | | | |
|---|---|---|---|---|---|---|
| Cell line | Tissue | Status | mutation | Reference | protein expression | Reference |
| NCI-H358 | Lung | Adenocarcinoma | — | — | — | — |
| NCI-H2122 | Lung | Adenocarcinoma | — | — | — | — |
| NCI-H2110 | Lung | Carcinoma, Non-Small-Cell Lung | — | — | — | — |
| NCI-H1792 | Lung | Adenocarcinoma | — | — | — | — |
| NCI-H1437 | Lung | Adenocarcinoma | — | — | — | — |
| MOR | Lung | Adenocarcinoma | — | — | — | — |
| COV362 | Ovary | Carcinoma | — | — | — | — |
| MKN-45 | Stomach | Adenocarcinoma | — | — | — | — |
| NCI-H838 | Lung | Adenocarcinoma | BCL11B: p.E508* | CCLE | SMARCA2 protein: +<br>SMARCA4 protein: − | Hoffman et al. 2014<br>Hoffman et al. 2014 |
| B1203L | Lung | Adenocarcinoma | ARID1A: p.Q1417*<br>ARID2: p.R572* | In this patent<br>In this patent | — | — |
| SBC-5 | Lung | Carcinoma, Small Cell | SMARCA4: p.RR1243fs | CCLE | SMARCA2 protein: −<br>SMARCA4 protein: − | Hoffman et al. 2014<br>Hoffman et al. 2014 |
| TOV-21G | Ovary | Adenocarcinoma, Clear Cell | ARID1A: p.N756fs, p.P549fs | CCLE | ARID1A protein: − | Ogiwara et al. 2019 |
| NCI-H1703 | Lung | Carcinoma, Squamous Cell | SMARCA4: Splie site | CCLE | SMARCA2 protein: −<br>SMARCA4 protein: − | Matsubara et al. 2012<br>Matsubara et al. 2012 |
| SNU-1327 | Lung | Adenocarcinoma | SMARCA4: p.Q160* | In this patent | — | — |
| NCI-H23 | Lung | Adenocarcinoma | SMARCA4: p.K1566N, p.E1567* | CCLE | SMARCA2 protein: −<br>SMARCA4 protein: − | Matsubara et al. 2012<br>Matsubara et al. 2012 |
| OVISE | Ovary | Adenocarcinoma, Clear Cell | ARID1A: p.H203fs, p.Q543fs<br>ARID1B: p.Y827* | CCLE<br>CCLE | ARID1A protein: − | Ogiwara et al. 2019 |
| NCI-H522 | Lung | Adenocarcinoma | SMARCA4: p.P270fs | CCLE | SMARCA2 protein: −<br>SMARCA4 protein: − | Matsubara et al. 2012<br>Matsubara et al. 2012 |
| SK-HEP-1 | Liver | Adenocarcinoma | SMARCA4: p.E1582* | CCLE | SMARCA2 protein: +<br>SMARCA4 protein: − | Hoffman et al. 2014<br>Hoffman et al. 2014 |

In Table 4, "Reference" indicates databases, documents and the like in which relevant gene mutations (mutation) or presence or absence of expression (protein expression) are reported, "CCLE" indicates a database prepared by Broad Institute: "Cancer Cell Line Encyclopedia (https://portals.broadinstitute.org/ccle), "Hoffman et al. 2014" indicates the document: "Hoffman et al., PNAS Feb. 25, 2014 111 (8), p. 3128-3133", "Matsubara et al., 2012" indicates the document: "Matsubara et al., Cancer Sci, February 2013, vol. 104, No. 2, p. 266-273", "Ogiwara et al., 2019" indicates the document: Ogiwara et al., Volume 35, Issue 2, 11 Feb. 2019, p. 177-190. e8", and "In this patent" indicates that the present inventors have confirmed the presence of a truncating mutation as information of mutation or expression which has not been reported in the literature.

In addition, specific examples of the mutation of a gene for a SWI/SNF complex factor which causes a decrease in activity of a SWI/SNF complex include, but are not limited to, ARID1A: p. Y551Lfs*72 (Insertion-Frameshift) (COSMIC Legacy Mutation ID: COSM 51423).

The method for "detection of a mutation of a gene for a SWI/SNF complex factor" in the present invention is not particularly limited, and examples thereof include the following method.

In the present invention, the phrase "detecting a mutation" means that a mutation on genome DNA is detected in principle. When the mutation on genome DNA is reflected in a change of a base in a transcription product or a change of an amino acid in a translation product, the meaning also includes detection of the change of the transcription product or the translation product (i.e. indirect detection).

The preferred aspect of the method of the present invention is a method for detecting a mutation by directly determining a nucleotide sequence of the region of a gene for a SWI/SNF complex factor in a cancer cell. In the present invention, the "region of a gene for a SWI/SNF complex factor" means a certain region on genome DNA which contains a gene for a SWI/SNF complex factor. The regions also each independently include, in addition to translated regions, untranslated regions such as an expression control region for the relevant gene (e.g. promotor region or enhancer region) and a 3'-end untranslated region for the relevant gene.

In this method, first, a DNA sample is prepared from a biological sample. Examples of the DNA sample include genome DNA samples, and cDNA samples prepared by reverse transcription from RNA.

The method for extracting genome DNA or RNA from a biological sample is not particularly limited, and a known method can be appropriately selected and used. Examples of the method for extracting genome DNA include a SDS phenol method (a method in which protein of a tissue stored in a urea-containing solution or ethanol is denatured with a proteinase (proteinase K), a surfactant (SDS) and phenol, and DNA is precipitated and extracted from the tissue with ethanol), and DNA extraction methods using Clean Columns (registered trademark, manufactured by NexTec Co., Ltd.), AquaPure (registered trademark, manufactured by Bio-Rad Laboratories, Inc.), ZR Plant/Seed DNA Kit (manufactured by Zymo Research), AquaGenomicSolution (registered trademark, manufactured by Mo Bi Tec GmbH), prepGEM (registered trademark, manufactured by ZyGEM LLC) and BuccalQuick (registered trademark, manufactured by TrimGen Corporation).

Examples of the method for extracting RNA from a biological sample and the method for preparing cDNA from the extracted RNA include methods similar to the above-mentioned method for detecting the expression level of GPX4 at a transcriptional level.

In this aspect, subsequently, DNA containing the region of a gene for a SWI/SNF complex factor is isolated, and the nucleotide sequence of the isolated DNA is determined. The isolation of DNA can be performed by PCR with genome DNA or RNA as a template, or the like using a pair of oligonucleotide primers designed to sandwich all or part of the region of a gene for a SWI/SNF complex factor. The determination of the nucleotide sequence of the isolated DNA can be performed by a method known to those skilled in the art, such as a Maxam-Gilbert method or a Sanger method. For the isolated DNA and the extracted DNA, it is also possible to use a next-generation sequencer which enables analysis such that nucleotide sequences of genes can be read rapidly and exhaustively, etc.

By comparing the determined nucleotide sequence of DNA or cDNA (for example, when the biological sample is a cancer patient-derived sample, the nucleotide sequence of DNA or cDNA derived from a non-cancer tissue of the same patient, or a known database), the presence or absence of a mutation in the region of a gene for a SWI/SNF complex factor in a cancer cell of the biological sample can be determined.

As the method for detecting a mutation in the region of a gene for a SWI/SNF complex factor, various methods capable of detecting a mutation can be used in addition to methods for directly determining the nucleotide sequence of DNA or cDNA.

For example, the detection of a mutation in the present invention can also be performed by the following method. First, a DNA or cDNA sample is prepared from a biological sample. Subsequently, an oligonucleotide probe is prepared which has a nucleotide sequence complementary to a nucleotide sequence containing a mutation site of the region of a gene for a SWI/SNF complex factor and is labeled with a reporter fluorescent dye and a quencher fluorescent dye. The oligonucleotide probe is hybridized to the DNA or cDNA sample, and the nucleotide sequence containing the mutation site of the region of a gene for a SWI/SNF complex factor is amplified using as a template the DNA or cDNA sample to which the oligonucleotide probe is hybridized. Fluorescence generated by the reporter fluorescent dye due to degradation of the oligonucleotide probe which is caused by the amplification is detected, and the detected fluorescence is then compared to a control. Examples of such a method include a double-dye probe method, so called a TaqMan (registered trademark) probe method.

In still another method, a DNA or cDNA sample is prepared from a biological sample. Subsequently, in a reaction system containing an intercalator which generated fluorescence when inserted between DNA double strands, a nucleotide sequence containing a mutation site of the region of a gene for a SWI/SNF complex factor is amplified using the DNA or cDNA sample as a template. The temperature of the reaction system is changed, a variation in intensity of fluorescence generated by the intercalator is detected, and the variation in intensity of the fluorescence with the detected change in temperature is compared to a control. Examples of such a method include a HRM (high resolution melting) analysis method.

In still another method, first, a DNA or cDNA sample is prepared from a biological sample. Subsequently, DNA containing all or part of the region of a gene for a SWISNF complex factor is amplified. Further, the amplified DNA is cleaved by a restriction enzyme. Subsequently, DNA fragments are separated according to the sizes thereof. Subsequently, the size of the detected DNA fragment is compared to a control. Examples of such a method include methods utilizing restriction fragment length polymorphism (RFLP), and a PCR-RFLP method.

In still another method, first, a DNA or cDNA sample is prepared from a biological sample. Subsequently, DNA containing all or part of the region of a gene for a SWI/SNF complex factor is amplified. Further, the amplified DNA is dissociated into single-stranded DNA. Subsequently, the dissociated single-stranded DNA is separated on a non-denaturing gel. The mobility of the separated single-stranded DNA on the gel is compared to a control. Examples of such a method include a PCR-SSCP (single-strand conformation polymorphism) method.

In still another method, first, a DNA or cDNA sample is prepared from a biological sample. Subsequently, DNA containing all or part of the region of a gene for a SWI/SNF complex factor is amplified. Further, the amplified DNA is separated on a gel in which the concentration of a DNA denaturant increases in steps. Subsequently, the mobility of the separated DNA on the gel is compared to a control. Examples of such a method include a denaturant gradient gel electrophoresis (DGGE) method.

As still another method, there is a method using DNA prepared from a biological sample and containing a mutation site of the region of a gene for a SWI/SNF complex factor, and a substrate on which an oligonucleotide probe hybridized to the DNA is fixed. Examples of such a method include a DNA array method.

In still another method, first, a DNA or cDNA sample is prepared from a biological sample. An "oligonucleotide primer having a nucleotide sequence complementary to bases on the 3' side of the bases of all or part of the region of a gene for a SWI/SNF complex factor by one base and a nucleotide sequence on the 3' side thereof" is prepared. Subsequently, with the DNA as a template, a dNTP primer elongation reaction is carried out using the primer. Subsequently, the primer elongation reaction product is applied to a mass analyzer to perform mass measurement. Subsequently, the gene type is determined from the result of the mass measurement. Subsequently, the determined gene type is compared to a control. Examples of such a method include a MALDI-TOF/MS method.

In still another method, first, a DNA or cDNA sample is prepared from a biological sample. Subsequently, an oligonucleotide probe consisting of 5'-"nucleotide sequence complementary to the bases of all or part of the region of a gene for a SWI/SNF complex factor and a nucleotide sequence on the 5' side thereof"-"nucleotide sequence which is not hybridized to bases on the 3' side of all or part of the region of a gene for a SWI/SNF complex factor by one base and a nucleotide sequence on the 3' side thereof"-3' (flap) is prepared. An "oligonucleotide probe having a nucleotide sequence complementary to the bases of all or part of the region of a gene for a SWI/SNF complex factor and a nucleotide sequence on the 3' side thereof" is prepared. Subsequently, the two oligonucleotide probes are hybridized to the prepared DNA or cDNA sample. Subsequently, the hybridized DNA is cleaved by a single-stranded DNA cleavage enzyme to liberate the flap. The single-stranded DNA cleavage enzyme is not particularly limited, and examples thereof include cleavases. In this method, subsequently, an oligonucleotide probe which has a sequence complementary to the flap and is labeled with reporter fluorescence and quencher fluorescence is hybridized to the flap. Subsequently, the intensity of generated fluorescence is measured. Subsequently, the measured fluorescence intensity is compared to a control. Examples of such a method include an Invader method.

In still another method, first, a DNA or cDNA sample is prepared from a biological sample. Subsequently, DNA containing all or part of the region of a gene for a SWISNF complex factor is amplified. The amplified DNA is dissociated into single-stranded DNA, and only one strand is separated from the dissociated single-stranded DNA. Subsequently, an elongation reaction is carried out base by base from near the bases of all or part of the region of a gene for a SWI/SNF complex factor, pyrophosphoric acid generated at this time is enzymatically caused to emit light, and the intensity of emission is measured. The measured fluorescence intensity is compared to a control. Examples of such a method include a Pyrosequencing method.

In still another method, first, a DNA or cDNA sample is prepared from a biological sample. Subsequently, DNA containing all or part of the region of a gene for a SWI/SNF complex factor is amplified. Subsequently, an "oligonucleotide primer having a nucleotide sequence complementary to bases on the 3' side of the bases of all or part of the region of a gene for a SWI/SNF complex factor by one base and a nucleotide sequence on the 3' side thereof" is prepared. Subsequently, with the amplified DNA as a template, a single-base elongation reaction is carried out using the prepared primer in the presence of a fluorescently labeled nucleotide. The polarization degree of fluorescence is measured. Subsequently, the measured polarization degree of fluorescence is compared to a control. Examples of such a method include an AcycloPrime method.

In still another method, first, a DNA or cDNA sample is prepared from a biological sample. Subsequently, DNA containing all or part of the region of a gene for a SWI/SNF complex factor is amplified. Subsequently, an "oligonucleotide primer having a nucleotide sequence complementary to bases on the 3' side of the bases of all or part of the region of a gene for a SWI/SNF complex factor by one base and a nucleotide sequence on the 3' side thereof" is prepared. Subsequently, with the amplified DNA as a template, a single-base elongation reaction is carried out using the prepared primer in the presence of a fluorescently labeled nucleotide. Subsequently, the type of base used for the single-base elongation reaction is determined. Subsequently, the determined type of base is compared to a control. Examples of such a method include a SNuPE method.

When the mutation is associated with a change of an amino acid in SWI/SNF complex factor protein (e.g. substitution, deletion, insertion or addition), the sample prepared from the biological sample may be protein. Here, for detecting a mutation, a method using a molecule binding specifically to a site at which a change of amino acids occurs due to the mutation, peptide mass fingerprinting method (PMF), a protein sequencer (Edman degradation method), or the like can be used.

For example, in a method for detecting protein using an antibody, first, a protein sample is prepared from a biological sample. Subsequently, an antigen-antibody reaction is carried out using an antibody specific to SWI/SNF complex factor protein (anti-SWI/SNF complex factor protein antibody), and SWI/SNF complex factor protein is detected. As such a method for detecting protein using an antibody, a method similar to the above-mentioned method for detecting protein using an antibody in the method for detecting the expression level of GPX4 at a translational level can be adjusted to the SWI/SNF complex factor protein, and adopted as appropriate. This method also has an advantage that additional information such as a form or a distribution state of cancer cells in a tissue can also be obtained immunohistochemically.

The type, the origin and the like of an antibody used are not particularly limited, and a monoclonal antibody is preferable. An oligoclonal antibody (mixture of several antibodies or dozens of antibodies) or a polyclonal antibody can also be used as long as it is possible to detect SWI/SNF complex factor protein with sufficient specificity. Functional fractions of antibodies such as Fab, Fab', $F(ab')_2$, Fv, scFv, sc $(Fv)_2$, dsFv and diabodies, and multimers (e.g. dimers, trimers, tetramers and polymers) thereof can also be used. The anti-SWI/SNF complex factor protein antibody may be a marketed product.

The SWI/SNF complex factor protein can also be detected by mass spectrometry (MS). In particular, analysis by a mass spectrometer coupled with liquid chromatography (LC/MS) is sensitive, and therefore advantageous. As a method for detection by mass spectrometry, a method similar to the above-mentioned method for detection by mass spectrometry in the method for detecting the expression level of GPX4 at a translational level can be adjusted to the SWI/SNF complex factor protein, and adopted as appropriate.

[Detection of Decrease in Expression of SWI/SNF Complex Factor]

The "decrease in expression of a SWI/SNF complex factor" normally means that the expression level is lower than a control (e.g. expression level in a healthy subject or a non-cancer tissue of the same patient). Examples of the method for detecting "a decrease in expression of a SWI/SNF complex factor" include a method in which the expression level of a SWI/SNF complex factor is detected at a transcriptional level or a translational level, and compared to the control.

In the method for detecting the expression level of a SWI/SNF complex factor at a transcriptional level, first, RNA or cDNA is prepared from a biological sample by the above-described method. Subsequently, an oligonucleotide primer or an oligonucleotide probe is used for an amplification reaction or a hybridization reaction, and an amplified product or a hybrid product thereof is detected. As such a method, a method similar to the above-mentioned method for detecting the expression level of GPX4 at a transcriptional level can be adjusted to the SWI/SNF complex factor, and adopted as appropriate.

In the method for detecting the expression level of a SWI/SNF complex factor at a translational level, first, a protein sample is prepared from a biological sample. Subsequently, an antigen-antibody reaction is carried out using an antibody specific to SWI/SNF complex factor protein, and SWI/SNF complex factor protein is detected. Such a method for detecting protein using an antibody is as described for the above-mentioned method for detecting SWI/SNF complex factor protein.

In the method for detecting the expression level of a SWI/SNF complex factor at a translational level, the SWI/SNF complex factor protein can also be detected by mass spectrometry (MS). Such a method for detection by mass spectrometry is as described for the above-mentioned method for detecting SWI/SNF complex factor protein.

It is known in the art that one of causes of a decrease in expression of a gene is excessive methylation of a promotor. Therefore, the presence or absence of a suppressed function of a SWI/SNF complex factor may be detected using methylation of a gene promotor for the SWI/SNF complex factor as an indicator. For detection of methylation of a promotor, it is possible to use, for example, a known method such as a method in which a change of a nucleotide sequence after treatment with bisulfite having an activity that converts methylated cytosine into uracil is directly detected by determination of the nucleotide sequence, or indirectly detected using a restriction endonuclease which can recognize (cleave) a nucleotide sequence before the bisulfite treatment and cannot recognize (cleave) a nucleotide sequence after the bisulfite treatment.

(Prediction of Sensitivity and Selection of Cancer Patient)

Thus, if a suppressed function of a SWI/SNF complex factor is detected from a biological sample, and the biological sample is a cancer cell, the cancer cell can be predicted to have sensitivity to a GPX4 inhibitor, and if the biological sample is a cancer cell contained in a cancer patient-derived sample, a cancer patient having the mutation detected in the cancer cell can be predicted to have sensitivity to treatment with a GPX4 inhibitor, and the cancer patient can be selected for cancer treatment with a GPX4 inhibitor.

Here, the "sensitivity to a GPX4 inhibitor" and the "sensitivity to treatment with a GPX4 inhibitor" is an indicator of whether or not the GPX4 inhibitor can exhibit a therapeutic effect on a cancer cell. The sensitivity includes acceleration of death of cancer cells and suppression of growth of cancer cells by the GPX4 inhibitor. The prediction of sensitivity includes not only determination of the presence or absence of sensitivity, but also evaluation of whether sensitivity can be expected or not, etc., and evaluation of the degree of sensitivity when the sensitivity is present (e.g. evaluation of whether high sensitivity can be expected, moderate sensitivity can be expected, or the like). Therefore, a patient for cancer treatment may be selected in line with, for example, a level at which moderate sensitivity can be expected depending on the type and the degree of the suppressed function of a SWI/SNF complex factor.

On the other hand, if a suppressed function of a SWI/SNF complex factor is not observed in a cancer patient-derived sample, the patient can be excluded from subjects for cancer treatment with a GPX4 inhibitor. This enables improvement of the success ratio of the treatment.

(GPX4)

Further, if GPX4 which is targeted by a GPX4 inhibitor according to the present invention is not normally expressed, it may be impossible to effectively perform cancer treatment with a GPX4 inhibitor. Therefore, in the cancer cell sensitivity prediction method, the cancer patient sensitivity prediction method and the cancer patient selection method, detection of a mutation and a decrease in expression of a gene for GPX4 can also be taken as an indicator.

As a method for detecting a mutation of a gene for GPX4, a method similar to the above-mentioned method for "detection of a gene for a SWI/SNF complex factor" can be adjusted to a mutation of a gene for GPX4, and adopted as appropriate. The method for detecting a decrease in expression of GPX4 is as described above.

<Method for Suppressing Growth of Cancer Cells and Method for Treating Cancer>

The present invention also provides:

a method for suppressing growth of cancer cells having a suppressed function of a SWI/SNF complex factor detected, the method comprising the step of:

contacting a GPX4 inhibitor with the cancer cell having the suppressed function of a SWI/SNF complex factor detected (herein, sometimes referred to as a "cancer cell growth inhibition method"); and a method for treating cancer, the method comprising the steps of:

(a) detecting the presence or absence of a suppressed function of a SWI/SNF complex factor in a cancer cell contained in a cancer patient-derived sample; and (b) administering a GPX4 inhibitor to a cancer patient having the suppressed function of a SWI/SNF complex factor detected in the cancer cell (herein, sometimes referred to as a "cancer treatment method").

In the cancer cell growth inhibition method and the cancer treatment method of the present invention, the detection of a suppressed function of a SWI/SNF complex factor and the GPX4 inhibitor are as described above.

The suppression of growth of cancer cells includes acceleration of death of the cancer cells and suppression of growth of the cancer cells. The method for contacting a GPX4 inhibitor with a cancer cell is not particularly limited, and examples thereof include a method in which a GPX4 inhibitor is added to a culture medium for the cancer cell.

The amount of the GPX4 inhibitor to be contacted with the cancer cell may be an amount effective for inhibiting GPX4 to suppress growth of cancer cells, and is appropriately selected according to the properties of a compound inhibiting GPX4, the type of cancer cell, and the like.

The administration of the GPX4 inhibitor to a cancer patient may be oral administration or parenteral administration (e.g. intravenous administration, arterial administration or topical administration).

The dosage of the GPX4 inhibitor administered to a cancer patient may be an amount effective for treating cancer by inhibiting GPX4, and cannot be determined definitely because it is appropriately selected according to the properties of a compound inhibiting GPX4, the age, the body weight, the symptom and the physical condition of a cancer patient, the advancement state of cancer, and the like. For example, when the GPX4 inhibitor is administered to a human, the daily dosage thereof is 0.001 to 100,000 mg, preferably 0.01 to 5,000 mg, in terms of the amount of the compound inhibiting GPX4. The frequency of administration of the GPX4 inhibitor to a cancer patient also cannot be determined definitely, and it is preferable that for example, the GPX4 inhibitor be administered once or in two to four divided doses daily, with the administration being repeated at appropriate intervals. The dosage and the frequency of administration can be appropriately increased or decreased if necessary at a physician's discretion.

In this way, GPX4 is further inhibited in cancer cells having a suppressed function of a SWI/SNF complex factor in a cancer patient, so that the cancer can be treated by acceleration of death and/or suppression of growth of the cancer cells.

The cancer to be treated is not particularly limited, and include at least one selected from the group consisting of lung cancer, ovary cancer, uterus cancer, liver cancer, stomach cancer, esophagus cancer, bowel cancer, pancreas cancer, prostate cancer, bladder cancer and kidney cancer, and among them, at least one selected from the group consisting of lung cancer, ovary cancer, liver cancer, stomach cancer and pancreas cancer is preferable.

<Reagent for Detecting Presence or Absence of Mutation>

The present invention also provides a reagent for detecting the presence or absence of a suppressed function of a SWI/SNF complex factor in the above-described method, the reagent comprising as an active ingredient the molecule of at least one of:

(i) an oligonucleotide primer binding specifically to a gene for a SWI/SNF complex factor;

(ii) an oligonucleotide probe binding specifically to a gene for a SWI/SNF complex factor; and (iii) an antibody binding specifically to SWI/SNF complex factor protein.

The oligonucleotide primer may be designed on the basis of nucleotide sequence information of genome DNA and cDNA for a SWI/SNF complex factor (e.g. Tables 1 to 3) so as to ensure that the primer is consistent with the above-mentioned method and an amplification region, and production of amplified products of genes other than a gene for a SWI/SNF complex factor is avoided as much as possible.

Those skilled in the art can design such an oligonucleotide primer by a conventional method. The oligonucleotide primer has a length of typically 15 to 50 bases, preferably 15 to 30 bases, and may have a larger or smaller length depending on a method and a purpose.

The oligonucleotide probe may be designed on the basis of nucleotide sequence information of genome DNA and cDNA for a SWI/SNF complex factor (e.g. Tables 1 to 3) so as to ensure that the probe is consistent with the above-mentioned method and a hybridization region, and hybridization to genes other than a gene for a SWI/SNF complex factor is avoided as much as possible. Those skilled in the art can design such an oligonucleotide probe by a conventional method. The oligonucleotide probe has a length of typically 15 to 200 bases, preferably 15 to 100 bases, still more preferably 15 to 50 bases, and may have a larger or smaller length depending on a method and a purpose.

It is preferable that the oligonucleotide probe be appropriately labeled and used. Examples of the method for performing labeling include a method in which using T4 polynucleotidekinase, the 5'-end of the oligonucleotide is phosphorylated with 32P to perform labeling; and a method in which using a DNA polymerase such as Klenow enzyme, a substrate base labeled with an isotope such as 32P, a fluorescent dye, biotin or the like with a random hexamer oligonucleotide or the like as a primer is incorporated (random priming method).

The oligonucleotide primer and the oligonucleotide probe can be prepared by, for example, a commercially available oligonucleotide synthesizing machine. It is also possible to prepare the oligonucleotide probe as a double-stranded DNA fragment obtained by restriction enzyme treatment or the like. The oligonucleotide primer and the oligonucleotide probe according to the present invention are not required to be composed only of a natural nucleotide (deoxyribonucleotide (DNA) or ribonucleotide (RNA)), and all or part thereof may be composed of a non-natural nucleotide. Examples of the non-natural nucleotide include PNA (polyamide nucleic acid), LNA (registered trademark, locked nucleic acid), ENA (registered trademark, 2'-0,4'-C-ethylene-bridged nucleic acids), and complexes thereof.

When the antibody binding specifically to the SWI/SNF complex factor protein is a polyclonal antibody, the antibody can be obtained by immunizing an immune animal with an antigen (e.g. SWI/SNF complex factor protein, a partial peptide thereof, or cells which express the protein or the peptide), and purifying antiserum of the animal by conventional means (e.g. salting-out, centrifugation, dialysis or column chromatography). The monoclonal antibody can be prepared by a hybridoma method or a recombinant DNA method.

Typical examples of the hybridoma method include a Kohler&Milstein method (Kohler&Milstein, Nature 1975; 256:495). The antibody-producing cell used in a cell fusion step in this method is a spleen cell, a lymph node cell, a peripheral blood leukocyte or the like of an animal (e.g. mouse, rat, hamster, rabbit, monkey or goat) immunized with an antigen (e.g. SWI/SNF complex factor protein, a partial peptide thereof, or cells which express the protein or the peptide). It is also possible to use antibody-producing cells obtained by applying an antigen in a culture medium to the cells or lymphocytes isolated in advance from animals which are not immunized. As a myeloma cell, any of various known cell lines can be used. The antibody-producing cell and the myeloma cell may be derived from different animal species as long as these cells can be fused with each other, and cells derived from the same animal species are preferable. The hybridoma is produced by, for example, cell fusion between a spleen cell obtained from a mouse immunized with an antigen and a mouse myeloma cell, and by subsequent screening, a hybridoma which produces a monoclonal antibody specific to SWI/SNF complex factor protein can be obtained. The monoclonal antibody to SWI/SNF complex factor protein can be obtained by culturing the hybridoma or from ascites fluid of a mammal given the hybridoma.

The recombinant DNA method is a method in which DNA encoding the antibody is cloned from a hybridoma, a B cell or the like, and incorporated into an appropriate vector, and the vector is introduced into a host cell (e.g. mammal cell line, Bacillus coli, yeast cell, insect cell or plant cell) to produce an antibody according to the present invention as a recombinant antibody (e.g. P. J. Delves, Antibody Production: Essential Techniques, 1997 WILEY, P. Shepherd and C. Dean Monoclonal Antibodies, 2000 OXFORD UNIVERSITY PRESS, Vandamme A M et al., Eur. J. Biochem. 1990; 192:767-775). In expression of DNA encoding an antibody, DNAs encoding a heavy chain or a light chain may be incorporated into different expression vectors to transform the host cell, or DNAs encoding a heavy chain and a light chain may be incorporated into a single expression vector to transform the host cell (e.g. WO 94/11523). The antibody can be obtained in a substantially pure and homogeneous form by culturing the host cell, separating the antibody from the inside of the host cell or the culture solution and purifying the antibody. For the separation and purification of the antibody, a common method which is used for purification of a polypeptide can be used. When a transgenic animal (e.g. bovine, goat, sheep or pig) into which an antibody gene is incorporated is prepared using a transgenic animal preparation technique, a large amount of a monoclonal antibody derived from the antibody gene can be obtained from milk from the transgenic animal.

On the basis of the thus-obtained antibodies or genes thereof, functional fractions of antibodies such as Fab, Fab', $F(ab')_2$, Fv, scFv, sc $(Fv)_2$, dsFv and diabodies, and multimers (e.g. dimers, trimers, tetramers and polymers) thereof can be prepared.

When the amount of an antibody bound to SWI/SNF complex factor protein is directly detected, the resulting anti-SWI/SNF complex factor protein antibody is directly labeled with an enzyme, a radioisotope, a fluorescent dye, an avidin-biotin system or the like and used. On the other hand, when an indirect detection method is carried out in which the amount of an antibody bound to SWI/SNF complex factor protein is detected using a secondary antibody etc., the resulting anti-SWI/SNF complex factor protein antibody (primary antibody) is not required to be labeled, and for the detection, a labeled molecule which recognizes the antibody (e.g. secondary antibody or protein A) may be used.

The reagent according to the present invention may comprise other ingredients acceptable for reagents, such as sterilized water, physiological saline, a buffering agent and a preservative if necessary in addition to the above-described molecule as an active ingredient.

<Method for Screening Compounds to be Used for Treatment of Cancer and Cancer Therapeutic Drug>

The present invention provides:

a method for screening compounds to be used for treatment of cancer containing a cancer cell having a suppressed function of a SWI/SNF complex factor detected, the method comprising the step of:

selecting a compound on the basis of whether GPX4 is inhibited or not (hereinafter, sometimes referred to as a "method for screening compounds).

By using each of compounds which inhibit GPX4 and are screened by the method for screening compounds, there can be provided a cancer therapeutic drug comprising a compound which inhibits GPX4 as an active ingredient, the cancer therapeutic drug being a therapeutic drug for cancer containing a cancer cell having a suppressed function of a SWI/SNF complex factor detected.

The test compound applied to the method for screening compounds according to the present invention is not particularly limited, and examples thereof include at least one selected from the group consisting of the above-described compound molecules listed as compounds which inhibit GPX4, polypeptides and polynucleotides. More specific examples of the test compound include synthetic low-molecular compound libraries, expressed products of gene libraries, peptide libraries, siRNA, antibodies, bacteria releasing substances, extracts and culture supernatants of cells (microorganisms, plant cells and animal cells), purified or partially purified polypeptides, marine organisms, plant or animal-derived extracts, and random phage peptide display libraries. The test compound may be a derivative of a known GPX4 inhibitor.

In the method for selecting a compound on the basis of whether GPX4 is inhibited or not (screening), a test compound may be applied to the system for confirmation of inhibition of activity or expression of GPX4, followed by detecting subsequent GPX4 activity or expression. When the result of detection shows that the activity or expression decreases as compared to GPX4 activity or expression in a control (e.g. a case where the test compound is not added), it can be evaluated that GPX4 is inhibited.

The "GPX4" which is evaluated for being inhibited or not by the compound in the screening is as described above.

The compound identified by the method for screening compounds according to the present invention can be formed into a cancer therapeutic drug as a medicament by appropriately mixing the compound with any of the pharmacologically acceptable additive ingredients mentioned for the GPX inhibitor above, etc. and subjecting the resulting mixture to formulation by a known pharmaceutical method. In particular, the compound can be formed into a therapeutic drug which is effective for cancer containing a cancer cell having a suppressed function of a SWI/SNF complex factor and is used for treating a cancer patient having a suppressed function of a SWI/SNF complex factor detected, and/or administered to the patient.

EXAMPLE

Hereinafter, the present invention will be described in more detail on the basis of Example, but the present invention is not limited to Examples below.

1. Experimental Material and Method (1) Cell Line

The cancer cell lines shown in Table 4 above: NCI-H358, NCI-H2122, NCI-H2110, NCI-H1792, NCI-H1437, MOR, COV362, MKN-45, NCI-H838, B1203L (Int J Cancer. 2006; 118:1992-7), SBC-5, TOV-21G, NCI-H1703, SNU-1327, NCI-H23, OVISE, NCI-H522 and SK-HEP-1 were used as cell lines to be tested in the present invention. The original sourced for the cell lines are shown in Table 5. As shown in Table 4 above, NCI-H23, NCI-H522, SBC-5, SK-HEP-1 and SNU-1327 are human cancer cell lines having a truncating mutation in a gene for SMARCA4, and NCI-H1703 is a human cancer cell line having a mutation at a splicing site of a gene for SMARCA4. NCI-H1703, NCI-H23, NCI-H522, SBC-5, SK-HEP-1 and NCI-H838 are human cancer cell lines in which expression of SMARCA4 protein is not detected in immunoblot analysis. NCI-H1703, NCI-H23, NCI-H522 and SBC-5 are human cancer cell lines in which SMARCA2 protein is not detected in immunoblot analysis. B1203L, OVISE and TOV-21G are human cancer cell lines having a truncating mutation in a gene for ARID1A, B1203L is a human cancer cell line having a truncating mutation in a gene for ARID2, OVISE is a human cancer cell line having a truncating mutation in a gene for ARID1B, and NCI-H838 is a human cancer cell line having a truncating mutation in a gene for BCL11B. On the other hand, NCI-H358, NCI-H2122, NCI-H2110, NCI-H1792, NCI-H1437, MOR, COV362 and MKN-45 are human cancer cell lines for which information about a loss-of-function mutation of a gene for a SWI/SNF complex factor and expression of protein has not been published.

(2) Small Interfering (si)RNA

For suppression of expression of GPX4, ON-TARGETplus Individual siRNA (manufactured by Dharmacon, Inc.) was used. For transfection, Lipofectamine RNAiMAX (manufactured by Thermo Fisher Scientific, product code: 13778150) was used. Non-target SIRNA (ON-TARGET plus Non-targeting Control, Dharmacon, Inc. product code: D-001810-01, SEQ ID NO: 60) was used as a negative control, and PLK1 (Dharmacon, Inc. product code: J-003290-09, SEQ ID NO: 59) was used as a positive control. For dilution of each siRNA, the siRNA was dissolved using a 1× siRNA buffer obtained by diluting a 5× siRNA buffer (manufactured by Dharmacon: B-002000-UB-100) by 5 times with nuclease free water (AM 9932 manufactured by Ambion, Inc.).

(3) Test for Suppression of Expression of GPX4

In the cancer cell lines described in (1) above and shown in Table 4, cell growth inhibition activity under suppression of expression of GPX4 was evaluated. Each cell line was seeded at 100 μL/well on a 96-well plate (manufactured by Greiner Bio-One GmbH) so as to attain the seeding density (1) or (2) shown in Table 5 below. For transfection evaluation, GPX4 siRNA (#1, #2 and #3), a negative control (ON-TARGET plus Non-targeting Control) and a positive control (PLK1 siRNA) shown in Table 6 below were used. The final concentration of each siRNA was 0.1 to 10 nM, and for transfection, Lipofectamine RNAiMAX (manufactured by Thermo Fisher Scientific, product code: 13778150) was used. The cells were cultured for 7 days, and the intracellular ATP which is a marker for cell survival was then measured using Cell Titer-Glo 2.0 Cell Viability Assay (manufactured by Promega Corporation). The cell growth inhibition ratio in suppression of expression of GPX4 was calculated, where the value for the cells transfected with the negative control and cultured for 7 days and the value for the cells transfected with the positive control and cultured for 7 days were defined as 0% and 100%, respectively.

Figure 2:
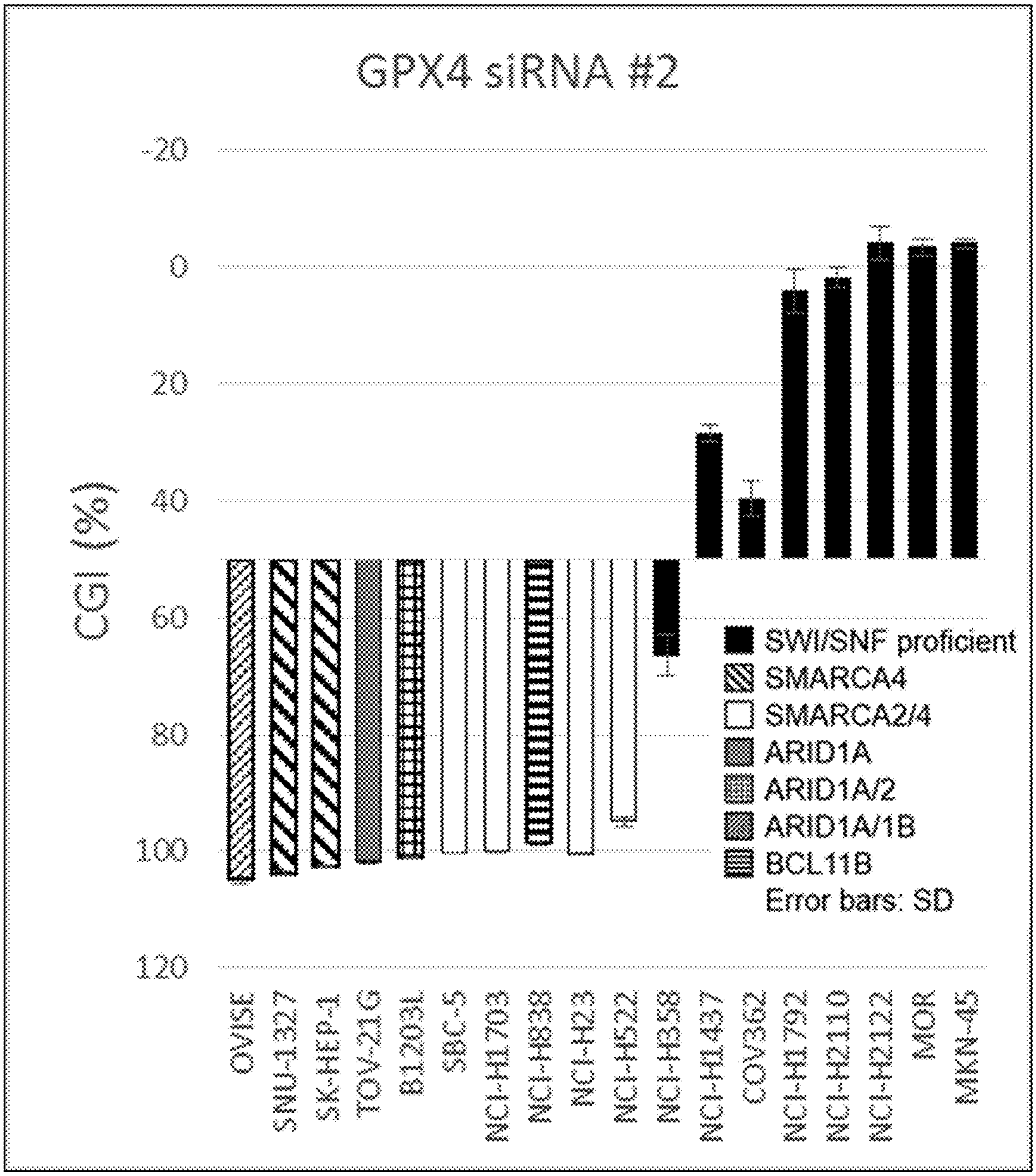
FIG. 2 is a graph showing cell growth inhibition ratios (CGI (%)) in suppression of expression of GPX4 (#2) in the cell lines shown in Table 4.
Figure 3:
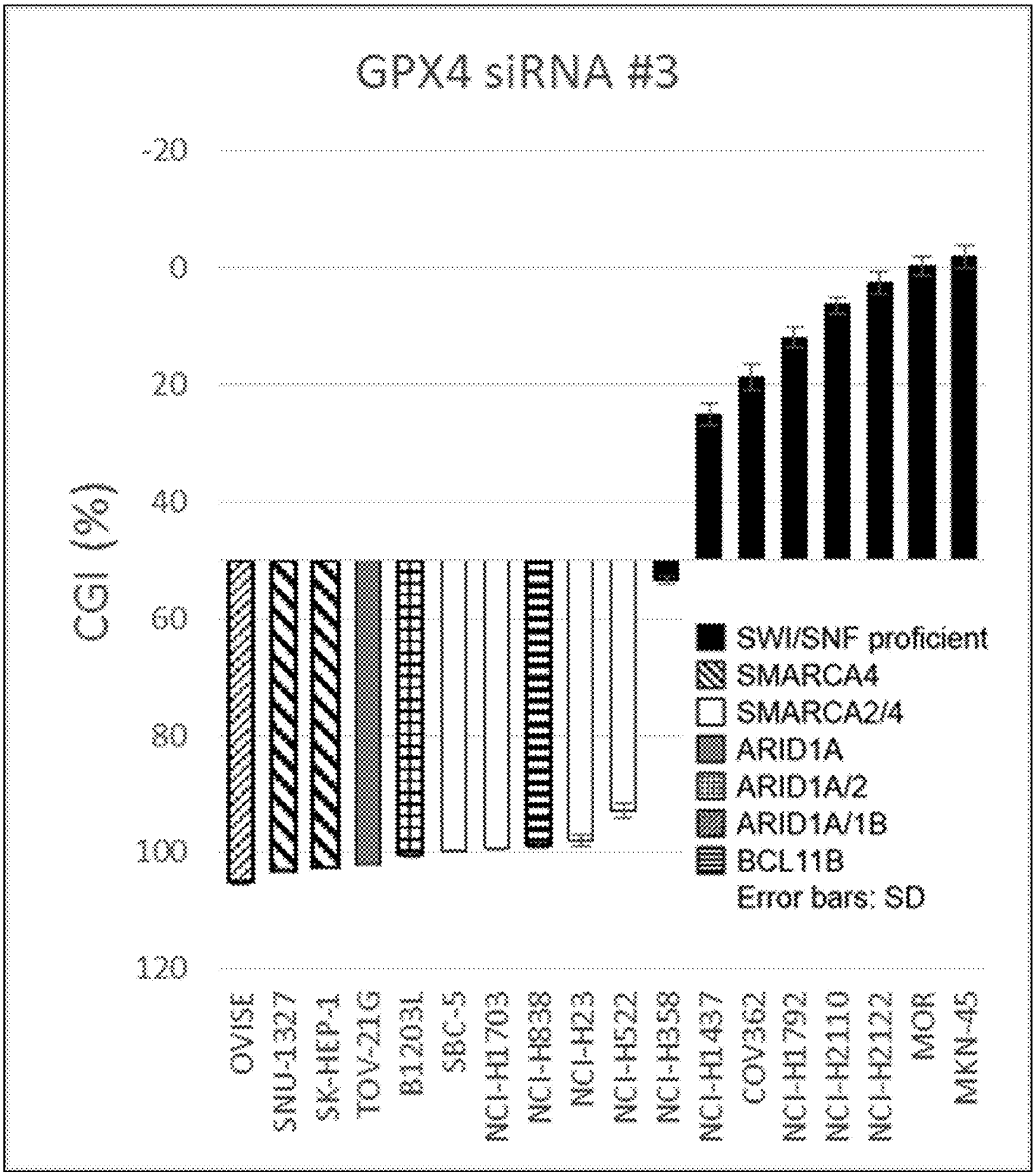
FIG. 3 is a graph showing cell growth inhibition ratios (CGI (%) in suppression of expression of GPX4 (#3) in the cell lines shown in Table 4.

FIG. 1 shows cell growth inhibition ratios (CGI (%)) in suppression of expression of GPX4 by GPX4 siRNA #1 or #2 in the cell lines (lung cancer cell lines) of NCI-H1792, MOR, NCI-H2110, NCI-H522, NCI-H23 and SNU-1327. FIG. 2 shows cell growth inhibition ratios (CGI (%)) in suppression of expression of GPX4 by GPX4 siRNA #2 and FIG. 3 shows cell growth inhibition ratios (CGI (%)) in suppression of expression of GPX4 by GPX4 siRNA #3 in the cell lines (including lung cancer cell lines, ovary cancer cell lines, liver cancer cell lines and stomach cancer cell lines) shown in Table 4 and tested at a time different from that for FIG. 1.

(4) Test for Inhibition of Activity of GPX4 1

In each cancer cell line, cell growth inhibition activity under a GPX4 inhibitor was evaluated. As the GPX4 inhibitor, ML210 (CAS No: 1360705-96-9) which is a low-molecular GPX4 inhibitor reported to be a compound inhibiting the enzymatic activity of GPX4:

[Formula 1]

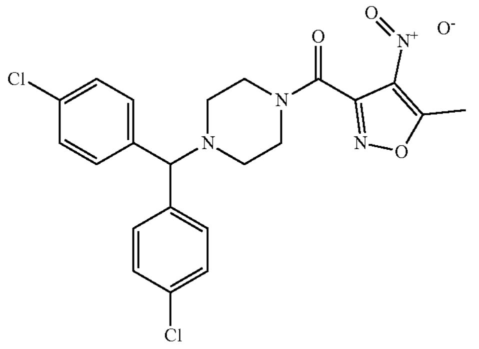

or RSL3 (CAS No: 1219810-16-8):

[Formula 2]

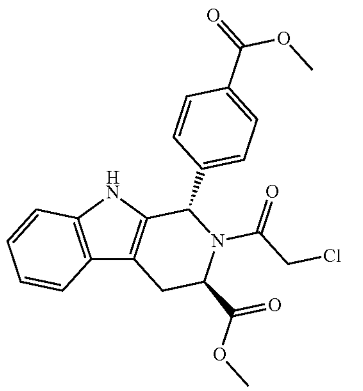

was used.

Figure 4:
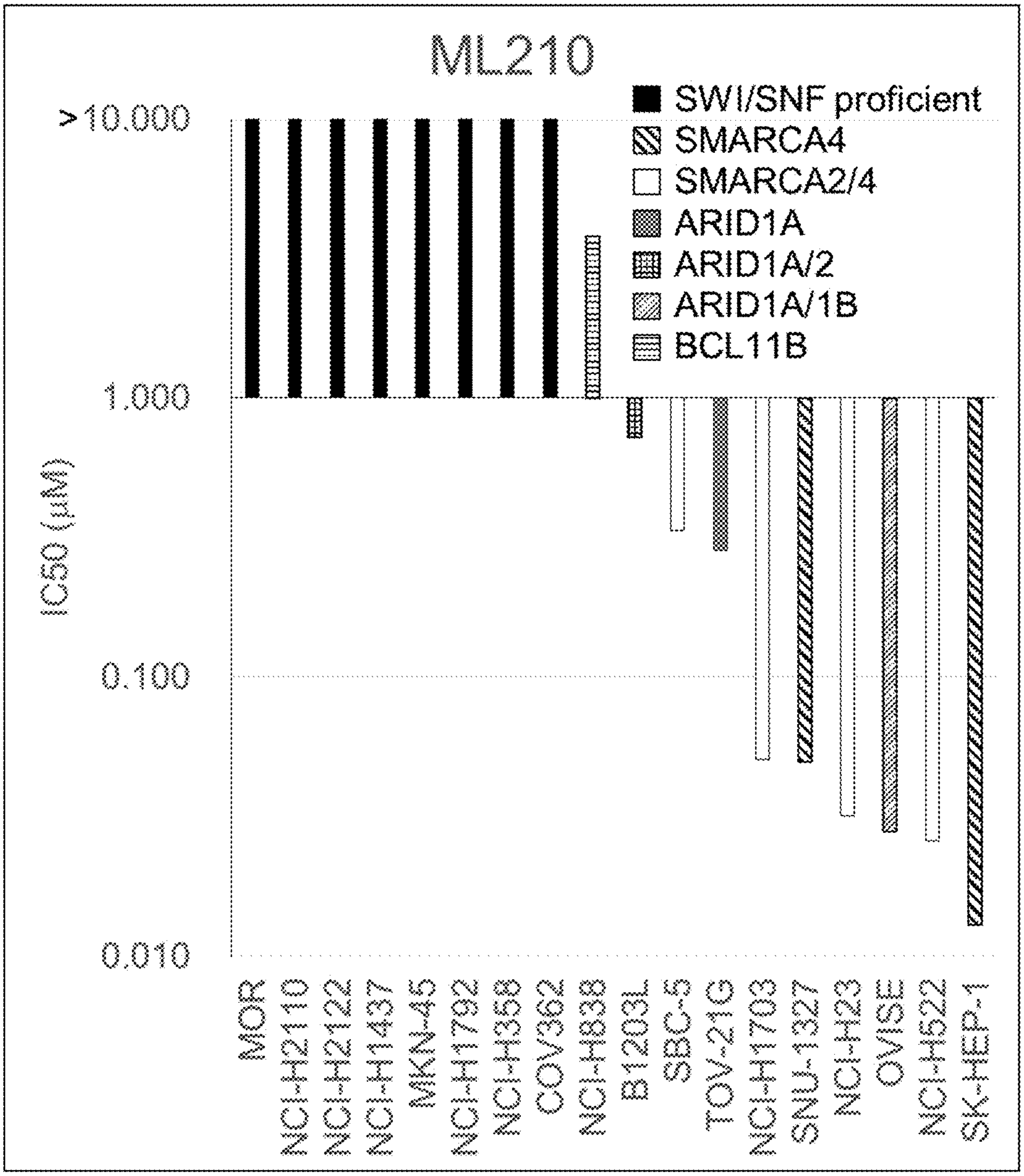
FIG. 4 is a graph showing IC50 (μM) in the cell lines shown in Table 4 when ML210 is used as a GPX4 inhibitor.
Figure 5:
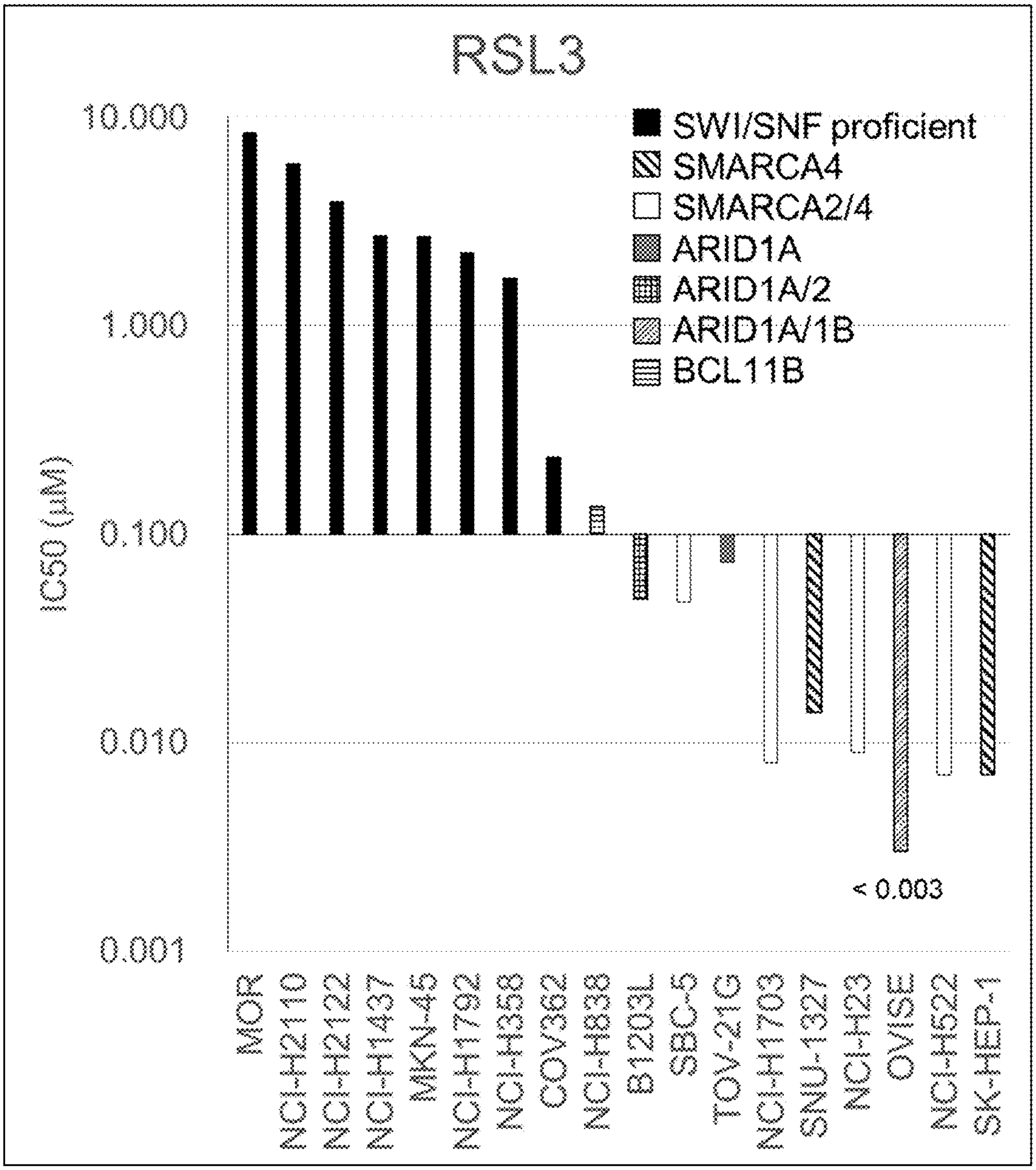
FIG. 5 is a graph showing IC50 (μM) in the cell lines shown in Table 4 when RSL3 is used as a GPX4 inhibitor.

These compounds were each added, and each cell line was seeded at 100 μL/well so as to attain the seeding density (2) shown in Table 5 below. The cells were cultured for 7 days, the intracellular ATP which is a marker for cell survival was then measured using Cell Titer-Glo 2.0 Cell Viability Assay (manufactured by Promega Corporation), and the cell survival rate was calculated, where the intracellular ATP level in each cancer cell line given only a solvent (dimethyl sulfoxide (DMSO) or water) for the compound and cultured for 7 days was defined as 100%. IC50 (50% inhibition concentration (μM) was calculated from a cell survival curve obtained from the concentration of each compound and the cell survival rate. FIG. 4 shows IC50 (μM) in the cell lines when ML210 was used as the GPX4 inhibitor, and FIG. 5 shows IC50 (μM) in the cell lines when RSL3 was used as the GPX4 inhibitor.

(5) Test for Suppression of Expression of GPX Family Protein

Figure 6:
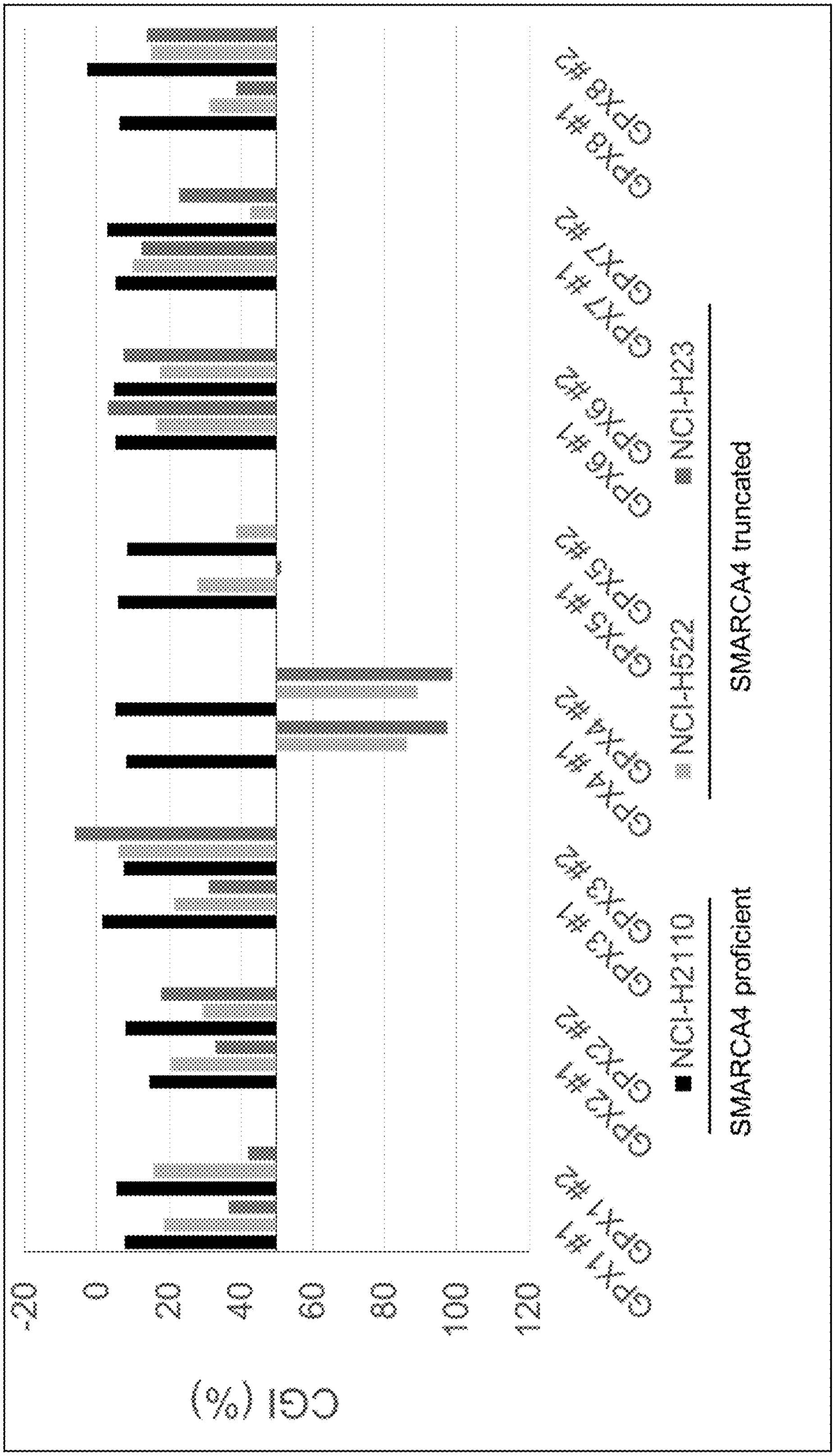
FIG. 6 is a graph showing cell growth inhibition ratios (CGI (%)) in suppression of expression of GPX family proteins in the cell lines of NCI-H2110, NCI-H522 and NCI-H23.

In the cancer cell lines, cell growth inhibition activity under suppression of expression of GPX1 to GPX8 which are GPX family proteins was evaluated. Each cell line was seeded at 100 L/well on a 96-well plate so as to attain the seeding density (2) shown in Table 5 below. For transfection evaluation, GPX1 siRNA (#1 and #2), GPX2 siRNA (#1 and #2), GPX3 siRNA (#1 and #2), GPX4 siRNA (#1 and #2), GPX5 siRNA (#1 and #2), GPX6 siRNA (#1 and #2), GPX7 siRNA (#1 and #2) and GPX8 siRNA (#1 and #2) (all from Dharmacon, Inc.) shown in Table 6 below were used, respectively. The final concentration of each siRNA was 5 nM or 10 nM, and for transfection, Lipofectamine RNAiMAX (Thermo Fisher Scientific, product code: 13778150) was used. The cells were cultured for 7 days, and the intracellular ATP which is a marker for cell survival was then measured using Cell Titer-Glo 2.0 Cell Viability Assay (manufactured by Promega Corporation). The cell growth inhibition ratio in suppression of expression of each GPX family protein was calculated, where the value for the cells transfected with the negative control and cultured for 7 days and the value for the cells transfected with the positive control and cultured for 7 days were defined as 0% and 100%, respectively. FIG. 6 shows cell growth inhibition ratios (CGI (%)) in suppression of expression of GPX family proteins in the cell lines of NCI-H2110, NCI-H522 and NCI-H23.

Figure 7:
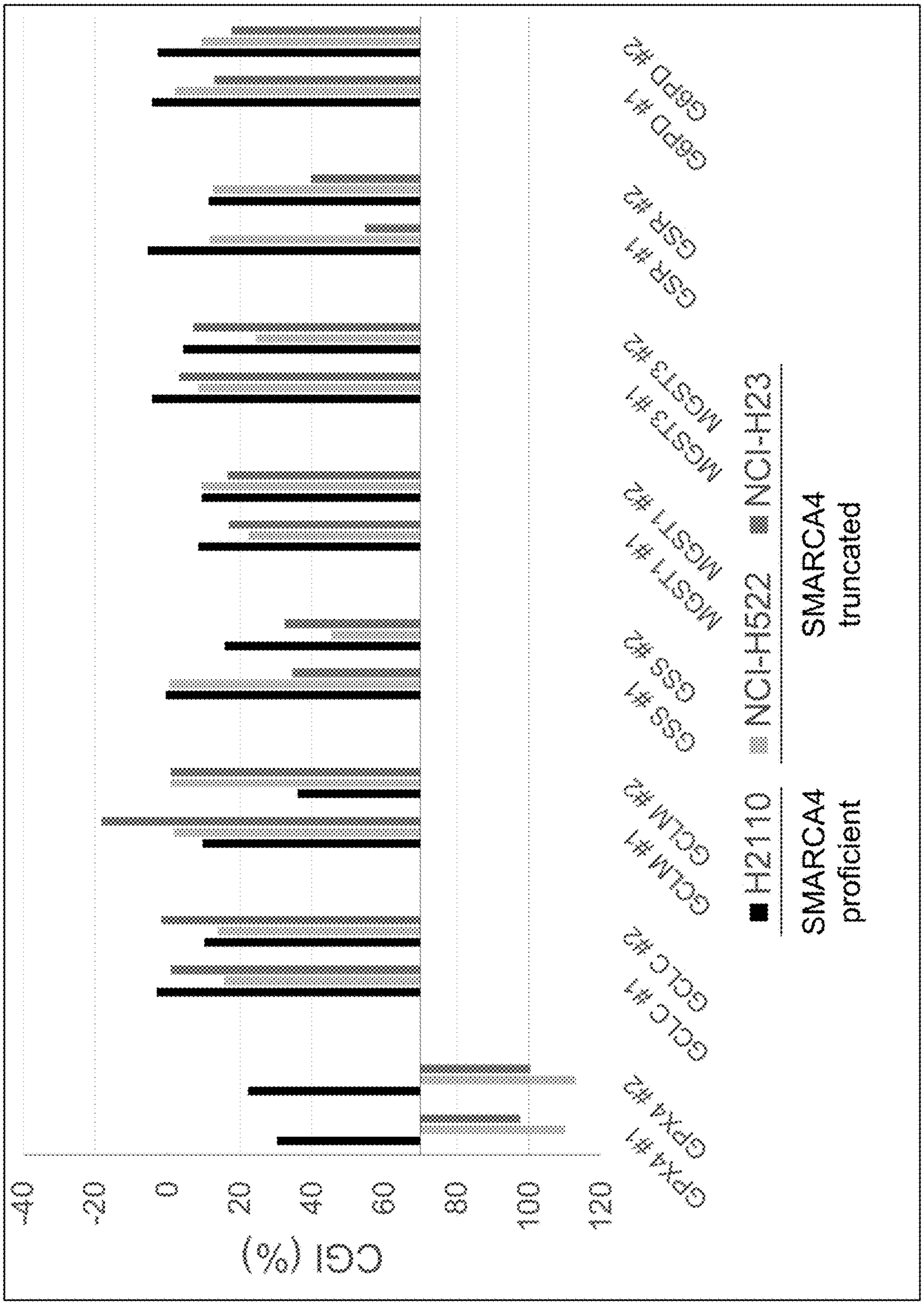
FIG. 7 is a graph showing cell growth inhibition ratios (CGI (%)) in suppression of expression of proteins involved in glutathione synthesis in the cell lines of NCI-H2110, NCI-H522 and NCI-H23.

(6) Test for Suppression of Expression of Protein Involved in Glutathione Synthesis In the cancer cell lines, cell growth inhibitory activity under suppression of expression of protein which is involved in glutathione synthesis (protein involved in glutathione synthesis) was evaluated. Each cell line was seeded at 100 μL/well on a 96-well plate so as to attain the seeding density (2) shown in Table 5 below. For the transfection assay, GPX4 siRNA (#1 and #2), GCLC siRNA (#1 and #2), GCLM siRNA (#1 and #2), GSS siRNA (#1 and #2), MGST1 siRNA (#1 and #2), MGST3 siRNA (#1 and #2), GSR siRNA (#1 and #2) and G6PD siRNA (#1 and #2) (all from Dharmacon, Inc.) shown in Table 6 below were used, respectively. The final concentration of each siRNA was 5 nM, and for transfection, Lipofectamine RNAiMAX (Thermo Fisher Scientific, product code: 13778150) was used. The cells were cultured for 7 days, and the intracellular ATP which is a marker for cell survival was then measured using Cell Titer-Glo 2.0 Cell Viability Assay (manufactured by Promega Corporation). The cell growth inhibition ratio in suppression of expression of each protein involved in glutathione synthesis was calculated, where the value for the cells transfected with the negative control and cultured for 7 days and the value for the cells transfected with the positive control and cultured for 7 days were defined as 0% and 100%, respectively. FIG. 7 shows cell growth inhibition ratios (CGI (%)) in suppression of expression of proteins involved in glutathione synthesis in the cell lines of NCI-H2110, NCI-H522 and NCI-H23.

TABLE 5

| Cell line | Culture solution | Seeding density (cells/well) (1) | Seeding density (cells/well) (2) | Original source |
|---|---|---|---|---|
| B1203L | RPMI-1640, 10% FBS | 2000 | 2000 | RIKEN Cell Bank* |
| COV362 | D-MEM(high glucose), 10% FBS | 2000 | 1000 | ECACC 07071910 |
| MKN-45 | RPMI-1640, 10% FBS | 3000 | 1500 | JCRB Cell Bank |
| MOR | RPMI-1640, 10% FBS | 5000 | 3000 | ECACC 84112312 |
| NCI-H1437 | RPMI-1640, 10% FBS | 1500 | 2000 | ATCC |
| NCI-H1703 | RPMI-1640, 10% FBS, 10 mM HEPES, 0.45% D-glucose, 1 mM Sodium Pyruvate | 1500 | 3000 | ATCC |
| NCI-H1792 | RPMI-1640, 10% FBS, 10 mM HEPES, 0.45% D-glucose, 1 mM Sodium Pyruvate | 3000 | 5000 | ATCC |
| NCI-H2110 | RPMI-1640, 10% FBS, 10 mM HEPES, 0.45% D-glucose, 1 mM Sodium Pyruvate | 5000 | 5000 | ATCC |
| NCI-H2122 | RPMI-1640, 10% FBS, 10 mM HEPES, 0.45% D-glucose, 1 mM Sodium Pyruvate | 3000 | 3000 | ATCC |
| NCI-H23 | RPMI-1640, 10% FBS, 10 mM HEPES, 0.45% D-glucose, 1 mM Sodium Pyruvate, 2 mM L-glutamine | 1500 | 1500 or 2000 | ATCC |
| NCI-H358 | RPMI-1640, 10% FBS | 3000 | 3000 | ATCC |
| NCI-H522 | RPMI-1640, 10% FBS, 10 mM HEPES, 0.45% D-glucose, 1 mM Sodium Pyruvate, 2 mM L-glutamine | 5000 | 2000 | ATCC |
| NCI-H838 | RPMI-1640, 10% FBS, 10 mM HEPES, 0.45% D-glucose, 1 mM Sodium Pyruvate | 500 | 1000 | ATCC |
| OVISE | RPMI-1640, 10% FBS | 4000 | 2000 | JCRB Cell Bank |
| SBC-5 | E-MEM, 10% FBS, 1% NEAA, 1 mM Sodium Pyruvate | 4000 | 4000 | JCRB Cell Bank |
| SK-HEP-1 | D-MEM(high glucose), 10% FBS | 2000 | 3000 | ATCC |
| SNU-1327 | RPMI-1640, 10% FBS, 25 mM HEPES | 5000 | 3000 | KCLB |
| TOV21G | MCDB105:medium199 = 1:1, 15% FBS, | 1000 | 2000 | ATCC |

ECACC: European Collection of Authenticated Cell Cultures
ATCC: American Type Culture Collection
KCLB: Korean Cell Line Bank
*B1203L was provided by the RIKEN BRC through the National Bio-Resource Project of the MEXT, Japan.

TABLE 6

| Duplex Catalogue No. | siRNA | GENE ID | NCBI Reference ID | GI Number | SEQ ID NO: |
|---|---|---|---|---|---|
| J-003290-09 | PLK1 | 5347 | NM_005030 | 34147632 | 59 |
| D-001810-01 | ON-TARGETplus Non-targeting Control | — | — | — | 60 |
| J-008982-05 | GPX1 siRNA #1 | 2876 | NM_000581 | 41406083 | 61 |
| J-008982-06 | GPX1 siRNA #2 | 2876 | NM_000581 | 41406083 | 62 |
| J-011675-06 | GPX2 siRNA #1 | 2877 | NM_002083 | 32967606 | 63 |
| J-011675-07 | GPX2 siRNA #2 | 2877 | NM_002083 | 32967606 | 64 |
| J-006485-06 | GPX3 siRNA #1 | 2878 | NM_002084 | 6006000 | 65 |
| J-006485-07 | GPX3 siRNA #2 | 2878 | NM_002084 | 6006000 | 66 |
| J-011676-06 | GPX4 siRNA #1 | 2879 | NM_002085 | 75709199 | 67 |
| J-011676-07 | GPX4 siRNA #2 | 2879 | NM_002085 | 75709199 | 68 |
| J-009445-20 | GPX5 siRNA #1 | 2880 | NM_003996 | 209977068 | 69 |
| J-009445-21 | GPX5 siRNA #2 | 2880 | NM_003996 | 209977068 | 70 |
| J-019309-10 | GPX6 siRNA #1 | 257202 | NM_182701 | 33186886 | 71 |
| J-019309-11 | GPX6 siRNA #2 | 257202 | NM_182701 | 33186886 | 72 |
| J-009875-09 | GPX7 siRNA #1 | 2882 | NM_015696 | 15618996 | 73 |
| J-009875-11 | GPX7 siRNA #2 | 2882 | NM_015696 | 15618996 | 74 |
| J-034902-07 | GPX8 siRNA #1 | 493869 | NM_001008397 | 56605999 | 75 |
| J-034902-08 | GPX8 siRNA #2 | 493869 | NM_001008397 | 56605999 | 76 |
| J-009212-09 | GCLC siRNA #1 | 2729 | NM_001498 | 45359851 | 77 |
| J-009212-10 | GCLC siRNA #2 | 2729 | NM_001498 | 45359851 | 78 |
| J-011670-09 | GCLM siRNA #1 | 2730 | NM_002061 | 53759142 | 79 |
| J-011670-10 | GCLM siRNA #2 | 2730 | NM_002061 | 53759142 | 80 |
| J-009586-05 | GSS siRNA #1 | 2937 | NM_000178 | 30581166 | 81 |
| J-009586-07 | GSS siRNA #2 | 2937 | NM_000178 | 30581166 | 82 |
| J-009248-05 | MGST1 siRNA #1 | 4257 | NM_145792 | 22035637 | 83 |
| J-009248-06 | MGST1 siRNA #2 | 4257 | NM_145792 | 22035637 | 84 |
| J-008382-09 | MGST3 siRNA #1 | 4259 | NM_004528 | 22035640 | 85 |
| J-008382-10 | MGST3 siRNA #2 | 4259 | NM_004528 | 22035640 | 86 |
| J-009647-07 | GSR siRNA #1 | 2936 | NM_000637 | 50301237 | 87 |
| J-009647-08 | GSR siRNA #2 | 2936 | NM_000637 | 50301237 | 88 |
| J-008181-18 | G6PD siRNA #1 | 2539 | NM_001042351 | 108773792 | 89 |
| J-008181-19 | G6PD siRNA #2 | 2539 | NM_001042351 | 108773792 | 90 |
| J-011676-05 | GPX4 siRNA #3 | 2879 | NM_002085 | 75709199 | 91 |

Table 5 shows seeding densities of the cell lines in the tests and culture solutions and original sources for the cell lines. Table 6 shows sequence numbers showing the sequences of the siRNAs, and IDs (gene IDs) in the NCBI RefSeq database, reference IDs (NCBI reference IDs) and GI numbers for genes whose expression is suppressed by the siRNAs.

(7) Test for Inhibition of Activity of GPX4 2 (Comparative Test with GCLC Inhibitor)

In each cancer cell line, cell growth inhibition activity under a GPX4 inhibitor was evaluated. As the GPX4 inhibitor, the ML210 or RSL3 was used. As a comparative control, buthionine sulphoximine (BSO, CAS No: 83730-53-4) that is an inhibitor of protein GCLC which is involved in glutathione synthesis (catalyst subunit of glutamate-cysteine ligase (GCL) that is a rate limiting enzyme for glutathione synthesis):

[Formula 3]

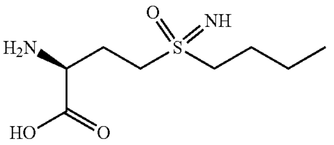

was used. These compounds were each added, and each cell line was seeded at 100 μL/well so as to attain the seeding density (2) shown in Table 5 above. The cells were cultured for 7 days, the intracellular ATP which is a marker for cell survival was then measured using Cell Titer-Glo 2.0 Cell Viability Assay (manufactured by Promega Corporation), and the cell survival rate was calculated, where the intracellular ATP level in each cancer cell line given only a solvent (dimethyl sulfoxide (DMSO) or water) for the compound and cultured for 7 days was defined as 100%. IC50 (50% inhibition concentration (μM) was calculated from a cell survival curve obtained from the concentration of each compound and the cell survival rate.

Figure 8:
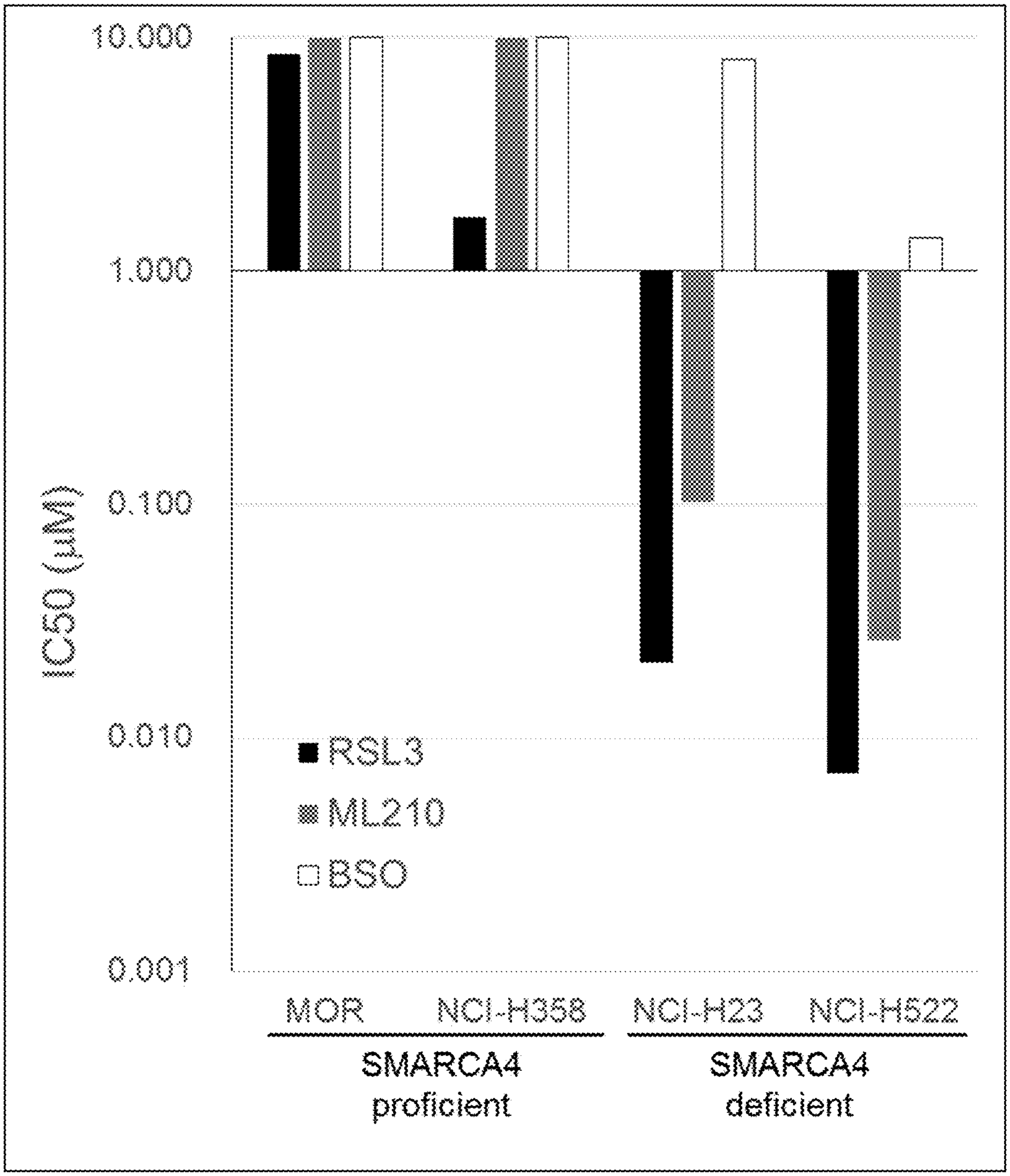
FIG. 8 is a graph showing IC50 (μM) in the cell lines MOR, NCI-H358, NCI-H23 and NCI-H522 when ML210, RSL3 or BSO is used.

FIG. 8 shows IC50 (μM) in the cell lines MOR, NCI-H 358, NCI-H23 and NCI-H522 when ML210, RSL3 or BSO is used.

(8) Test for Drug Efficacy of ML210 on SK-HEP-1 Tumor-Bearing Mouse

For examining the efficacy of the GPX4 inhibitor on SWI/SNF complex factor-deficient cancer in vivo, a test was conducted in which ML210 was administered to mice in which SK-HEP-1 (human cancer cell line suppressing a function of SMARCA4) was transplanted (SK-HEP-1 tumor-bearing mice). Specifically, first, SK-HEP-1 was cultured in vitro, and collected using a solution at 2.5 g/L-tripsin/1 mmol-EDTA (manufactured by Nacalai tesque, product code: 35554-64) on the day of inoculation to the mice, and the cells were suspended at 2.5 E7 cells/mL in a solution of Matrigel (manufactured by Corning Incorporated, product name: 356234) diluted with the Hanks' Balanced Salt solution (manufactured by Sigma-Aldrich Co. LLC, product code: H 9269) (final concentration: 50%). 0.2 mL of the prepared cell suspension was transplanted into the groin of each of BALB/c-nu/nu mice (CAnN. Cg-Foxn 1 <nu>/CrlCrlj, Charles River, Inc.).

Figure 9:
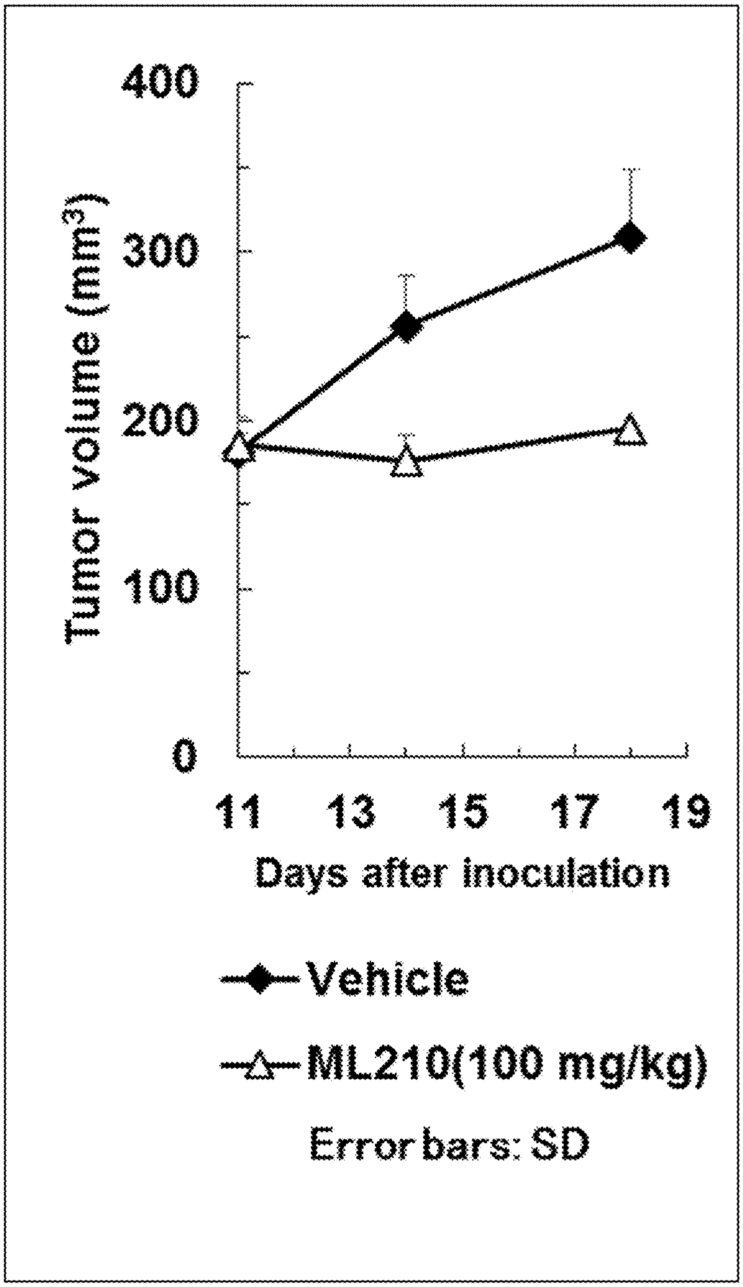
FIG. 9 is a graph showing a relationship between the volume of a tumor and the time after inoculation of SK-HEP-1 in each group of SK-HEP-1 tumor-bearing mice (ML210 or vehicle).

Subsequently, to mice (SK-HEP-1 tumor-bearing mice) for which the engraftment of the tumor (cancer cell) had been confirmed, a dosing liquid obtained by suspending ML210 at a predetermined concentration in a mixed liquid of 10% dimethyl sulfoxide (manufactured by Wako Company, product code: 043-07216), 10% Cremophor (manufactured by Sigma-Aldrich Co. LLC, product code: C5135), 15% polyethylene glycol 400 (manufactured by Wako Company, product code: 161-09065) and 15% hydroxypropyl-β-cyclodextrin (manufactured by Nihon Shokuhin Kako Co., Ltd., product code: 7585-39-9) was orally administered at a predetermined dose (20 mL/kg) once a day to a daily dosage of 100 mg/kg upon the confirmation of the implantation. The day of inoculation of SK-HEP-1 was defined as day 0, administration of ML210 was started on day 11, and the volume of the tumor was measured on days 11, 14 and 18. The minor diameter and the major diameter of the tumor were measured using an electronic caliper (manufactured by Mitutoyo Corporation, product code: CD-15AX), and the volume of the tumor was calculated by the least square method. For SK-HEP-1 tumor-bearing mice given only the mixed liquid (vehicle) which does not contain ML210, similarly the day of inoculation of SK-HEP-1 was defined as day 0, administration of the vehicle was started on day 11, and the volume of the tumor was measured on days 11, 14 and 18. FIG. 9 shows a relationship between the volume of the tumor in the group of SK-HEP-1 tumor-bearing mice given ML210 (ML210) or the group of SK-HEP-1 tumor-bearing mice given the mixed liquid (Vehicle: without administration of ML210) (Tumor Volume) and the time after inoculation of SK-HEP-1 (Days after inoculation).

2. Results (1) Test for Suppression of Expression of GPX4

In cancer cell lines having a deficient mutation in a gene for SMARCA4 that is a SWI/SNF complex factor and/or having no SMARCA4 protein detected by immunoblot analysis, cell growth was markedly inhibited to the extent that the cell growth inhibition ratio was 90% or more in the test for suppression of expression of GPX4 as shown in FIG. 1. Further, even in cancer cell lines having a deficient mutation in a gene for at least one of SWI/SNF complex factors in addition to SMARCA4 (e.g. SMARCA2, ARID1A, ARID1B, ARID2 and BCL11B) and/or having at least one of these factors whose expression was not detected by immunoblot analysis, cell growth was markedly inhibited to the extent that the cell growth inhibition ratio was 90% or more when expression of GPX 4 was suppressed as shown in FIGS. 2 and 3. These results show that survival of a cancer cell line having a suppressed function of a SWI/SNF complex factor heavily depends on the function of GPX4.

(2) Test for Inhibition of Activity of GPX4 1

When a GPX4 inhibitor was added to cancer cell lines having a deficient mutation in a gene for at least one of SWI/SNF complex factors (e.g. SMARCA4, SMARCA2, ARID1A, ARID1B, ARID2 and BCL11B) and/or having at least one of these factors whose expression was not detected by immunoblot analysis, cell growth was markedly inhibited as compared to cell lines having no suppressed function of a SWI/SNF complex factor in the test for inhibition of activity of GPX4 1 as shown in FIGS. 4 and 5.

The results in (1) and (2) above show that inhibition (suppression of expression and inhibition of activity) of GPX4 is effective for suppressing growth of cancer cells having a suppressed function of a SWI/SNF complex factor (obtaining antitumor activity).

(3) Test for Suppression of Expression of GPX Family Protein

In cancer cell lines having a deficient mutation in a gene for SMARCA4 that is a SWI/SNF complex factor and/or having no SMARCA4 protein detected by immunoblot analysis, cell growth was markedly inhibited only when expression of GPX4, in particular, among GPX family proteins, was suppressed in the test for suppression of expression of GPX family protein as shown in FIG. 6. This result shows that inhibition of GPX4 is important for obtaining antitumor activity against a cancer cell having a suppressed function of a SWI/SNF complex factor (e.g. SMARCA4).

(4) Test for Suppression of Expression of Protein Involved in Glutathione Synthesis In cancer cell lines having a deficient mutation in a gene for SMARCA4 that is a SWI/SNF complex factor and/or having no SMARCA4 protein detected by immunoblot analysis, cell growth was markedly inhibited only when expression of GPX4, in particular, among proteins involved in glutathione synthesis, was suppressed in the test for suppression of expression of protein involved in glutathione synthesis as shown in FIG. 7. This result also shows that inhibition of GPX4 is important for obtaining antitumor activity against a cancer cell having a suppressed function of a SWI/SNF complex factor (e.g. SMARCA4).

(5) Test for Inhibition of Activity of GPX4 2 (Comparative Test with GCLC Inhibitor)

When a GPX4 inhibitor was added to cancer cell lines having a deficient mutation in a gene for SMARCA4 that is a SWI/SNF complex factor and/or having no SMARCA4 protein detected by immunoblot analysis, cell growth was markedly inhibited as compared to BSO which is a GCLC inhibitor in the test for inhibition of activity of GPX4 2 as shown in FIG. 8. This result also shows that inhibition of GPX4 is effective for obtaining antitumor activity against a cancer cell having a suppressed function of a SWI/SNF complex factor (e.g. SMARCA4).

(6) Test for Drug Efficacy of ML210 on SK-HEP-1 Tumor-Bearing Mouse

As shown in FIG. 9, the GPX4 inhibitor exhibited antitumor activity even in vivo against cancer (tumor) containing a cancer cell (cancer cell suppressing a function of SMARCA4) having a deficient mutation in a gene for SMARCA4 that is a SWI/SNF complex factor and/or having no SMARCA4 protein detected by immunoblot analysis. Specifically, in the group of SK-HEP-1 tumor-bearing mice given ML210, an increase in volume of the tumor was suppressed as compared to the group given the vehicle, and marked antitumor activity was observed.

Industrial Applicability

As described above, according to the present invention, it is possible to efficiently predict sensitivity to cancer treatment with a GPX4 inhibitor using a suppressed function of a SWI/SNF complex factor as an indicator. In addition, according to the present invention, it is possible to detect the presence or absence of a suppressed function of a SWI/SNF complex factor in a cancer patient-derived sample and select a patient having the mutation detected, followed by subjecting the patient to treatment of cancer with a GPX4 inhibitor. This enables significant improvement of cancer treatment outcomes. By using a probe or a primer against a gene for a SWI/SNF complex factor and an antibody against a SWI/SNF complex factor, companion diagnosis can be efficiently performed by detection of the presence or absence of such a suppressed function of the SWI/SNF complex factor.

[Sequence Listing Free Text]

SEQ ID NO: 2
<223> Xaa represents selenocysteine
SEQ ID NO: 59
<223> PLK1
SEQ ID NO: 60
<223> ON-TARGETplus Non-targeting Control
SEQ ID NO: 61
<223> GPX1 siRNA #1
SEQ ID NO: 62
<223> GPX1 siRNA #2
SEQ ID NO: 63
<223> GPX2 siRNA #1
SEQ ID NO: 64
<223> GPX2 siRNA #2
SEQ ID NO: 65
<223> GPX3 siRNA #1
SEQ ID NO: 66
<223> GPX3 siRNA #2
SEQ ID NO: 67
<223> GPX4 siRNA #1
SEQ ID NO: 68
<223> GPX4 siRNA #2
SEQ ID NO: 69
<223> GPX5 siRNA #1
SEQ ID NO: 70
<223> GPX5 siRNA #2
SEQ ID NO: 71
<223> GPX6 siRNA #1
SEQ ID NO: 72
<223> GPX6 siRNA #2
SEQ ID NO: 73
<223> GPX7 siRNA #1
SEQ ID NO: 74
<223> GPX7 siRNA #2
SEQ ID NO: 75
<223> GPX8 siRNA #1
SEQ ID NO: 76
<223> GPX8 siRNA #2
SEQ ID NO: 77
<223> GCLC siRNA #1
SEQ ID NO: 78
<223> GCLC siRNA #2
SEQ ID NO: 79
<223> GCLM siRNA #1
SEQ ID NO: 80
<223> GCLM siRNA #2
SEQ ID NO: 81
<223> GSS siRNA #1
SEQ ID NO: 82
<223> GSS siRNA #2
SEQ ID NO: 83
<223> MGST1 siRNA #1
SEQ ID NO: 84
<223> MGST1 siRNA #2
SEQ ID NO: 85
<223> MGST3 siRNA #1
SEQ ID NO: 86
<223> MGST3 siRNA #2
SEQ ID NO: 87
<223> GSR siRNA #1
SEQ ID NO: 88
<223> GSR siRNA #2
SEQ ID NO: 89
<223> G6PD siRNA #1
SEQ ID NO: 90
<223> G6PD siRNA #2
SEQ ID NO: 91
<223> GPX4 siRNA #3

[Sequence Listing]

The invention claimed is:

1. A method of treating cancer in a patient, the method comprising identifying, or having identified, a patient as having a cancer comprising a cancer cell exhibiting decreased activity of a SWI/SNF complex factor compared to the SWI/SNF complex factor's activity in a normal control cell; and administering to the patient a compound that inhibits glutathione peroxidase 4 (GPX4).

2. The method of claim 1, wherein the decreased activity of the SWI/SNF complex factor in the cancer cell is due to decreased expression of the SWI/SNF complex factor in the cancer cell compared to in the normal control cell.

3. The method of claim 2, comprising determining, or having determined, the level of mRNA encoding the SWI/SNF complex factor in a sample of cancer cells from the patient, as a measure of expression of the SWI/SNF complex factor in the cancer cell.

4. The method of claim 2, wherein the SWI/SNF complex factor is a BAF complex factor.

5. The method of claim 2, wherein the SWI/SNF complex factor is at least one of the following: SMARCA2, SMARCA4, ARID1A, ARID1B, ARID2, and BCL11B.

6. The method of claim 1, comprising measuring, or having measured, the decreased activity of the SWI/SNF complex factor in a sample of cancer cells obtained from the patient.

7. A method of treating cancer in a patient, the method comprising identifying, or having identified, a patient as having a cancer comprising a cancer cell that has a loss-of-function mutation in a gene encoding a SWI/SNF complex factor; and administering to the patient a compound that inhibits glutathione peroxidase 4 (GPX4).

8. The method of claim 7, wherein the SWI/SNF complex factor is a BAF complex factor.

9. The method of claim 7, wherein the SWI/SNF complex factor is at least one of the following factors: SMARCA2, SMARCA4, ARID1A, ARID1B, ARID2, or BCL11B.

10. The method of claim 7, comprising detecting, or having detected, the mutation in a sample of cancer cells obtained from the patient.

11. The method of claim 1, wherein the compound is administered to the patient in an amount effective for treating the patient's cancer.

12. A method of treating cancer in a patient, the method comprising determining, or having determined, that the patient comprises a gene encoding a SWI/SNF complex factor that has a loss-of-function mutation; and administering to the patient a compound that inhibits GPX4.

13. The method of claim 12, wherein the SWI/SNF complex factor is a BAF complex factor.

14. The method of claim 12, wherein the SWI/SNF complex factor is at least one of the following factors: SMARCA2, SMARCA4, ARID1A, ARID1B, ARID2, or BCL11B.

15. The method of claim 12, wherein the compound is administered to the patient in an amount effective for treating the patient's cancer.

16. A method of treatment comprising assaying, or having assayed, an activity of a SWI/SNF complex factor in a sample of cancer cells obtained from a patient;

determining that the activity of the SWI/SNF complex factor in the cancer cells is decreased compared to the activity of the SWI/SNF complex in a normal control cell;

selecting a cancer treatment for the patient, wherein the treatment comprises a compound that inhibits GPX4; and administering to the patient the treatment comprising the compound that inhibits GPX4.

17. The method of claim 16, wherein the SWI/SNF complex factor is a BAF complex factor.

18. The method of claim 16, wherein the SWI/SNF complex factor is at least one of the following factors: SMARCA2, SMARCA4, ARID1A, ARID1B, ARID2, or BCL11B.

19. A method of screening for an anti-cancer compound, the method comprising:

providing a plurality of compounds identified as inhibiting GPX4, providing a cancer cell line identified as having decreased activity of a SWI/SNF complex factor compared to the activity of the SWI/SNF complex factor in a control cell line;

assaying each of the plurality of compounds for its ability to inhibit growth of cells of the cancer cell line and thereby determining that one or more of the compounds inhibits growth of the cells of the cancer cell line; and selecting one of the one or more compounds as potentially useful for treating a cancer characterized as having decreased activity of the SWI/SNF complex factor.

20. The method of claim 19, further comprising:

administering the selected compound to a tumor-bearing animal model for a human cancer, wherein the tumor comprises a SWI/SNF complex factor-deficient cancer; and determining that the selected compound inhibits growth of the tumor in the animal model compared to tumor growth in a control animal to which the selected compound was not administered.

* * * * *